US008216807B2

(12) United States Patent
Adams et al.

(10) Patent No.: US 8,216,807 B2
(45) Date of Patent: Jul. 10, 2012

(54) ANTIBODIES TO LYMPHOTOXIN-α

(75) Inventors: Camellia W. Adams, Mountain View, CA (US); Jane L. Grogan, San Francisco, CA (US); Austin L. Gurney, San Francisco, CA (US); Krista McCutcheon, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/026,069

(22) Filed: Feb. 11, 2011

(65) Prior Publication Data

US 2011/0208673 A1 Aug. 25, 2011

Related U.S. Application Data

(63) Continuation of application No. 11/871,136, filed on Oct. 11, 2007, now Pat. No. 7,923,011.

(60) Provisional application No. 60/829,257, filed on Oct. 12, 2006, provisional application No. 60/938,999, filed on May 18, 2007.

(51) Int. Cl.
*C12P 21/04* (2006.01)
*C12N 15/00* (2006.01)
*C12N 5/07* (2010.01)
*C07H 21/02* (2006.01)
*C07H 21/04* (2006.01)

(52) U.S. Cl. ............... 435/70.21; 435/455; 435/328; 435/331; 435/354; 536/23.53; 536/23.1

(58) Field of Classification Search ............... None
See application file for complete search history.

(56) References Cited

U.S. PATENT DOCUMENTS

| | | | |
|---|---|---|---|
| 3,773,919 A | 11/1973 | Boswell | |
| RE30,985 E | 6/1982 | Cartaya | |
| 4,560,655 A | 12/1985 | Baker | |
| 4,657,866 A | 4/1987 | Kumar | |
| 4,676,980 A | 6/1987 | Segal et al. | |
| 4,767,704 A | 8/1988 | Cleveland et al. | |
| 4,816,567 A | 3/1989 | Cabilly et al. | |
| 4,920,196 A | 4/1990 | Aggarwal | |
| 4,927,762 A | 5/1990 | Darfler | |
| 4,959,457 A | 9/1990 | Bringman | |
| 5,122,469 A | 6/1992 | Mather et al. | |
| 5,188,969 A | 2/1993 | Arai et al. | |
| 5,264,365 A | 11/1993 | Georgiou et al. | |
| 5,427,908 A | 6/1995 | Dower et al. | |
| 5,432,018 A | 7/1995 | Dower et al. | |
| 5,498,530 A | 3/1996 | Schatz et al. | |
| 5,500,362 A | 3/1996 | Robinson et al. | |
| 5,508,192 A | 4/1996 | Georgiou et al. | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,569,825 A | 10/1996 | Lonberg et al. | |
| 5,571,894 A | 11/1996 | Wels et al. | |
| 5,573,905 A | 11/1996 | Lerner et al. | |
| 5,580,717 A | 12/1996 | Dower et al. | |
| 5,587,458 A | 12/1996 | King et al. | |
| 5,591,669 A | 1/1997 | Krimpenfort et al. | |
| 5,624,821 A | 4/1997 | Winter et al. | |
| 5,641,870 A | 6/1997 | Rinderknecht et al. | |
| 5,648,237 A | 7/1997 | Carter | |
| 5,648,260 A | 7/1997 | Winter et al. | |
| 5,658,727 A | 8/1997 | Barbas et al. | |
| 5,661,004 A * | 8/1997 | Browning et al. | ........... 435/69.1 |
| 5,670,149 A | 9/1997 | Browning et al. | |
| 5,683,688 A | 11/1997 | Aggarwal et al. | |
| 5,723,286 A | 3/1998 | Dower et al. | |
| 5,731,168 A | 3/1998 | Carter et al. | |
| 5,733,743 A | 3/1998 | Johnson et al. | |
| 5,747,023 A | 5/1998 | Goeddel et al. | |
| 5,750,373 A | 5/1998 | Garrard et al. | |
| 5,789,199 A | 8/1998 | Joly et al. | |
| 5,795,964 A | 8/1998 | Browning et al. | |
| 5,821,337 A | 10/1998 | Carter et al. | |
| 5,824,509 A | 10/1998 | Aggarwal et al. | |
| 5,837,234 A | 11/1998 | Gentile et al. | |
| 5,837,242 A | 11/1998 | Holliger et al. | |
| 5,840,523 A | 11/1998 | Simmons et al. | |
| 5,869,046 A | 2/1999 | Presta et al. | |
| 5,925,351 A | 7/1999 | Browning et al. | |
| 5,969,108 A | 10/1999 | McCafferty et al. | |
| 6,027,888 A | 2/2000 | Georgiou et al. | |
| 6,083,715 A | 7/2000 | Georgiou et al. | |
| 6,171,586 B1 | 1/2001 | Lam et al. | |
| 6,172,197 B1 | 1/2001 | McCafferty et al. | |

(Continued)

FOREIGN PATENT DOCUMENTS

CA 2388245 4/2001

(Continued)

OTHER PUBLICATIONS

Aggarwal et al., "Human Tumor Necrosis Factor" *Journal of Biological Chemistry* 260(4):2345-2354 (1985).
Aggarwal et al., "Lymphotoxin and Tumor Necrosis Factor: Qualitative and Quantitative Differences in Their Receptors and Signal Transduction in Various Cell Types" *Cytokines and Lipocortins in Inflammation and Differentiation*, Wiley-Liss, Inc. pp. 375-384 (1990).
Aggarwal, "Comparative Analysis of the Structure and Function of TNF-α and TNFβ" *Tumor Necrosis Factors: Structure, Function and Mechanism of Action*, Aggarwal and Vicek, eds., pp. 61-78 (1992).
Agyekum et al., "Expression of lymphotoxin-beta (LT-beta) in chronic inflammatory conditions" *Journal of Pathology* 199(1):115-121 (Jan. 2003).

(Continued)

*Primary Examiner* — Shulamith H Shafer
(74) *Attorney, Agent, or Firm* — Jennifer K. Holmes

(57) ABSTRACT

The invention provides various antibodies that bind to lymphotoxin-α, methods for making such antibodies, compositions and articles incorporating such antibodies, and their uses in treating, for example, an autoimmune disorder. The antibodies include murine, chimeric, and humanized antibodies.

13 Claims, 32 Drawing Sheets

U.S. PATENT DOCUMENTS

| | | |
|---|---|---|
| 6,267,958 B1 | 7/2001 | Andya et al. |
| 6,312,691 B1 | 11/2001 | Browning et al. |
| 6,403,087 B1 | 6/2002 | Browning et al. |
| 6,528,624 B1 | 3/2003 | Idusogie et al. |
| 6,602,684 B1 | 8/2003 | Umana et al. |
| 6,669,941 B1 | 12/2003 | Browning et al. |
| 6,737,056 B1 | 5/2004 | Presta |
| 7,001,598 B2 | 2/2006 | Browning et al. |
| 7,011,974 B2 | 3/2006 | Wood et al. |
| 7,029,872 B2 | 4/2006 | Gerngross et al. |
| 7,030,080 B2 | 4/2006 | Browning et al. |
| 7,056,695 B2 | 6/2006 | Dahiyat et al. |
| 7,057,022 B2 | 6/2006 | Smith et al. |
| 7,138,501 B2 * | 11/2006 | Ruben et al. ............. 530/388.23 |
| 7,262,039 B1 | 8/2007 | Narimatsu et al. |
| 7,273,707 B2 | 9/2007 | Kuai et al. |
| 2002/0004587 A1 | 1/2002 | Miller et al. |
| 2002/0039580 A1 | 4/2002 | Browning et al. |
| 2002/0136719 A1 | 9/2002 | Shenoy et al. |
| 2002/0164328 A1 | 11/2002 | Shinkawa et al. |
| 2002/0197254 A1 | 12/2002 | Browning et al. |
| 2003/0115614 A1 | 6/2003 | Kanda et al. |
| 2003/0157108 A1 | 8/2003 | Presta |
| 2003/0175884 A1 | 9/2003 | Umana et al. |
| 2004/0018590 A1 | 1/2004 | Gerngross et al. |
| 2004/0058394 A1 | 3/2004 | Garber et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0259150 A1 | 12/2004 | Nakamura et al. |
| 2005/0037003 A1 | 2/2005 | Browning et al. |
| 2005/0123546 A1 | 6/2005 | Umana et al. |
| 2005/0129614 A1 | 6/2005 | Rosen et al. |
| 2005/0163747 A1 | 7/2005 | Hilbert et al. |
| 2005/0260201 A1 | 11/2005 | Le et al. |
| 2005/0266004 A1 | 12/2005 | Giles-Komar et al. |
| 2005/0271663 A1 | 12/2005 | Ignatovich et al. |
| 2005/0276805 A1 | 12/2005 | Hanai et al. |
| 2006/0025576 A1 | 2/2006 | Miller et al. |
| 2006/0029604 A1 | 2/2006 | Gerngross et al. |
| 2006/0034828 A1 | 2/2006 | Gerngross et al. |
| 2006/0034830 A1 | 2/2006 | Gerngross et al. |
| 2006/0063254 A1 | 3/2006 | Kanda et al. |
| 2006/0064781 A1 | 3/2006 | Kanda et al. |
| 2006/0067930 A1 | 3/2006 | Adams et al. |
| 2006/0078990 A1 | 4/2006 | Kanda et al. |
| 2006/0078991 A1 | 4/2006 | Kanda et al. |
| 2006/0121037 A1 | 6/2006 | Le et al. |
| 2006/0134102 A1 | 6/2006 | LePage et al. |
| 2006/0147448 A1 | 7/2006 | Gommerman et al. |
| 2006/0147452 A1 | 7/2006 | Kang et al. |
| 2006/0222644 A1 | 10/2006 | Garber et al. |
| 2006/0222646 A1 | 10/2006 | Treacy |
| 2007/0010009 A1 | 1/2007 | Kanda et al. |
| 2007/0048300 A1 | 3/2007 | Taylor et al. |
| 2007/0111281 A1 | 5/2007 | Sondermann et al. |

FOREIGN PATENT DOCUMENTS

| | | |
|---|---|---|
| EP | 218868 | 4/1987 |
| EP | 288088 | 10/1988 |
| EP | 0 308 936 B1 | 3/1989 |
| EP | 212489 | 11/1994 |
| EP | 1585477 | 6/2003 |
| EP | 1539793 | 1/2004 |
| EP | 1585547 | 7/2004 |
| EP | 1593393 | 11/2005 |
| EP | 0954333 | 6/2006 |
| WO | WO 87/00195 | 1/1987 |
| WO | WO 90/03430 | 4/1990 |
| WO | WO 91/00360 | 1/1991 |
| WO | WO 92/00329 | 1/1992 |
| WO | WO 92/20373 | 11/1992 |
| WO | WO 93/08829 | 5/1993 |
| WO | WO 93/16185 | 8/1993 |
| WO | WO 94/04690 | 3/1994 |
| WO | WO 94/13808 | 6/1994 |
| WO | 94/29351 | 12/1994 |
| WO | WO 96/16673 | 6/1996 |
| WO | WO 97/04801 | 2/1997 |
| WO | WO 97/17852 | 5/1997 |
| WO | 97/30087 | 8/1997 |
| WO | WO 98/02463 | 1/1998 |
| WO | WO 98/56418 A2 | 12/1998 |
| WO | WO 98/58964 | 12/1998 |
| WO | WO 99/22764 | 5/1999 |
| WO | WO 99/51642 | 10/1999 |
| WO | 00/61739 | 10/2000 |
| WO | 01/29246 A1 | 4/2001 |
| WO | 03/011878 A2 | 2/2003 |
| WO | 03/035835 A2 | 5/2003 |
| WO | 03/084570 A1 | 10/2003 |
| WO | 03/085119 A1 | 10/2003 |
| WO | WO 2004/039329 | 5/2004 |
| WO | WO 2004/056312 A2 | 7/2004 |
| WO | 2004/078140 | 9/2004 |
| WO | 2004/078140 A2 | 9/2004 |
| WO | 2005/035586 A1 | 4/2005 |
| WO | 2005/035778 A1 | 4/2005 |
| WO | 2005/044859 | 5/2005 |
| WO | WO 2005/053742 A1 | 6/2005 |
| WO | WO 2005/067477 | 7/2005 |
| WO | WO 2005/097832 | 10/2005 |
| WO | 2006/014679 A1 | 2/2006 |
| WO | 2006/014683 A2 | 2/2006 |
| WO | 2006/014685 A1 | 2/2006 |
| WO | 2006/014725 A1 | 2/2006 |
| WO | 2006014726 A2 | 2/2006 |
| WO | WO 2006/114284 | 11/2006 |

OTHER PUBLICATIONS

American College of Rheumatology Subcommittee on Rheumatoid Arthritis Guidelines, "Guidelines for the Management of Rheumatoid Arthritis" *Arthritis and Rheumatism* 46(2):328-346 (Feb. 2002).

*American Type Culture Collection Catalogue of Cell Lines and Hybridomas*, sixth edition pp. 346-349 (1988).

Androlewicz et al., "Lymphotoxin is expressed as a heteromeric complex with a distinct 33-kDa glycoprotein on the surface of an activated human T cell hybridoma" *Journal of Biological Chemistry* 267(4):2542-2547 (Feb. 5, 1992).

Arie et al., "Chaperone Function of FkpA, A Heat Shock Prolyl Isomerase, in the Periplasm of *Escherichia coli*" *Molecular Microbiology* 39(1):199-210 (2001).

Barbas et al., "In Vitro Evolution of a Neutralizing Human Antibody to Human Immunodeficiency Virus Type 1 to Enhance Affinity and Broaden Strain Cross-Reactivity" *Proc Natl Acad Sci U S A.* 91(9):3809-3813 (Apr. 1994).

Barnes and Sato., "Methods for Growth of Cultured Cells in Serum-Free Medium" *Analytical Biochemistry* 102:255-270 (1980).

Bass et al., "Hormone Phage: An Enrichment Method for Variant Proteins with Altered Binding Properties" *Proteins: Structure, Function, and Genetics* 8(4):309-314 (1990).

Boerner et al., "Production of Antigen-Specific Human Monoclonal Antibodies From In Vitro-Primed Human Splenocytes" *J Immunol.* 147(1):86-95 (Jul. 1991).

Bothmann and Pluckthun, "The Periplasmic *Escherichia coli* Peptidylprolyl cis,trans-Isomerase FkpA" *J Bio Chem.* 275(22):17100-17105 (Jun. 2000).

Brennan et al., "Preparation of bispecific antibodies by chemical recombination of monoclonal immunoglobulin $G_1$ fragments" *Science* 229(4708):81-83 (Jul. 5, 1985).

Brodeur et al., "Mouse-Human Myeloma Partners for the Production of Heterohybridomas" *Monoclonal Antibody Production Techniques and Applications*, New York:Marcel Dekker, Inc. pp. 51-63 (1987).

Browning et al., "Characterization of surface lymphotoxin forms use of specific monoclonal antibodies and soluble receptors" *J. of Immunology* 154:33-46 (Jan. 1, 2001).

Browning et al., "Lymphotoxin and an associated 33-kDa glycoprotein are expressed on the surface of an activated human T cell hybridoma" *J. Immunol.* 147(4):1230-1237 (Aug. 15, 1991).

Bruggemann et al., "Designer Mice: The Production of Human Antibody Repertoires in Transgenic Animals" *Year Immunol.* 7:33-40 (1993).

Buch et al., "True infliximab resistance in rheumatoid arthritis: a role for lymphotoxin alpha?" *Annals of the Rheumatic Diseases* 63(10) :1344-1346 (Oct. 2004).

Burton, D.R., "Immunoglobulin G: Functional Sites" *Molecular Immunology* 22(3) :161-206 (1985).

Carter et al., "High Level *Escherichia coli* Expression and Production of a Bivalent Humanized Antibody Fragment" *Bio/Technology* 10(2) :163-167 (Feb. 1992).

Carter et al., "Humanization of an Anti-p185$^{HER2}$ Antibody for Human Cancer Therapy" *Proc Natl Acad Sci U S A*. 89(10) :4285-4289 (May 1992).

Cathcart et al., "Experimental arthritis in a nonhuman primate. I. Induction by bovine type II collagen" *Laboratory Investigations* 54:26-31 (1986).

Chaplin et al., "Development and maturation of secondary lymphoid tissues" *Annual Reviews in Immunology* 17:399-433 (1999).

Chen et al., "Chaperone Activity of DsbC" *J Bio Chem.* 274(28):19601-19605 (Jul. 1999).

Chen et al., "Selection and Analysis of an Optimized Anti-VEGF Antibody: Crystal Structure of an Affinity-matured Fab in Complex with Antigen" *Journal of Molecular Biology* 293(4):865-881 (1999).

Chiang, Eugene et al., "Targeted depletion of lymphotoxin-alpha-expressing TH1 and TH17 cells inhibits autoimmune disease" *Nature Medicine* 15(7):766-773 (Jul. 2009).

Chothia and Lesk, "Canonical Structures for the Hypervariable Regions of Immunoglobulins" *J Mol Biol.* 196(4):901-917 (Aug. 20, 1987).

Clackson et al., "Making Antibody Fragments Using Phage Display Libraries" *Nature* 352(6336):624-628 (Aug. 15, 1991).

Clynes et al., "Fc Receptors Are Required in Passive and Active Immunity to Melanoma" *Proc Natl Acad Sci U S A*. 95(2) :652-656 (Jan. 1998).

Cole et al., "The EBV-Hybridoma Technique and Its Application to Human Lung Cancer" *Monoclonal Antibodies and Cancer Therapy*, New York:Alan R. Liss, Inc. pp. 77-96 (1985).

Coligan et al., "Animal Models of Acute and Chronic Gradt-Versus-Host Disease" *Current Protocols in Immunology* (unit 4.3), New York:John Wiley & Sons, Inc. (1998).

Coligan et al., "Delayed-Type Hypersensitivity" *Current Protocols in Immunology* (Unit 4.5), New York:John Wiley & Sons, Inc. (1993).

Coligan et al., "Skin Allograft rejection" *Current Protocols in Immunology* (Unit 4.4), New York:John Wiley & Sons, Inc. (1991).

Courtenay et al., "Immunisation against heterologous type II collagen induces arthritis in mice" *Nature* 283:666-668 (1980).

Crea et al., "Chemical Synthesis of Genes for Human Insulin" *Proc Natl Acad Sci U S A*. 75(12) :5765-5769 (Dec. 1978).

Cunningham and Wells, "High-Resolution Epitope Mapping of hGH-Receptor Interactions by Alanine-Scanning Mutagenesis" *Science* 244:1081-1085 (Jun. 2, 1989).

*Current Protocols in Immunology* (unit 15.5, National Institutes of Health), Coligen et al., John Wiley & Sons, Inc. (1995).

Dohi et al., "Elimination of colonic patches with lymphotoxin beta receptor-Ig prevents Th2 cell-type colitis" *J. of Immunology* 167(5) :2781-2790 (Sep. 1, 2001).

Duncan and Winter, "The Binding Site for Clq on IgG" *Nature* 332:738-740 (Apr. 21, 1988).

Durie et al., "Prevention of collagen-induced arthritis with an antibody to gp39, the ligand for CD40" *Science* 261:1328-1330 (1993).

Ellman et al., "Biosynthetic Method for Introducing Unnatural Amino Acids Site-Specifically into Proteins" *Meth. Enzym.* 202:301-336 (1991).

Endres et al., "Mature follicular dendritic cell networks depend on expression of lymphotoxin beta receptor by radioresistant stromal cells and of lymphotoxin beta and tumor necrosis factor by B cells" *Journal of Immunology* 189(1) :159-168 (1999).

Eugster et al., "Differential effects of TNF and LTalpha in the host defense against *M. bovis* BCG"*European J. Immunol.* 31(6) :1935-1943 (Jun. 2001).

Fava et al., "A role for the lymphotoxin/LIGHT axis in the pathogenesis of murine collagen-induced arthritis" *Journal of Immunology* 171(1) :115-126 (Jul. 1, 2003).

Futterer et al., "The Lymphotoxin β Receptor Controls Organogenesis and Affinity Maturation in Peripheral Lymphoid Tissues" *Immunity* 9:59-70 (1998).

Gazzano-Santoro et al., "A non-radioactive complement-dependent cytotoxicity assay for anti-CD20 monoclonal antibody" *J Immunol Methods*. 202(2) :163-171 (Mar. 28, 1997).

Gescuk, et al., "Novel Therapeutic Agents for Systemic Lupus Erythematosus" *Current Opinion in Rheumatology* 14:515-521 (2002).

Goding, "Production of Monoclonal Antibodies" *Monoclonal Antibodies: Principles and Practice*, Academic Press, pp. 56-103 (1986).

Gommerman et al., "A role for surface lymphotoxin in experimental autoimmune encephalomyelitis independent of LIGHT" *Journal of Clinical Investigation* 112(5) :755-767 (Sep. 2003).

Gommerman et al., "Manipulation of lymphoid microenvironments in nonhuman primates by an inhibitor of the lymphotoxin pathway" *Journal of Clinical Investigation* 110(9) :1359-1369 (Nov. 2002).

Gorman et al., "Mammalian cell expression" *Current Opinion in Biotechnology* 1(1) :36-47 (Oct. 1990).

Gorman et al., "Transient Production of Proteins Using an Adenovirus Transformed Cell Line" *DNA Prot. Eng. Tech*. 2(1) :3-10 (1990).

Graham et al., "Characteristics of a Human Cell Line Transformed by DNA from Human Adenovirus Type 5" *J Gen Virol*. 36(1) :59-72 (Jul. 1977).

Grewal et al., "Requirement for CD40 ligand in costimulation induction, T cell activation, and experimental allergic encephalomyelitis" *Science* 273:1864-1867 (1996).

Griffiths et al., "Human anti-self antibodies with high specificity from phage display libraries" *EMBO Journal* 12(2) :725-734 (Feb. 1993).

Gruber et al., "Efficient Tumor Cell Lysis Mediated by a Bispecific Single Chain Antibody Expressed in *Escherichia coli*" *Journal of Immunology* 152:5368-5374 (1994).

Guss et al., "Structure of the IgG-Binding Regions of Streptococcal Protein G" *EMBO Journal* 5(7) :1567-1575 (1986).

Hakimi et al., "Reduced immunogenicity and improved pharmacokinetics of humanized anti-Tac in cynomolgus monkeys" *J Immunol*. 147(4) :1352-1359 (Aug. 15, 1991).

Ham and McKeehan, "Media and Growth Requirements" *Methods in Enzymology* 58:44-93 (1979).

Han et al., "Blockade of lymphotoxin pathway exacerbates autoimmune arthritis by enhancing the Th1 response" *Arthritis and Rheumatism* 52(10) :3202-3209 (Oct. 2005).

Hara et al., "Overproduction of Penicillin-Binding Protein 7 Suppresses Thermosensitive Growth Defect at Low Osmolarity Due to an spr Mutation of *Escherichia coli*" *Microb Drug Resist*. 2(1) :63-72 (1996).

Harris, "Production of humanized monoclonal antibodies for in vivo imaging and therapy" *Biochemical Society Transactions* 23(4) :1035-1038 (Nov. 1995).

Hawkins et al., "Selection of Phage Antibodies by Binding Affinity Mimicking Affinity Maturation" *J Mol Biol*. 226:889-896 (1992).

Holliger et al., ""Diabodies": Small Bivalent and Bispecific Antibody Fragments" *Proc Natl Acad Sci U S A*. 90:6444-6448 (Jul. 1993).

Holmdahl et al., "Collagen induced arthritis as an experimental model for rheumatoid arthritis. Immunogenetics, pathogenesis and autoimmunity" *APMIS* 97(7):575-584 (Jul. 1989).

Holmdahl et al., "Role of T lymphocytes in murine collagen induced arthritis" *Agents and Actions* 19:295-305 (1986).

Hoogenboom et al., "By-passing immunisation. Human antibodies from synthetic repertoires of germline VH gene segments rearranged in vitro" *J. Mol. Biol*. 227(2):381-388 (Sep. 20, 1992).

Hurle and Gross, "Protein Engineering Techniques for Antibody Humanization" *Curr Opin Biotechnol*. 5:428-433 (1994).

Imagawa, D. et al., "Anti-tumor Necrosis Factor Antibody Enhances Allograft Survival in Rats" *J. of Surgical Research*, San Diego, CA 48(4) :345-348 (Apr. 1, 1990).

Issekutz et al., "Treatment of established adjuvant arthritis in rats with monoclonal antibody to CD18 and very late activation antigen-4 integrins suppresses neutrophil and T-lymphocyte migration to the joints and improves clinical disease" *Immunology* 88:569-576 (1996).

Jackson et al., "In vitro antibody maturation. Improvement of a high affinity, neutralizing antibody against IL-1 beta" *Journal of Immunology* 154(7) :3310-3319 (Apr. 1, 1995).

Jaffers et al., "Monoclonal Antibody Therapy, Anti-Idiotypic and Non-Anti-Idiotypic Antibodies to OKT3 Arising Despite Intense Immunosuppression" *Transplantation* 41(5) :572-578 (May 1986).

Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6) :2551-2555 (Mar. 15, 1993).

Jakobovits et al., "Germ-line Transmission and Expression of a Human-Derived Yeast Artificial Chromosome" *Nature* 362(6417) :255-258 (Mar. 18, 1993).

Jamieson et al., "Collagen-Induced Arthritis in Rats Assessment by Serial Magnification Radiography" *Invest. Radiol.* 20:324-330 (1985).

Johnson & Chiswell, "Human antibody engineering" *Current Opinion in Structural Biology* 3:564-571 (1993).

Jones et al., "Replacing the Complementarity-Determining Regions in a Human Antibody with Those From a Mouse" *Nature* 321(6069) :522-525 (May 29, 1986).

Joosten et al., "Anticytokine treatment of established type II collagen-induced arthritis in DBA/1 mice. A comparative study using anti-TNFα, anti-IL-1α/β, and IL-1Ra" *Arthritis and Rheumatism* 39(5):797-809 (1996).

Joosten et al., "IL-1αβ Blockade Prevents Cartilage and Bone Destruction in Murine Type II Collagen-Induced Arthritis, Whereas TNF-α Blockade Only Ameliorates Joint Inflammation" *J Immunol.* 163:5049-5055 (1999).

Junghans et al., "Anti-Tac-H, a Humanized Antibody to the Interleukin 2 Receptor with New Features for Immunotherapy in Malignant and Immune Disorders" *Cancer Research* 50(5) :1495-1502 (Mar. 1, 1990).

Kabat et al. *Sequences of Proteins of Immunological Interest*, 5th edition, Bethesda, MD:NIH vol. 1:688-696 (1991).

Kanda et al., "Comparison of cell lines for stable production of fucose-negative antibodies with enhanced ADCC" *Biotechnology Bioengineering* 94(4) :680-688 (Jul. 5, 2006).

Khazaeli et al., "Phase I trial of multiple large doses of murine monoclonal antibody CO17-1A. II. Pharmacokinetics and immune response" *J Natl. Cancer Inst.* 80(12) :937-942 (Aug. 17, 1988).

Kohler and Milstein, "Continuous Cultures of Fused Cells Secreting Antibody of Predefined Specificity" *Nature* 256(5517) :495-497 (Aug. 7, 1975).

Kollias et al., "Complementation of lymphotoxin alpha knockout mice with tumor necrosis factor-expressing transgenes rectifies defective splenic structure and function" *Journal of Exp. Med.* 188(4) :745 (Aug. 17, 1998).

Korner et al., "Distinct roles for lymphotoxin-alpha and tumor necrosis factor in organogenesis and spatial organization of lymphoid tissue" *European Journal of Immunology* 27(10) :2600-2609 (Oct. 1997).

Kostelny et al., "Formation of a Bispecific Antibody by, the Use of Leucine Zippers" *Journal of Immunology* 148(5) :1547-1553 (Mar. 1, 1992).

Kozbor et al., "A Human Hybrid Myeloma for Production of Human Monoclonal Antibodies" *J Immunol.* 133(6) :3001-3005 (Dec. 1, 1984).

Kraus et al. *Acta Neurologica Scandinavica* 105(4) :300-308 (2002).

Kunkel et al., "Rapid and Efficient Site-specific Mutagenesis Without Phenotypic Selection" *Methods in Enzymology* 154:367-382 (1987).

Lehninger, A.L., "The amino acid building blocks of protein" *Biochemistry*, 2nd edition, New York, NewYork:Worth Publishers pp. 71-92 (1975).

Lindmark et al., "Binding of Immunoglobulins to Protein A and Immunoglobulin Levels in Mammalian Sera" *J Immunol Meth.* 62:1-13 (1983).

Littlefield, J. W., "Selection of Hybrids From Matings of Fibroblasts In Vitro and Their Presumed Recombinants" *Science* 145:709-710 (Aug. 14, 1964).

Lowman and Wells, "Monovalent Phage Display: A Method for Selecting Variant Proteins from Random Libraries" *Methods: A Companion to Methods in Enzymology* 3:205-216 (Dec. 1991).

MacEwan et al., "TNF ligands and receptors—a matter of life and death." *British Journal of Pharmacology* 135(4) :855-875 (Feb. 2002).

Mackay et al., "Lymphotoxin but not tumor necrosis factor functions to maintain splenic architecture and humoral responsiveness in adult mice" *European Journal of Immunology* 27(8) :2033-2042 (Aug. 1997).

Maini et al., "Monoclonal anti-TNFα antibody as a probe of pathogenesis and therapy of rheumatoid disease" *Immunol. Rev.* 144:195-223 (1995).

Margolis et al., "Ribonuclease and deoxyribonuclease activity in hyaluronidase preparations" *Analytical Biochemistry* 35(1) :77-81 (May 1970).

Marks et al., "By-passing immunization: building high affinity human antibodies by chain shuffling" *Bio/Technology* 10(7) :779-783 (Jul. 1992).

Marks et al., "By-Passing Immunization: Human Antibodies From V-gene Libraries Displayed on Phage" *J Mol Biol.* 222(3) :581-597 (Dec. 5, 1991).

Mather et al., "Culture of Testicular Cells in Hormone-Supplemented Serum-Free Medium" *Annals N.Y. Acad. Sci.* 383:44-68 (1982).

Mather, "Establishment and Characterization of Two Distinct Mouse Testicular Epithelial Cell Lines" *Biol Reprod.* 23:243-252 (1980).

Matsumoto et al., "Involvement of distinct cellular compartments in the abnormal lymphoid in organogenesis in lymphotoxin-alpha-deficient mice and alymphoplasia (aly) mice defined by the chimeric analysis" *J. Immunol.* 163(3) :1584-1591 (Aug. 1, 1999).

Matsumoto et al., "Lymphotoxin-alpha-deficient and TNF receptor-I-deficient mice define developmental and functional characteristics of germinal centers" *Immunol. Rev.* 156:137-144 (Apr. 1997).

Matusevicius, "Multiple sclerosis: the proinflammatory cytokines lymphotoxin-alpha and tumour necrosis factor-alpha are upregulated in cerebrospinal fluid mononuclear cells" *J. Neuroimm.* 66(1-2) :115-123 (May 1996).

Mauri et al., "LIGHT, a new member of the TNF superfamily, and lymphotoxin α are ligands for herpesvirus entry mediator" *Immunity* 8(1) :21-30 (Jan. 1998).

McCafferty et al., "Phage antibodies: filamentous phage displaying antibody variable domains" *Nature* 348:552-554 (Dec. 6, 1990).

Miller et al., "Monoclonal antibody therapeutic trials in seven patients with T-cell lymphoma" *Blood* 62:988-995 (1983).

Miller, "Structural studies on cartilage collagen employing limited cleavage and solubilization with pepsin" *Biochemistry* 11(26):4903-4909 (Dec. 19, 1972).

Milstein and Cuello, "Hybrid Hybridomas and Their Use in Immunohistochemistry" *Nature* 305:537-540 (Oct. 6, 1983).

Morimoto et al., "Abnormalities in CD4+ T-lymphocytes subsets in inflammatory rheumatic diseases" *Am. J. Med.* 84(5):817-825 (1988).

Morimoto et al., "Single-step purification of F(ab')$_2$ fragments of mouse monoclonal antibodies (immunoglobulins G1) by hydrophobic interaction high performance liquid chromatography using TSKgel Phenyl-5PW" *J Biochem Biophys Methods* 24(1-2) :107-117 (Mar. 1992).

Morrison et al., "Chimeric Human Antibody Molecules: Mouse Antigen-Binding Domains with Human Constant Region Domains" *Proc. Natl. Acad. Sci. USA* 81(21) :6851-6855 (Nov. 1984).

Munson and Rodbard, "LIGAND: A Versatile Computerized Approach for Characterization of Ligand-Binding Systems" *Analytical Biochemistry* 107(1) :220-229 (Sep. 1, 1980).

Murphy et al., "The lineage decisions of helper T cells" *Nature Reviews: Immunology* 2(12) :933-944 (Dec. 2002).

Nickoloff et al., "Severe combined immunodeficiency mouse and human psoriatic skin chimeras. Validation of a new animal model" *Am J Pathol.* 146(3) :580-588 (Mar. 1995).

Noren et al., "A general method for site-specific incorporation of unnatural amino acids into proteins" *Science* 244(4901) :182-188 (Apr. 14, 1989).

Oi and Herzenberg, "Immunoglobulin-Producing Hybrid Cell Lines" *Selected methods in cellular immunology*, Mishell BB, Shiigi S, San Francisco: Freeman, Chapter 17, pp. 351-372 (1981).
Okazaki et al., "Fucose depletion from human IgG1 oligosaccharide enhances binding enthalpy and association rate between IgG1 and FcgammaRIIIa" *J Mol Biol*. 336(5):1239-1249 (Mar. 5, 2004).
Papac et al., "A High-Throughput Microscale Method to Release N-Linked Oligosaccharides from Glycoproteins for Matrix-Assisted Laser Desorption/Ionization Time-of-Flight Mass Spectrometric Analysis" *Glycobiology* 8(5):445-454 (1998).
Paul et al., "Lymphotoxin" *Ann. Rev. Immunol*. 6:407-438 (1988).
Pennica et al., "Human tumour necrosis factor: precursor structure, expression and homology to lymphotoxin" *Nature* 312(5996):724-729 (Dec. 20, 1984).
Pitzalis et al., "The preferential accumulation of helper-inducer T lymphocytes in inflammatory lesions: evidence for regulation by selective endothelial and homolytic adhesion" *European Journal of Immunology* 18(9):1397-1404 (1988).
Plant et al., "Astroglial-derived lymphotoxin-alpha exacerbates inflammation and demyelination, but not remyelination" *Glia* 49(1):1-14 (Jan. 1, 2005).
Pluckthun, A., "Mono- and bivalent antibody fragments produced in *Escherichia coli*: engineering, folding and antigen binding" *Immunol. Revs*. 130:151-188 (1992).
Potocnik et al., "Expression of activation antigens on T cells in rheumatoid arthritis patients" *Scand. J. Immunol*. 31(2):213-224 (1990).
Powell et al., "Lymphotoxin and tumor necrosis factor-alpha production by myelin basic protein-specific T cell clones correlates with encephalitogenicity" *International Immunology* 2(6):539-544 (1990).
Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).
Presta et al., "Humanization of an Antibody Directed Against IgE" *J Immunol*. 151(5):2623-2632 (Sep. 1, 1993).
Presta, "Antibody Engineering" *Current Opinion in Structural Biology* 2:593-596 (1992).
Ramm and Pluckthun, "The Periplasmic *Escherichia coli* Peptidylprolyl cis,trans Isomerase FkpA" *J Biol Chem*. 275(22):17106-17113 (Jun. 2000).
Ravetch and Kinet, "Fc Receptors" *Annu. Rev. Immunol*. 9:457-492 (1991).
Rennert et al., "Lymph node genesis is induced by signaling through the lymphotoxin beta receptor" *Immunity* 9(1):71-79 (Jul. 1998).
Ridley et al., "Monocyte activation in rheumatoid arthritis: evidence for in situ activation and differentiation in joints" *Br. J. Rheumatology* 29(2):84-88 (1990).
Riechmann et al., "Reshaping Human Antibodies for Therapy" *Nature* 332:323-327 (Mar. 24, 1988).
Ripka et al., "Two Chinese Hamster Ovary Glycosylation Mutants Affected in the Conversion of GDP-Mannose to GDP-Fucose" *Archives of Biochemistry & Biophysics* 249(2):533-545 (Sep. 1986).
Ruddle, "Tumor Necrosis Factor (TNF-α) and Lymphotoxin (TNF-β)" *Current Opinion in Immunology* 4:327-332 (1992).
Saito et al., "The participation of tumor necrosis factor in the pathogenesis of lung allograft rejection in the rat" *Transplantation* 55(5):967-972 (May 1993).
Sambrook et al, "Molecular Cloning: A Laboratory Manual" (Sections 4.21-4.41), Cold Spring Harbor Laboratory Press, 2nd edition, New York (1989).
Schier et al., "Identification of Functional and Structural Amino-Acid Residues by Parsimonious Mutagenesis." *Gene*. 169:147-155 (1996).
Schon et al., "Murine psoriasis-like disorder induced by naive CD4+ T cells" *Nat Med*. 3(2):183-188 (Feb. 1997).
Sean Riminton et al., "Challenging cytokine redundancy: inflammatory cell movement and clinical course of experimental autoimmune encephalomyelitis are normal in lymphotoxin-deficient, but not tumor necrosis factor-deficient, mice" *Journal of Experimental Medicine* 187(9):1517-1528 (May 4, 1998).

Sears et al., "Effects of monoclonal antibody immunotherapy on patients with gastrointestinal adenocarcinoma" *J Biol Response Mod*. 3(2):138-150 (1984).
Seki et al., "Type II collagen-induced murine arthritis: induction of arthritis depends on antigen-presenting cell function as well as susceptibility of host to an anticollagen immune response" *J. Immunol*. 148:3093-3099 (1992).
Selmaj et al., "Cytokine cytotoxicity against oligodendrocytes. Apoptosis induced by lymphotoxin" *Journal of Immunology* 147(5):1522-1529 (Sep. 1, 1991).
Selmaj et al., "Identification of lymphotoxin and tumor necrosis factor in multiple sclerosis lesions" *J. Clin. Invest*. 87(3):949-954 (Mar. 1991).
Shalaby et al., "Development of Humanized Bispecific Antibodies Reactive with Cytotoxic Lymphocytes and Tumor Cells Overexpressing the HER2 Protooncogene" *Journal of Experimental Medicine* 175:217-225 (Jan. 1, 1992).
Shawler et al., "Human immune response to multiple injections of murine monoclonal IgG" *J Immunol*. 135(2):1530-1535 (1985).
Shields et al., "High Resolution Mapping of the Binding Site on Human IgG1 for FcγRI, FcγRII, FcγRIII, and FcRn and Design of IgG1 Variants with Improved Binding to the FcγR" *Journal of Biological Chemistry* 276(9):6591-6604 (2001).
Sims et al., "A Humanized CD18 Antibody Can Block Function Without Cell Destruction" *The Journal of Immunology* 151(4):2296-2308 (Aug. 15, 1993).
Skerra, "Bacterial expression of immunoglobulin fragments" *Curr. Opin. Immunol*. 5:256-262 (1993).
Small et al., "Analysis of a Transgenic Mouse Containing Simian Virus 40 and v-myc Sequences" *Molecular & Cellular Biology* 5:642-648 (1985).
Sprent et al., "T cell memory" *Annu Rev Immunol*. 20:551-579 (2002).
Spriggs, "Tumor Necrosis Factor: Basic Principles and Preclinical Studies" *Biologic Therapy of Cancer*, DeVita et al., J.B. Lippincott Co. pp. 354-377 (1991).
Stepien et al., "The tumour necrosis factor family of receptors/ligands in the serum of patients with rheumatoid arthritis" *European Cytokine Network* 9(2):145-154 (Jun. 1998).
Suen et al., "A critical role for lymphotoxin in experimental allergic encephalomyelitis" *Journal of Experimental Medicine* 186(8):1233-1240 (Oct. 20, 1997).
Suresh et al., "Bispecific Monoclonal Antibodies from Hybrid Hybridomas" *Methods in Enzymology* 121:210-228 (1986).
Takemura et al., "Lymphoid neogenesis in rheumatoid synovitis" *Journal of Immunology* 167(2):1072-1080 (Jul. 15, 2001).
Tanabe et al., "Combined immunosuppressive therapy with low dose FK506 and antimetabolites in rat allogeneic heart transplantation" *Transplantation* 58(1):23-27 (Jul. 15, 1994).
Thomas and Quinn, "Functional differentiation of dendritic cells in rheumatoid arthritis: role of CD86 in the synovium" *J. Immunol*. 156(8):3074-3086 (1996).
Thomas et al., "Rheumatoid synovium is enriched in mature antigen-presenting dendritic cells" *J. Immunol*. 152(5):2613-2623 (1994).
Traunecker et al., "Bispecific Single Chain Molecules (Janusins) Target Cytotoxic Lymphocytes on HIV Infected Cells" *EMBO Journal* 10(12):3655-3659 (1991).
Tutt et al., "Trispecific F(ab')3 derivatives that use cooperative signaling via the TCR/CD3 complex and CD2 to activate and redirect resting cytotoxic T cells" *J Immunol*. 147(1):60-69 (Jul. 1991).
Urlaub and Chasin, "Isolation of Chinese Hamster Cell Mutants Deficient in Dihydrofolate Reductase Activity" *Proc Natl Acad Sci U S A*. 77(7):4216 (Jul. 1980).
Vaswani and Hamilton, "Humanized antibodies as potential therapeutic drugs" *Ann Allergy Asthma & Immunol*. 1:105-115 (1998).
Verhoeyen et al., "Reshaping Human Antibodies: Grafting an Antilysozyme Activity" *Science* 239:1534-1536 (Mar. 1988).
Vieira et al., "Production of single-stranded plasmic DNA" *Meth Enzymol*. 153:3-11 (1987).
Voshkuhl et al., "T helper 1 (Th1) functional phenotype of human myelin basic protein-specific T lymphocytes." *Autoimmunity* 15(2):137-143 (1993).

Ware et al., "The Ligands and Receptors of the Lymphotoxin System" *Pathways for Cytolysis, Current Topics Microbiol. Immunol.*, Springer-Verlag pp. 175-218 (1995).

Waterhouse et al., "Combinatorial infection and in vivo recombination: a strategy for making large phage antibody repertoires" *Nucleic Acids Research* 21:2265-2266 (1993).

Wernick et al., "IgG and IgM rheumatoid factor synthesis in rheumatoid synovial membrane cell cultures" *Arthritis and Rheumatism* 28(7):742-752 (1985).

Weyand et al., "The power of the third dimension: tissue architecture and autoimmunity in rheumatoid arthritis" *Current Opinion in Rheumatology* 15(3):259-266 (May 2003).

Williams et al., "Anti-tumor necrosis factor ameliorates joint disease in murine collagen-induced arthritis" *Proc Natl Acad Sci U S A.* 89:9784-9788 (1992).

Williams et al., "Synergy between anti-CD4 and anti-tumor necrosis factor in the amelioration of established collagen-induced arthritis" *Proc. Natl. Acad. Sci. USA* 91:2762-2766 (1994).

Wolyniec et al., "Reduction of Antigen-Induced Airway Hyperreactivity and Eosinophilia in ICAM-1-Deficient Mice." *Am J Respir Cell Mol Biol.* 18:777-785 (1998).

Wong et al., "MsSOD Induction by TNF and Its Protective Role" *Tumor Necrosis Factors: The Molecules and their Emerging Role in Medicine*, Beutler, B., Raven Press pp. 473-484 (1992).

Wong et al., "Tumor Necrosis Factor" *Human Monocytes*, Academic Press pp. 195-215 (1989).

Wooley et al., "Influence of a Recombinant Human Soluble Tumor Necrosis Factor Receptor FC Fusion Protein on Type II Collagen-Induced Arthritis in Mice" *J Immunol.* 151(11):6602-6607 (1993).

Worm et al., "Lymphotoxin-alpha is an important autocrine factor for CD40+ interleukin-4-mediated B-cell activation in normal and atopic donors" *Immunology* 94(3):395-402 (Jul. 1998).

Wu et al., "Reversal of spontaneous autoimmune insulitis in nonobese diabetic mice by soluble lymphotoxin receptor" *Journal of Experimental Medicine* 193(11):1327-1332 (Jun. 4, 2001).

Wu et al., "Signal via lymphotoxin-beta R on bone marrow stromal cells is required for an early checkpoint of NK cell development" *Journal of Immunology* 166(3):1684-1689 (Feb. 1, 2001).

Yamane-Ohnuki et al., "Establishment of FUT8 knockout Chinese hamster ovary cells: an ideal host cell line for producing completely defucosylated antibodies with enhanced antibody-dependent cellular cytotoxicity" *Biotechnol Bioeng.* 87(5):614-622 (Sep. 5, 2004).

Yelton et al., "Affinity Maturation of the BR96 Anti-Carcinoma Antibody by Codon-Based Mutagenesis" *The Journal of Immunology* 155:1994-2004 (1995).

Zipp et al., "Genetic control of multiple sclerosis: increased production of lymphotoxin and tumor necrosis factor-alpha by HLA-DR2+ T cells" *Annals of Neurology* 38(5):723-730 (Nov. 1995).

Zoller et al., "Oligonucleotide-Directed Mutagenesis Using M13-Derived Vectors: An Efficient and General Procedure for the Production of Point Mutations in Any Fragment of DNA" *Nucleic Acids Research* 10:6487-6504 (1987).

Pfeffer, K., "Biological functions of tumor necrosis factor cytokines and their receptors" *Cytokine & Growth Factor Reviews* 14:185-191 (2003).

\* cited by examiner

2C8 Chimera Light Chain

DIVMTQSHKFMSTSVGDRVSITCKASQAVSSAVAWYQQKPGQSPKLQIYSASHRYTGVPD
RFTGSGSGTDFTFTISSVQAEDLAVYYCQQHYSTPWTFGGGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQUENCE ID NO:32)

2C8 Chimera Heavy Chain

EVQLQQSGPELVKPGASVKLSCKASGYTFTSYVIHWVKQKPGQGLEWIGYNNPYNDGTNY
NEKFKGKATLTSDKSSSTAYMELSSLTSEDSAVYYCSRPTMLPWFAYWGQGTTLTVSAAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQUENCE ID NO:33)

*FIG. 1A*

3F12 Chimera Light Chain:

DIVMSQSPSSLAVSVGEKVTMSCKSSQSLLYSTNQKNFLAWYQQKPGQSPKLLIYWASTR
DSGVPDRFTGSGSGTDFTLTISSVKAEDLAVYYCQQYYSYPRTFGGGTKLEIKRTVAAPS
VFIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO:34)

3F12 Chimera Heavy Chain:

QGQLQQSGAELMKPGASVKISCKATGYTFSSYWIEWVKQRPGHGLEWIGEISPGSGSTNY
NEEFKGKATFTADKSSNTAYIQLSSLSTSEDSAVYYCADGYHGYWGQGTTLTVSSAKTTG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK (SEQ ID NO:35)

3F12 Chimera Heavy-chain Variable Region:

QGQLQQSGAELMKPGASVKISCKATGYTFSSYWIEWVKQRPGHGLEWIGEISPGSGSTNY
NEEFKGKATFTADKSSNTAYIQLSSLSTSEDSAVYYCADGYHGYWGQGTTLTVSS
(SEQ ID NO:31)

*FIG. 1B*

Anti-LTα 3F12.2D3 Light-chain Variable Region:

DIVMSQSPSSLAVSVGEKVTMSCKSSQSLLYSTNQKNFLAWYQQKPGQSPKLLIYWASTRDSGV
PDRFTGSGSGTDFTLTISSVKAEDLAVYYCQQYYSYPRTFGGGTKLEIK (SEQ ID NO:36)

Anti-LTα 3F12.2D3 Light-chain Constant Region:

**RADAAPTVSIFPPSSEQLTSGGASVVCFLNNFYPKDINVKWKIDGSERQNGVLNSWTDQDSKDS
TYSMSSTLTLTKDEYERHNSYTCEATHKTSTSPIVKSFNRNEC** (SEQ ID NO:37)

(Highlighted in bold are residues that were identified from various chemical/enzymatic cleavages)

*FIG. 1C*

Anti-LTα 3F12.2D3 Heavy-chain Variable Region:

QGQLQQSGAELMKPGASVKISCKATGYTFSSYWIEWVKQRPGHGLEWIGEISPGSGSTNYNEEF
KGKATFTADKSSNTAYIQLSSLTSEDSAVYYCADGYHGYWGQGTPLTVSS (SEQ ID NO:38)

Anti-LTα 3F12.2D3 Heavy-chain Constant Region:

**AKTTPPSVYPLAPGCGDTTGSSVTLGCLVKGYFPESVTVTWNSGSLSSSVHTFPALLQSGLYTM
SSSVTVPSSTWPSQTVTCSVAHPASSTTVDKKLEPSGPISTINPCPPCKECHKCPAPNLEGGPSVFIFPPN
IKDVLMISLTPKVTCVVVDVSEDDPDVQISWFVNNVEVHTAQTQTHREDYN**STIRVVSTLPIQ
HQDWMSGKEFKCKVNNKDLPSPIERTISKIKGLVRAPQVYILPPPAEQLSRKDVSLTCLVVGFN
PGDISVEWTSNGHTEENYKDTAPVLDSDGSYFIYSKLNMRTSKWEKTDSFSCNVRHEGLKNYYL
KKTISRSPG** (SEQ ID NO:39)

* Indicates glycosylation site (Highlighted in bold are residues that were identified from various chemical/enzymatic cleavages)

*FIG. 1D*

Light Chain

```
                    10         20          30         40
2C8        DIVMTQSHKFMSTSVGDRVSITC [KASQAVSSAVA] WYQQKP
             *    ****  *       *        *
hu2C8.v2   DIQMTQSPSSLSASVGDRVTITC [RASQAVSSAVA] WYQQKP
                                     **  ***
hum kI     DIQMTQSPSSLSASVGDRVTITC [RASQSISNYLA] WYQQKP 50         60         70         80
2C8        GQSPKLQIY [SASHRYT] GVPDRFTGSGSGTDFTFTISSVQA
             **                    *  *            *     *  *
hu2C8.v2   GKAPKLQIY [SASHRYT] GVPSRFSGSGSGTDFTLTISSLQP
                *       *    ****
hum kI     GKAPKLLIY [AASSLES] GVPSRFSGSGSGTDFTLTISSLQP 90        100
2C8        EDLAVYYC [QQHYSTPWT] FGGGTKVEIKR (SEQ ID NO:23)
             *  *                  *
hu2C8.v2   EDFATYYC [QQHYSTPWT] FGQGTKVEIKR (SEQ ID NO:24)
                                   ** *
hum kI     EDFATYYC [QQYNSLPWT] FGQGTKVEIKR (SEQ ID NO:40)
```

FIG. 2A

Heavy Chain

```
                    10        20         30         40
2C8        EVQLQQSGPELVKPGASVKLSCKAS [GYTFTSYVIH] WVKQK
             **   **    *   *  **    *                        *
hu2C8.v2   EVQLVESGGGLVQPGGSLRLCAAS [GYTFTSYVIH] WVRQA
                                              *   *  ***
hum III    EVQLVESGGGLVQPGGSLRLCAAS [GFTFSSYAMS] WVRQA 50     a     60                   70         80
2C8        PGQGLEWIG [YNNPYNDGTNYNEKFKG] KATLTSDKSSSTAYM
              *   *                                *  **     *   *
hu2C8.v2   PGKGLEWVG [YNNPYNDGTNYNEKFKG] RATISSDKSKNTAYL
                *      ******** * ****        *   * *    *
hum III    PGKGLEWVS [VISGDGGSTYYADSVKG] RFTISRDNSKNTLYL 90        100        110        130
2C8        ELSSLTSEDSAVYYCSR [PTMLPWFAY] WGQGTTLTVSA
(SEQ ID NO:25)
             *** **  *                            **   *
hu2C8.v2   QMNSLRAEDTAVYYCSR [PTMLPWFAY] WGQGTLVTVSS
(SEQ ID NO:26)
                       *  ********
hum III    QMNSLRAEDTAVYYCAR [GRGGGSD-Y] WGQGTLVTVSS
(SEQ ID NO:41)
```

FIG. 2B

Light Chain for 2C8.v7

DIQMTQSPSSLSASVGDRVTITCRASQAVSSAVAWYQQKPGKAPKLLIYSASHRYTGVPS
RFSGSGSGTDFTLTISSLQPEDFATYYCQQHYSTPWTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO:42)

Heavy Chain for 2C8.v7

EVQLVESGGGLVQPGGSLRLSCAASGYTFTSYVIHWVRQAPGKGLEWVGYNNPYNDGTNY
NEKFKGRATISSDKSKNTAYLQMNSLRAEDTAVYYCSRPTMLPWFAYWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:43)

Light Chain for 2C8.v12

DIQMTQSPSSLSASVGDRVTITCRASQAVSSAVAWYQQKPGKAPKLLIYSASHRYTGVPS
RFSGSGSGTDFTLTISSLQPEDFATYYCQQHYSTPWTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO:44)

Heavy Chain for 2C8.v12

EVQLVESGGGLVQPGGSLRLSCAASGYTFTSYVIHWVRQAPGKGLEWVGYNNPYNDGTNY
NEKFKGRFTISSDKSKNTAYLQMNSLRAEDTAVYYCSRPTMLPWFAYWGQGTLVTVSSAS
TKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO:45)

*FIG. 2C*

Light Chain

```
                          10         20        abcdef  30               40
3F12         DIVMSQSPSSLAVSVGEKVTMSC   {KSSQSLLYSTNQKNFLA}   WYQQKP
              *  *       **   **    **
hu3F12.v5    DIQMTQSPSSLSASVGDRVTITC   {KSSQSLLYSTNQKNFLA}   WYQQKP
                                        **  ******** *
hum kI       DIQMTQSPSSLSASVGDRVTITC   {RASQSIS-------NYLA}  WYQQKP 50            60         70        80
3F12         GQSPKLLIY   {WASTRDS}   GVPDRFTGSGSGTDFTLTISSVKAEDLAVY
              **                      * *                 *** *
hu3F12.v5    GKAPKLLIY   {WASTRDS}   GVPSRFSGSGSGTDFTLTISSLQPEDFATY
                           *   ***
hum kI       GKAPKLLIY   {AASSLES}   GVPSRFSGSGSGTDFTLTISSLQPEDFATY 90         100
3F12         YC   {QQYYSYPRT}   FGGGTKLEIKR     (SEQ ID NO:27)
                                       *  *
hu3F12.v5    YC   {QQYYSYPRT}   FGQGTKVEIKR     (SEQ ID NO:28)
                    * * *
hum kI       YC   {QQYNSLPWT}   FGQGTKVEIKR     (SEQ ID NO:40)
```

*FIG. 3A*

Heavy Chain

```
                       10         20             30              40
3F12         QGQLQQSGAELMKPGASVKISCKAT   {GYTFSSYWIE}   WVKQR
              *   **    ** **   * ***  *                          *  *
hu3F12.v5    EVQLVESGGGLVQPGGSLRLSCAAS   {GYTFSSYWIE}   WVRQA
                                             *    ***
humhviii     EVQLVESGGGLVQPGGSLRLSCAAS   {GFTFSSYAMS}   WVRQA 50      a    60             70         80
3F12         PGKGLEWIG   {EISPGSGSTNYNEEFKG}   KATFTADKSSNTAYI
                *      *                       *    *  * *         *
hu3F12.v5    PGKGLEWVG   {EISPGSGSTNYNEEFKG}   RATFSADNSKNTAYL
                           *    *   *** *  ****    *  *   *       *
humhviii     PGKGLEWVS   {VISGDGGSTYYADSVKG}   RFTISRDNSKNTLYL abc          90         100           110
3F12         QLSSLSTSEDSAVYYCAD   {GYH-G--Y}   WCQGTTLTVSSA
(SEQ ID NO:29)
                **   ** *                                   **
hu3F12.v5    QMNSL-RAEDTAVYYCAD   {GYH-G--Y}   WGQGTLVTVSSA
(SEQ ID NO:30)
                      *           *** **
humhviii     QMNSL-RAEDTAVYYCAR   {GRGGGSDY}   WGQGTLVTVSSA
(SEQ ID NO:41)
```

*FIG. 3B*

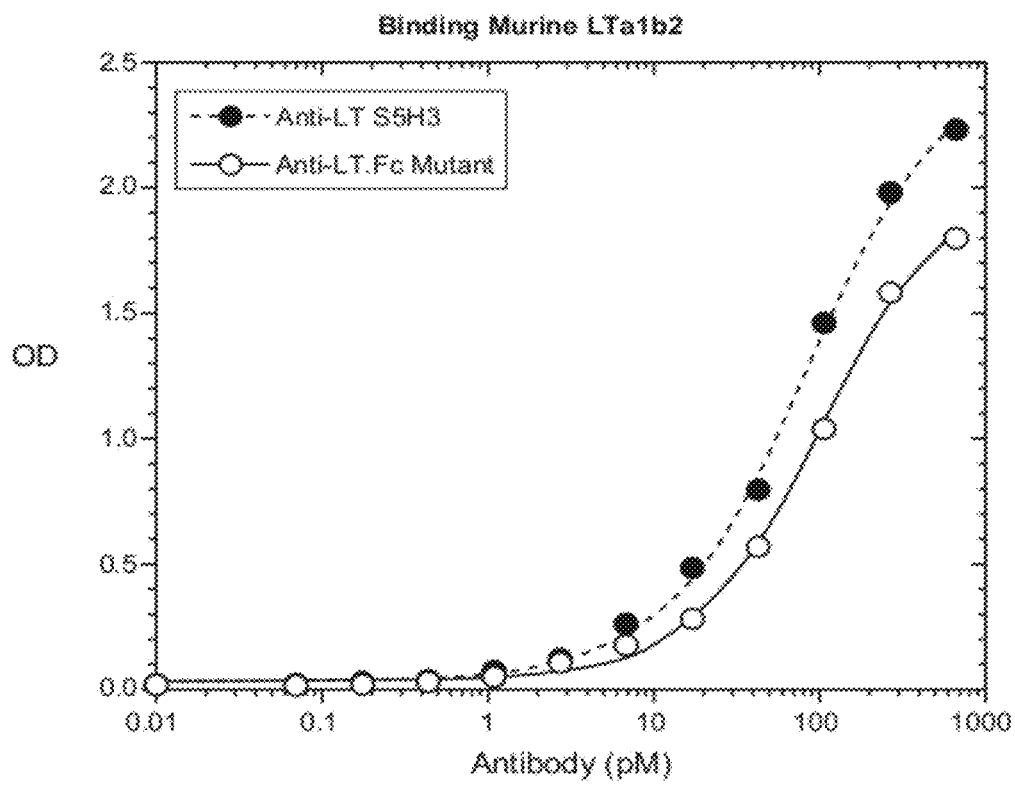
FIG. 11A
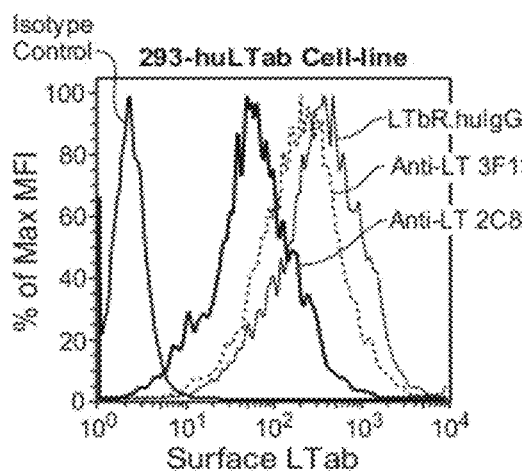 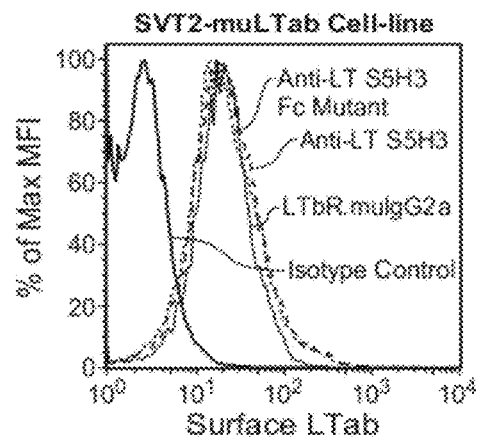
FIG. 11B  FIG. 11C

Variable Light Domain

```
                         10         20         30         40
chim.2C8    DIVMTQSHKFMSTSVGDRVSITC [KASQAVSSAVA] WYQQKP
             *  ****  *        *         *
hu2C8.vX    DIQMTQSPSSLSASVGDRVTITC [RASQAVSSAVA] WYQQKP
                                     **  ***
hum kI      DIQMTQSPSSLSASVGDRVTITC [RASQSISNYLA] WYQQKP 50         60         70         80
chim.2C8    GQSPKLQIY [SASHRYT] GVPDRFTGSGSGTDFTFTISSVQA
             **    *                *  *          *    *  *
hu2C8.vX    GKAPKLLIY [SASHRYT] GVPSRFSGSGSGTDFTLTISSLQP
                         *  ****
hum kI      GKAPKLLIY [AASSLES] GVPSRFSGSGSGTDFTLTISSLQP 90        100
chim.2C8    EDLAVYYC [QQHYSTPWT] FGGGTKVEIKR (SEQ ID NO:23)
              * *       **                *
hu2C8.vX    EDFATYYC [QESYSTPWT] FGQGTKVEIKR (SEQ ID NO:102)
                       *** *
hum kI      EDFATYYC [QQYNSLPWT] FGQGTKVEIKR (SEQ ID NO:40)
```

FIG. 18A

Variable Heavy Domain

```
                        10         20         30
chim.2C8    EVQLQQSGPELVKPGASVKLSCKAS [GYTFTSYVIH] WVKQK
              **   **  *   *  **      *                *  *
hu2C8.vX    EVQLVESGGGLVQPGGSLRLSCAAS [GYTFTSYVIH] WVRQA
                                          *  *   ***
hum III     EVQLVESGGGLVQPGGSLRLSCAAS [GFTFSSYAMS] WVRQA 50    a       60         70         80
chim.2C8    PGQGLEWIG [YNNPYNDGTNYNEKFKG] KATLTSDKSSSTAYM
              *    *              *                **  **   **    *
hu2C8.vX    PGKGLEWVG [YNNPYNAGTNYNEKFKG] RFTISSDKSKNTAYL
                *      ********  *  ****           *  *        *
hum III     PGKGLEWVA [VISGDGGSTYYADSVKG] RFTISRDNSKNTLYL abc        90       100ab        110
chim.2C8    ELSSLTSEDSAVYYCSR [PTMLPWP-AY] WGQGTTLTVSA
(SEQ ID NO:25)
              ***  **   *                              **   *
hu2C8.vX    QMNSLRAEDTAVYYCSR [PTMLPWP-AY] WGQGTLVTVSS
(SEQ ID NO:103)
                            *    *********
hum III     QMNSLRAEDTAVYYCAR [GRVGYSLYDY] WGQGTLVTVSS
(SEQ ID NO:41)
```

FIG. 18B

Light Chain Variable

```
                          10         20        abcdef 30
3F12chim      DIVMSQSPSSLAVSVGEKVTMSC [KSSQSLLYSTNQKNFLA] WYQQK
               * *         **       **     **
3F12.v14      DIQMTQSPSSLSASVGDRVTITC [KSSQSLLYSTNQKNFLA] WYQQK
                                             **
hum kI        DIQMTQSPSSLSASVGDRVTITC [RASQ-------SISNYLA] WYQQK 40         50         60         70         80
3F12chim      PGQSPKLLIY [WASTRDS] GVPDRFTGSGSGTDFTLTISSVKA
               **                    *  *                ***
3F12.v14      PGKAPKLLIY [WASTRDS] GVPSRFSGSGSGTDFTLTISSLQP
                 *  ***
hum kI        PGKAPKLLIY [AASSLES] GVPSRFSGSGSGTDFTLTISSLQP 90           100
3F12chim      EDLAVYYC [QQYYSYPRT] FGGGTKLEIKR (SEQ ID NO:27)
                * *                    *    *
3F12.v14      EDFATYYC [QQYYSYPRT] FGQGTKVEIKR (SEQ ID NO:108)
                            * * *
hum kI        EDFATYYC [QQYNSLPWT] FGQGTKVEIKR (SEQ ID NO:40)
```

*FIG. 26A*

Heavy Chain Variable

```
                       10         20         30         40
3F12chim      QGQLQQSGAELMKPGASVKISCKAT [GYTFSSYWIE] WVKQR
               **    **    **   **  *  ***    * *              * *
3F12.v14      EVQLVESGGGLVQPGGSLRLSCAAS [GYTFSSYWIE] WVRQA
                                                 *    ***
humhviii      EVQLVESGGGLVQPGGSLRLSCAAS [GFTFSSYAMS] WVRQA 50   a    60         70         80
3F12chim      PGHGLEWIG [EISPGSGSTNYNEEFKG] KATFTADKSSNTAYI
                   *     *    *     *   *        *   *   *    *
3F12.v14      PGKGLEWVG [EINPGSGSTIYNEKFKG] RATFSADNSKNTAYL
                 *  * ****   *  ****      *  *    *
humhviii      PGKGLEWVS [VISGDGGSTYYADSVKG] RFTISRDNSKNTLYL abc      90      100ab        110
3F12chim      QLSSLSTEDSAVYYCAD [GYR-----GY] WGQGTTLTVSS
(SEQ ID NO:29)
                **   **  *                        **
3F12.v14      QMNSLRAEDTAVYYCAD [GYR-----GY] WGQGTLVTVSS
(SEQ ID NO:109)
                                *  *******
humhviii      QMNSLRAEDTAVYYCAR [GRVGYSLYDY] WGQGTLVTVSS
(SEQ ID NO:41)
```

*FIG. 26B*

ANTIBODIES TO LYMPHOTOXIN-α

RELATED APPLICATIONS

This application is a Continuation of U.S. application Ser. No. 11/871,136, filed Oct. 11, 2007, now U.S. Pat. No. 7,923,011 which claims the benefit of priority of U.S. Provisional Application Ser. No. 60/829,257 filed on 12 Oct. 2006, and of U.S. Provisional Application Ser. No. 60/938,999 filed on 18 May 2007, which are incorporated by reference in their entirety.

FIELD OF THE INVENTION

The present invention concerns antibodies and their uses to treat autoimmune disorders. More particularly, the present invention concerns antibodies that bind to lymphotoxin-α and may also block binding of the lymphotoxin-α ligand to one or more receptors.

BACKGROUND OF THE INVENTION

TNF and LT

Autoimmune diseases remain clinically important diseases in humans. As the name implies, autoimmune diseases wreak their havoc through the body's own immune system. While the pathological mechanisms differ among individual types of autoimmune diseases, one general mechanism involves the binding of certain antibodies (referred to herein as self-reactive antibodies or autoantibodies) present. Physicians and scientists have identified more than 70 clinically distinct autoimmune diseases, including rheumatoid arthritis (RA), multiple sclerosis (MS), vasculitis, immune-mediated diabetes, and lupus such as systemic lupus erythematosus (SLE). While many autoimmune diseases are rare—affecting fewer than 200,000 individuals—collectively, these diseases afflict millions of Americans, an estimated five percent of the population, with women disproportionately affected by most diseases. The chronic nature of these diseases leads to an immense social and financial burden.

Tumor Necrosis Factor (TNF)-related proteins are recognized in the art as a large family of proteins having a variety of activities ranging from host defense to immune regulation to apoptosis. TNF was first identified as a serum-derived factor that was cytotoxic for several transformed cell lines in vitro and caused necrosis of certain tumors in vivo. A similar factor in the superfamily was identified and referred to as lymphotoxin ("LT"). Due to observed similarities between TNF and LT in the early 1980's, it was proposed that TNF and LT be referred to as TNF-α and TNF-β, respectively. Scientific literature thus makes reference to both nomenclatures. As used in the present application, the term "TNF" refers to TNF-α. Later research revealed two forms of lymphotoxin, referred to as LTα and LTβ. US 2005-0129614 describes another polypeptide member of the TNF ligand super-family based on structural and biological similarities, designated TL-5.

Members of the TNF family of proteins exist in membrane-bound forms that act locally through cell-cell contact, or as secreted proteins. A family of TNF-related receptors react with these proteins and trigger a variety of signalling pathways including cell death or apoptosis, cell proliferation, tissue differentiation, and proinflammatory responses. TNF-α by itself has been implicated in inflammatory diseases, autoimmune diseases, viral, bacterial, and parasitic infections, malignancies, and/or neurodegenerative diseases and is a useful target for specific biological therapy in diseases such as RA and Crohn's disease.

Cloning of the TNF and LTα proteins and further characterization of their respective biological activities reveal that the proteins differ in many aspects. Aggarwal et al., *Cytokines and Lipocortins in Inflammation and Differentiation*, Wiley-Liss, Inc. 1990, pp. 375-384. For instance, LTα is a secreted, soluble protein of approximately 20 kDa (25 kDa if N- and O-glycosylated). TNF, in contrast, has no site for glycosylation and is synthesized with an apparent transmembrane domain that results in the original protein transcript being cell associated. Proteolysis of the cell-associated TNF protein results in the release of the soluble form of the protein having a molecular weight of approximately 19 kDa. TNF is produced primarily by activated macrophages, whereas LT is produced by activated lymphocytes. Wong et al., *Tumor Necrosis Factors: The Molecules and their Emerging Role in Medicine*, Beutler, B., ed., Raven Press (1991), pp. 473-484. The sequences encoding TNF and LTα also differ. TNF and LTα share only approximately 32% amino acid sequence identity. Regarding the different biological activities of TNF and LTα, TNF increases production of endothelial-cell interleukin-1 ("IL-1"), whereas LTα has little effect thereon. Further, TNF induces production of macrophage-colony-stimulating factor from macrophages, whereas LTα has no effect thereon. These and other biological activities are discussed in Aggarwal, *Tumor Necrosis Factors: Structure, Function and Mechanism of Action*, Aggarwal and Vicek, eds. (1992), pp. 61-78.

TNF and LTα are described further in the review articles by Spriggs, "Tumor Necrosis Factor Basic Principles and Preclinical Studies," *Biologic Therapy of Cancer*, DeVita et al., eds., J.B. Lippincott Company (1991) Ch. 16, pp. 354-377; Ruddle, *Current Opinion in Immunology*, 4:327-332 (1992); Wong et al., "Tumor Necrosis Factor," *Human Monocytes*, Academic Press (1989), pp. 195-215; and Paul et al., *Ann. Rev. Immunol.*, 6:407-438 (1988).

In non-tumor cells, TNF and TNF-related cytokines are active in a variety of immune responses. Both TNF and LTα ligands bind to and activate TNF receptors (p55 or p60 and p75 or p80; herein called "TNF-R").

Cell-surface LT complexes have been characterized in CD4+ T cell hybridoma cells (II-23.D7), which express high levels of LT (Browning et al., *J. Immunol.*, 147: 1230-1237 (1991); Androlewicz et al., *J. Biol. Chem.*, 267: 2542-2547 (1992)). The expression and biological roles of LTβ-R, LT subunits, and surface LT complexes are reviewed in Ware et al., "The ligands and receptors of the lymphotoxin system", in *Pathways for Cytolysis, Current Topics Microbiol. Immunol.*, Springer-Verlag, pp. 175-218 (1995).

LTα expression is induced and LTα secreted primarily by activated T and B lymphocytes and natural killer (NK) cells. Among the T helper cell subclasses, LTα appears to be produced by Th1 but not Th2 cells. LTα has also been detected in melanocytes. LTβ (also called p33) has been identified on the surface of T lymphocytes, T cell lines, B cell lines and lymphokine-activated killer (LAK) cells. Studies have shown that LTD is not functional in the absence of LTα.

LTα exists either as a homotrimer (LTα3) or a heterotrimer with LTβ. These heterotrimers contain either two subunits of LTα and one subunit of LTβ (LTα2β1), or one subunit of LTα and two of LTβ (LTα1β2).

The only known cell-surface receptors for the LTα homotrimer are the two TNF receptors, p55 and p75. However, the LTαβ heterotrimer, LTα1β2, does not bind to the TNF receptors and instead binds to a member of the TNF receptor superfamily, lymphotoxin β receptor (referred to herein as LTβ-R). The heterotrimeric form LTα2β1 likely binds TNF receptors.

LTβ-R has a well-described role both in the development of the immune system and in the functional maintenance of a number of cells in the immune system, including follicular dendritic cells and a number of stromal cell types (Matsumoto et al., *Immunol. Rev.* 156:137 (1997)). Known ligands to the LTβ-R include not only LTα1β2, but also a second ligand called LIGHT (Mauri et al., *Immunity* 8:21 (1998)). Activation of LTβ-R has been shown to induce the apoptotic death of certain cancer cell lines in vivo (U.S. Pat. No. 6,312,691). Humanized antibodies to LTβ-R and methods of use thereof are provided in US 2004-0058394 and stated as being useful for treating or reducing the advancement, severity, or effects of neoplasia in humans. Further, EP 1585547 (WO 2004/058183) (LePage and Gill) discloses combination therapies that include a composition that activates LTβ-R signaling in combination with one or more other chemotherapeutic agents, as well as therapeutic methods and screening methods for identifying agents that in combination with a LTβ-R agonist agent have an additive effect on tumor inhibition.

LT is important for lymphoneogenesis, as evident from knockout mice. See Futterer et al. *Immunity,* 9 (1): 59-70 (1998), showing that mice deficient in LTβ-R lacked lymph nodes and Peyer's patches and also showing impaired antibody affinity maturation. Rennert et al., *Immunity,* 9 (1): 71-9 (1998) reported that an agonist monoclonal antibody against LTβ-R restored the ability to make lymph nodes in LTα knockout mice. See also Wu et al., *J. Immunology,* 166 (3): 1684-9 (2001) and Endres et al., *J. Exp. Med.,* 189 (1): 159-68 (1999); Dohi et al., *J. Immunology,* 167 (5): 2781-90 (2001); and Matsumoto et al., *J. Immunology,* 163 (3): 1584-91 (1999). Korner et al. *Eur. J. Immun.,* 27 (10): 2600-9 (1997) reported that mice lacking both TNF and LT showed retarded B-cell maturation and serum immunoglobulin deficiencies, whereas mice lacking only TNF showed no such deficiencies.

In addition, LT is important for inflammation. LTα is overexpressed in the pancreas of RIP.LTα transgenic mice, which have shown inflammation, increased chemokine expression, and a lymphoid-like structure, and in which overexpression of LTβ alone has demonstrated no additional inflammation. Further, LTα-deficient mice exhibit impaired TNF-α production, and defective splenic architecture and function are restored when such mice are crossed to TNF-transgene (Kollias, *J. Exp. Med.,* 188:745 (1998); Chaplin, *Ann Rev Imm* 17:399 (1999)), and decreased TNF levels are restored after pathogenic challenge (Eugster, *Eur. J. Immun.* 31:1935 (2001)).

When TNF-α or LTα$_3$ interacts with the TNF receptors TNFRI and/or TNFRII, the result is proinflammatory responses and/or apoptosis. When LTα1β2 interacts with the receptor LTβ-R, the result is lymphoneogenesis and induction of chemokines and adhesion molecules. Autoimmune diseases are associated with lymphoneogenesis and inflammatory responses, and there is increased LT expression in patients with autoimmune disease, including MS, inflammatory bowel disease (IBD), and RA (Weyand et al., *Curr. Opin. Rheumatol.,* 15: 259-266 (2003); Selmaj et al., *J. Clin. Invest.,* 87: 949-954 (1991); Matusevicius et al., *J. Neuroimm.,* 66: 115-123 (1996); Powell et al., *International Immunology,* 2 (6): 539-44 (1990); Zipp et al., *Annals of Neurology,* 38/5: 723-730 (1995); Voskuhl et al., *Autoimmunity* 15 (2): 137-43 (1993); Selmaj et al., *J. Immunology,* 147: 1522-29 (1991); Agyekum et al., *Journal Pathology,* 199 (1): 115-21 (2003); and Takemura et al., *J. Immunol.,* 167: 1072 (2001)).

As to MS specifically, serum LTα correlates with lesions/disease burden in MS (Kraus et al., *Acta Neurologica Scandinavica,* 105 (4): 300-8 (2002)). LTα is involved in demyelination but not remyelination in an in vivo cuprizone model, whereas TNF-α is required for both (Plant et al., *Glia* 49:1-14 (2005)).

As to RA specifically, levels of human LTα3 and TNF-α in RA patients are elevated over those of normal donors (Stepien, *Eur Cytokine Net* 9: 145 (1998)). The roles of LTα in RA include: serum LTα is present in some RA patients, increased LTα protein is present in synovium, the LT pathway is associated with ectopic lymphoneogenesis in synovium, and there is increased LTβ-R expression on fibroblast-like synoviocytes in RA patients. In addition, a case report discloses that neutralizing LTα3 is beneficial for an infliximab-resistant RA patient (Buch et al., *Ann. Rheum. Dis.,* 63: 1344-46 (2004)). Also, Han et al., *Arthrit. Rheumat.,* 52: 3202-3209 (2005) describes that blockading the LT pathway exacerbates autoimmune arthritis by enhancing the Th1 response.

Preclinical efficacy for prevention and treatment with LTβR-Ig in collagen-induced arthritis (CIA) is shown in Fava et al., *J. Immunology,* 171 (1): 115-26 (2003). Further, LTα-deficient mice are resistant to experimental autoimmune encephalomyelitis (EAE) (Suen et al., *J. Exp. Med,* 186: 1233-40 (1997); Sean Riminton et al., *J. Exp. Med,* 187 (9): 1517-28 (1998)). There is also published efficacy of LTβR-Ig in EAE (Gommerman et al., *J. Clin. Invest,* 112 (5): 755-67 (2003)). Also, LTβR-Ig disrupts lymphogenesis in mice. Mackay et al., *Europ. J. Immunol.* 27 (8): 2033-42 (1997)). Further, administration of LTβR-Ig decreases insulin-dependent diabetes mellitus (IDDM) in non-obese diabetic mice (Wu et al., *J. Exp. Med,* 193 (11): 1327-32 (2001)). The role of LT in lymphogenesis in non-human primates was investigated by Gommerman et al., *J. Clin. Invest.* 110 (9): 1359-69 (2002) using LTβR-Ig. Further, LTα-deficient mice are less susceptible to *M. bovis* BCG than TNF-α-deficient mice. Eugster et al., *Europ. J. Immunol.,* 31: 1935 (2001).

LT has also been used to treat cancer. See U.S. Pat. No. 5,747,023.

Antibodies

Antibodies are proteins that exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are responsible for the binding specificity of each particular antibody for its particular antigen. However, the variability is not evenly distributed throughout the variable domains of antibodies. It is concentrated in three segments called complementarity determining regions (CDRs) both in the light-chain and the heavy-chain variable domains. The more highly conserved portions of the variable domains are called the framework regions (FRs). The variable domains of native heavy and light chains each comprise four FRs, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy-chain constant regions that correspond to the different classes of immunoglobulins are called α, δ, ε, γ, and μ, respectively. Of the human immunoglobulin classes, only human IgG1, IgG2, IgG3, and IgM are known to activate complement, and human IgG1 and IgG3 mediate antibody-dependent cell-mediated cytotoxicity (ADCC) more effectively than IgG2 and IgG4.

Two main approaches have been used to develop therapeutic compounds that inhibit TNF-α. The first, exemplified by infliximab, a chimeric monoclonal antibody to TNF-α also known as REMICADE®, is to neutralize TNF-α action by using a specific monoclonal antibody of high affinity and potency to prevent binding of TNF-α to its receptors. The second, exemplified by etanercept, also known as ENBREL®, is to inhibit TNF-α by using a TNF receptor-based molecule that functions as a "decoy" to reduce the binding of TNF-α to its natural receptors. Although both types of molecules can prevent the binding of TNFα to its receptors, receptor-based inhibitors such as etanercept will also prevent receptor binding of LTα.

In the patent literature, antibodies to cachectin (TNF), disclosed by EP 212489, are reported as useful in diagnostic immunoassays and in therapy of shock in bacterial infections. EP 218868 discloses monoclonal antibodies to human TNF and their uses. EP 288,088 discloses anti-TNF antibodies, and their utility in immunoassay diagnosis of pathologies, in particular Kawasaki's pathology and bacterial infection. Anti-TNF antibodies are also described, for example, in EP 1585477 (Giles-Komar et al.); US 2006-0147452; US 2006-0222646; and US 2006-0121037. A method of treating RA by using a single-domain antibody polypeptide construct that antagonizes human TNFα's binding to a receptor is described in US 2005-0271663. Methods of treating RA using anti-TNF receptor fusion proteins are described in US 2005-0260201. Methods for treating a TNF-mediated disease using a composition comprising methotrexate and an anti-TNF antibody, including RA, Crohn's disease, and acute and chronic immune diseases associated with transplantation, are described in EP 1593393. Antibodies that bind to TNF-R include those described in U.S. Pat. No. 7,057,022. Novel proteins with TNF-alpha antagonist activity are described in U.S. Pat. No. 7,056,695. US 2006-0147448 discloses treatment of immunological renal disorders by LT pathway inhibitors.

LTβ and LTβ/LTα complexes and LTβ-R and antibodies thereto as well as LTβ blocking agents are described, for example, in WO 1992/00329; WO 1994/13808; U.S. Pat. Nos. 5,661,004; 5,795,964; EP 0954333; U.S. Pat. Nos. 5,670,149; 5,925,351; US 2005-0037003; U.S. Pat. Nos. 6,403,087; 6,669,941; 6,312,691; 7,001,598; 7,030,080; US 2006-0222644; and US 2005-0163747. The application US 2006-0134102 discloses LTβ-R agents in combination with chemotherapeutic agents. Antibodies to the LTβ-R are described in US 2005-0281811. See also WO 2006/114284 regarding use of LTβ-R antibodies to prevent and/or treat obesity and obesity-related disorders. Humanized antibodies specific for the LTβ-R alone or in combination with chemotherapeutic agent(s) in therapeutic methods are disclosed in EP 1539793. LTα and antibodies thereto are described, for example, in U.S. Pat. Nos. 4,959,457; 5,824,509; 4,920,196; and 5,683,688; US 2005-0266004 (WO 2005/067477) and U.S. Pat. No. 5,188,969 (EP 347728B1). See also US 2002-0039580; WO 2004/039329; and US 2002-0197254 regarding LTβ or LTβ-R technology. Multivalent antibodies (that bind the TNF receptor superfamily) are described, for example, in US 2002-0004587 and US 2006-0025576.

There is a continuing need in the art to produce antibodies, in particular, therapeutic antibodies having improved function, such as anti-LTα antibodies or fragments thereof that block LTβ, since LTα has more interactions with the various receptors than TNF-α or LTβ alone.

SUMMARY OF THE INVENTION

The invention is in part based on the identification of a variety of antagonists of the LT biological pathway, which is a biological/cellular process presenting as an important therapeutic target. The invention provides compositions and methods based on interfering with LTα activation, including but not limited to interfering with LTα binding to various receptors.

Accordingly, the invention is as claimed. In one aspect, the invention provides an isolated anti-lymphotoxin-α (LTα) antibody comprising at least one complementarity-determining region (CDR) sequence selected from the group consisting of:

(a) a CDR-L1 sequence comprising amino acids A1-A11, wherein A1-A11 is KASQAVSSAVA (SEQ ID NO:1) or RASQAVSSAVA (SEQ ID NO:2), or comprising amino acids A1-A17, wherein A1-A17 is KSSQSLLYSTNQKNFLA (SEQ ID NO:3) or KSSQSLLYSANQKNFLA (SEQ ID NO:4) or KSSQSLLYSTNQKNALA (SEQ ID NO:6), where N is any amino acid (chimeric 2C8 or humanized 2C8.v2/2C8.vX or chimeric 3F12/humanized 3F12.v5/humanized 3F12.v14, or 3F12 clone 14 or 17, respectively);

(b) a CDR-L2 sequence comprising amino acids B1-B7, wherein B1-B7 is SASHRYT (SEQ ID NO:7) or WASTRDS (SEQ ID NO:8) (chimeric 2C8/humanized 2C8.v2/humanized 2C8.vX or chimeric 3F12/humanized 3F12.v5/humanized 3F12.v14, respectively);

(c) a CDR-L3 sequence comprising amino acids C1-C9, wherein C1-C9 is QQHYSTPWT (SEQ ID NO:9) or QENYSTPWT (SEQ ID NO:11) or QQYYSYPRT (SEQ ID NO:13) or QQYASYPRT (SEQ ID NO:14) or QQYYAYPRT (SEQ ID NO:15), where N is any amino acid (chimeric 2C8/humanized 2C8.v2 or 2C8 clone G7 or chimeric 3F12/humanized 3F12.v5/humanized 3F12.v14 or 3F12 clone 20 or 3F12 clone 21, respectively);

(d) a CDR-H1 sequence comprising amino acids D1-D10, wherein D1-D10 is GYTFTSYVIH (SEQ ID NO:16) or GYTFSSYWIE (SEQ ID NO:17) (chimeric 2C8/humanized 2C8.v2/humanized 2C8.vX or chimeric 3F12/humanized 3F12.v5/humanized 3F12.v14, respectively);

(e) a CDR-H2 sequence comprising amino acids E1-E17, wherein E1-E17 is YNNPYNDGTNYNEKFKG (SEQ ID NO:1-8) or EISPGSGSTNYNEEFKG (SEQ ID NO:19) or YNNPYNAGTNYNEKFKG (SEQ ID NO:101) or EIN-PGSGSTIYNEKFKG (SEQ ID NO:110), wherein N is any amino acid (chimeric 2C8/humanized 2C8.v2 or chimeric 3F12/humanized 3F12.v5, or humanized 2C8.vX, or humanized 3F12.v14, respectively); and (f) a CDR-H3 sequence comprising amino acids F1-F9, wherein F1-F9 is PTMLPWFAY (SEQ ID NO:20), or comprising amino acids F1-F5, wherein F1-F5 is GYHGY (SEQ ID NO:21) or GYHGA (SEQ ID NO:22) (chimeric 2C8/humanized 2C8.v2/humanized 2C8.vX or chimeric 3F12/humanized 3F12.v5/humanized 3F12.v14 or 3F12 clone 12, respectively).

Preferably, SEQ ID NO:3 is KSSQSLLYSTAQKNFLA (SEQ ID NO:5) (3F12 clone 15). In another preferred aspect, SEQ ID NO:11 is QESYSTPWT (SEQ ID NO:10) (2C8 clone A8/humanized 2C8.vX) or QEVYSTPWT (SEQ ID NO:12) (2C8 clone H6).

In a further preferred embodiment, the CDR-L1 sequence is SEQ ID NO:2 or 3 or 4 or 6.

In another preferred aspect, the antibody comprises either (i) all of the CDR-L1 to CDR-L3 amino acid sequences of SEQ ID NOS:1 or 2 and 7 and 9, or of SEQ ID NOS:1 or 2 and 7 or 8 and 11, or of SEQ ID NOS:3, 8, and 13, or of SEQ ID NOS:4, 5, or 6, 8, and 13, or of SEQ ID NOS:3, 8, and 14 or 15, or of SEQ ID NOS:4, 5, or 6, 8, and 14 or 15; or (ii) all of the CDR-H1 to CDR-H3 amino acid sequences of SEQ ID NOS:16, 18, and 20, or all of SEQ ID NOS:16, 101, and 20, or all of SEQ ID NOS:17, 19, and 21 or 22, or all of SEQ ID NOS:17, 110, and 21.

In a still further preferred aspect, the antibody comprises either all of SEQ ID NOS:1 or 2 and 7 and 9, or all of SEQ ID NOS:16, 18, and 20, or all of SEQ ID NOS:16, 101, and 20. In an alternative embodiment, the antibody comprises either all of SEQ ID NOS:3, 8, and 13, or all of SEQ ID NOS:17, 19, and 21 or 22. In an alternative embodiment, the antibody comprises either all of SEQ ID NOS:4, 8, and 14, or all of SEQ ID NOS:17, 110, and 21. In other embodiments, the antibody comprises (i) all of the CDR-L1 to CDR-L3 amino acid sequences of SEQ ID NOS:1 or 2, 7 and 9, or of SEQ ID NOS:1 or 2 and 7 or 8 and 11, or of SEQ ID NOS:3, 8, and 13, or of SEQ ID NOS:4, 5, or 6, 8, and 13, or of SEQ ID NOS:3, 8, and 14 or 15, or of SEQ ID NOS:4, 5, or 6, 8, and 14 or 15; and (ii) all of the CDR-H1 to CDR-H3 amino acid sequences of SEQ ID NOS:16, 18, and 20, or of SEQ ID NOS:16, 101, and 20, or of SEQ ID NOS:17, 19, and 21 or 22, or of SEQ ID NOS:17, 110, and 21.

In addition, the antibodies herein are preferably chimeric or humanized, most preferably humanized. A humanized antibody of the invention may comprise one or more suitable human and/or human consensus non-CDR (e.g., framework) sequences in its heavy- and/or light-chain variable domains, provided the antibody exhibits the desired biological characteristics (e.g., a desired binding affinity). Preferably, at least a portion of such humanized antibody framework sequence is a human consensus framework sequence.

In some embodiments, one or more additional modifications are present within the human and/or human consensus non-CDR sequences. In one embodiment, the heavy-chain variable domain of an antibody of the invention comprises at least a portion of (preferably all of) a human consensus framework sequence, which in one embodiment is the subgroup III consensus framework sequence. In one embodiment, an antibody of the invention comprises a variant subgroup III consensus framework sequence modified at least one amino acid position. For example, in one embodiment, a variant subgroup III consensus framework sequence may comprise a substitution at one or more of positions 71, 73, and/or 78. In one embodiment, said substitution is R71A, N73T, and/or N78A, in any combination thereof, preferably all three. In another embodiment, these antibodies comprise or further comprise at least a portion of (preferably all of) a human κ light-chain consensus framework sequence. In a preferred embodiment, an antibody of the invention comprises at least a portion of (preferably all of) a human κ subgroup I framework consensus sequence.

The amino acid position/boundary delineating a CDR of an antibody can vary, depending on the context and the various definitions known in the art (as described below). Some positions within a variable domain may be viewed as hybrid hypervariable positions in that these positions can be deemed to be within a CDR under one set of criteria while being deemed to be outside a CDR under a different set of criteria. One or more of these positions can also be found in extended CDRs (as further defined below). The invention provides antibodies comprising modifications in these hybrid hypervariable positions. In one embodiment, these hybrid hypervariable positions include one or more of positions 26-30, 33-35B, 47-49, 57-65, 93, 94, and 102 in a heavy-chain variable domain. In one embodiment, these hybrid hypervariable positions include one or more of positions 24-29, 35-36, 46-49, 56, and 97 in a light-chain variable domain. In one embodiment, an antibody of the invention comprises a variant human subgroup consensus framework sequence modified at one or more hybrid hypervariable positions.

In another preferred aspect, the antibody binds to LTα3 and blocks the interaction of LTα3 with tumor necrosis factor receptor-1 (TNFRI) and tumor necrosis factor receptor-2 (TNFRII). Preferably, it binds also to one or more LTαβ complexes and especially on the cell surface. Preferably, it also blocks the function of one or more LTαβ complexes. Also, it preferably decreases levels of inflammatory cytokines associated with rheumatoid arthritis in an in vitro arthritis assay such as an in vitro collagen-induced arthritis assay or an in vitro antibody-induced arthritis assay.

In some aspects, such as the murine S5H3 antibody, the antibody does not block the interaction of LTαβ with LTβ-R. In other aspects, the antibody does block the interaction of LTαβ with LTβ-R. Preferably, the antibody modulates LTαβ-expressing cells. In other embodiments, the anti-LTα antibody substantially neutralizes at least one activity of at least one LTα protein. Preferably, the antibody herein targets any cell expressing LTβ, and more preferably depletes LTβ-positive or -secreting cells.

The preferred antibody binds LTα with an affinity of at least about $10^{-12}$M (picomolar levels), and more preferably at least about $10^{-13}$ M. Also preferred is an IgG antibody, more preferably human IgG. Human IgG encompasses any of the human IgG isotypes of IgG1, IgG2, IgG3, and IgG4. Murine IgG encompasses the isotypes of IgG1, 2a, 2b, and 3. More preferably, the murine IgG is IgG2a and the human IgG is IgG1. In other preferred embodiments of the human IgG, the VH and VL sequences provided are joined to human IgG1 constant region.

In another embodiment, the invention provides an anti-LTα antibody having a light-chain variable domain comprising SEQ ID NO:23 or 24, or a heavy-chain variable domain comprising SEQ ID NO:25 or 26, or having light-chain and heavy-chain variable domains comprising both SEQ ID NOS: 23 and 25, or comprising both SEQ ID NOS:24 and 26.

In a still further embodiment, the invention provides an anti-LTα antibody having a light-chain variable domain comprising SEQ ID NO:27 or 28, or a heavy-chain variable domain comprising SEQ ID NO:29 or 30 or 31, or having light-chain and heavy-chain variable domains comprising both SEQ ID NOS:27 and 29, or comprising both SEQ ID NOS:27 and 30, or comprising both SEQ ID NOS:27 and 31, or comprising both SEQ ID NOS:28 and 30, or comprising both SEQ ID NOS:28 and 31.

In a still further aspect, the invention provides an anti-LTα antibody having a light-chain variable domain comprising SEQ ID NO:102, or a heavy-chain variable domain comprising SEQ ID NO:103, or having light-chain and heavy-chain variable domains comprising both SEQ ID NOS:102 and 103.

In a still further aspect, the invention provides an anti-LTα antibody having a light-chain variable domain comprising SEQ ID NO:108, or a heavy-chain variable domain comprising SEQ ID NO:109, or having light-chain and heavy-chain variable domains comprising both SEQ ID NOS:108 and 109.

In other preferred embodiments, the antibody has an Fc region. In one aspect, such Fc region is a wild-type (or native-sequence) Fc region. In another embodiment, the antibody further comprises one or more amino acid substitutions in its Fc region that result in the polypeptide exhibiting at least one of the following properties: increased FcγR binding, increased antibody-dependent cell-mediated cytotoxicity (ADCC), increased complement-dependent cytotoxicity (CDC), decreased CDC, increased ADCC and CDC function, increased ADCC but decreased CDC function, increased FcRn binding, and increased serum half life, as compared to an antibody having a native-sequence Fc region. More preferably, the antibody further comprises one or more amino acid substitutions in its Fc region that result in it having increased ADCC function as compared to the same antibody having a native-sequence Fc region.

In a particularly preferred embodiment, the antibody has amino acid substitutions in its Fc region at any one or any combination of positions that are 268D, or 298A, or 326D, or 333A, or 334A, or 298A together with 333A, or 298A together with 334A, or 239D together with 332E, or 239D together with 298A and 332E, or 239D together with 268D and 298A and 332E, or 239D together with 268D and 298A and 326A and 332A, or 239D together with 268D and 298A and 326A and 332E, or 239D together with 268D and 283L and 298A and 332E, or 239D together with 268D and 283L and 298A and 326A and 332E, or 239D together with 330L and 332E and 272Y and 254T and 256E, or 250Q together with 428L, or 265A, or 297A, wherein the 265A substitution is in the absence of 297A and the 297A substitution is in the absence of 265A. In one particular embodiment, the Fc region has from one to three such amino acid substitutions, for example, substitutions at positions 298, 333, and 334, and more preferably the combination of 298A, 333A, and 334A. The letter after the number in each of these designations represents the changed amino acid at that position.

Such anti-LTα antibodies effect varying degrees of disruption of the LTα/LTβ signaling pathway. For example, in one embodiment, the invention provides an anti-LTα antibody (preferably humanized) wherein the monovalent affinity of the antibody to human LTα (e.g., affinity of the antibody as a Fab fragment to human LTα) is about the same as or greater than that of a murine antibody (e.g., affinity of the murine antibody as a Fab fragment to human LTα) produced by a hybridoma cell line deposited under American Type Culture Collection Accession Number (ATCC) PTA-7538 (hybridoma murine Lymphotoxin alpha2 beta1 s5H3.2.2). The monovalent affinity is preferably expressed as a Kd value and/or is measured by optical biosensor that uses surface plasmon resonance (SPR) (BIACORE® technology) or radioimmunoassay.

Further antibodies herein include those with any of the properties above having reduced fusose relative to the amount of fucose on the same antibody produced in a wild-type Chinese hamster ovary cell. More preferred are those antibodies having no fucose.

In another embodiment, the invention provides an antibody composition comprising the antibodies described herein having an Fc region, wherein about 20-100% of the antibodies in the composition comprise a mature core carbohydrate structure in the Fc region that lacks a fucose. Preferably, such composition comprises antibodies having an Fc region that has been altered to change one or more of the ADCC, CDC, or pharmacokinetic properties of the antibody compared to a wild-type IgG Fc sequence by substituting an amino acid selected from the group consisting of A, D, E, L, Q, T, and Y at any one or any combination of positions of the Fc region selected from the group consisting of: 238, 239, 246, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 309, 312, 314, 315, 320, 322, 324, 326, 327, 329, 330, 331, 332, 333, 334, 335, 337, 338, 340, 360, 373, 376, 378, 382, 388, 389, 398, 414, 416, 419, 428, 430, 434, 435, 437, 438 and 439.

The above-described antibody composition is more preferably one wherein the antibody further comprises an Fc substitution that is 268D or 326D or 333A together with 334A, or 298A together with 333A, or 298A together with 334A, or 239D together with 332E, or 239D together with 298A and 332E, or 239D together with 268D and 298A and 332E, or 239D together with 268D and 298A and 326A and 332A, or 239D together with 268D and 298A and 326A and 332E, or 239D together with 268D and 283L and 298A and 332E, or 239D together with 268D and 283L and 298A and 326A and 332E, or 239D together with 330L and 332E, wherein the letter after the number in each of these designations represents the changed amino acid at that position.

The above-described antibody composition is additionally preferably one wherein the antibody binds an FcγRIII. The composition is preferably one wherein the antibody has ADCC activity in the presence of human effector cells or has increased ADCC activity in the presence of human effector cells compared to the otherwise same antibody comprising a human wild-type IgG1 Fc. The composition is also preferably one wherein the antibody binds the FcγRIII with better affinity, or mediates ADCC more effectively, than a glycoprotein with a mature core carbohydrate structure including fucose attached to the Fc region of the glycoprotein. In addition, the composition is preferably one wherein the antibody has been produced by a Chinese hamster ovary (CHO) cell, preferably a Lec13 cell. The composition is also preferably one wherein the antibody has been produced by a mammalian cell lacking a fucosyltransferase gene, more preferably the FUT8 gene.

In one embodiment, the above-described composition is one wherein the antibody is free of bisecting N-acetylglucosamine (GlcNAc) attached to the mature core carbohydrate structure. In an alternative embodiment, the composition is one wherein the antibody has bisecting GlcNAc attached to the mature core carbohydrate structure.

In another aspect, the above-described composition is one wherein the antibody has one or more galactose residues attached to the mature core carbohydrate structure. In an alternative embodiment, the composition is one wherein the antibody is free of one or more galactose residues attached to the mature core carbohydrate structure.

In a further aspect, the above-described composition is one wherein the antibody has one or more sialic acid residues attached to the mature core carbohydrate structure. In an alternative aspect, the composition is one wherein the antibody is free of one or more sialic acid residues attached to the mature core carbohydrate structure.

The above-described composition preferably comprises at least about 2% afucosylated antibodies, more preferably at least about 4% afucosylated antibodies, still more preferably at least about 10% afucosylated antibodies, even more preferably at least about 19% afucosylated antibodies, and most preferably about 100% afucosylated antibodies.

Also included herein is an anti-idiotype antibody that specifically binds any of the antibodies herein.

A therapeutic agent for use in a host subject preferably elicits little to no immunogenic response against the agent in said subject. In one embodiment, the invention provides a chimeric or humanized antibody that elicits and/or is expected to elicit a human anti-mouse antibody response (HAMA) at a substantially reduced level compared to a murine antibody in a host subject. In another example, the invention provides a chimeric or humanized antibody that elicits and/or is expected to elicit minimal or no human anti-mouse antibody response (HAMA). In one example, an antibody of the invention elicits an anti-mouse antibody response that is at or below a clinically acceptable maximum level.

Antibodies of the invention can be used to modulate one or more aspects of LTα-associated effects, including but not limited to LTα receptor activation, downstream molecular signaling, cell proliferation, cell migration, cell survival, cell morphogenesis, and angiogenesis. These effects can be modulated by any biologically relevant mechanism, including disruption of ligand (e.g., LTα), binding to and blocking the LTα3 receptor or one or both of the heterodimeric receptors, as well as receptor phosphorylation, and/or receptor multimerization.

In another aspect, the invention provides a method of inhibiting LTα-activated cell proliferation, said method comprising contacting a cell or tissue with an effective amount of one or more of the antibodies of the invention.

In a preferred embodiment, such LTα-actived cell proliferation is due to an autoimmune disorder, more preferably RA, MS, Sjogren's syndrome, lupus, myasthenia gravis, or IBD, or cancer, especially breast cancer, lung cancer, prostate cancer, a lymphoma, or leukemia. In another preferred embodiment, the method further comprises contacting the cell or tissue with a second medicament, wherein the first medicament is one or more of the antibodies herein. In a still further preferred embodiment, the cell or tissue is a mammalian cell or tissue, more preferably human, and still more preferably the method is an in vivo method. In such preferred in vivo method, preferably, the subject having the cell or tissue, most preferably a human subject, is administered the effective amount of the antibodies herein, such as by intravenous or subcutaneous administration.

In another embodiment, the invention provides a method of treating an autoimmune disorder in a subject comprising administering to the subject an effective amount of the antibody of the invention. Preferably, the autoimmune disorder is selected from the group consisting of rheumatoid arthritis (RA), lupus, Wegener's disease, inflammatory bowel disease (IBD), idiopathic thrombocytopenic purpura (ITP), thrombotic thrombocytopenic purpura (TTP), autoimmune thrombocytopenia, multiple sclerosis (MS), psoriasis, IgA nephropathy, IgM polyneuropathies, myasthenia gravis, vasculitis, diabetes mellitus, Reynaud's syndrome, Sjögren's syndrome, glomerulonephritis, Hashimoto's thyroiditis, Graves' disease, helicobacter-pylori gastritis, and chronic hepatitis C.

Preferably, the autoimmune disorder is RA, MS, Sjögren's syndrome, lupus, myasthenia gravis, or IBD, more preferably the autoimmune disorder is RA, IBD, lupus, or MS. More preferably, the lupus is systemic lupus erythematosus or lupus nephritis, and the IBD is Crohn's disease or ulcerative colitis.

In other aspects, the antibody is a naked antibody. In a further aspect, the antibody is conjugated with another molecule, such as a cytotoxic agent.

In another aspect, the method is such that the antibody is administered intravenously. In an alternative aspect, the antibody is administered subcutaneously.

In another embodiment, the subject has RA and the antibody induces a major clinical response in the subject.

In a further aspect, the subject has an abnormal level of one or more regulatory cytokines, anti-nuclear antibodies (ANA), anti-rheumatoid factor (RF) antibodies, creatinine, blood urea nitrogen, anti-endothelial antibodies, anti-neutrophil cytoplasmic antibodies (ANCA), infiltrating CD20 cells, anti-double stranded DNA (dsDNA) antibodies, anti-Sm antibodies, anti-nuclear ribonucleoprotein antibodies, anti-phospholipid antibodies, anti-ribosomal P antibodies, anti-Ro/SS-A antibodies, anti-Ro antibodies, anti-La antibodies, antibodies directed against Sjögren's-associated antigen A or B (SS-A or SS-B), antibodies directed against centromere protein B (CENP B) or centromere protein C (CENP C), autoantibodies to ICA69, anti-Smith antigen (Sm) antibodies, anti-nuclear ribonucleoprotein antibodies, anti-ribosomal P antibodies, autoantibodies staining the nuclear or perinuclear zone of neutrophils (pANCA), anti-*Saccharomyces cerevisiae* antibodies, cross-reactive antibodies to GM1 ganglioside or GQ1b ganglioside, anti-acetylcholine receptor (AchR), anti-AchR subtype, or anti-muscle specific tyrosine kinase (MuSK) antibodies, serum anti-endothelial cell antibodies, IgG or anti-desmoglein (Dsg) antibodies, anti-centromere, anti-topoisomerase-1 (Scl-70), anti-RNA polymerase or anti-U3-ribonucleoprotein (U3-RNP) antibodies, anti-glomerular basement membrane (GBM) antibodies, anti-glomerular basement membrane (GBM) antibodies, anti-mitochondrial (AMA) or anti-mitochondrial M2 antibodies, anti-thyroid peroxidase (TPO), anti-thyroglobin (TG) or anti-thyroid stimulating hormone receptor (TSHR) antibodies, anti-nucleic (AN), anti-actin (AA) or anti-smooth muscle antigen (ASM) antibodies, IgA anti-endomysial, IgA anti-tissue transglutaminase, IgA anti-gliadin or IgG anti-gliadin antibodies, anti-CYP21A2, anti-CYP11A1 or anti-CYP17 antibodies, anti-ribonucleoprotein (RNP), or myositis-specific antibodies, anti-myelin associated glycoprotein (MAG) antibodies, anti-hepatitis C virus (HCV) antibodies, anti-GM1 ganglioside, anti-sulfate-3-glycuronyl paragloboside (SGPG), or IgM anti-glycoconjugate antibodies, IgM anti-ganglioside antibody, anti-thyroid peroxidase (TPO), anti-thyroglobin (TG) or anti-thyroid stimulating hormone receptor (TSHR) antibodies, anti-myelin basic protein or anti-myelin oligodendrocytic glycoprotein antibodies, IgM rheumatoid factor antibodies directed against the Fc portion of IgG, anti-Factor VIII antibodies, or a combination thereof.

In another preferred aspect of this method, the antibody is administered no more than about once every other week, more preferably about once a month, to the subject.

In another embodiment, a second medicament, wherein the antibody is a first medicament, is administered to the subject in an effective amount to treat the subject in the methods above. Such second medicament is preferably an immunosuppressive agent, an antagonist that binds a B-cell surface marker, a BAFF antagonist, a disease-modifying anti-rheumatic drug (DMARD), an integrin antagonist, a non-steroidal anti-inflammatory drug (NSAID), a cytokine antagonist, or a combination thereof. Additionally, it may be a hyaluronidase glycoprotein as an active delivery vehicle. Most preferably it is a DMARD or methotrexate.

In another embodiment, the subject has never been previously treated with a medicament for the disorder. In a further aspect, the subject has never been previously treated with a TNF antagonist.

In an alternative embodiment, the subject has been previously treated with a medicament for the disorder, preferably with a TNF antagonist (such as an anti-TNF antibody or a TNF receptor-Ig such as etanercept) or a DMARD.

In another embodiment, the invention provides a method of treating RA in a subject comprising administering to the subject an effective amount of an antibody of this invention. In this method, preferably the antibody induces a major clinical response in the subject. More preferably, the subject has been treated with a medicament for the disorder, preferably with a TNF antagonist (such as an anti-TNF antibody or a TNF receptor-Ig such as etanercept) or a DMARD. In another preferred aspect of this method, the antibody is administered no more than about once every other week, more preferably about once a month, to the subject.

In another embodiment of this RA treatment method, a second medicament, wherein the antibody is a first medicament, is administered to the subject being treated for RA in an effective amount to treat the subject. Such second medicament is preferably an immunosuppressive agent, an antagonist that binds a B-cell surface marker, a BAFF antagonist, a disease-modifying anti-rheumatic drug (DMARD), an integrin antagonist, a non-steroidal anti-inflammatory drug (NSAID), a cytokine antagonist, or a combination thereof. Additionally, it may be a hyaluronidase glycoprotein as an active delivery vehicle. Most preferably it is a DMARD or methotrexate. Preferably, the antibody used for treating RA is administered subcutaneously or intravenously. Further it may be a naked antibody or conjugated, e.g., to a cytotoxic agent. In another preferred aspect of this method, the antibody is administered no more than about once every other week, more preferably about once a month, to the subject.

The invention also provides a composition comprising the antibody of any of the preceding embodiments and a carrier, such as a pharmaceutically acceptable carrier.

Another aspect of the invention is an isolated nucleic acid encoding an antibody of any one of the preceding embodiments. Expression vectors comprising such nucleic acid, and those encoding the antibodies of the invention, are also provided. Also provided is a host cell comprising a nucleic acid encoding an antibody of the invention. Any of a variety of host cells can be used. In one embodiment, the host cell is a prokaryotic cell, for example, E. coli. In another embodiment, the host cell is a eukaryotic cell, for example a yeast cell or mammalian cell such as a Chinese Hamster Ovary (CHO) cell.

In another aspect, the invention provides methods for making an antibody of the invention. For example, the invention provides a method of making or producing an anti-LTα antibody (which, as defined herein includes full length and fragments thereof, provided they contain an Fc region), said method comprising culturing a suitable host cell comprising a nucleic acid encoding an antibody of the invention (preferably comprising a recombinant vector of the invention encoding said antibody (or fragment thereof)), under conditions to produce the antibody, and recovering said antibody. The antibody may be recovered from the host cell or host cell culture. In a preferred embodiment, the antibody is a naked antibody. In another preferred embodiment, the antibody is conjugated with another molecule, the other molecule preferably being a cytotoxic agent.

Still another aspect of the invention is an article of manufacture comprising a container and a composition contained therein, wherein the composition comprises an antibody of any of the preceding embodiments and a package insert indicating that the composition can be used to treat the indication the antibody is intended for, such as an autoimmune disorder. A second medicament, as noted above, may be added to such article, for example, in a separate container, in addition to the antibody, which is the first medicament.

In a further aspect, the invention encompasses a hybridoma deposited at the ATCC on Apr. 19, 2006 under Deposit No. PTA-7538. Further provided is an antibody secreted by such a hybridoma.

If the autoimmune disease is RA specifically, one aspect is a method wherein the patient has never been previously administered a medicament for the RA. An alternative aspect is a method wherein the patient has been previously administered at least one medicament for the RA, more preferably wherein the patient was not responsive to at least one medicament that was previously administered. The previously administered medicament or medicaments to which the patient may be non-responsive include an immunosuppressive agent, cytokine antagonist, integrin antagonist, corticosteroid, analgesic, DMARD, NSAID, or CD20 antagonist, and more preferably an immunosuppressive agent, cytokine antagonist, integrin antagonist, corticosteroid, DMARD, NSAID, or CD20 antagonist, such as a CD20 antibody, which is preferably not rituximab or a humanized 2H7. Most preferably, such previously administered medicament(s) are a DMARD or a TNF inhibitor such as anti-TNF-alpha antibody or TNF-Ig.

In another preferred aspect of the invention for using the antibodies herein to treat an autoimmune disease such as RA, the patient has exhibited an inadequate response to one or more TNF inhibitors or to one or more DMARDs. More preferably, the RA is early RA or incipient RA.

In another embodiment, a method is provided wherein at least about three months after the administration of the antibody herein to a patient with RA or joint damage, an imaging test is given that measures a reduction in bone or soft tissue joint damage as compared to baseline prior to the administration, and the amount of the antibody administered is effective in achieving a reduction in the joint damage. In a preferred aspect, the test measures a total modified Sharp score. In a preferred aspect, the method further comprises an additional administration to the patient of the antibody herein in an amount effective to achieve a continued or maintained reduction in joint damage as compared to the effect of a prior administration of the antibody. In a further aspect, the antibody herein is additionally administered to the patient even if there is no clinical improvement in the patient at the time of the testing after a prior administration. The clinical improvement is preferably determined by assessing the number of tender or swollen joints, conducting a global clinical assessment of the patient, assessing erythrocyte sedimentation rate, assessing the amount of C-reactive protein level, or using composite measures of disease activity.

Preferred second medicaments for treatment of RA and joint damage include an immunosuppressive agent, a DMARD, a pain-control agent, an integrin antagonist, a NSAID, a cytokine antagonist, a bisphosphonate, an antagonist to a B-cell surface marker such as, for example, BR3-Fc, BR3 antibody, CD20 antibody, CD40 antibody, CD22 antibody, CD23 antibody, or a combination thereof. If the second medicament is a DMARD, preferably it is selected from the group consisting of auranofin, chloroquine, D-penicillamine, injectable gold, oral gold, hydroxychloroquine, sulfasalazine, myocrisin, and methotrexate. If the second medicament is a NSAID, preferably it is selected from the group consisting of: fenbufen, naprosyn, diclofenac, etodolac, indomethacin, aspirin and ibuprofen. If the second medicament is an immunosuppressive agent, it is preferably selected from the group consisting of etanercept, infliximab, adalimumab, leflunomide, anakinra, azathioprine, and cyclophosphamide. Other groups of preferred second medicaments include anti-alpha4, etanercept, infliximab, etanercept, adalimumab, kinaret, efalizumab, osteoprotegerin (OPG), anti-receptor activator of NFκB ligand (anti-RANKL), anti-receptor activator of NFκB-Fc (RANK-Fc), pamidronate, alendronate, actonel, zolendronate, clodronate, methotrexate, azulfidine, hydroxychloroquine, doxycycline, leflunomide, sulfasalazine (SSZ), prednisolone, interleukin-1 receptor antagonist, prednisone, or methylprednisolone. Another preferred group of second medicaments includes infliximab, an infliximab/methotrexate (MTX) combination, MTX, etanercept, a corticosteroid, cyclosporin A, azathioprine, auranofin, hydroxychloroquine (HCQ), combination of prednisolone, MTX, and SSZ, combinations of MTX, SSZ, and HCQ, the combination of cyclophosphamide, azathioprine, and HCQ, and the combination of adalimumab with MTX More preferably, the corticosteroid is prednisone, prednisolone, methylprednisolone, hydrocortisone, or dexamethasone. In another preferred embodiment, the second medicament is MTX, which is more preferably administered perorally or parenterally.

In another aspect, the treatment methods herein further comprise re-treating the patient by re-administering an effective amount of the antibody herein to the patient. Preferably, the re-treatment is commenced at least about 24 weeks after the first administration of the antibody. In another embodiment, a second re-treatment is commenced, and more preferably wherein the second re-treatment is commenced at least about 24 weeks after the second administration of the antibody. In another embodiment, where the autoimmune disease is RA, joint damage has been reduced after the re-treatment. In an alternative embodiment, no clinical improvement is observed in the patient at the time of the testing after the re-treatment, especially wherein the clinical improvement is determined by assessing the number of tender or swollen joints, conducting a global clinical assessment of the patient, assessing erythrocyte sedimentation rate, assessing the amount of C-reactive protein level, or using composite measures of disease activity.

In another aspect, the invention herein provides a method for advertising an antibody herein or a pharmaceutically acceptable composition thereof comprising promoting, to a target audience, the use of the antibody or pharmaceutical composition thereof for treating a patient or patient population exhibiting an autoimmune disease such as RA, MS, lupus, or an IBD.

In another aspect, the invention provides an article of manufacture comprising, packaged together, a pharmaceutical composition comprising an antibody herein and a pharmaceutically acceptable carrier and a label stating that the antibody or pharmaceutical composition is indicated for treating patients with an autoimmune disease such as RA, MS, lupus, or an IBD. In a preferred embodiment, the article further comprises a container comprising a second medicament, wherein the antibody herein is a first medicament, further comprising instructions on the package insert for treating the patient with an effective amount of the second medicament, which is preferably methotrexate.

In a still further aspect, the invention provides a method for packaging an antibody herein or a pharmaceutical composition of the antibody comprising combining in a package the antibody or pharmaceutical composition and a label stating that the antibody or pharmaceutical composition is indicated for treating patients exhibiting an autoimmune disease such as RA, MS, lupus, or an IBD.

BRIEF DESCRIPTION OF THE DRAWINGS

FIG. 1A depicts the full-length sequences for the 2C8 chimera light and heavy chains (SEQ ID NOS:32 and 33, respectively).

FIG. 1B depicts the full-length sequences for the 3F12 chimera light and heavy chains (SEQ ID NOS:34 and 35, respectively), as well as the 3F12 chimera heavy-chain variable region (SEQ ID NO:31).

FIG. 1C depicts the sequence of the light-chain variable region for an improved 3F12 chimera (referred to as chimera2 in the examples below) (3F12.2D3) (SEQ ID NO:36) and the sequence of the light-chain constant region of 3F12.2D3 (SEQ ID NO:37). The bold type of the residues indicates those identified from various chemical/enzymatic cleavages.

FIG. 1D depicts the sequence of the heavy-chain variable region for an improved 3F12 chimera (3F12.2D3) (SEQ ID NO:38) and the sequence of the heavy-chain constant region of 3F12.2D3 (SEQ ID NO:39). The bold type of the residues indicates those identified from various chemical/enzymatic cleavages, and the asterisk indicates a glycosylation site.

FIG. 2A depicts alignment of sequences of the variable light chain for the following: chimeric 2C8 antibody (SEQ ID NO:23), humanized 2C8.v2 (SEQ ID NO: 24), and human kappa subgroup I consensus sequence (SEQ ID NO:40). The CDR sequences of each are shown in brackets, and asterisks are used to show differences among the aligned sequence amino acid residues.

FIG. 2B depicts alignment of sequences of the variable heavy chain for the following: chimeric 2C8 antibody (SEQ ID NO:25), humanized 2C8.v2 (SEQ ID NO:26), and human subgroup III consensus sequence (SEQ ID NO:41). The CDR sequences of each are shown in brackets, and asterisks are used to show differences among the aligned sequence amino acid residues.

FIG. 2C depicts the light- and heavy-chain sequences for versions 2C8.v7 and2C8.v12 (SEQ ID NOS:42-45).

FIG. 3A depicts alignment of sequences of the variable light chain for the following: chimeric 3F12 antibody (SEQ ID NO:27), humanized 3F12.v5 (SEQ ID NO:28), and human kappa subgroup I consensus sequence (SEQ ID NO:40). The CDR sequences of each are shown in brackets, and asterisks are used to show differences among the aligned sequence amino acid residues.

FIG. 3B depicts alignment of sequences of the variable heavy chain for the following: original chimeric 3F12 antibody (not 3F12.2D3) (SEQ ID NO:29), humanized 3F12.v5 (SEQ ID NO:30), and human subgroup III consensus sequence (SEQ ID NO:41). The CDR sequences of each are shown in brackets, and asterisks are used to show differences among the aligned sequence amino acid residues.

FIG. 4A shows the results of preventative use of the anti-LTα antibody versus a Fc DANA mutation (anti-LT.Fc-mutant) and a TNFRII.Fc mutant (a TNFR.Ig immunoadhesin) as well as a control isotype (anti-ragweed IgG2a monoclonal antibody). FIG. 4B shows that the anti-LTα antibody inhibited development of arthritis in an AIA model when administered therapeutically, versus control isotype and TNFRII.Fc mutant.

FIG. 5A shows that S5H3 inhibited arthritis in a CIA-preventative model, versus a Fc DANA mutation (anti-LT.Fc mutant) as well as a control isotype (anti-ragweed IgG2a monoclonal antibody) and was comparable to a TNFRII.Fc mutant. FIG. 5B shows that the S5H3 anti-LTα antibody inhibited development of arthritis in a CIA model when administered therapeutically, versus control isotype, and was comparable to the TNFRII.Fc mutant.

FIG. 11A shows through enzyme-linked immunosorbent assay (ELISA) results that hamster-murine chimeric anti-LTα S5H3 antibody binds to murine LTα1β2 complex, as does the anti-LT.Fc mutant.

FIG. 11B shows FACS assay results for binding of chimeric anti-LTα antibodies 3F12 and 2C8 to the LTα on the surface of human cells complexed with LTβ. They are compared to LTβ-receptor.huIgG1 and isotype control huIgG1 (trastuzumab).

FIG. 11C shows FACS assay results for binding of hamster-murine chimeric anti-LTα antibody S5H3 to the LTα on the surface of murine cells complexed with LTβ. It is compared to LTβ-receptor murine IgG2a, anti-LT S5H3Fc mutant, and isotype control (anti-IL122 muIgG2a).

FIG. 18A depicts alignment of sequences of the variable light chain for the following: chimeric 2C8 antibody (SEQ ID NO:23), humanized 2C8.vX (SEQ ID NO:102), and human kappa subgroup I consensus sequence (SEQ ID NO:40). The CDR sequences of each are shown in brackets, and asterisks are used to show differences among the aligned sequence amino acid residues.

FIG. 18B depicts alignment of sequences of the variable heavy chain for the following: chimeric 2C8 antibody (SEQ ID NO:25), humanized 2C8.vX (SEQ ID NO:103), and human subgroup III consensus sequence (SEQ ID NO:41). The CDR sequences of each are shown in brackets, and asterisks are used to show differences among the aligned sequence amino acid residues.

FIG. 25B-D show the results of gating using the CD4, CD8, and CD19 antibodies, respectively.

FIG. 26A depicts alignment of sequences of the variable light chain for the following: chimeric 3F12 antibody (SEQ ID NO:27), humanized 3F12.v14 (SEQ ID NO:108), and human kappa subgroup I consensus sequence (SEQ ID NO:40). The CDR sequences of each are shown in brackets, and asterisks are used to show differences among the aligned sequence amino acid residues.

FIG. 26B depicts alignment of sequences of the variable heavy chain for the following: chimeric 3F12 antibody (SEQ ID NO:29), humanized 3F12.v14 (SEQ ID NO:109), and human subgroup III consensus sequence (SEQ ID NO:41). The CDR sequences of each are shown in brackets, and asterisks are used to show differences among the aligned sequence amino acid residues.

DETAILED DESCRIPTION OF THE PREFERRED EMBODIMENTS

General Techniques

Figure 4A:
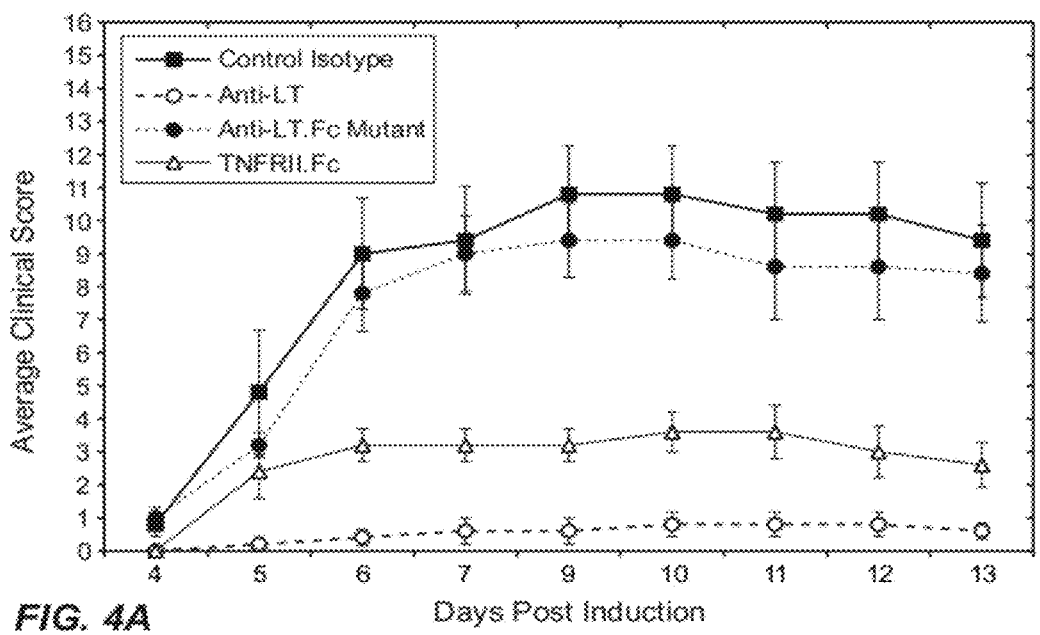
FIGS. 4A and 4B show that hamster-murine chimeric anti-LTα antibody S5H3 inhibits antibody-induced arthritis (AIA).

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction*, (Mullis et al., ed., 1994); *A Practical Guide to Molecular Cloning* (Perbal Bernard V., 1988); *Phage Display: A Laboratory Manual* (Barbas et al., 2001).

Definitions

"Lymphotoxin-α or "LTα" is defined herein as a biologically active polypeptide having the amino acid sequence shown in FIG. 2A of U.S. Pat. No. 5,824,509. LTα is defined to specifically exclude human TNFα or its natural animal analogues (Pennica et al., *Nature* 312:20/27: 724-729 (1984) and Aggarwal et al., *J. Biol. Chem.* 260: 2345-2354 (1985)). LTα is defined to specifically exclude human LTβ as defined, for example, in U.S. Pat. No. 5,661,004.

"Lymphotoxin-α3 trimer" or "LTα3" refers to a homotrimer of LTα monomers. This homotrimer is anchored to the cell surface by the LTβ, transmembrane and cytoplasmic domains.

"Lymphotoxin-αβ" or "LTαβ" or "LTαβ complex" refers to a heterotrimer of LTα with LTβ. These heterotrimers contain either two subunits of LTα and one subunit of LTβ (LTα2β1), or one subunit of LTα and two of LTβ (LTα1β2).

"Tumor necrosis factor receptor-I" or "TNFRI" and "tumor necrosis factor receptor-II" or "TNFRII" refer to cell-surface TNF receptors for the LTαβ homotrimer, also known as p55 and p75, respectively.

"Lymphotoxin-β receptor" or "LTβ-R" refers to the receptor to which the LTαβ heterotrimers bind.

"Regulatory cytokines" are cytokines the abnormal levels of which indicate the presence of an autoimmune disorder in a patient. Such cytokines include, for example, interleukin-1 (IL-1), IL-2, IL-3, IL-4, IL-5, IL-69 IL-7, IL-8, IL-10, IL-12, IL-13, IL-14, IL-15, IL-18, IL-23, IL-24, IL-25, IL-26, BLyS/April, TGF-α, TGF-β, interferon-α (IFN-α), IFN-β, IFN-γ, MIP-1, MIF, MCP-1, M-CSF or G-CSF, a lymphotoxin, LIGHT, 4-1BB ligand, CD27 ligand, CD30 ligand, CD40 ligand, Fas ligand, GITR ligand, OX40 ligand, RNAK ligand, THANK, TRAIL, TWEAK and VEG1. This group includes TNF family members, which include but are not limited to, TNF-α, LTs such as LTα, LTβ, and LIGHT. For a review of the TNF superfamily, see MacEwan, *Br. J. Pharmacology* 135: 855-875 (2002). Preferably, the regulatory cytokine is an IL such as IL-1b or IL-6 and/or a TNF family member.

"Inflammatory cytokines associated with rheumatoid arthritis" refer to IL-6, IL-1b, and TNFα, associated with RA pathology, which can be inhibited systemically and or in the joints in an in vitro collagen-induced arthritis assay.

"LTαβ-expressing cells" are cells that express or secrete the LTαβ heterotrimers.

The expression "modulates LTαβ-expressing cells" refers to depleting or altering proteins made by the cells such as cytokines, chemokines, or growth factors, with the cells including, for example, monocytes, dendritic cells, T cells, and B cells.

The terms "antibody" and "immunoglobulin" are used interchangeably in the broadest sense and include monoclonal antibodies (e.g., full-length or intact monoclonal antibodies), polyclonal antibodies, multivalent antibodies, and multispecific antibodies (e.g., bispecific antibodies so long as they exhibit the desired biological activity), and may also include certain antibody fragments (as described in greater detail herein). An antibody can be chimeric, human, humanized, and/or affinity matured.

"Antibody fragments" comprise only a portion of an intact antibody, wherein the portion preferably retains at least one, more preferably most or all, of the functions normally associated with that portion when present in an intact antibody. In one embodiment, an antibody fragment comprises an antigen-binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function, and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment. In one embodiment, an antibody of the invention is a one-armed antibody as described in WO 2005/063816, for example, an antibody comprising Fc mutations constituting "knobs" and "holes". For example, a hole mutation can be one or more of T366A, L368A and/or Y407V in an Fc polypeptide, and a cavity mutation can be T366W. Examples of antibody fragments include Fab, Fab', F(ab')$_2$, and Fv fragments; diabodies; linear antibodies; single-chain antibody molecules; and multispecific antibodies formed from antibody fragments.

For the purposes herein, an "intact antibody" is one comprising heavy and light variable domains as well as an Fc region.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that typically include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in, e.g., bacterial, non-animal eukaryotic, animal, or plant cells (see, e.g., U.S. Pat. No. 4,816,567). The "monoclonal antibodies" may also be isolated from phage antibody libraries using the techniques described in, e.g., Clackson et al., *Nature*, 352:624-628 (1991) and Marks et al., *J. Mol. Biol.*, 222:581-597 (1991).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues that are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence, although the FR regions may include one or more amino acid substitutions that improve binding affinity. The number of these amino acid substitutions in the FR is typically no more than six in the H chain, and no more than three in the L chain. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332: 323-329 (1988); and Presta, *Curr. Op. Struct. Biol.*, 2:593-596 (1992). See also Vaswani and Hamilton, *Ann. Allergy, Asthma & Immunol.* 1: 105-115 (1998); Harris, *Biochem. Soc. Transactions* 23:1035-1038 (1995); Hurle and Gross, *Curr. Op. Biotech.* 5:428-433 (1994). The humanized antibody includes a PRIMATIZED® antibody wherein the antigen-binding region of the antibody is derived from an antibody produced by, e.g., immunizing macaque monkeys with the antigen of interest. Methods of making humanized antibodies are known in the art.

A "human antibody" is one that possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues. Human antibodies can also be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991).

An "affinity-matured" antibody is an antibody with one or more alterations in one or more CDRs thereof that result in an improvement in the affinity of the antibody for antigen, compared to a parent antibody that does not possess those alteration(s). Preferred affinity matured antibodies will have nanomolar or even picomolar affinities for the target antigen. Affinity-matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al., *Proc Nat. Acad. Sci, USA* 91:3809-3813 (1994); Schier et al., *Gene* 169:147-155 (1995); Yelton et al., *J. Immunol.* 155:1994-2004 (1995); Jackson et al., *J. Immunol.* 154(7):3310-9 (1995); and Hawkins et al., *J. Mol. Biol.* 226:889-896 (1992).

An "antigen" is a predetermined antigen to which an antibody can selectively bind. The target antigen may be polypeptide, carbohydrate, nucleic acid, lipid, hapten, or another naturally occurring or synthetic compound. Preferably, the target antigen is α polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than five, and more preferably four or less, and still more preferably three or less, pre-existing amino acid changes are present. Where pre-existing amino acid changes are present in a VH, preferably those changes are only at three, two, or one of positions 71, 73, and 78; for instance, the histidine residues at those positions may be alanine residues. In one embodiment, the VL acceptor human framework is identical in sequence to the VL human immunoglobulin framework sequence or human consensus framework sequence.

A "human consensus framework" is a framework that represents the most commonly occurring amino acid residue in a selection of human immunoglobulin VL or VH framework sequences. Generally, the selection of human immunoglobulin VL or VH sequences is from a subgroup of variable domain sequences. Typically, this subgroup of sequences is a subgroup as in Kabat et al., supra. In one embodiment, for the VL, the subgroup is subgroup kappa I as in Kabat et al., supra. In one embodiment, for the VH, the subgroup is subgroup III as in Kabat et al, supra.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences:

EVQLVESGGGLVQPGGSLRLSCAAS (SEQ ID NO: 46)-H1-

WVRQAPGKGLEWVG (SEQ ID NO: 47)-H2-

RFTISRDNSKNTLYLQMNSLRAEDTAVYYCAR (SEQ ID NO: 48)-

H3-WGQGTLVTVSS (SEQ ID NO: 49), where N is any amino acid residue.

In another embodiment, the VH subgroup III consensus framework amino acid sequence comprises at least a portion or all of each of the following sequences:

EVQLVESGGGLVQPGGSLRLSCAAS (SEQ ID NO: 46)-H1-

WVRQAPGKGLEWVG (SEQ ID NO: 47)-H2-

RATFSADNSKNTAYLQMNSLRAEDTAVYYCAD (SEQ ID NO: 50)-

H3-WGQGTLVTVSS (SEQ ID NO: 49), where N is any amino acid residue.

A "VL subgroup I consensus framework" comprises the consensus sequence obtained from the amino acid sequences in variable light kappa subgroup I of Kabat et al., supra. In one embodiment, the VL subgroup I consensus framework amino acid sequence comprises at least a portion or all of each of the following sequences:

DIQMTQSPSSLSASVGDRVTITC- (SEQ ID NO: 51)

L1-WYQQKPGKAPKLQIY- (SEQ ID NO: 52)

L2-GVPSRFSGSGSGTDFTLTISSLQPEDFATYYC- (SEQ ID NO: 53)

L3-FGQGTKVEIKR. (SEQ ID NO: 54)

In another embodiment, the VL subgroup I consensus framework amino acid sequence comprises at least a portion or all of each of the following sequences:

DIQMTQSPSSLSASVGDRVTITC- (SEQ ID NO: 51)

L1-WYQQKPGKAPKLLIY- (SEQ ID NO: 55)

L2-GVPSRFSGSGSGTDFTLTISSLQPEDFATYYC- (SEQ ID NO: 53)

L3-FGQGTKVEIKR. (SEQ ID NO: 54)

The term "complementarity-determining region", or "CDR", when used herein refers to the regions of an antibody variable domain that are hypervariable in sequence and/or form structurally defined loops. Generally, antibodies comprise six hypervariable regions; three in the VH (H1, H2, H3), and three in the VL (L1, L2, L3). A number of CDR delineations are in use and are encompassed herein. The Kabat CDRs are based on sequence variability and are the most commonly used (Kabat et al., supra). Chothia refers instead to the location of the structural loops (Chothia and Lesk, *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
| --- | --- | --- | --- | --- |
| L1 | L24-L34 | L24-L34 | L24-L32 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H32B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H52-H56 | H47-H58 |
| H3 | H95-H102 | H95-H102 | H95-H102 | H93-H101 |

CDRs may comprise "extended CDRs" as follows: 24-36 or 24-34 (L1), 46-56 or 50-56 (L2), and 89-97 (L3) in the VL, and 26-35 (H1), 50-65 or 49-65 (H2), and 93-102, 94-102, or 95-102 (H3) in the VH. The variable domain residues are numbered according to Kabat et al., supra, for each of these definitions. Throughout the present specification and claims, the numbering of the residues in an immunoglobulin heavy chain is that of the EU index as in Kabat et al., supra. The "EU index as in Kabat" refers to the residue numbering of the human IgG1 EU antibody.

An "unmodified human framework" is a human framework that has the same amino acid sequence as the acceptor human framework, e.g. lacking human to non-human amino acid substitution(s) in the acceptor human framework.

An "altered CDR" for the purposes herein is a CDR comprising one or more (e.g. one to about 16) amino acid substitution(s) therein.

An "un-modified CDR" for the purposes herein is a CDR having the same amino acid sequence as a non-human antibody from which it was derived, i.e. one lacking one or more amino acid substitutions.

"Framework" or "FR" residues are those variable domain residues other than the CDR residues as herein defined.

A "blocking" antibody or an "antagonist" antibody is one that inhibits or reduces biological activity of the antigen it binds. Preferred blocking antibodies or antagonist antibodies substantially or completely inhibit the biological activity of the antigen.

An "agonist antibody", as used herein, is an antibody that mimics at least one of the functional activities of a polypeptide of interest.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable-domain residue numbering as in Kabat" or "amino acid position numbering as in Kabat", and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or CDR of the variable domain. For example, a heavy-chain variable domain may include a single amino acid insert (residue 52a according to Kabat) after residue 52 of H2 and inserted residues (e.g. residues 82a, 82b, and 82c, etc according to Kabat) after heavy-chain FR residue 82. The Kabat numbering of residues may be determined for a given antibody by alignment at regions of homology of the sequence of the antibody with a "standard" Kabat-numbered sequence.

A "parent polypeptide" is a polypeptide comprising an amino acid sequence that lacks one or more of the Fc-region modifications disclosed herein and that differs in effector function compared to a polypeptide variant as herein disclosed. The parent polypeptide may comprise a native-sequence Fc region or an Fc region with pre-existing amino acid sequence modifications (such as additions, deletions, and/or substitutions).

The term "Fc region" is used to define a C-terminal region of an immunoglobulin heavy chain. The "Fc region" may be a native-sequence Fc region or a variant Fc region. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The Fc region of an immunoglobulin generally comprises two constant domains, CH2 and CH3. The last residue, lysine, in the heavy chain of IgG1 can, but does not have to, be present as the terminal residue in the Fc in the mature protein.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22: 161-206 (1985).

The "CH3 domain" comprises the stretch of residues C-terminal to a CH2 domain in an Fc region (i.e. from about amino acid residue 341 to about amino acid residue 447 of an IgG)

A "functional Fc region" possesses an "effector function" of a native-sequence Fc region. Exemplary "effector functions" include C1q binding; CDC; Fc receptor binding; ADCC; phagocytosis; down regulation of cell-surface receptors (e.g. LT receptor), etc. Such effector functions generally require the Fc region to be combined with a binding domain (e.g. an antibody variable domain) and can be assessed using various assays as herein disclosed, for example.

A "native-sequence Fc region" or "wild-type Fc region" comprises an amino acid sequence identical to the amino acid sequence of an Fc region found in nature. Native-sequence human Fc regions are known in the art and include a native-sequence human IgG1 Fc region (non-A and A allotypes); native-sequence human IgG2 Fc region; native-sequence human IgG3 Fc region; and native-sequence human IgG4 Fc region, as well as naturally occurring allelic variants thereof.

A "variant Fc region" comprises an amino acid sequence that differs from that of a native-sequence Fc region by virtue of at least one "amino acid modification" as herein defined. Preferably, the variant Fc region has at least one amino acid substitution compared to a native-sequence Fc region or to the Fc region of a parent polypeptide, e.g. from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, more preferably at least about 90% homology therewith, and most preferably at least about 95% homology therewith.

The term "Fc region-containing polypeptide" refers to a polypeptide, such as an antibody or immunoadhesin (see definitions herein), which comprises an Fc region.

The terms "Fc receptor" and "FcR" are used to describe a receptor that binds to the Fc region of an IgG antibody. The preferred FcR is a native-sequence human FcR. In one embodiment, the FcR is a FcγR that includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131, and/or FcγRIIA-H131. FcRs are reviewed in Ravetch and Kinet, *Annu. Rev. Immunol* 9:457-492 (1991); Capel et al., *Immunomethods* 4:25-34 (1994); and de Haas et al., *J. Lab. Clin. Med.*, 126:330-341 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *Eur. J. Immunol.* 24:2429-2434 (1994)).

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.*, 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMCs) and NK cells. Alternatively, or additionally, ADCC activity of the molecule of interest may be assessed in vivo, e.g., in a animal model such as that disclosed in Clynes et al., *PNAS* (USA) 95:652-656 (1998).

"Human effector cells" are leukocytes that express one or more FcRs and perform effector functions. Preferably, the cells express at least FcγRIII and perform ADCC effector function. Examples of human leukocytes that mediate ADCC include PBMCs, NK cells, monocytes, cytotoxic T cells, and neutrophils; with PBMCs and NK cells being preferred. The effector cells may be isolated from a native source thereof, e.g. from blood or PBMCs as described herein.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g. as described in Gazzano-Santoro et al., *J. Immunol. Methods* 202:163 (1996), may be performed.

A polypeptide with a variant IgG Fc having "altered" FcR binding affinity or ADCC activity is one that has either enhanced or diminished FcR binding activity (FcγR or FcRn) and/or ADCC activity compared to a parent polypeptide or to a polypeptide comprising a native-sequence Fc region. The variant Fc that "exhibits increased binding" to an FcR binds at least one FcR with better affinity than the parent polypeptide. The improvement in binding compared to a parent polypeptide may be about three-fold, preferably about 5-, 10-, 25-, 50-, 60-, 100-, 150-, 200-, and up to 500-fold, or about 25% to 1000% improvement in binding. The polypeptide variant that "exhibits decreased binding" to an FcR binds at least one FcR with less affinity than a parent polypeptide. The decrease in binding compared to a parent polypeptide may be about 40% or more decrease in binding. Such Fc variants that display decreased binding to an FcR may possess little or no appreciable binding to an FcR, e.g., about 0-20% binding to the FcR compared to a native-sequence IgG Fc region.

The polypeptide having a variant Fc that binds an FcR with "better affinity" or "higher affinity" than a polypeptide or parent polypeptide having wild-type or native-sequence IgG Fc is one that binds any one or more of the above identified FcRs with substantially better binding affinity than the parent polypeptide with native-sequence Fc, when the amounts of polypeptide with variant Fc and parent polypeptide in the binding assay are essentially the same. For example, the variant Fc polypeptide with improved FcR binding affinity may display from about two-fold to about 300-fold, preferably, from about three-fold to about 170-fold, improvement in FcR binding affinity compared to the parent polypeptide, where FcR binding affinity is determined as known in the art.

The polypeptide comprising a variant Fc region that "exhibits increased ADCC" or mediates ADCC in the presence of human effector cells more effectively than a polypeptide having wild-type IgG Fc is one that in vitro or in vivo is substantially more effective at mediating ADCC, when the amounts of polypeptide with variant Fc region and the polypeptide with wild-type Fc region used in the assay are essentially the same. Generally, such variants will be identified using the in vitro ADCC assay as herein disclosed, but other assays or methods for determining ADCC activity, e.g. in an animal model, etc, are contemplated. The preferred variant is from about five-fold to about 100-fold, more preferably from about 25- to about 50-fold, more effective at mediating ADCC than the wild-type Fc.

An "amino acid modification" refers to a change in the amino acid sequence of a predetermined amino acid sequence. Exemplary modifications include an amino acid substitution, insertion, and/or deletion. The preferred amino acid modification herein is a substitution.

An "amino acid modification at" a specified position, e.g. of the Fc region, refers to the substitution or deletion of the specified residue, or the insertion of at least one amino acid residue adjacent to the specified residue. By insertion "adjacent to" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, and other amino acid residue analogues such as those described in Eliman et al., *Meth. Enzym.* 202:301-336 (1991). For generation of such non-naturally occurring amino acid residues, the procedures of Noren et al., *Science* 244:182 (1989) and Eliman et al., supra, can be used. Briefly, these procedures involve chemically activating a suppressor tRNA with a non-naturally occurring amino acid residue followed by in vitro transcription and translation of the RNA.

The term "conservative" amino acid substitution as used within this invention is meant to refer to amino acid substitutions that substitute functionally equivalent amino acids. Conservative amino acid changes result in silent changes in the amino acid sequence of the resulting polypeptide. For example, one or more amino acids of a similar polarity act as functional equivalents and result in a silent alteration within the amino acid sequence of the polypeptide. In general, substitutions within a group may be considered conservative with respect to structure and function. However, the skilled artisan will recognize that the role of a particular residue is determined by its context within the three-dimensional structure of the molecule in which it occurs. For example, Cys residues may occur in the oxidized (disulfide) form, which is less polar than the reduced (thiol) form. The long aliphatic portion of the Arg side chain may constitute a critical feature of its structural or functional role, and this may be best conserved by substitution of a nonpolar, rather than another basic, residue. Also, it will be recognized that side chains containing aromatic groups (Trp, Tyr, and Phe) can participate in ionic-aromatic or "cation-pi" interactions. In these cases, substitution of one of these side chains with a member of the acidic or uncharged polar group may be conservative with respect to structure and function. Residues such as Pro, Gly, and Cys (disulfide form) can have direct effects on the main-chain conformation, and often may not be substituted without structural distortions.

An "amino acid insertion" refers to the incorporation of at least one amino acid into a predetermined amino acid sequence. While the insertion will usually consist of the insertion of one or two amino acid residues, the present application contemplates larger "peptide insertions", e.g., insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

The "hinge region" is generally defined as stretching from Glu216 to Pro230 of human IgG1 (Burton, *Molec. Immunol.* 22: 161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e., residues 233 to 239 of the Fc region.

"C1q" is a polypeptide that includes a binding site for the Fc region of an immunoglobulin. C1q together with two serine proteases, C1r and C1s, forms the complex C1, the first component of the CDC pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g., the α chain thereof) that is responsible for binding an Fc region. One useful binding domain is the extracellular domain of an FcR α chain.

"Functional fragments" of the antibodies of the invention comprise a portion of an intact antibody, generally including the antigen-binding or variable region of the intact antibody or the Fc region of an antibody that retains FcR binding capability. Examples of antibody fragments include linear antibodies, single-chain antibody molecules, and multispecific antibodies formed from antibody fragments.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen-recognition and binding site of an antibody (i.e., is "heterologous"), and an immunoglobulin constant-domain sequence. The adhesin part of an immunoadhesin molecule typically is a contiguous amino acid sequence comprising at least the binding site of a receptor or a ligand. The immunoglobulin constant-domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM. For example, useful immunoadhesins as second medicaments herein include polypeptides that comprise the B-lymphocyte stimulator (BLyS) binding portions of a BLyS receptor without the transmembrane or cytoplasmic sequences of the BLyS receptor. In one embodiment, the extracellular domain of BR3 (BLyS receptor 3), TACI (transmembrane activator and calcium-modulator and cyclophilin ligand interactor), or BCMA (B-cell maturation antigen) is fused to a constant domain of an immunoglobulin sequence.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

An "on-rate" or "rate of association" or "association rate" or "$k_{on}$" according to this invention can be determined with the surface plasmon resonance technique using a BIACORE®-2000 or a BIACORE®-3000 (BIAcore, Inc., Piscataway, N.J.) optical biosensor at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 μM) before injection at a flow rate of 5 μl/minute to achieve approximately 10 response units (RU) of coupled protein. Following the injection of 1M ethanolamine to block unreacted groups, for kinetics measurements, two-fold serial dilutions of Fab (0.78 nM to 500 nM) are injected in phosphate-buffered saline (PBS) with 0.05% TWEEN™ 20 (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2™) by simultaneous fitting the association and dissociation sensorgram. The equilibrium dissociation constant (Kd) was calculated as the ratio $k_{off}/k_{on}$. See, e.g., Chen et al., *J. Mol. Biol* 293:865-881 (1999). However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

The "Kd" or "Kd value" according to this invention is, in one embodiment, measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen et al., *J. Mol. Biol* 293:865-881 (1999)). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (consistent with assessment of an anti-VEGF antibody, Fab-12, in Presta et al., *Cancer Res.* 57:4593-4599 (1997)). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% TWEEN™-20 in PBS. When the plates have dried, 150 µl/well of scintillant (MicroScint-20; Packard) is added, and the plates are counted on a TOPCOUNT™ gamma counter (Packard) for ten minutes. Concentrations of each Fab that give less than or equal to 20% of maximal binding are chosen for use in competitive binding assays.

The phrase "substantially similar" or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, more preferably less than about 40%, still more preferably less than about 30%, even more preferably less than about 20%, and most preferably less than about 10% as a function of the value for the reference/comparator antibody.

The phrase "substantially reduced," or "substantially different," as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, more preferably greater than about 20%, still more preferably greater than about 30%, even more preferably greater than about 40%, and most preferably greater than about 50% as a function of the value for the reference/comparator antibody.

"Percent (%) amino acid sequence identity" and "homology" with respect to a peptide or polypeptide sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN™ (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, authored by Genentech, Inc. The source code of ALIGN-2 has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described herein using the ALIGN-2 computer program.

A "disorder" is any condition that would benefit from treatment with an antibody or method of the invention, regardless of mechanism, but including inhibiting or blocking the action of LTα3 or LTαβ and/or by depleting LTα-positive cells. This condition includes, but is not limited to, a medical condition or illness mediated by or related to elevated expression or activity, or abnormal activation, of LTα3 and/or LTαβ by any cell. This includes chronic and acute disorders such as those pathological conditions that predispose the mammal to the disorder in question.

An "autoimmune disorder" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disorder, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

As used herein, an "autoimmune disorder" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis (MS), opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, IBD, including Crohn's disease and ulcerative colitis, ANCA-associated vasculitis, lupus, MS, Sjögren's syndrome, Graves' disease, IDDM, pernicious anemia, thyroiditis, and glomerulonephritis. Still more preferred are RA, IBD, lupus, and MS, and more preferred RA and IBD, and most preferred RA.

Specific examples of other autoimmune disorders as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spinooptical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immunovasculitis, CNS vasculitis, cutaneous vasculitis, hypersensitivity vasculitis, necrotizing vasculitis such as fibrinoid necrotizing vasculitis and systemic necrotizing vasculitis, ANCA-negative vasculitis, and ANCA-associated vasculitis such as Churg-Strauss syndrome (CSS), Wegener's granulomatosis, and microscopic polyangiitis), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, antiphospholipid antibody syndrome, motoneuritis, allergic neuritis, Behçet's disease/syndrome, Castleman's syndrome, Goodpasture's syndrome, Reynaud's syndrome, Sjögren's syndrome, Stevens-Johnson syndrome, pemphigoid or pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, preferably allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (opthalmopathy or thyroid-associated opthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs. NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to antispermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigenantibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

As used herein, "rheumatoid arthritis" or "RA" refers to a recognized disease state that may be diagnosed according to the 2000 revised American Rheumatoid Association criteria for the classification of RA, or any similar criteria, and includes active, early, and incipient RA, as defined below. Physiological indicators of RA include symmetric joint swelling, which is characteristic though not invariable in rheumatoid arthritis. Fusiform swelling of the proximal interphalangeal (PIP) joints of the hands as well as metacarpophalangeal (MCP), wrists, elbows, knees, ankles, and metatarsophalangeal (MTP) joints are commonly affected and swelling is easily detected. Pain on passive motion is the most sensitive test for joint inflammation, and inflammation and structural deformity often limit the range of motion for the affected joint. Typical visible changes include ulnar deviation of the fingers at the MCP joints, hyperextension, or hyperflexion of the MCP and PIP joints, flexion contractures of the elbows, and subluxation of the carpal bones and toes. The subject with RA may be resistant to DMARDs, in that the DMARDs are not effective or fully effective in treating symptoms. Further candidates for therapy according to this invention include those who have experienced an inadequate response to previous or current treatment with TNF inhibitors such as etanercept, infliximab, and/or adalimumab because of toxicity or inadequate efficacy (for example, etanercept for 3 months at 25 mg twice a week or at least 4 infusions of infliximab at 3 mg/kg).

A patient with "active rheumatoid arthritis" means a patient with active and not latent symptoms of RA. Subjects with "early active rheumatoid arthritis" are those subjects with active RA diagnosed for at least eight weeks but no longer than four years, according to the revised 1987 ACR criteria for the classification of RA. Subjects with "early rheumatoid arthritis" are those subjects with RA diagnosed for at least eight weeks but no longer than four years, according to the revised 1987 ACR criteria for classification of RA. Early RA includes, for example, juvenile-onset RA, juvenile idiopathic arthritis (JIA), or juvenile RA (JRA).

Patients with "incipient RA" have early polyarthritis that does not fully meet ACR criteria for a diagnosis of RA, but is associated with the presence of RA-specific prognostic biomarkers such as anti-CCP and shared epitope. They include patients with positive anti-CCP antibodies who present with polyarthritis, but do not yet have a diagnosis of RA, and are at high risk for going on to develop bona fide ACR criteria RA (95% probability).

"Joint damage" is used in the broadest sense and refers to damage or partial or complete destruction to any part of one or more joints, including the connective tissue and cartilage, where damage includes structural and/or functional damage of any cause, and may or may not cause joint pain/arthalgia. It includes, without limitation, joint damage associated with or resulting from inflammatory joint disease as well as non-inflammatory joint disease. This damage may be caused by any condition, such as an autoimmune disease, especially arthritis, and most especially RA. Exemplary such conditions include acute and chronic arthritis, RA including juvenile-onset RA, juvenile idiopathic arthritis (JIA), or juvenile RA (JRA), and stages such as rheumatoid synovitis, gout or gouty arthritis, acute immunological arthritis, chronic inflammatory arthritis, degenerative arthritis, type II collagen-induced arthritis, infectious arthritis, septic arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), rheumatic autoimmune disease other than RA, and significant systemic involvement secondary to RA (including but not limited to vasculitis, pulmonary fibrosis or Felty's syndrome). For purposes herein, joints are points of contact between elements of a skeleton (of a vertebrate such as an animal) with the parts that surround and support it and include, but are not limited to, for example, hips, joints between the vertebrae of the spine, joints between the spine and pelvis (sacroiliac joints), joints where the tendons and ligaments attach to bones, joints between the ribs and spine, shoulders, knees, feet, elbows, hands, fingers, ankles, and toes, but especially joints in the hands and feet.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, prevention of metastasis, decreasing of the rate of disease progression, amelioration or palliation of the disease state, and remission or improved prognosis. In some embodiments, the antibodies of the invention are used to delay development of a disease or disorder. A subject is successfully "treated" for example, for an autoimmune disorder if, after receiving a therapeutic amount of an antibody of the invention according to the methods of the present invention, the subject shows observable and/or measurable reduction in or absence of one or more signs and symptoms of the particular disease.

In one preferred embodiment of successful treatment, the antibody induces a major clinical response in a subject with RA. For purposes herein, a "major clinical response" is defined as achieving an American College of Rheumatology 70 response (ACR 70) for six consecutive months. ACR response scores are categorized as ACR 20, ACR 50, and ACR 70, with ACR 70 being the highest level of sign and symptom control in this evaluation system. ACR response scores measure improvement in RA disease activity, including joint swelling and tenderness, pain, level of disability, and overall patient and physician assessment. An example of a different type of antibody that induces a major clinical response as recognized by the FDA and as defined herein is etanercept (ENBREL®).

An "effective amount" refers to an amount effective, at dosages and for periods of time necessary, to achieve the desired therapeutic or prophylactic result.

A "therapeutically effective amount" of a medicament herein may vary according to factors such as the disease state, age, sex, and weight of the individual, and the ability of the medicament, e.g., antibody, to elicit a desired response in the individual. A therapeutically effective amount is also one in which any toxic or detrimental effects of the drug in question, e.g., antibody, are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{88}$, $Sm^{153}$, $Bi^{212}$, $P^{32}$ and radioactive isotopes of Lu), chemotherapeutic agents, and toxins such as small-molecule toxins or enzymatically active toxins of bacterial, fungal, plant, or animal origin, or fragments thereof.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; CDP323, an oral alpha-4 integrin inhibitor; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antibiotic chromophores); other antibiotics such as aclacinomycin, actinomycin, authramycin, azaserine, bleomycin, cactinomycin, carabicin, caminomycin, carzinophilin, chromomycin, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), and deoxydoxorubicin), epirubicin, esorubicin, idarubicin, marcellomycin, mitomycins such as mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, and zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; and folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); and pharmaceutically acceptable salts, acids, or derivatives of any of the above.

The term "cytokine" is a generic term for proteins released by one cell population that act on another cell as intercellular mediators. Examples of such cytokines are lymphokines, monokines, interleukins (ILs) such as IL-1, IL-1α, IL-2, IL-3, IL-4, IL-5, IL-6, IL-7, IL-8, IL-9, IL-11, IL-12, and IL-15, including PROLEUKIN® rIL-2, a TNF such as TNF-α or TNF-β, and other polypeptide factors including leukocyte-inhibitory factor (LIF) and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof. A "cytokine antagonist" is a molecule that inhibits or antagonizes such cytokines by any mechanism, including, for example, antibodies to the cytokine, antibodies to the cytokine receptor, and immunoadhesins.

For purposes herein, "tumor necrosis factor alpha" or "TNF-alpha" or "TNFα" refers to a human TNF-alpha molecule comprising the amino acid sequence as described in Pennica et al., Nature, 312:721 (1984) or Aggarwal et al., J. Biol. Chem., 260:2345 (1985).

A "TNF antagonist" or "TNF inhibitor" is defined herein as a molecule that decreases, blocks, inhibits, abrogates, or otherwise interferes with TNFα activity in vitro, in situ, and/or preferably in vivo. Such an agent inhibits, to some extent, a biological function of TNF-alpha, generally through binding to TNF-alpha and neutralizing its activity. A suitable TNF antagonist can also decrease block, abrogate, interfere, prevent and/or inhibit TNF RNA, DNA, or protein synthesis, TNFα release, TNFα receptor signaling, membrane TNFα cleavage, TNFα activity, and TNFα production and/or synthesis. Such TNF antagonists include, but are not limited to, anti-TNFα antibodies, antigen-binding fragments thereof, specified mutants or domains thereof that bind specifically to TNFα that, upon binding to TNFα, destroy or deplete cells expressing the TNFα in a mammal and/or interfere with one or more functions of those cells, a soluble TNF receptor (e.g., p55, p70 or p85) or fragment, fusion polypeptides thereof, a small-molecule TNF antagonist, e.g., TNF binding protein I or II (TBP-I or TBP-II), nerelimonmab, CDP-571, infliximab (REMICADE®), etanercept (ENBREL®), adalimumab (HUMIRA™), CDP-571, CDP-870, afelimomab, lenercept, and the like), antigen-binding fragments thereof, and receptor molecules that bind specifically to TNFα, compounds that prevent and/or inhibit TNFα synthesis, TNFα release, or its action on target cells, such as thalidomide, tenidap, phosphodiesterase inhibitors (e.g, pentoxifylline and rolipram), A2b adenosine receptor agonists, and A2b adenosine receptor enhancers, compounds that prevent and/or inhibit TNFα receptor signaling, such as mitogen-activated protein (MAP) kinase inhibitors, compounds that block and/or inhibit membrane TNFα cleavage, such as metalloproteinase inhibitors, compounds that block and/or inhibit TNFα activity, such as angiotensin-converting enzyme (ACE) inhibitors (e.g., captopril), and compounds that block and/or inhibit TNFα production and/or synthesis, such as MAP kinase inhibitors. The preferred antagonist comprises an antibody or an immunoadhesin. Examples of TNF antagonists specifically contemplated herein are etanercept (ENBREL®), infliximab (REMICADE®), and adalimumab (HUMIRA™).

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; hormone-replacement therapy; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

The term "growth factor" refers to proteins that promote growth, and include, for example, hepatic growth factor; fibroblast growth factor; vascular endothelial growth factor; nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, -β, and -γ; and colony stimulating factors (CSFs) such as macrophage-CSF (M-CSF), granulocyte-macrophage-CSF (GM-CSF), and granulocyte-CSF (G-CSF). As used herein, the term growth factor includes proteins from natural sources or from recombinant cell culture and biologically active equivalents of the native-sequence growth factor, including synthetically produced small-molecule entities and pharmaceutically acceptable derivatives and salts thereof.

The term "integrin" refers to a receptor protein that allows cells both to bind to and to respond to the extracellular matrix and is involved in a variety of cellular functions such as wound healing, cell differentiation, homing of tumor cells, and apoptosis. They are part of a large family of cell adhesion receptors that are involved in cell-extracellular matrix and cell-cell interactions. Functional integrins consist of two transmembrane glycoprotein subunits, called alpha and beta, that are non-covalently bound. The alpha subunits all share some homology to each other, as do the beta subunits. The receptors always contain one alpha chain and one beta chain. Examples include Alpha6beta1, Alpha3beta1, Alpha7beta1, LFA-1, etc. As used herein, the term "integrin" includes proteins from natural sources or from recombinant cell culture and biologically active equivalents of the native-sequence integrin, including synthetically produced small-molecule entities and pharmaceutically acceptable derivatives and salts thereof.

An "integrin antagonist" is a molecule that inhibits or antagonizes such integrins by any mechanism, including, for example, antibodies to the integrin. Examples of "integrin antagonists or antibodies" herein include an LFA-1 antibody, such as efalizumab (RAPTIVA®) commercially available from Genentech, or other CD11/11a and CD18 antibodies, or an alpha 4 integrin antibody such as natalizumab (ANTEGREN®) available from Biogen, or diazacyclic phenylalanine derivatives (WO 2003/89410), phenylalanine derivatives (WO 2003/70709, WO 2002/28830, WO 2002/16329 and WO 2003/53926), phenylpropionic acid derivatives (WO 2003/10135), enamine derivatives (WO 2001/79173), propanoic acid derivatives (WO 2000/37444), alkanoic acid derivatives (WO 2000/32575), substituted phenyl derivatives (U.S. Pat. Nos. 6,677,339 and 6,348,463), aromatic amine derivatives (U.S. Pat. No. 6,369,229), ADAM disintegrin domain polypeptides (US 2002/0042368), antibodies to alphavbeta3 integrin (EP 633945), aza-bridged bicyclic amino acid derivatives (WO 2002/02556), etc.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone, such as SOLU-MEDROL® methylprednisolone sodium succinate), dexamethasone or dexamethasone triamcinolone, hydrocortisone, and betamethasone. The preferred corticosteroids herein are prednisone, methylprednisolone, hydrocortisone, or dexamethasone.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); trocade (Ro32-355); a peripheral sigma receptor antagonist such as ISR-31747; alkylating agents such as cyclophosphamide; bromocriptine; danazol; dapsone; glutaraldehyde (which masks the MHC antigens, as described in U.S. Pat. No. 4,120, 649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, rimexolone, and dexamethasone; dihydrofolate reductase inhibitors such as methotrexate (oral or subcutaneous); anti-malarial agents such as chloroquine and hydroxychloroquine; sulfasalazine; leflunomide; cytokine release inhibitors such as SB-210396 and SB-217969 monoclonal antibodies and a MHC II antagonist such as ZD2315; a PG1 receptor antagonist such as ZD4953; a VLA4 adhesion blocker such as ZD7349; anti-cytokine or anti-cytokine receptor antibodies including anti-interferon-alpha, -beta, or -gamma antibodies, anti-TNF-alpha antibodies (infliximab (REMICAD®) or adalimumab), anti-TNF-alpha immunoadhesin (etanercept), anti-TNF-beta antibodies, interleukin-1 (IL-1) blockers such as recombinant HuIL-1Ra and IL-1B inhibitor, anti-interleukin-2 (IL-2) antibodies and anti-IL-2 receptor antibodies; IL-2 fusion toxin; anti-L3T4 antibodies; leflunomide; heterologous anti-lymphocyte globulin; OPC-14597; NISV (immune response modifier); an essential fatty acid such as gammalinolenic acid or eicosapentaenoic acid; CD-4 blockers and pan-T antibodies, preferably anti-CD3 or anti-CD4/CD4a antibodies; co-stimulatory modifier (e.g., CTLA4-Fc fusion, also known as ABATACEP™); anti-interleukin-6 (IL-6) receptor antibodies and antagonists; anti-LFA-1 antibodies, including anti-CD11a and anti-CD18 antibodies; soluble peptide containing a LFA-3-binding domain (WO 1990/08187); streptokinase; IL-10; transforming growth factor-beta (TGF-beta); streptodornase; RNA or DNA from the host; FK506; RS-61443; enlimomab; CDP-855; PNP inhibitor; CH-3298; GW353430; 4162W94, chlorambucil; deoxyspergualin; rapamycin; T-cell receptor (Cohen et al., U.S. Pat. No. 5,114, 721); T-cell receptor fragments (Offner et al., *Science*, 251: 430-432 (1991); WO 1990/11294; Janeway, *Nature*, 341: 482-483 (1989); and WO 91/01133); BAFF antagonists such as BAFF antibodies and BR3 antibodies; zTNF4 antagonists (Mackay and Mackay, *Trends Immunol.*, 23:113-5 (2002)); biologic agents that interfere with T cell helper signals, such as anti-CD40 receptor or anti-CD40 ligand (CD154), including blocking antibodies to CD40-CD40 ligand (e.g., Durie et al., *Science*, 261: 1328-30 (1993); Mohan et al., *J. Immunol.*, 154: 1470-80 (1995)) and CTLA4-Ig (Finck et al., *Science*, 265: 1225-7 (1994)); and T-cell receptor antibodies (EP 340, 109) such as T10B9. Some preferred immunosuppressive agents herein include cyclophosphamide, chlorambucil, azathioprine, leflunomide, MMF, or methotrexate.

Examples of "disease-modifying anti-rheumatic drugs" or "DMARDs" include chloroquine, hydroxycloroquine, myocrisin, auranofin, sulfasalazine, methotrexate, leflunomide, etanercept, infliximab (plus oral and subcutaneous methotrexate), azathioprine, D-penicilamine, gold salts (oral), gold salts (intramuscular), minocycline, cyclosporine including cyclosporine A and topical cyclosporine, staphylococcal protein A (Goodyear and Silverman, *J. Exp. Med.*, 197, (9), p 1125-39 (2003)), including salts and derivatives thereof, etc.

Examples of "non-steroidal anti-inflammatory drugs" or "NSAIDs" include aspirin, acetylsalicylic acid, ibuprofen and ibuprofen retard, fenoprofen, piroxicam, flurbiprofen, naproxen, ketoprofen, naproxen, tenoxicam, benorylate, diclofenac, naproxen, nabumetone, indomethacin, ketoprofen, mefenamic acid, diclofenac, fenbufen, azapropazone, acemetacin, tiaprofenic acid, indomethacin, sulindac, tolmetin, phenylbutazone, diclofenac and diclofenac retard, cyclooxygenase (COX)-2 inhibitors such as GR 253035, MK966, celecoxib (CELEBREX®); 4-(5-(4-methylphenyl)-3-(trifluoromethyl)-1H-pyrazol-1-yl), benzenesulfonamide and valdecoxib (BEXTRA®), and meloxicam (MOBIC®), including salts and derivatives thereof, etc. Preferably, they are aspirin, naproxen, ibuprofen, indomethacin, or tolmetin. Such NSAIDs are optionally used with an analgesic such as codenine, tramadol, and/or dihydrocodinine or narcotic such as morphine.

A "B cell" is a lymphocyte that matures within the bone marrow, and includes a naïve B cell, memory B cell, or effector B cell (plasma cells). The B cell herein may be a normal or non-malignant B cell.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., *Proc. Natl. Acad. Sci.* (USA) 82:1766 (1985), for example. The preferred CD20 is non-human primate or human CD20, most preferably human CD20.

The "CD22" antigen, or "CD22," also known as BL-CAM or Lyb8, is a type I integral membrane glycoprotein with molecular weight of about 130 (reduced) to 140 kD (unreduced). It is expressed in both the cytoplasm and cell membrane of B-lymphocytes. CD22 antigen appears early in B-cell lymphocyte differentiation at approximately the same stage as the CD19 antigen. Unlike other B-cell markers, CD22 membrane expression is limited to the late differentiation stages comprised between mature B cells (CD22+) and plasma cells (CD22–). The CD22 antigen is described, for example, in Wilson et al., *J. Exp. Med.* 173:137 (1991) and Wilson et al., *J. Immunol.* 150:5013 (1993).

An "antagonist to a B-cell surface marker" is a molecule that, upon binding to a B-cell surface marker, destroys or depletes B cells in a mammal and/or interferes with one or more B-cell functions, e.g. by reducing or preventing a humoral response elicited by the B cell. The antagonist preferably is able to deplete B cells (i.e. reduce circulating B-cell levels) in a mammal treated therewith. Such depletion may be achieved via various mechanisms such as ADCC and/or CDC, inhibition of B-cell proliferation and/or induction of B-cell death (e.g. via apoptosis). Antagonists included within the scope of the present invention include antibodies, synthetic or native-sequence peptides, immunoadhesins, and small-molecule antagonists that bind to a B-cell surface marker, optionally conjugated with or fused to another molecule. The preferred antagonist comprises an antibody or immunoadhesin. It includes BLyS antagonists such as immunoadhesins, and is preferably lumiliximab (anti-CD23), CD20, CD22, or BR3 antibody or BLyS immunoadhesin. The BLyS immunoadhesin preferably is selected from the group consisting of BR3 immunoadhesin comprising the extracellular domain of BR3, TACI immunoadhesin comprising the extracellular domain of TACI, and BCMA immunoadhesin comprising the extracellular domain of BCMA. The most preferred BR3 immunoadhesin is hBR3-Fc of SEQ ID NO:2 of WO 2005/00351 and US 2005/0095243. See also US 2005/0163775 and WO 2006/068867. Another preferred BLyS antagonist is an anti-BLyS antibody, more preferably wherein the anti-BLyS antibody binds BLyS within a region of BLyS comprising residues 162-275, or an anti-BR3 antibody, more preferably wherein the anti-BR3 antibody binds BR3 in a region comprising residues 23-38 of human BR3.

Examples of CD20 antibodies include: "C2B8," which is now called "rituximab" ("RITUXAN®") (U.S. Pat. No. 5,736,137) and fragments thereof that retain the ability to bind CD20; the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 to situmomab" antibody (BEXXAR™) commercially available from Corixa (see, also, U.S. Pat. No. 5,595,721); murine monoclonal antibody "1F5" (Press et al. *Blood* 69(2):584-591 (1987) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); a humanized 2H7 (WO 2004/056312 (Lowman et al.) and as set forth below); HUMAX-CD20™ fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003)); the human monoclonal antibodies set forth in WO 2004/035607 (Teeling et al.); AME-133™ antibodies (Applied Molecular Evolution); GA101 (GlycArt; US 2005/0123546); A20 antibody or variants thereof such as chimeric or humanized A20 antibody (cA20, hA20, respectively) (US 2003/0219433, Immunomedics); and monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)). The preferred CD20 antibodies herein are chimeric, humanized, or human CD20 antibodies, more preferably rituximab, a humanized 2H7, chimeric or humanized A20 antibody (Immunomedics), and HUMAX-CD20™ human CD20 antibody (Genmab).

Purely for the purposes herein and unless indicated otherwise, a "humanized 2H7" refers to a humanized CD20 antibody, or an antigen-binding fragment thereof, wherein the antibody is effective to deplete primate B cells in vivo. The antibody includes those set forth in US 2006/0062787 and the figures thereof, and including those antibodies the sequences of which are provided in US 2006/0188495. See also US 2006/0034835 and US 2006/0024300. In a summary of various preferred embodiments of the invention, the V region of variants based on 2H7 version 16 as disclosed in US 2006/0062787 will have the amino acid sequences of v16 except at the positions of amino acid substitutions that are indicated in the table below. Unless otherwise indicated, the 2H7 variants will have the same L chain as that of v16.

| 2H7 version | Heavy chain ($V_H$) changes | Light chain ($V_L$) changes | Fc changes |
|---|---|---|---|
| 16 | — | | |
| A | — | — | S298A, E333A, K334A |
| B | N100A | M32L | |
| C | N100A | M32L | S298A, E333A, K334A |
| D | D56A, N100A | S92A | |
| E | D56A, N100A | M32L, S92A | S298A, E333A, K334A |
| F | D56A, N100A | M32L, S92A | S298A, E333A, K334A, E356D, M358L |
| G | D56A, N100A | M32L, S92A | S298A, K334A, K322A |
| H | D56A, N100A | M32L, S92A | S298A, E333A, K334A, K326A |
| I | D56A, N100A | M32L, S92A | S298A, E333A, K334A, K326A, N434W |
| J | — | — | K334L |

The preferred humanized 2H7 is an intact antibody or antibody fragment having the sequence of version 16, or any of the versions shown above.

"BAFF antagonists" herein are any molecules that block the activity of BAFF or BR3. They include immunoadhesins comprising a portion of BR3, TACI, or BCMA that binds BAFF, or variants thereof that bind BAFF. In other embodiments, the BAFF antagonist is a BAFF antibody. A "BAFF antibody" is an antibody that binds BAFF, and preferably binds BAFF within a region of human BAFF comprising residues 162-275 of human BAFF. In another embodiment, the BAFF antagonist is BR3 antibody. A "BR3 antibody" is an antibody that binds BR3, and is preferably one that binds BR3 within a region of human BR3 comprising residues 23-38 of human BR3. The sequences of human BAFF and human BR3 are found, for example, in US 2006/0062787. Other examples of BAFF-binding polypeptides or BAFF antibodies can be found in, e.g., WO 2002/092620, WO 2003/014294, Gordon et al., *Biochemistry* 42(20):5977-5983 (2003), Kelley et al., *J. Biol. Chem.*, 279(16):16727-16735 (2004), WO 1998/18921, WO 2001/12812, WO 2000/68378 and WO 2000/40716.

"Chronic" administration refers to administration of the medicament(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "mammal" refers to any animal classified as a mammal, including humans, domestic and farm animals, and zoo, sports, or pet animals, such as dogs, horses, cats, cows, etc. Preferably, the mammal herein is human.

A "package insert" refers to instructions customarily included in commercial packages of medicaments that contain information about the indications, usage, dosage, administration, contraindications, other medicaments to be combined with the packaged product, and/or warnings concerning the use of such medicaments, etc.

A "kit" is any manufacture (e.g., a package or container) comprising at least one reagent, e.g., a medicament for treatment of an autoimmune disease such as RA, lupus, MS, or IBD. The manufacture is preferably promoted, distributed, or sold as a unit for performing the methods of the present invention.

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

A "medicament" is an active drug to treat the disorder in question or its symptoms or side effects.

The term "about" as used herein refers to the usual error range for the respective value readily known to the skilled person in this technical field.

Modes for Carrying Out the Invention

In one embodiment, the invention contemplates an isolated LTα antibody comprising at least one CDR sequence selected from the group consisting of:

(a) a CDR-L1 sequence comprising amino acids A1-A11, wherein A1-A11 is KASQAVSSAVA (SEQ ID NO:1) or RASQAVSSAVA (SEQ ID NO:2), or comprising amino acids A1-A17, wherein A1-A17 is KSSQSLLYSTNQKNFLA (SEQ ID NO:3) or KSSQSLLYSANQKNFLA (SEQ ID NO:4) or KSSQSLLYSTNQKNALA (SEQ ID NO:6), where N is any amino acid (chimeric 2C8 or humanized 2C8.v2/2C8.vX or chimeric 3F12/humanized 3F12.v5/humanized 3F12.v14, or 3F12 clone 14 or 17, respectively);

(b) a CDR-L2 sequence comprising amino acids B1-B7, wherein B1-B7 is SASHRYT (SEQ ID NO:7) or WASTRDS (SEQ ID NO:8) (chimeric 2C8/humanized 2C8.v2/humanized 2C8.vX or chimeric 3F12/humanized 3F12.v5/humanized 3F12.v14, respectively);

(c) a CDR-L3 sequence comprising amino acids C1-C9, wherein C1-C9 is QQHYSTPWT (SEQ ID NO:9) or QENYSTPWT (SEQ ID NO:11) or QQYYSYPRT (SEQ ID NO:13) or QQYASYPRT (SEQ ID NO:14) or QQYYAYPRT (SEQ ID NO:15), where N is any amino acid (chimeric 2C8/humanized 2C8.v2 or 2C8 clone G7 or chimeric 3F12/humanized 3F12.v5/humanized 3F12.v14 or 3F12 clone 20 or 3F12 clone 21, respectively);

(d) a CDR-H1 sequence comprising amino acids D1-D10, wherein D1-D10 is GYTFTSYVIH (SEQ ID NO:16) or GYTFSSYWIE (SEQ ID NO:17) (chimeric 2C8/humanized 2C8.v2/humanized 2C8.vX or chimeric 3F12/humanized 3F12.v5/humanized 3F12.v14, respectively);

(e) a CDR-H2 sequence comprising amino acids E1-E17, wherein E1-E17 is YNNPYNDGTNYNEKFKG (SEQ ID NO:18) or EISPGSGSTNYNEEFKG (SEQ ID NO:19) or YNNPYNAGTNYNEKFKG (SEQ ID NO:101) or EINPGSGSTIYNEKFKG (SEQ ID NO:110), wherein N is any amino acid (chimeric 2C8/humanized 2C8.v2 or chimeric 3F12/humanized 3F12.v5, or humanized 2C8.vX, or humanized 3F12.v14, respectively); and (f) a CDR-H3 sequence comprising amino acids F1-F9, wherein F1-F9 is PTMLPWFAY (SEQ ID NO:20), or comprising amino acids F1-F5, wherein F1-F5 is GYHGY (SEQ ID NO:21) or GYHGA (SEQ ID NO:22) (chimeric 2C8/humanized 2C8.v2/humanized 2C8.vX or chimeric 3F12/humanized 3F12.v5/humanized 3F12.v14 or 3F12 clone 12, respectively).

In one preferred embodiment, SEQ ID NO:3 is KSSQSLLYSTAQKNFLA (SEQ ID NO:5) (3F12 clone 15). In a further preferred embodiment, SEQ ID NO:11 is QESYSTPWT (SEQ ID NO:10) (2C8 clone A8/humanized 2C8.vX) or QEVYSTPWT (SEQ ID NO:12) (2C8 clone H6).

In another preferred embodiment, the CDR-L1 sequence is SEQ ID NO:2 or 3 or 4 or 6.

In another preferred aspect, the antibody comprises either (i) all of the CDR-L1 to CDR-L3 amino acid sequences of SEQ ID NOS:1 or 2 and 7 and 9, or of SEQ ID NOS:1 or 2 and 7 or 8 and 11, or of SEQ ID NOS:3, 8, and 13, or of SEQ ID NOS:4, 5, or 6, 8, and 13, or of SEQ ID NOS:3, 8, and 14 or 15, or of SEQ ID NOS:4, 5, or 6, 8, and 14 or 15; or (ii) all of the CDR-H1 to CDR-H3 amino acid sequences of SEQ ID NOS:16, 18, and 20, or all of SEQ ID NOS:16, 101, and 20, or all of SEQ ID NOS:17, 19, and 21 or 22, or all of SEQ ID NOS:17, 110, and 21.

In another aspect, the antibody comprises either all of SEQ ID NOS:1 or 2 and 7 and 9, or all of SEQ ID NOS:16, 18, and 20, or all of SEQ ID NOS:16, 101, and 20. In an alternative embodiment, the antibody comprises either all of SEQ ID NOS:3, 8, and 13, or all of SEQ ID NOS:17, 19, and 21 or 22. In an alternative embodiment, the antibody comprises either all of SEQ ID NOS:4, 8, and 14, or all of SEQ ID NOS:17, 110, and 21. In other embodiments, the antibody comprises (i) all of the CDR-L1 to CDR-L3 amino acid sequences of SEQ ID NOS:1 or 2, 7 and 9, or of SEQ ID NOS:1 or 2 and 7 or 8 and 11, of SEQ ID NOS:3, 8, and 13, or of SEQ ID NOS:4, 5, or 6, 8, and 13, or of SEQ ID NOS:3, 8, and 14 or 15, or of SEQ ID NOS:4, 5, or 6, 8, and 14 or 15; and (ii) all of the CDR-H1 to CDR-H3 amino acid sequences of SEQ ID NOS:16, 18, and 20, or of SEQ ID NOS:16, 101, and 20, or of SEQ ID NOS:17, 19, and 21 or 22, or of SEQ ID NOS:17, 110, and 21.

One preferred aspect is an anti-LTα antibody having a light-chain variable domain comprising SEQ ID NO:23 or 24, or a heavy-chain variable domain comprising SEQ ID NO:25 or 26, or having light-chain and heavy-chain variable domains comprising both SEQ ID NOS:23 and 25 or both SEQ ID NOS:24 and 26. Further preferred is an anti-LTα antibody having a light-chain variable domain comprising SEQ ID NO:27 or 28, or a heavy-chain variable domain comprising SEQ ID NO:29, 30, or 31, or having light-chain and heavy-chain variable domains comprising both SEQ ID NOS:27 and 29, or both SEQ ID NOS:27 and 30, or both SEQ ID NOS:27 and 31, or both SEQ ID NOS:28 and 30, or both SEQ ID NOS:28 and 31. In a still further aspect, the invention provides an anti-LTα antibody having a light-chain variable domain comprising SEQ ID NO:102, or a heavy-chain variable domain comprising SEQ ID NO:103, or having light-chain and heavy-chain variable domains comprising both SEQ ID NOS:102 and 103. In a still further aspect, the invention provides an anti-LTα antibody having a light-chain variable domain comprising SEQ ID NO:108, or a heavy-chain variable domain comprising SEQ ID NO:109, or having light-chain and heavy-chain variable domains comprising both SEQ ID NOS:108 and 109.

Antibodies in other embodiments comprise a human κ subgroup 1 consensus framework sequence, and/or they comprise a heavy-chain human subgroup III consensus framework sequence, wherein the framework sequence preferably comprises a substitution at position 71, 73, and/or 78. Such substitutions are preferably R71A, N73T, or N78A, or any combination thereof, most preferably all three.

The antibodies of this invention preferably bind to LTα3 and block the interaction of LTα3 with TNFRI and TNFRII. Preferably, they also bind to LTαβ complex and especially on the cell surface. Preferably, they also block LTαβ function, and/or preferably contain an Fc region, and/or decrease levels of inflammatory cytokines associated with RA in an in vitro collagen-induced arthritis assay or an in vitro antibody-induced arthritis assay.

Further preferred antibodies block the interaction of LTαβ with LTβ-R and/or modulate LTαβ-expressing cells. In other preferred embodiments, the anti-LTα antibody herein substantially neutralizes at least one activity of at least one LTα protein. Preferably, the antibody herein targets any cell expressing LTα, and preferably depletes LTα-positive or -secreting cells.

Preferred antibodies herein bind LTα with an affinity of at least about $10^{-12}$ M, more preferably at least about $10^{-13}$ M. The antibodies also preferably are of the IgG isotype, such as IgG1, IgG2a, IgG2b, or IgG3, more preferably human IgG, and most preferably IgG1 or IgG2a.

Another preferred antibody has a monovalent affinity to human LTα that is about the same as or greater than the monovalent affinity to human LTα of a murine antibody produced by a hybridoma cell line deposited under American Type Culture Collection Accession Number PTA-7538 (hybridoma murine Lymphotoxin alpha2 beta1 s5H3.2.2).

As is well established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Fold difference in binding affinity can be quantified in terms of the ratio of the monovalent binding affinity value of a humanized antibody (e.g., in Fab form) and the monovalent binding affinity value of a reference/comparator antibody (e.g., in Fab form) (e.g., a murine antibody having donor CDR sequences), wherein the binding affinity values are determined under similar assay conditions.

Thus, in one embodiment, the fold difference in binding affinity is determined as the ratio of the Kd values of the humanized antibody in Fab form and said reference/comparator Fab antibody. For example, in one embodiment, if an antibody of the invention (A) has an affinity that is "three-fold lower" than the affinity of a reference antibody (M), then if the Kd value for A is 3x, the Kd value of M would be 1x, and the ratio of Kd of A to Kd of M would be 3:1. Conversely, in one embodiment, if an antibody of the invention (C) has an affinity that is "three-fold greater" than the affinity of a reference antibody (R), then if the Kd value for C is 1x, the Kd value of R would be 3x, and the ratio of Kd of C to Kd of R would be 1:3. Any assays known in the art, including those described herein, can be used to obtain binding affinity measurements, including, for example, an optical biosensor that uses SPR (BIACORE® technology), RIA, and ELISA. Preferably, the measurement is by optical biosensor or radioimmunoassay.

The antibodies herein are preferably chimeric or humanized, more preferably humanized, and still more preferably antibodies wherein at least a portion of their framework sequence is a human consensus framework sequence.

Another embodiment herein is an anti-idiotype antibody that specifically binds the antibody herein.

Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives, e.g., X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as RIA or ELISA.

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, Monoclonal *Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal, e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-SEPHAROSE™ medium) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high-affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy-chain and light-chain constant-domain ($C_H$ and $C_L$) sequences for the homologous murine sequences (U.S. Pat. No. 4,816,567 and Morrison, et al., *Proc. Natl. Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

The present invention encompasses humanized antibodies. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. Nature 321:522-525 (1986); Riechmann et al. Nature 332:323-327 (1988); Verhoeyen et al. Science 239:1534-1536 (1988)), by substituting CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework for the humanized antibody (Sims et al., J. Immunol. 151:2296 (1993); Chothia et al., J. Mol. Biol. 196:901 (1987). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al. J. Immunol., 151:2623 (1993).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

The humanized antibody may be an antibody fragment, such as a Fab, which is optionally conjugated with one or more cytotoxic agent(s) in order to generate an immunoconjugate. Alternatively, the humanized antibody may be a full-length antibody, such as a full-length IgG1 antibody.

Human Antibodies and Phage Display Methodology

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); and U.S. Pat. No. 5,545,807; and WO 1997/17852.

Alternatively, phage-display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the LT$\alpha$ cell. Phage display can be performed in a variety of formats, reviewed in, e.g, Johnson and Chiswell, Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991) or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al, Journal of Biochemical and Biophysical Methods 24:107-117 (1992) and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See, e.g., WO 1993/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the LTα protein. Other such antibodies may combine a LTα binding site with a binding site for another protein. Alternatively, an anti-LTα arm may be combined with an arm that binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), or NKG2D or other NK-cell-activating ligand, so as to focus and localize cellular defense mechanisms to the LTβ-expressing cell. Bispecific antibodies may also be used to localize cytotoxic agents to cells that express LTα. These antibodies possess a LTα-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')$_2$ bispecific antibodies).

WO 1996/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO 1998/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy-chain/light-chain pairs, where the two chains have different specificities (Millstein et al., *Nature,* 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 1993/08829, and in Traunecker et al., *EMBO J.,* 10:3655-3659 (1991).

According to a different approach, antibody variable domains with the desired binding specificities (antibody-antigen combining sites) are fused to immunoglobulin constant-domain sequences. Preferably, the fusion is with an Ig heavy-chain constant domain, comprising at least part of the hinge, $C_H2$, and $C_H3$ regions. It is preferred to have the first heavy-chain constant region ($C_H1$) containing the site necessary for light-chain bonding, present in at least one of the fusions. DNAs encoding the immunoglobulin heavy-chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a preferred embodiment of this approach, the bispecific antibodies are composed of a hybrid immunoglobulin heavy chain with a first binding specificity in one arm, and a hybrid immunoglobulin heavy-chain/light-chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 1994/04690. For further details of generating bispecific antibodies see, for example, Suresh et al., *Methods in Enzymology,* 121:210 (1986).

In another approach (U.S. Pat. No. 5,731,168), the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 1991/00360, WO 1992/20373, and EP 03089). Heteroconjugate antibodies may be made using any convenient cross-linking methods. Suitable cross-linking agents are well known in the art, and are disclosed, for example, in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describes a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describes the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Holliger et al., *Proc. Natl. Acad. Sci. USA,* 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen-binding sites (e.g., tetravalent antibodies), which can be readily produced by recombinant expression of nucleic acid encoding the polypeptide chains of the antibody. The multivalent antibody can comprise a dimerization domain and three or more antigen-binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen-binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable-domain polypeptides. The multivalent antibody herein may, for instance, comprise from about two to about eight light-chain variable-domain polypeptides. The light-chain variable-domain polypeptides contemplated herein comprise a light-chain variable-domain and, optionally, further comprise a CL domain.

Vectors, Host Cells, and Recombinant Methods

Selection and Transformation of Host Cells

Suitable host cells for cloning or expressing the recombinant monoclonal antibodies, immunoadhesins, and other polypeptide antagonists described herein are prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full-length antibody, antibody fragments, and antibody fusion proteins can be produced in bacteria, in particular when glycosylation and Fc effector functions are not needed, such as when the therapeutic antibody is conjugated to a cytotoxic agent (e.g., a toxin) and the immunoconjugate by itself shows effectiveness in tumor cell destruction. Full-length antibodies have greater half life in circulation. Production in *E. coli* is faster and more cost efficient. For expression of antibody fragments and polypeptides in bacteria, see, e.g., U.S. Pat. Nos. 5,648,237; 5,789,199; and 5,840,523, which describe translation-initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells. For general monoclonal antibody production, see also U.S. Pat. No. 7,011,974.

In addition to prokaryotes, eukaryotic microbes such as filamentous fungi or yeast are suitable cloning or expression hosts for antibody-encoding, such as LTα-antibody-encoding, vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of, e.g., glycosylated LTα-binding antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (e.g., 293 or 293 cells subcloned for growth in suspension culture, Graham et al., *J. Gen Virol.* 36:59 (1977)); baby hamster kidney cells (BHK, e.g., ATCC CCL 10); Chinese hamster ovary cells/-DHFR(CHO, Urlaub et al., *Proc. Natl. Acad. Sci. USA* 77:4216 (1980)), including, but not limited to CHO K1, CHO pro3⁻, CHO DG44, CHO DUXB11, Lec13, B-Ly1, and CHO DP12 cells, preferably a CHO DUX (DHFR-) or subclone thereof (herein called "CHO DUX"); C127 cells, mouse L cells; Ltk⁻ cells; mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse myeloma cells; NS0; hybridoma cells such as mouse hybridoma cells; COS cells; mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with expression or cloning vectors for production of the LTβ-binding antibody herein, and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 1990/03430; WO 1987/00195; or US Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one particular aspect, a suitable medium contains a basal medium component such as a DMEM/HAM F-12 based formulation (for composition of DMEM and HAM F12 media and especially serum-free media, see culture media formulations in the *American Type Culture Collection Catalogue of Cell Lines and Hybridomas*, Sixth Edition, 1988, pages 346-349) (the formulations of medium as described in U.S. Pat. No. 5,122,469 may be appropriate) with suitably modified, if necessary, concentrations of some components such as amino acids, salts, sugar, and vitamins, and optionally containing glycine, hypoxanthine, and thymidine; recombinant human insulin, hydrolyzed peptone, such as PROTEASE PEPTONE 2 and 3™, PRIMATONE HS™ or PRIMATONE RL™ (Difco, USA; Sheffield, England), or the equivalent; a cell-protective agent, such as PLURONIC F68™ or the equivalent PLURONIC™ polyol; GENTAMYCIN™ antibiotic; and trace elements. Preferably the cell culture media is serum free.

In one aspect of the invention, antibody production is conducted in large quantity by a fermentation process. Various large-scale fed-batch fermentation procedures are available for production of recombinant proteins. Large-scale fermentations have at least about 1000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 100 liters in volumetric capacity, and can range from about one liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., *J Bio Chem* 274:19601-19605 (1999); U.S. Pat. Nos. 6,083,715 and 6,027,888; Bothmann and Pluckthun, *J. Biol. Chem.* 275: 17100-17105 (2000); Ramm and Pluckthun, *J. Biol. Chem.* 275:17106-17113 (2000); and Arie et al., *Mol. Microbiol.* 39:199-210 (2001).

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, U.S. Pat. Nos. 5,264,365; 5,508,192; and Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system herein.

Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulphonylfluoride (PMSF) may be included in any of the foregoing steps to inhibit proteolysis, and antibiotics may be included to prevent the growth of adventitious contaminants.

In one embodiment, the antibody protein produced herein is further purified to obtain preparations that are substantially homogeneous for further assays and uses. Standard protein purification methods known in the art can be employed. The following procedures are exemplary of suitable purification procedures: hydroxylapatite chromatography, chromatography on heparin SEPHAROSE™, gel electrophoresis, dialysis, fractionation on immunoaffinity columns, ethanol precipitation, reverse-phase HPLC, chromatography on silica, chromatography on an anion- or cation-exchange resin (such as DEAE or a polyaspartic acid column), chromatofocusing, SDS-PAGE, ammonium sulfate precipitation, and gel filtration using, for example, SEPHADEX™ G-75 resin. Affinity chromatography is a preferred purification technique. For analytical-scale purification, smaller volumes are passed through columns and used; for preparative- or commercial-scale purification to produce quantities of antibody useful in therapeutic applications, larger volumes are employed. The skilled artisan will understand which scale should be used for which application. Preferably, preparative scale is employed for this invention.

The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled-pore glass or poly(styrenedivinyl)benzene allow for faster flow rates and shorter processing times than can be achieved with agarose. Where the antibody comprises a $C_H3$ domain, the BAKERBOND ABX™ resin (J. T. Baker, Phillipsburg, N.J.) is useful for purification.

For Protein A chromatography, the solid phase to which Protein A is immobilized is preferably a column comprising a glass or silica surface, more preferably a controlled pore glass column or a silicic acid column. In some applications, the column has been coated with a reagent, such as glycerol, to prevent nonspecific adherence of contaminants. The solid phase is then washed to remove contaminants non-specifically bound to the solid phase. Finally, the antibody of interest is recovered from the solid phase by elution.

Following any preliminary purification step(s), the mixture comprising the antibody of interest and contaminants may be subjected to low pH hydrophobic-interaction chromatography using an elution buffer at a pH between about 2.5-4.5, preferably performed at low salt concentrations (e.g., from about 0 to 0.25M salt).

Generating Variant Antibodies Exhibiting Reduced or Absence of HAMA Response

Reduction or elimination of a HAMA response is a significant aspect of clinical development of suitable therapeutic agents. See, e.g., Khaxzaeli et al., *J. Natl. Cancer Inst.,* 80:937 (1988); Jaffers et al., *Transplantation,* 41:572 (1986); Shawler et al., *J. Immunol.,* 135:1530 (1985); Sears et al., *J. Biol. Response Mod,* 3:138 (1984); Miller et al., *Blood,* 62:988 (1983); Hakimi et al., *J. Immunol.,* 147:1352 (1991); Reichmann et al., *Nature,* 332:323 (1988); and Junghans et al., *Cancer Res,* 50:1495 (1990). In some embodiments herein, the invention provides antibodies that are humanized such that HAMA response is reduced or eliminated. Variants of these antibodies can further be obtained using routine methods known in the art, some of which are further described below.

For example, an amino acid sequence from an antibody as described herein can serve as a starting (parent) sequence for diversification of the framework and/or CDR sequence(s). A selected framework sequence to which a starting CDR sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence, as such frameworks have been demonstrated to have minimal, or no, immunogenicity in human patients.

Where the acceptor is derived from a human immunoglobulin, one may optionally select a human framework sequence based on its homology to the donor framework sequence by aligning the donor framework sequence with various human framework sequences in a collection of human framework sequences and selecting the most homologous framework sequence as the acceptor.

In one embodiment, human consensus frameworks herein are from, or derived from, VH subgroup III and/or VL kappa subgroup I consensus framework sequences.

Thus, the VH acceptor human framework may comprise one, two, three, or all of the following framework sequences:

```
FR1 comprising
EVQLVESGGGLVQPGGSLRLSCAAS,              (SEQ ID NO: 46)

FR2 comprising
WVRQAPGKGLEWVG,                         (SEQ ID NO: 47)

FR3 comprising FR3 comprises
RFTISRDNSKNTLYLQMNSLRAEDTAVYYCAR,       (SEQ ID NO: 48)
or RATFSADNSKNTAYLQMNSLRAEDTAVYYCAD,       (SEQ ID NO: 50)
and FR4 comprising
WGQGTLVTVSS.                            (SEQ ID NO: 49)
```

The VL acceptor human framework may comprise one, two, three, or all of the following framework sequences:

```
FR1 comprising
DIQMTQSPSSLSASVGDRVTITC,                (SEQ ID NO: 51)

FR2 comprising
WYQQKPGKAPKLQIY,                        (SEQ ID NO: 52)
or

WYQQKPGKAPKLLIY,                        (SEQ ID NO: 55)

FR3 comprising
GVPSRFSGSGSGTDFTLTISSLQPEDFATYYC,       (SEQ ID NO: 53)
and

FR4 comprising
FGQGTKVEIKR.                            (SEQ ID NO: 54)
```

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal, usually only four, three, two, or one amino acid difference relative to the human immunoglobulin sequence or consensus framework sequence.

CDR residues of the non-human antibody are incorporated into the VL and/or VH acceptor human frameworks. For example, one may incorporate residues corresponding to the Kabat CDR residues, the Chothia hypervariable loop residues, the AbM residues, and/or the contact residues. Optionally, the extended CDR residues as follows are incorporated: 24-34 (L1), 50-56 (L2) and 89-97 (L3), 26-35 (H1), 50-65 or 49-65 (H2) and 93-102, 94-102, or 95-102 (H3).

"Incorporation" of CDR residues can be achieved in various ways, e.g., nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the CDR residues are changed to non-human residues, or by synthesizing nucleic acid encoding the desired sequence, etc.

CDR-grafted variants may be generated by Kunkel mutagenesis of nucleic acid encoding the human acceptor sequences, using a separate oligonucleotide for each CDR. Kunkel et al., *Methods Enzymol.* 154:367-382 (1987). Appropriate changes can be introduced within the framework and/or CDR, using routine techniques, to correct and re-establish proper CDR-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins that bind to a ligand, such as an antigen. Using the techniques of phage (mid) display allows the generation of large libraries of protein variants that can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, *Proteins*, 8:309 (1990); Lowman and Wells, *Methods. A Companion to Methods in Enzymology*, 3:205 (1991)). In a monovalent phagemid display system, the gene fusion is expressed at low levels and wild-type gene III proteins are also expressed so that infectivity of the particles is retained. Methods of generating peptide libraries and screening those libraries have been disclosed in many patents (e.g., U.S. Pat. Nos. 5,723,286; 5,432,018; 5,580,717; 5,427,908; and 5,498,530).

Libraries of antibodies have been prepared in a number of ways including by altering a single gene by inserting random DNA sequences or cloning a family of related genes. Methods for displaying antibodies or antigen-binding fragments using phage(mid) display are described in U.S. Pat. Nos. 5,750,373; 5,733,743; 5,837,242; 5,969,108; 6,172,197; 5,580,717; and 5,658,727. The library is then screened for expression of antibodies or antigen-binding proteins with the desired characteristics.

The sequence of oligonucleotides includes one or more of the designed codon sets for the CDR residues to be altered. A codon set is a set of different nucleotide triplet sequences used to encode desired variant amino acids. Codon sets can be represented using symbols to designate particular nucleotides or equimolar mixtures of nucleotides as shown below according to the IUB code.

| IUB CODES |
|---|
| G Guanine |
| A Adenine |
| T Thymine |
| C Cytosine |
| R (A or G) |
| Y (C or T) |
| M (A or C) |
| K (G or T) |
| S (C or G) |
| W (A or T) |
| H (A or C or T) |
| B (C or G or T) |
| V (A or C or G) |
| D (A or G or T) H |
| N (A or C or G or T) |

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid-phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used herein, have sequences that allow for hybridization to a variable-domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable-region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that in Crea et al., *Proc. Nat'l. Acad. Sci. USA*, 75:5765 (1978).

The DNA template is generated by those vectors that are derived from bacteriophage M13 vectors (the commercially available M13 mp 18 and M13 mp 19 vectors are suitable), or that contain a single-stranded phage origin of replication as described by Viera et al., *Meth. Enzymol.*, 153:3 (1987). Thus, the DNA to be mutated can be inserted into one of these vectors to generate single-stranded template. Production of the single-stranded template is described in sections 4.21-4.41 of Sambrook et al., supra.

To alter the native DNA sequence, the oligonucleotide is hybridized to the single stranded template under suitable hybridization conditions. A DNA-polymerizing enzyme, for example, T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabeled with a $^{32}P$ phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously, the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.*, 153:3 (1987). Thus, the DNA that is to be mutated must be inserted into one of these vectors in order to generate single-stranded template. Production of the single-stranded template is described in sections 4.21-4.41 of Sambrook et al., supra.

In another method, a library can be generated by providing upstream and downstream oligonucleotide sets, each set having a plurality of oligonucleotides with different sequences. These sequences are established by the codon sets provided within the sequence of the oligonucleotides. The upstream and downstream oligonucleotide sets, along with a variable-domain template nucleic acid sequence, can be used in a polymerase chain reaction (PCR) to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent-accessible and highly diverse positions in a CDR. As described above, a codon set is a set of different nucleotide triplet sequences used to encode desired variant amino acids.

Antibody selectants that meet the desired criteria, as selected through appropriate screening/selection steps, can be isolated and cloned using standard recombinant techniques.

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino-acid analysis, non-denaturing size-exclusion high-pressure liquid chromatography (HPLC), mass spectrometry, ion-exchange chromatography, and papain digestion.

In certain embodiments of the invention, the antibodies produced herein are analyzed for their biological activity. In some embodiments, the antibodies herein are tested for their antigen-binding activity. The antigen-binding assays known in the art and useful herein include, without limitation, any direct or competitive-binding assays using techniques such as Western blots, radioimmunoassays, ELISA (enzyme linked immunosorbent assay), "sandwich" immunoassays, immunoprecipitation assays, fluorescent immunoassays, and protein A immunoassays.

In one embodiment, the present invention contemplates an altered antibody that possesses some but not all effector functions, which make it a desired candidate for many applications in which the half life of the antibody in vivo is important, yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include PBMCs and NK cells. Alternatively, or additionally, ADCC activity of the molecule of interest may be assessed in vivo, e.g., in an animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g., as described in Gazzano-Santoro et al., *J. Immunol. Methods* 202:163 (1996), may be performed. FcRn binding and in vivo clearance/half life determinations can also be performed using methods known in the art.

Antibody Variants

In some embodiments, amino-acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced into the subject antibody amino acid sequence at the time that the sequence is made.

A useful method for identification of certain residues or regions of the antibody that are preferred locations for mutagenesis is called "alanine-scanning mutagenesis" as described by Cunningham and Wells, *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the CDRs, but FR alterations are also contemplated. Conservative substitutions are shown in Table A under the heading of "preferred substitutions." If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (as described, for example, in A. L. Lehninger, *Biochemistry, second ed.*, pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more CDR residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several CDR sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. For location of candidate CDR sites for modification, alanine-scanning mutagenesis can be performed to identify CDR residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The antibodies of the present invention preferably have the native-sequence Fc region. However, it may be desirable to introduce one or more amino acid modifications into an Fc region thereof, generating a Fc-region variant. The Fc-region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine. These antibodies would nonetheless retain substantially the same characteristics required for therapeutic utility as compared to their wild-type counterpart. Such amino acid substitutions may, e.g., improve or reduce other Fc function or further improve the same Fc function, increase antigen-binding affinity, increase stability, alter glycosylation, or include allotypic variants. The antibodies may further comprise one or more amino acid substitutions in the Fc region that result in the antibody exhibiting one or more of the properties selected from increased FcγR binding, increased ADCC, increased CDC, decreased CDC, increased ADCC and CDC function, increased ADCC but decreased CDC function (e.g., to minimize infusion reaction), increased FcRn binding, and increased serum half life, as compared to the same antibodies that have the wild-type Fc region. These activities can be measured by the methods described herein. For example, see WO 1999/51642. See also Duncan and Winter, Nature 322: 738-40 (1988); U.S. Pat. No. 5,648,260; U.S. Pat. No. 5,624,821; and WO 1994/29351 concerning other examples of Fcregion variants.

For additional amino acid alterations that improve Fc function, see, e.g., U.S. Pat. No. 6,737,056. Any of the antibodies of the present invention may further comprise at least one amino acid substitution in the Fc region that decreases CDC activity, for example, comprising at least the substitution K322A. See U.S. Pat. No. 6,528,624 (Idusogie et al.).

In another preferred embodiment, the antibody has amino acid substitutions at any one or any combination of positions that are 268D, or 298A, or 326D, or 333A, or 334A, or 298A together with 333A, or 298A together with 334A, or 239D together with 332E, or 239D together with 298A and 332E, or 239D together with 268D and 298A and 332E, or 239D together with 268D and 298A and 326A and 332A, or 239D together with 268D and 298A and 326A and 332E, or 239D together with 268D and 283L and 298A and 332E, or 239D together with 268D and 283L and 298A and 326A and 332E, or 239D together with 330L and 332E and 272Y and 254T and 256E, or 250Q together with 428L, or 265A, or 297A, wherein the 265A substitution is in the absence of 297A and the 297A substitution is in the absence of 265A. The letter after the number in each of these designations represents the changed amino acid at that position.

Mutations that improve ADCC and CDC include substitutions at one to three positions of the Fc region, including positions 298, 333, and/or 334 of the Fc region (Eu numbering of residues), especially S298A together with E333A and K334A (S298A/E333A/K334A, or synonymously a combination of 298A, 333A, and 334A), also referred to herein as the triple Ala mutant. K334L increases binding to CD16. K322A results in reduced CDC activity; K326A or K326W enhances CDC activity. D265A results in reduced ADCC activity.

Stability variants are variants that show improved stability with respect to, e.g., oxidation and deamidation.

A further type of amino acid variant of the antibody alters the original glycosylation pattern of the antibody. Such altering includes deleting one or more carbohydrate moieties found in the antibody, and/or adding one or more glycosylation sites that are not present in the antibody. Glycosylation variants that increase ADCC function are described, e.g., in WO 2003/035835. See also US 2006/0067930.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US 2003/0157108 (Presta). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in, e.g., WO 2003/011878, Jean-Mairet et al. and U.S. Pat. No. 6,602,684 (Umana et al.). Antibodies with at least one galactose residue in the oligosaccharide attached to an Fc region of the antibody are reported, for example, in WO 1997/30087 (Patel et al.). See, also, WO 1998/58964 (Raju) and WO 1999/22764 (Raju) concerning antibodies with altered carbohydrate attached to the Fc region thereof. See also US 2005/0123546 (Umana et al.); US 2004/0072290 (Umana et al.); US 2003/0175884 (Umana et al.); WO 2005/044859 (Umana et al.); and US 2007/0111281 (Sondermann et al.) on antigen-binding molecules with modified glycosylation, including antibodies with an Fc region containing N-linked oligosaccharides; and US 2007/0010009 (Kanda et al.)

One preferred glycosylation antibody variant herein comprises an Fc region wherein a carbohydrate structure attached to the Fc region has reduced fucose or lacks fucose, which may improve ADCC function. Specifically, antibodies are contemplated herein that have reduced fusose relative to the amount of fucose on the same antibody produced in a wild-type CHO cell. That is, they are characterized by having a lower amount of fucose than they would otherwise have if produced by native CHO cells. Preferably the antibody is one wherein less than about 10% of the N-linked glycans thereon comprise fucose, more preferably wherein less than about 5% of the N-linked glycans thereon comprise fucose, and most preferably, wherein none of the N-linked glycans thereon comprise fucose, i.e., wherein the antibody is completely without fucose, or has no fucose.

Such "defucosylated" or "fucose-deficient" antibodies may be produced, for example, by culturing the antibodies in a cell line such as that disclosed in, for example, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; US 2006/0063254; US 2006/0064781; US 2006/0078990; US 2006/0078991; Okazaki et al. *J. Mol. Biol.* 336:1239-1249 (2004); and Yamane-Ohnuki et al., *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US 2003/0157108 A1 (Presta) and WO 2004/056312 A1 (Adams et al., especially at Example 11) and knockout cell lines, such as alpha-1,6-fucosyltransferase gene, FUT8-knockout CHO cells (Yamane-Ohnuki et al., Biotech. Bioeng. 87: 614 (2004)). See also Kanda et al., *Biotechnol. Bioeng.*, 94: 680-8 (2006). US 2007/0048300 (Biogen-IDEC) discloses a method of producing aglycosylated Fc-containing polypeptides, such as antibodies, having desired effector function, as well as aglycosylated antibodies produced according to the method and methods of using such antibodies as therapeutics, all being applicable herein. Additionally, U.S. Pat. No. 7,262, 039 relates to a polypeptide having an alpha-1,3-fucosyltransferase activity, including a method for producing a fucose-containing sugar chain using the polypeptide.

See also US 2006/024304 (Gerngross et al.); U.S. Pat. No. 7,029,872 (Gerngross); US 2004/018590 (Gerngross et al.); US 2006/034828 (Gerngross et al.); US 2006/034830 (Gerngross et al.); US 2006/029604 (Gerngross et al.); WO 2006/014679 (Gerngross et al.); WO 2006/014683 (Gerngross et al.); WO 2006/014685 (Gerngross et al.); WO 2006/014725 (Gerngross et al.); and WO 2006/014726 (Gerngross et al.) on recombinant glycoproteins and glycosylation variants that are applicable herein.

In another embodiment, the invention provides an antibody composition comprising the antibodies described herein having an Fc region, wherein about 20-100% of the antibodies in the composition comprise a mature core carbohydrate structure in the Fc region that lacks a fucose. Preferably, such composition comprises antibodies having an Fc region that has been altered to change one or more of the antibody-dependent cell-mediated cytotoxicity (ADCC), complement-dependent cytotoxicity (CDC), or pharmacokinetic properties of the antibody compared to a wild-type IgG Fc sequence by substituting an amino acid selected from the group consisting of A, D, E, L, Q, T, and Y at any one or any combination of positions of the Fc region selected from the group consisting of: 238, 239, 246, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 309, 312, 314, 315, 320, 322, 324, 326, 327, 329, 330, 331, 332, 333, 334, 335, 337, 338, 340, 360, 373, 376, 378, 382, 388, 389, 398, 414, 416, 419, 428, 430, 434, 435, 437, 438, and 439.

The composition is more preferably one wherein the antibody further comprises an Fc substitution that is 268D or 326D or 333A together with 334A, or 298A together with 333A, or 298A together with 334A, or 239D together with 332E, or 239D together with 298A and 332E, or 239D together with 268D and 298A and 332E, or 239D together with 268D and 298A and 326A and 332A, or 239D together with 268D and 298A and 326A and 332E, or 239D together with 268D and 283L and 298A and 332E, or 239D together with 268D and 283L and 298A and 326A and 332E, or 239D together with 330L and 332E, wherein the letter after the number in each of these designations represents the changed amino acid at that position.

The composition is additionally preferably one wherein the antibody binds an FcγRIII. The composition further is preferably such that the antibody has ADCC activity in the presence of human effector cells or has increased ADCC activity in the presence of human effector cells compared to the otherwise same antibody comprising a human wild-type IgG1 Fc region.

The composition is also preferably one wherein the antibody binds the FcγRIII with better affinity, or mediates ADCC more effectively, than a glycoprotein with a mature core carbohydrate structure including fucose attached to the Fc region of the glycoprotein. In addition, the composition is preferably one wherein the antibody has been produced by a CHO cell, preferably a Lec13 cell. The composition is also preferably one wherein the antibody has been produced by a mammalian cell lacking a fucosyltransferase gene, more preferably the FUT8 gene.

In one aspect, the composition is one wherein the antibody is free of bisecting N-acetylglucosamine (GlcNAc) attached to the mature core carbohydrate structure. Alternatively, the composition is such that the antibody has bisecting GlcNAc attached to the mature core carbohydrate structure.

In another aspect, the composition is one wherein the antibody has one or more galactose residues attached to the mature core carbohydrate structure. Alternatively, the composition is such that the antibody is free of one or more galactose residues attached to the mature core carbohydrate structure.

In a further aspect, the composition is one wherein the antibody has one or more sialic acid residues attached to the mature core carbohydrate structure. Alternatively, the composition is such that the antibody is free of one or more sialic acid residues attached to the mature core carbohydrate structure.

This composition preferably comprises at least about 2% afucosylated antibodies. The composition more preferably comprises at least about 4% afucosylated antibodies. The composition still more preferably comprises at least about 10% afucosylated antibodies. The composition even more preferably comprises at least about 19% afucosylated antibodies. The composition most preferably comprises about 100% afucosylated antibodies.

Immunoconjugates

The invention also pertains to immunoconjugates, or antibody-drug conjugates (ADC), comprising an antibody conjugated to a cytotoxic agent such as a chemotherapeutic agent, a drug, a growth-inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, e.g., drugs to kill or inhibit tumor cells in the treatment of cancer (Syrigos and Epenetos, *Anticancer Research* 19:605-614 (1999); Niculescu-Duvaz and Springer, *Adv. Drug Del. Rev.* 26:151-172 (1997); and U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., *Lancet,* 603-05 (1986); Thorpe, "Antibody Carriers Of Cytotoxic Agents In Cancer Therapy: A Review," in Monoclonal Antibodies '84: Biological And Clinical Applications, A. Pinchera et al. (eds), pp. 475-506 (1985)). Maximal efficacy with minimal toxicity is sought thereby. Both polyclonal antibodies and monoclonal antibodies have been reported as useful in these strategies (Rowland et al., *Cancer Immunol. Immunother.,* 21:183-87 (1986)). Drugs used in these methods include daunomycin, doxorubicin, methotrexate, and vindesine. Toxins used in antibody-toxin conjugates include bacterial toxins such as diphtheria toxin, plant toxins such as ricin, small-molecule toxins such as geldanamycin (Mandler et al., *J. Nat. Cancer Inst.,* 92(19):1573-1581 (2000); Mandler et al., *Bioorganic & Med. Chem. Letters,* 10:1025-1028 (2000); and Mandler et al., *Bioconjugate Chem.,* 13: 786-791 (2002)), maytansinoids (EP 1391213 and Liu et al., *Proc. Natl. Acad. Sci. USA,* 93: 8618-8623 (1996)), and calicheamicin (Lode et al., *Cancer Res.,* 58:2928 (1998); and Hinman et al., Cancer Res., 53:3336-3342 (1993)). Without being limited to any one theory, the toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, for example, WO 1994/11026.

Conjugates of an antibody and one or more small-molecule toxins, such as a calicheamicin, maytansinoid, trichothecene, and CC1065, and the derivatives of these toxins that have toxin activity, are also contemplated herein.

In the ADCs of the invention, an antibody (Ab) is conjugated to one or more drug moieties (D), e.g., about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

Ab-(L-D)$_p$   Formula I

Nucleophilic groups on antibodies include, but are not limited to: (i) N-terminal amine groups, (ii) side-chain amine groups, e.g., lysine, (iii) side-chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups that may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Domen et al., *J. Chromatog.,* 510: 293-302 (1990)). In another embodiment, proteins containing N-terminal serine or threonine residues can react with sodium meta-periodate, resulting in production of an aldehyde in place of the first amino acid (Geoghegan and Stroh, *Bioconjugate Chem.,* 3:138-146 (1992) and U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide that does not destroy the desired properties of the conjugate.

In yet another embodiment, the antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

The ADCs herein are optionally prepared with cross-linker reagents, such as, for example, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate), which are commercially available (e.g., from Pierce Biotechnology, Inc., Rockford, Ill., U.S.A). See pages 467-498, 2003-2004 Applications Handbook and Catalog.

Antibody Derivatives

The antibodies of the present invention can be further modified to contain additional nonproteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations of the antibodies used in accordance with the present invention are prepared for storage by mixing an antibody having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or polyethylene glycol (PEG).

A further formulation and delivery method herein involves that described, for example, in WO 2004/078140, including the ENHANZE™ drug delivery technology (Halozyme Inc.). This technology is based on a recombinant human hyaluronidase (rHuPH20). rHuPH20 is a recombinant form of the naturally occurring human enzyme approved by the FDA that temporarily clears space in the matrix of tissues such as skin. That is, the enzyme has the ability to break down hyaluronic acid (HA), the space-filling "gel"-like substance that is a major component of tissues throughout the body. This clearing activity is expected to allow rHuPH20 to improve drug delivery by enhancing the entry of therapeutic molecules through the subcutaneous space. Hence, when combined or co-formulated with certain injectable drugs, this technology can act as a "molecular machete" to facilitate the penetration and dispersion of these drugs by temporarily opening flow channels under the skin. Molecules as large as 200 nanometers may pass freely through the perforated extracellular matrix, which recovers its normal density within approximately 24 hours, leading to a drug delivery platform that does not permanently alter the architecture of the skin.

Hence, the present invention includes a method of delivering an antibody herein to a tissue containing excess amounts of glycosaminoglycan, comprising administering a hyaluronidase glycoprotein (sHASEGP) (this protein comprising a neutral active soluble hyaluronidase polypeptide and at least one N-linked sugar moiety, wherein the N-linked sugar moiety is covalently attached to an asparagine residue of the polypeptide) to the tissue in an amount sufficient to degrade glycosaminoglycans sufficiently to open channels less than about 500 nanometers in diameter; and administering the antibody to the tissue comprising the degraded glycosaminoglycans.

In another embodiment, the invention includes a method for increasing the diffusion of an antibody herein that is administered to a subject comprising administering to the subject a sHASEGP polypeptide in an amount sufficient to open or to form channels smaller than the diameter of the antibody and administering the antibody, whereby the diffusion of the therapeutic substance is increased. The sHASEGP and antibody may be administered separately or simultaneously in one formulation, and consecutively in either order or at the same time.

Exemplary anti-LTα antibody formulations are described in WO 1998/56418, which include a liquid multidose formulation comprising the anti-LTα antibody at 40 mg/mL, 25 mM acetate, 150 mM trehalose, 0.9% benzyl alcohol, 0.02% polysorbate 20 at pH 5.0 that has a minimum shelf life of two years storage at 2-8° C. Another anti-LTα formulation of interest comprises 10 mg/mL antibody in 9.0 mg/mL sodium chloride, 7.35 mg/mL sodium citrate dihydrate, 0.7 mg/mL POLYSORBATE 80™ surfactant, and Sterile Water for Injection, pH 6.5. Yet another aqueous pharmaceutical formulation comprises 10-30 mM sodium acetate from about pH 4.8 to about pH 5.5, preferably at pH 5.5, POLYSORBATE as a surfactant in an amount of about 0.01-0.1% v/v, trehalose at an amount of about 2-10% w/v, and benzyl alcohol as a preservative (U.S. Pat. No. 6,171,586). Lyophilized formulations adapted for subcutaneous administration are described, for example, in WO 1997/04801 and U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antibody are also contemplated. See, for example, US 2002/0136719 (Shenoy et al.).

The formulation herein may also contain more than one active compound (a second medicament as noted above) as necessary for the particular indication being treated, preferably those with complementary activities that do not adversely affect each other. For example, it may be desirable to further provide a cytotoxic agent, chemotherapeutic agent, cytokine antagonist, integrin antagonist, or immunosuppressive agent (e.g., one that acts on T cells, such as cyclosporin or an antibody that binds T cells, e.g., one that binds LFA-1). The type and effective amounts of such second medicaments depend, for example, on the amount of antibody present in the formulation, the type of disease or disorder or treatment, the clinical parameters of the subjects, and other factors discussed above. These are generally used in the same dosages and with administration routes as described herein or from about 1 to 99% of the heretofore employed dosages. The preferred such medicaments are noted above.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug-delivery systems (for example, liposomes, albumin microspheres, microemulsions, nano-particles, and nanocapsules), or in macroemulsions. Such techniques are disclosed, for example, in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in-vivo administration must be sterile. This is readily accomplished by filtration through sterile filtration membranes.

Uses

An antibody of the present invention may be used in, for example, in vitro, ex vivo, and in vivo therapeutic methods. Antibodies of the invention can be used as an antagonist to partially or fully block the specific LTα activity in vitro, ex vivo, and/or in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects, or in other mammalian subjects having the antigen with which an antibody of the invention cross-reacts (e.g., chimpanzee, baboon, marmoset, cynomolgus, rhesus, pig, or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen to which an antibody of the invention binds. Still further, the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig, or mouse) for veterinary purposes or as an animal model of human disease. Regarding the latter, such animal models may be useful for evaluating the therapeutic efficacy of antibodies of the invention (e.g., testing of dosages and time courses of administration). The antibodies of the invention can be used to treat, inhibit, delay progression of, prevent/delay recurrence of, ameliorate, or prevent autoimmune diseases, disorders, or conditions as defined herein.

In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies that do not necessarily prevent ligand binding but interfere with receptor activation, thereby inhibiting any responses that would normally be initiated by the ligand binding. The invention also encompasses antibodies that either preferably or exclusively bind to ligand-receptor complexes. An antibody of the invention can also act as an agonist of a particular antigen receptor, thereby potentiating, enhancing, or activating either all or partial activities of the ligand-mediated receptor activation.

The antibody may be a naked antibody or alternatively is conjugated with another molecule, such as a cytotoxic agent. The antibody is preferably administered intravenously or subcutaneously, most preferably subcutaneously.

In one embodiment, the subject has never been previously treated with drug(s), such as immunosuppressive agent(s), to treat the disorder, and in a particular embodiment has never been previously treated with a TNF antagonist. In an alternative embodiment, the subject has been previously treated with drug(s) to treat the disorder, including with a TNF antagonist.

In a still further aspect, the patient has relapsed with the disorder. In an alternative embodiment, the patient has not relapsed with the disorder.

In another aspect, the antibody herein is the only medicament administered to the subject to treat the disorder. In an alternative aspect, the antibody herein is one of the medicaments used to treat the disorder.

In a further aspect, the subject only has RA as an autoimmune disorder. Alternatively, the subject only has MS as an autoimmune disorder. Still alternatively, the subject only has lupus, or ANCA-associated vasculitis, or Sjögren's syndrome as an autoimmune disorder. In all cases autoimmune disorder is defined above.

In a still further embodiment, the subject has an abnormal level of one or more regulatory cytokines, anti-nuclear antibodies (ANA), anti-rheumatoid factor (RF) antibodies, creatinine, blood urea nitrogen, anti-endothelial antibodies, anti-neutrophil cytoplasmic antibodies (ANCA), infiltrating CD20 cells, anti-double stranded DNA (dsDNA) antibodies, anti-Sm antibodies, anti-nuclear ribonucleoprotein antibodies, anti-phospholipid antibodies, anti-ribosomal P antibodies, anti-Ro/SS-A antibodies, anti-Ro antibodies, anti-La antibodies, antibodies directed against Sjögren's-associated antigen A or B (SS-A or SS-B), antibodies directed against centromere protein B (CENP B) or centromere protein C (CENP C), autoantibodies to ICA69, anti-Smith antigen (Sm) antibodies, anti-nuclear ribonucleoprotein antibodies, anti-ribosomal P antibodies, autoantibodies staining the nuclear or perinuclear zone of neutrophils (pANCA), anti-*Saccharomyces cerevisiae* antibodies, cross-reactive antibodies to GM1 ganglioside or GQ1b ganglioside, anti-acetylcholine receptor (AchR), anti-AchR subtype, or anti-muscle specific tyrosine kinase (MuSK) antibodies, serum anti-endothelial cell antibodies, IgG or anti-desmoglein (Dsg) antibodies, anti-centromere, anti-topoisomerase-1 (Scl-70), anti-RNA polymerase or anti-U3-ribonucleoprotein (U3-RNP) antibodies, anti-glomerular basement membrane (GBM) antibodies, anti-glomerular basement membrane (GBM) antibodies, anti-mitochondrial (AMA) or anti-mitochondrial M2 antibodies, anti-thyroid peroxidase (TPO), anti-thyroglobin (TG) or anti-thyroid stimulating hormone receptor (TSHR) antibodies, anti-nucleic (AN), anti-actin (AA) or anti-smooth muscle antigen (ASM) antibodies, IgA anti-endomysial, IgA anti-tissue transglutaminase, IgA anti-gliadin or IgG anti-gliadin antibodies, anti-CYP21A2, anti-CYP11A1 or anti-CYP17 antibodies, anti-ribonucleoprotein (RNP), or myosytis-specific antibodies, anti-myelin associated glycoprotein (MAG) antibodies, anti-hepatitis C virus (HCV) antibodies, anti-GM1 ganglioside, anti-sulfate-3-glycuronyl paragloboside (SGPG), or IgM anti-glycoconjugate antibodies, IgM anti-ganglioside antibody, anti-thyroid peroxidase (TPO), anti-thyroglobin (TG) or anti-thyroid stimulating hormone receptor (TSHR) antibodies, anti-myelin basic protein or anti-myelin oligodendrocytic glycoprotein antibodies, IgM rheumatoid factor antibodies directed against the Fc portion of IgG, anti-Factor VIII antibodies, or a combination thereof.

The parameters for assessing efficacy or success of treatment of an autoimmune disorder (which includes an autoimmune-related disease) will be known to the physician of skill in the appropriate disease. Generally, the physician of skill will look for reduction in the signs and symptoms of the specific disease. The following are by way of examples.

In one embodiment, the methods and compositions of the invention are useful to treat RA. RA is characterized by inflammation of multiple joints, cartilage loss, and bone erosion that leads to joint destruction and ultimately reduced joint function. Additionally, since RA is a systemic disease, it can have effects in other tissues such as the lungs, eyes, and bone marrow.

If the subject has RA, which is a preferred indication herein, preferably the antibodies herein induce a major clinical response in the subject.

The antibodies herein can be used as first-line therapy in patients with early RA (i.e., methotrexate (MTX) naive), or in combination with, e.g., MTX or cyclophosphamide. Alternatively, the antibodies can be used in treatment as second-line therapy for patients who were, for example, refractory to DMARD and/or TNF inhibitor, and/or MTX, in combination with, e.g., MTX. The LTα-binding antibodies can also be administered in combination with B-cell mobilizing agents such as integrin antibodies that mobilize B cells into the bloodstream for more effective killing. The LTβ-binding antibodies are useful to prevent and control joint damage, delay structural damage, decrease pain associated with inflammation in RA, and generally reduce the signs and symptoms in moderate-to-severe RA. The RA patient can be treated with the LTα antibody prior to, after, or together with treatment with other drugs used in treating RA (see combination therapy described herein). Patients who had previously failed DMARDs and/or had an inadequate response to MTX alone are, in one embodiment, treated with a LTα-binding antibody. In another embodiment, such patients are administered humanized LTα-binding antibody plus cyclophosphamide or LTα-binding antibody plus MTX. Most preferably, the antibodies herein are administered with MTX for treatment of RA, and not with high-dose steroids.

One method of evaluating treatment efficacy in RA is based on American College of Rheumatology (ACR) criteria, which are used to measure the percentage of improvement in tender and swollen joints, among other things. The RA patient can be scored at, for example, ACR 20 (20 percent improvement) compared with no antibody treatment (e.g., baseline before treatment) or treatment with placebo. Other ways of evaluating the efficacy of antibody treatment include X-ray scoring such as the Sharp X-ray score used to score structural damage such as bone erosion and joint space narrowing. Patients can also be evaluated for the prevention of or improvement in disability based on Health Assessment Questionnaire (HAQ) score, AIMS score, or SF-36 at time periods during or after treatment. The ACR 20 criteria may include 20% improvement in both tender (painful) joint count and swollen joint count plus a 20% improvement in at least three of five additional measures:

1. patient's pain assessment by visual analog scale (VAS),
2. patient's global assessment of disease activity (VAS),
3. physician's global assessment of disease activity (VAS),
4. patient's self-assessed disability measured by the Health Assessment Questionnaire, and
5. acute phase reactants, CRP or ESR.

The ACR 50 and 70 are defined analogously. Preferably, the patient is administered an amount of an LTα-binding antibody of the invention effective to achieve at least a score of ACR 20, preferably at least ACR 30, more preferably at least ACR 50, even more preferably at least ACR 70, and most preferably at least ACR 75.

Psoriatic arthritis has unique and distinct radiographic features. For psoriatic arthritis, joint erosion and joint space narrowing can be evaluated by the Sharp score as well. The antibodies disclosed herein can be used to prevent the joint damage as well as reduce disease signs and symptoms of the disorder.

Yet another aspect of the invention is a method of treating lupus, including systemic lupus erythematosus (SLE) and lupus nephritis, by administering to the subject having such disease an effective amount of an antibody of the invention. For example, SLEDAI scores provide a numerical quantitation of disease activity. The SLEDAI is a weighted index of 24 clinical and laboratory parameters known to correlate with disease activity, with a numerical range of 0-103. See Gescuk and Davis, *Current Opinion in Rheumatology*, 14: 515-521 (2002). Antibodies to double-stranded DNA are believed to cause renal flares and other manifestations of lupus. Patients undergoing antibody treatment can be monitored for time to renal flare, which is defined as a significant, reproducible increase in serum creatinine, urine protein, or blood in the urine. Alternatively or in addition, patients can be monitored for levels of antinuclear antibodies and antibodies to double-stranded DNA. Treatments for SLE include high-dose corticosteroids and/or cyclophosphamide (HDCC).

Spondyloarthropathies are a group of disorders of the joints, including ankylosing spondylitis, psoriatic arthritis, and Crohn's disease. Treatment success can be determined by validated patient and physician global assessment measuring tools.

Various medications are used to treat psoriasis; treatment differs directly in relation to disease severity. Patients with a more mild form of psoriasis typically utilize topical treatments, such as topical steroids, anthralin, calcipotriene, clobetasol, and tazarotene, to manage the disease, while patients with moderate and severe psoriasis are more likely to employ systemic (methotrexate, retinoids, cyclosporine, PUVA, and UVB) therapies. Tars are also used. These therapies are disadvantageous due to safety concerns, time-consuming regimens, and/or inconvenient processes of treatment. Furthermore, some require expensive equipment and dedicated space in the office setting. Such systemic medications can produce serious side effects, including hypertension, hyperlipidemia, bone-marrow suppression, liver disease, kidney disease, and gastrointestinal upset. Also, the use of phototherapy can increase the incidence of skin cancers. In addition to the inconvenience and discomfort associated with the use of topical therapies, phototherapy and such systemic treatments also require cycling patients on and off therapy and monitoring lifetime exposure due to their side effects.

Treatment efficacy for psoriasis is assessed by monitoring changes in clinical signs and symptoms of the disease, including Physician's Global Assessment (PGA) changes, Psoriasis Area and Severity Index (PASI) scores, and Psoriasis Symptom Assessment (PSA), compared with the baseline condition. The patient can be measured periodically throughout treatment on the Visual Analog Scale (VAS) used to indicate the degree of itching experienced at specific time points.

Assays

Ligand/receptor binding studies may be carried out in any known assay method, such as competitive-binding assays, direct and indirect sandwich assays, and immunoprecipitation assays. Cell-based assays and animal models can be used to understand the interaction between the ligands and receptors identified herein and the development and pathogenesis of the conditions and diseases referred to herein.

In one approach, mammalian cells may be transfected with the ligands or receptors described herein, and the ability of the antibody herein to inhibit binding or activity is analyzed. Suitable cells can be transfected with the desired gene, and monitored for activity. Such transfected cell lines can then be used to test the ability of antibody, for example, to modulate LTαβ complex expression of the cells.

In addition, primary cultures derived from transgenic animals can be used in the cell-based assays. Techniques to derive continuous cell lines from transgenic animals are well known in the art. See, e.g., Small et al., *Mol. Cell. Biol.,* 5:642-648 (1985).

One suitable cell-based assay is the addition of epitope-tagged ligand (e.g., LTα) to cells that have or express the respective receptor, and the analysis of binding (in the presence or absence of prospective antibodies) by FACS staining with anti-tag antibody. In another assay, the ability of the antibody herein to inhibit the expression of LTαβ complex on cells expressing such complex is assayed. For example, suitable expressing cell lines are cultured in the presence or absence of prospective antibodies and the modulation of LTαβ complex expression can be measured by $^3$H-thymidine incorporation or cell number.

The results of the cell-based in vitro assays can be further verified using in vivo animal models. Many animal models can be used to test the efficacy of the antibodies identified herein in relation to, for instance, immune-related disease. The in vivo nature of such models makes them particularly predictive of responses in human patients. Animal models of immune-related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail-vein injection, spleen implantation, intraperitoneal implantation, and implantation under the renal capsule.

Graft-versus-host disease is an example of a disease for which an animal model has been designed. Graft-versus-host disease occurs when immunocompetent cells are transplanted into immunosuppressed or tolerant patients. The donor cells recognize and respond to host antigens. The response can vary from life-threatening severe inflammation to mild cases of diarrhea and weight loss. Graft-versus-host disease models provide a means of assessing T-cell reactivity against MHC antigens and minor transplant antigens. A suitable procedure is described in detail in *Current Protocols in Immunology,* Eds. Cologan et al., (John Wiley & Sons, Inc., 1994), unit 4.3.

An animal model for skin allograft rejection tests the ability of T cells to mediate in vivo tissue destruction to measure their role in anti-viral immunity, and is described, for example, in *Current Protocols in Immunology,* supra, unit 4.4. Other transplant rejection models useful to test the antibodies herein include the allogeneic heart-transplant models described by Tanabe et al., *Transplantation,* 58:23 (1994) and Tinubu et al., *J. Immunol.,* 4330-4338 (1994).

Animal models for delayed-type hypersensitivity provide an assay of cell-mediated immune function. Delayed-type hypersensitivity reactions are a T-cell-mediated in vivo immune response characterized by inflammation that does not reach a peak until after a period of time has elapsed after challenge with an antigen. These reactions also occur in tissue-specific autoimmune diseases such as MS and experimental autoimmune encephalomyelitis (EAE, a model for MS). A suitable, exemplary model is described in detail in *Current Protocols in Immunology,* supra, unit 4.5.

The collagen-induced arthritis (CIA) model is considered a suitable model for studying potential drugs or biologics active in human arthritis because of the many immunological and pathological similarities to human RA, the involvement of localized major histocompatibility, complete class-II-restricted T-helper lymphocyte activation, and the similarity of histological lesions. Features of this CIA model that are similar to that found in RA patients include: erosion of cartilage and bone at joint margins (as can be seen in radiographs), proliferative synovitis, and symmetrical involvement of small and medium-sized peripheral joints in the appendicular, but not the axial, skeleton. Jamieson et al., *Invest. Radiol.* 20: 324-9 (1985). Furthermore, IL-1 and TNF-α appear to be involved in CIA as well as in RA. Joosten et al., *J. Immunol.* 163: 5049-5055 (1999). TNF-neutralizing antibodies, and separately, TNFR.Fc, reduced the symptoms of RA in this model (Williams et al., *Proc. Natl. Acad. Sci. USA,* 89:9784-9788 (1992); Wooley et al., *J. Immunol.,* 151: 6602-6607 (1993)).

In this model for RA, type II collagen is purified from bovine articular cartilage (Miller, *Biochemistry* 11:4903 (1972)) and used to immunized mice (Williams et al, *Proc. Natl. Acad. Sci. USA,* 91:2762 (1994)). Symptoms of arthritis include erythema and/or swelling of the limbs as well as erosions or defects in cartilage and bone as determined by histology. This widely used model is also described, for example, by Holmdahl et al., *APMIS,* 97:575 (1989), in *Current Protocols in Immunology,* supra, units 15.5, and in Issekutz et al., *Immunology,* 88:569 (1996).

A model of asthma has been described in which antigen-induced airway hyper-reactivity, pulmonary eosinophilia, and inflammation are induced by sensitizing an animal with ovalbumin and challenging the animal with the same protein delivered by aerosol. Animal models such as rodent and nonhuman primate models exhibit symptoms similar to atopic asthma in humans upon challenge with aerosol antigens. Suitable procedures to test the antibodies herein for suitability in treating asthma include those described by Wolyniec et al., *Am. J. Respir. Cell Mol. Biol.*, 18:777 (1998).

Additionally, the antibodies herein can be tested in the SCID/SCID mouse model for immune disorders. For example, as described by Schon et al., *Nat. Med.*, 3:183 (1997), the mice demonstrate histopathologic skin lesions resembling psoriasis. Another suitable model is the human skin/SCID mouse chimera prepared as described by Nickoloff et al., *Am. J. Path.*, 146:580 (1995).

Dosage

For the prevention or treatment of disease, the appropriate dosage of an antibody of the invention (when used alone or in combination with a second medicament as noted below) will depend, for example, on the type of disease to be treated, the type of antibody, the severity and course of the disease, whether the antibody is administered for preventive or therapeutic purposes, previous therapy, the patient's clinical history and response to the antibody, and the discretion of the attending physician. The dosage is preferably efficacious for the treatment of that indication while minimizing toxicity and side effects.

The antibody is suitably administered to the patient at one time or over a series of treatments. Depending on the type and severity of the disease, about 1 μg/kg to 500 mg/kg (preferably about 0.1 mg/kg to 400 mg/kg) of antibody is an initial candidate dosage for administration to the patient, whether, for example, by one or more separate administrations, or by continuous infusion. One typical daily dosage might range from about 1 μg/kg to 500 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 400 mg/kg. Thus, one or more doses of about 0.5 mg/kg, 2.0 mg/kg, 4.0 mg/kg or 10 mg/kg or 50 mg/kg or 100 mg/kg or 300 mg/kg or 400 mg/kg (or any combination thereof) may be administered to the patient. Such doses may be administered intermittently, e.g., every week or every three weeks (e.g., such that the patient receives from about two to about twenty, e.g., about six doses of the antibody). An initial higher loading dose, followed by one or more lower doses, may be administered. An exemplary dosing regimen comprises administering an initial loading dose of about 4 to 500 mg/kg, followed by a weekly maintenance dose of about 2 to 400 mg/kg of the antibody. However, other dosage regimens may be useful. The progress of this therapy is easily monitored by conventional techniques and assays.

For the treatment of an autoimmune disorder, the therapeutically effective dosage will typically be in the range of about 50 mg/m$^2$ to about 3000 mg/m$^2$, preferably about 50 to 1500 mg/m$^2$, more preferably about 50-1000 mg/m$^2$. In one embodiment, the dosage range is about 125-700 mg/m$^2$. For treating RA, in one embodiment, the dosage range for the humanized antibody is about 50 mg/m$^2$ or 125 mg/m$^2$ (equivalent to about 200 mg/dose) to about 1000 mg/m$^2$, given in two doses, e.g., the first dose of about 200 mg is administered on day one followed by a second dose of about 200 mg on day 15. In different embodiments, the dosage is about any one of 50 mg/dose, 80 mg/dose, 100 mg/dose, 125 mg/dose, 150 mg/dose, 200 mg/dose, 250 mg/dose, 275 mg/dose, 300 mg/dose, 325 mg/dose, 350 mg/dose, 375 mg/dose, 400 mg/dose, 425 mg/dose, 450 mg/dose, 475 mg/dose, 500 mg/dose, 525 mg/dose, 550 mg/dose, 575 mg/dose, or 600 mg/dose, or 700 mg/dose, or 800 mg/dose, or 900 mg/dose, or 1000 mg/dose, or 1500 mg/dose.

In treating disease, the LTα-binding antibodies of the invention can be administered to the patient chronically or intermittently, as determined by the physician of skill in the disease.

A patient administered a drug by intravenous infusion or subcutaneously may experience adverse events such as fever, chills, burning sensation, asthenia, and headache. To alleviate or minimize such adverse events, the patient may receive an initial conditioning dose(s) of the antibody followed by a therapeutic dose. The conditioning dose(s) will be lower than the therapeutic dose to condition the patient to tolerate higher dosages.

The antibodies herein may be administered at a frequency that is within the skill and judgment of the practicing physician, depending on various factors noted above, for example, the dosing amount. This frequency includes twice a week, three times a week, once a week, bi-weekly, or once a month, In a preferred aspect of this method, the antibody is administered no more than about once every other week, more preferably about once a month.

Route of Administration

The antibodies used in the methods of the invention (as well as any second medicaments) are administered to a subject or patient, including a human patient, in accord with suitable methods, such as those known to medical practitioners, depending on many factors, including whether the dosing is acute or chronic. These routes include, for example, parenteral, intravenous administration, e.g., as a bolus or by continuous infusion over a period of time, by subcutaneous, intramuscular, intra-arterial, intraperitoneal, intrapulmonary, intracerebrospinal, intra-articular, intrasynovial, intrathecal, intralesional, or inhalation routes (e.g., intranasal). Parenteral infusions include intramuscular, intravenous, intraarterial, intraperitoneal, or subcutaneous administration. In addition, the antibody is suitably administered by pulse infusion, particularly with declining doses of the antibody. Preferred routes herein are intravenous or subcutaneous administration, most preferably subcutaneous.

In one embodiment, the antibody herein is administered by intravenous infusion, and more preferably with about 0.9 to 20% sodium chloride solution as an infusion vehicle.

Combination Therapy

In any of the methods herein, one may administer to the subject or patient along with the antibody herein an effective amount of a second medicament (where the antibody herein is a first medicament), which is another active agent that can treat the condition in the subject that requires treatment; for example, if the condition is an autoimmune disorder, the second medicament is a drug that can treat the autoimmune disorder, alone or with another active agent. For treatment of autoimmune disorders, the second medicament includes, for example, a chemotherapeutic agent, an immunosuppressive agent, an antagonist (such as an antibody) that binds a B-cell surface marker such as rituximab or humanized 2H7, a BAFF antagonist, a DMARD, a cytotoxic agent, an integrin antagonist such as a CD11 or CD18 antagonist including CD11a or CD18 antibodies, e.g., efalizumab (RAPTIVA®), a NSAID, a cytokine antagonist, such as a TNF antagonist, an anti-rheumatic agent, a muscle relaxant, a narcotic, an analgesic, an anesthetic, a sedative, a local anesthetic, a neuromuscular blocker, an antimicrobial, an antipsoriatic, a corticosteriod, an anabolic steroid, an erythropoietin, an immunizing agent, an immunoglobulin, a radiopharmaceutical, an antidepressant, an antipsychotic, a stimulant, an asthma medication, a beta agonist, an inhaled steroid, an epinephrine, a cytokine, cells for repressing B-cell autoantibody secretion as set forth in WO 2005/027841, a hyaluronidase glycoprotein as an active delivery vehicle as set forth in, for example, WO 2004/078140, or a combination thereof.

For treatment of proliferative diseases such as cancer, the second medicament would include, for example, chemotherapeutic agents, hormones, cytotoxic agents, and other biologics such as antibodies to HER-2, to VEGF, to B-cell surface antigens such as TAHO antigen (e.g., US 2006/0251662), CD20, and CD22, and to EGF/EGF-R.

Preferably, such second medicament for autoimmune diseases is an immunosuppressive agent, an antagonist that binds a B-cell surface marker (such as an antibody, e.g., CD20 antibody or CD22 antibody), a BAFF antagonist, a DMARD, an integrin antagonist, a hyaluronidase glycoprotein (as an active delivery vehicle), a NSAID, a cytokine antagonist, more preferably a TNF (e.g., TNF-alpha), CD11, or CD18 antagonist, or a combination thereof. More preferably, it is methotrexate, a TNF antagonist, an antagonist to a B-cell surface marker, or a DMARD.

The type of such second medicament depends on various factors, including the type of autoimmune disorder, the severity of the disease, the condition and age of the patient, the type and dose of first medicament employed, etc.

The antibodies herein can be administered concurrently, sequentially, or alternating with the second medicament or upon non-responsiveness with other therapy. Thus, the combined administration of a second medicament includes co-administration (concurrent administration), using separate formulations or a single pharmaceutical formulation, and consecutive administration in either order, wherein preferably there is a time period while both (or all) medicaments simultaneously exert their biological activities. All these second medicaments may be used in combination with each other or by themselves with the first medicament, so that the expression "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with the same administration routes as the first medicaments, or from about 1 to 99% of the dosages of the first medicaments. If such second medicaments are used at all, preferably, they are used in lower amounts than if the first medicament were not present, especially in subsequent dosings beyond the initial dosing with the first medicament, so as to eliminate or reduce side effects caused thereby.

For the treatment of RA, for example, the patient can be treated with an antibody of the invention in conjunction with any one or more of the following drugs: integrin antagonists, DMARDs (e.g., MTX), NSAIDs, cytokine inhibitors such as HUMIRA™ (adalimumab; Abbott Laboratories), ARAVA® (leflunomide), REMICADE® (infliximab; Centocor Inc., of Malvern, Pa.), ENBREL® (etanercept; Immunex, WA), corticosteroids, or COX-2 inhibitors. DMARDs commonly used in RA include hydroxycloroquine, sulfasalazine, methotrexate, leflunomide, etanercept, infliximab, azathioprine, D-penicillamine, Gold (oral), Gold (intramuscular), minocycline, cyclosporine, or Staphylococcal protein A immunoadsorption. Adalimumab is a human monoclonal antibody that binds to TNFα. Infliximab is a chimeric monoclonal antibody that binds to TNFα. Etanercept is an "immunoadhesin" fusion protein consisting of the extracellular ligand binding portion of the human 75 kD (p75) tumor necrosis factor receptor (TNFR) linked to the Fc portion of a human IgG1.

For conventional treatment of RA, see, e.g., American College of Rheumatology Subcommittee on Rheumatoid Arthritis Guidelines, *Arthritis & Rheumatism* 46(2): 328-346 (2002). In a specific embodiment, the RA patient is treated with an LTα antibody of the invention in conjunction with MTX. An exemplary dosage of MTX is about 7.5-25 mg/kg/wk. MTX can be administered orally and subcutaneously.

For the treatment of ankylosing spondylitis, psoriatic arthritis, and Crohn's disease, the patient can be treated with an antibody of the invention in conjunction with, for example, REMICADE® (infliximab; from Centocor Inc., Malvern, Pa.) or ENBREL® (etanercept; Amgen, Calif.).

Treatments for SLE include high-dose corticosteroids and/or cyclophosphamide (HDCC) in conjunction with the antibodies herein.

For the treatment of psoriasis, patients can be administered a LTβ-binding antibody in conjunction with topical treatments, such as topical steroids, anthralin, calcipotriene, clobetasol, and tazarotene, or with MTX, retinoids, cyclosporine, PUVA and UVB therapies, and integrin antagonists such as anti-CD11a or anti-CD18 antibodies, including, e.g., efalizumab (RAPTIVA®). In one embodiment, the psoriasis patient is treated with the LTα-binding antibody sequentially or concurrently with cyclosporine or with efalizumab.

In certain embodiments, an immunoconjugate comprising the antibody herein conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, a ribonuclease, or a DNA endonuclease.

Articles of Manufacture

In another embodiment of the invention, articles of manufacture containing materials useful for the treatment of the disorders described above are provided. In one aspect, the article of manufacture comprises (a) a container comprising the antibodies herein (preferably the container comprises the antibody and a pharmaceutically acceptable carrier or diluent within the container); and (b) a package insert with instructions for treating the disorder in a patient.

In a preferred embodiment, the article of manufacture herein further comprises a container comprising a second medicament, wherein the antibody is a first medicament. This article further comprises instructions on the package insert for treating the patient with the second medicament, in an effective amount. The second medicament may be any of those set forth above, with an exemplary second medicament being an antagonist binding to a B-cell surface marker (e.g., a CD20 antibody), a BAFF antagonist, an immunosuppressive agent, including MTX and corticosteroids, an integrin antagonist, a cytokine antagonist such as a TNF, CD11, or CD18 antagonist, or a combination thereof. The preferred second medicaments are a steroid, a cytokine antagonist, and/or an immunosuppressive agent.

In this aspect, the package insert is on or associated with the container. Suitable containers include, for example, bottles, vials, syringes, etc. The containers may be formed from a variety of materials such as glass or plastic. The container holds or contains a composition that is effective for treating the disorder in question and may have a sterile access port (for example, the container may be an intravenous solution bag or a vial having a stopper pierceable by a hypodermic injection needle). At least one active agent in the composition is the antibody herein. The label or package insert indicates that the composition is used for treating the particular disorder in a patient or subject eligible for treatment with specific guidance regarding administration of the compositions to the patients, including dosing amounts and intervals of antibody and any other medicament being provided. Package insert refers to instructions customarily included in commercial packages of therapeutic products that contain information about the indications, usage, dosage, administration, contra-indications, and/or warnings concerning the use of such therapeutic products. The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

In a specific embodiment of the invention, an article of manufacture is provided comprising, packaged together, a pharmaceutical composition comprising an antibody herein and a pharmaceutically acceptable carrier and a label stating that the antibody or pharmaceutical composition is indicated for treating patients with an autoimmune disease such as RA, MS, lupus, or IBD.

In a preferred embodiment the article of manufacture herein further comprises a container comprising a second medicament, wherein the antibody is a first medicament, and which article further comprises instructions on the package insert for treating the patient with the second medicament, in an effective amount. The second medicament may be any of those set forth above, with an exemplary second medicament being those set forth above, including, especially for RA treatment, an immunosuppressive agent, a corticosteroid, a DMARD, an integrin antagonist, a NSAID, a cytokine antagonist, a bisphosphonate, or a combination thereof, more preferably a DMARD, NSAID, cytokine antagonist, integrin antagonist, or immunosuppressive agent. Most preferably, the second medicament is methotrexate or a DMARD if the disease is RA.

In another aspect, the invention provides a method for packaging or manufacturing an antibody herein or a pharmaceutical composition thereof comprising combining in a package the antibody or pharmaceutical composition and a label stating that the antibody or pharmaceutical composition is indicated for treating patients with an autoimmune disease such as RA, MS, lupus, or IBD.

Methods of Advertising

The invention herein also encompasses a method for advertising an antibody herein or a pharmaceutically acceptable composition thereof comprising promoting, to a target audience, the use of the antibody or pharmaceutical composition thereof for treating a patient or patient population with an autoimmune disease such as RA, MS, lupus, or IBD.

Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the treatment methods herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed, generally in public places. More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or individual contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments. The advertising may be individualized or customized based on user characterizations defined by service interaction and/or other data such as user demographics and geographical location.

The following are non-limiting examples of the methods and compositions of the invention. It is understood that various other embodiments may be practiced, given the general description provided above. The disclosures of all citations in the specification are expressly incorporated herein by reference.

EXAMPLE 1

Preparation of Anti-Human and Anti-Murine LTα Monoclonal Antibodies and Hamster-Murine Chimeras Anti-human LTα monoclonal antibodies 2C8 and 3F12 were generated as follows: BALB/c mice (Charles River Laboratories, Wilmington, Del.) were hyperimmunized by injection with 5 µg/dose of purified recombinant human LTα expressed in *E. coli* (Genentech, Inc., South San Francisco, Calif.; Genentech Lot#8360-2B; see also Spriggs, "Tumor Necrosis Factor: Basic Principles and Preclinical Studies," *Biologic Therapy of Cancer*, DeVita et al., eds., J.B. Lippincott Company (1991) Ch. 16, pp. 354-377; Ruddle, *Current Opinion in Immunology*, 4:327-332 (1992); Wong et al., "Tumor Necrosis Factor," *Human Monocytes*, Academic Press (1989), pp. 195-215; Aggarwal et al., *Cytokines and Lipocortins in Inflammation and Differentiation*, Wiley-Liss, Inc. 1990, pp. 375-384; and Paul et al., *Ann. Rev. Immunol.*, 6:407-438 (1988)) in DETOX™ adjuvant (RIBI ImmunoChem Research, Inc., Hamilton, Mo.). Specifically, 10 µg LTα3 was mixed with 50 µL of the adjuvant and injected subcutaneously into the rear footpads of mice (strain BALB/c) on days 1, 4, 15, 29, 41, 56, and 71. Serum was collected on Days 15 and 56 for detection of anti-LTα3-specific antibodies by binding ELISA.

On day 75, the animals were sacrificed, spleens were harvested, and 3×10E7 cells were fused with 5×10E7 cells of the mouse myeloma line X63-Ag8.653 using 50% polyethylene glycol (PEG) 4000 by an established procedure (Oi and Herzenberg, in *Selected Methods in Cellular Immunology*, B. Mishel and S. Schiigi, eds., (W.J.Freeman Co., San Francisco, Calif., 1980)). The fused cells were plated into 96-well microtiter plates at a density of 2×10E5 cells/well containing HAT medium for selection (Littlefield, *Science*, 145:709 (1964)). After 12 days, the supernatants were harvested and screened for antibody production by direct ELISA. The supernatants harvested from each hybridoma lineage were purified by affinity chromatography (Pharmacia fast protein liquid chromatography (FPLC); Pharmacia, Uppsala, Sweden). The purified antibody preparations were then sterile filtered (0.2-μm pore size; Nalgene, Rochester N.Y.) and stored at 4° C. in phosphate-buffered saline (PBS).

Anti-murine LTα monoclonal antibody S5H3 was generated as follows: Armenian hamsters were immunized with recombinant mouse LTα2β1 (R&D Systems Inc. (1008-LY)). The hamsters were immunized with 2 μg of antigen by footpad for 12 injections, with an IP boost of 2 μg of antigen once. The lymph nodes and spleen were fused by PEG treatment. Primary screening was done by ELISA on Immunogen-vs. Genentech-manufactured murine LTα-6His (murine LTα with six histidines attached at the C-terminal end). Detection was done with peroxidase-conjugated AFFINIPURE™ goat anti-Armenian hamster IgG (H+L) (Jackson ImmunoResearch 127-035-160). Secondary screening was performed by FACS on irrelevant transfected HEK 293 cells vs. HEK 293 cells stably transfected with murine LTαβ (under G418 selection). Detection was performed using R-phycoerythrin-conjugated AFFINIPURE™ F(ab')2 goat anti-Armenian hamster IgG (H+L) (Jackson ImmunoResearch 127-116-160). The hybridoma from which this antibody was derived was deposited with ATCC as Deposit No. PTA-7538 (hybridoma murine Lymphotoxin alpha2 beta1 s5H3.2.2).

All anti-murine and anti-human LTα antibodies generated in these experiments were selected for recognition of LTα3. These were then screened for (a) blocking of binding of LTα3 to TNFR1 and TNFR11 by ELISA, (b) binding of LTαβ by ELISA and FACS of cells stably transfected with LTα and LTβ, and (c) blocking of LTαβ interaction with the LTβ receptor by ELISA. Antibodies 3F12, 2C8, and S5H3 were selected because they all bound and neutralized LTα3 and LTαβ.

For use in the murine in vivo studies described below, the hamster anti-murine LTα hybridoma was cloned as a hamster/mouse chimera. Total RNA was extracted from S5H3 hybridoma cells using a RNEASY MINI™ kit (Qiagen) and the manufacturer's suggested protocol. RT-PCR was accomplished using a Qiagen ONE-STEP™ kit, and primers were designed to amplify the light- and heavy-chain variable domains and add restriction enzyme sites for cloning.

For construction of the light chain of this chimeric antibody S5H3, two sequential cloning steps were used. In the first step, RT-PCR, ClaI and AscI sites were added, using primer set one, allowing cloning into a pRK-based vector simply to amplify DNA for sequencing. After the DNA sequence of the light-chain variable domain was obtained, a round of PCR was performed, using this plasmid as template, in order to add EcoRV and KpnI sites that are compatible with the expression vector.

For construction of the heavy chain of S5H3, likewise two cloning steps were used. Specifically, RT-PCR was used to amplify cDNA and add ClaI and AscI sites for cloning into a vector for sequencing. Subsequently, this plasmid was used as template for PCR to add BsiWI and ApaI sites that are compatible with the expression vector.

For RT-PCR, the primers used were as follows:

```
S5H3 light-chain set one:
5' primer:
                                      (SEQ ID NO: 56)
GGA TCA TCG ATA CAR CTN GTV YTN CAN CAR TCN CC 3' primer:
                                      (SEQ ID NO: 57)
GGT AAC GGC GCG CCG YTC AGA AGA TGG TGG RAA S5H3 light-chain set two:
5' primer:
                                      (SEQ ID NO: 58)
GGA TCC GAT ATC CAG CTG GTA TTG ACC CAA TCT 3' primer:
                                      (SEQ ID NO: 59)
GGA TCA GGT ACC GCT GCC AAA AAC ACA CGA CCC S5H3 heavy chain set one:
5' primer:
                                      (SEQ ID NO: 60)
TGA TAA TCG ATG ARG TNC CAT TTR GTN GAR 3' primer:
                                      (SEQ ID NO: 61)
TAG TAA GGC GCG CCT GGT CAG GGA NCC NGA RTT CCA S5H3 heavy chain set two:
5' primer:
                                      (SEQ ID NO: 62)
TGA TCG CGT ACG CTG AGG TTC AAT TGG TTG AG 3' primer:
                                      (SEQ ID NO: 63)
TGA TCG TGG GCC CTT TGT TGT GGC TGA GGA GAC GG
``` wherein R=A or G, Y=C or T, and N=all four nucleic acids A, G, C, and T. Purified PCR products for the light-chain variable domain were cloned into a pRK mammalian cell expression vector (pRK.LPG2.mukappa) containing the murine kappa constant domain. For the heavy chain, PCR products were cloned into a pRK mammalian cell expression vector (pRK.LPG10.mulgG2a) encoding the murine CH1, hinge, CH2, and CH3 domains of murine isotype IgG2a. These vectors are derivatives of previously described vectors for expression of IgGs in 293 cells (Shields et al., *J. Biol. Chem.*, 276:6591-6604 (2000) and Gorman et al., *DNA Prot Eng Tech*, 2:3-10 (1990)). For S5H3 chimeric antibody expression, the plasmids for the light and heavy chains were transiently co-transfected into 293 cells (an adenovirus-transformed human embryonic kidney cell line (Graham et al., *J. Gen. Virol.*, 36:59-74 (1977)) or CHO cells. The antibody protein was purified from cell-culture supernatants by protein A affinity chromatography.

The LTα3 binding ELISA was carried out as follows: Microtiter wells were coated with a 1 μg/ml LTα3 in 50 mM carbonate buffer solution (50 μl/well) overnight. The unadsorbed solution was aspirated from the wells. Wells were blocked with 200 μL PBS containing 5 mg/ml bovine serum albumin (PBS-BSA) for 2 hours. 50 μL of test sample appropriately diluted in PBS-BSA was added to each well, incubated for one hour, and washed with PBS containing 0.05% TWEEN-20™ surfactant. 100 μL of horse radish peroxidase-labeled goat anti-mouse IgG in PBS-BSA buffer was added to each well and incubated for one hour. Each well was washed with PBS/0.05% TWEEN-20™ surfactant and then citrate phosphate buffer, pH 5, containing 0.1 mg o-phenylenediamine/ml (substrate solution), and aqueous 30% $H_2O_2$ was added to each well. The wells were incubated for 30 minutes; then the reaction was stopped with 50 μL 2.5M sulfuric acid $H_2SO_4$, and absorbance was read at 490 nm.

The LTα3-blocking ELISA, the LTαβ-binding ELISA and FACS assays, and the LTαβ-blocking ELISA were carried out by procedures described further below.

EXAMPLE 2

Sequencing, Humanization, and Affinity Maturation of Anti-LTα Antibody 3F12

1. De Novo Sequencing of Anti-LTα 3F12 Using LTQ-FTMS-MS/MS Analysis and Edman Degradation Because the hybridoma cell line 3F12.2D3 was lost from the frozen cell line bank, anti-LTα monoclonal antibody protein, purified from ascites 3F12.2D3, was submitted for sequencing at a concentration of about 3.0 mg/mL in PBS. The antibody (Ab) was separated on 4-20% TRIS™ HCl SDS-PAGE under reducing conditions and each resolved heavy chain (HC) and light chain (LC) was subjected to N-terminal sequencing (25-30 residues were sequenced) to establish monoclonality. The HC was found to be blocked with a pyroglutamyl group that made the N-terminal amino acid inaccessible to Edman sequencing. The blocking group was subsequently removed using the pyroglutamate aminopeptidase enzyme (PGAP) and the HC chain subjected to sequencing again. Both the HC and LC were confirmed to be monoclonal. The Ab was then treated with various enzymatic and chemical cleavages according to a strategy described in *Analytical Biochemistry*, 35:77-86 (2006). In brief, these consisted of the enzymes trypsin, endo Lys-C, Asp-N, and chemical treatments with CNBr and dilute acid (Asp/Pro cleavage).

Chemical cleavages generated a mixture of peptides that were sequenced on model 494 PROCISE™ sequencers and identified using Genentech's SEQSORT program (SEQSORT is a utility program designed to make the output produced by the programs in Pittsburgh Supercomputing Center's sequence analysis suite more manageable and readable). These chemical cleavages allowed identification of the constant region of the HC and LC by identity with antibodies in protein sequence databases. Peptides generated from the enzymatic digestions were collected from capillary RP-HPLC separations and the peptide masses measured using MALDI-TOF analysis. Peptides with masses that did not match the constant regions were subjected to further analysis using Edman degradation or liquid chromatography-electrospray ionization tandem mass spectrometry (LC-MS/MS) on an LTQ-FT mass spectrometer. Sequences of the variable regions of the HC and LC were derived from peptides with overlapping sequences obtained by the various proteolytic cleavages.

For analysis of the peptides by LC-MS/MS a micro-capillary C18 reverse-phase chromatography column (0.15×150 mm i.d., 5 µm, 300 Å) was employed using a flow rate of 1 mL/minute on an AGILENT™ 1100 series capillary LC system. Solvent A was applied, and a gradient from 2 to 80% solvent B was applied, solvent A consisting of 0.1% v/v formic acid in water and solvent B consisting of 0.1% v/v formic acid in acetonitrile. The LC was coupled in-line with the LTQ-FT mass spectrometer, and peptides with m/z between 350 and 1800 were analyzed in data-dependent mode with the five most abundant species in each full mass range survey scan being selected for collision-induced dissociation (CID). The resulting CID spectra were screened with the search program MASCOT to find exact matches to database sequences, and potentially novel sequences were determined by manual de novo interpretation. Peptides that could not be completely sequenced or that contained the isobaric amino acid pairs of leucine/isoleucine and glutamine/lysine were analyzed further using Edman degradation.

A Fab portion of anti-LTα was obtained from papain digestion of the intact antibody followed by size-exclusion chromatography. Masses of both heavy-chain and light-chain components of the Fab were obtained by quadruple-TOF mass spectrometry after inter-chain disulfides were reduced. The experimental masses corresponded to those calculated based on the obtained sequences of the heavy chain and light chain to within 0.5 Da each.

Sequence of anti-LTα light chain for chimera 3F12.2D3:

(SEQ ID NO: 64)
DIVMSQSPSSLAVSVGEKVTMSCKSSQSLLYSTNQKNFLAWYQQKPGQSP

KLLIYWASTRDSGVPDRFTGSGSGTDFTLTISSVKAEDLAVYYCQQYYSY

PRTFGGGTKLEIKRADAAPTVSIFPPSSEQLTSGGASVVCFLNNFYPKDI

NVKWKIDGSERQNGVLNSWTDQDSKDSTYSMSSTLTLTKDEYERHNSYTC

EATHKTSTSPIVKSFNRNEC

Sequence of anti-LTα heavy-chain variable region spanning into constant region for chimera 3F12.2D3:

(SEQ ID NO: 65)
QGQLQQSGAELMKPGASVKISCKATGYTFSSYWIEWVKQRPGHGLEWIGE

ISPGSGSTNYNEEFKGKATFTADKSSNTAYIQLSSLSTSEDSAVYYCADG

YHGYWGQGTTLTVSSAKTTPPSVYPLAPGCGDTTGSSVTLGCLVKGYFPE

SVTVTWNSGSLSSSVHTFPALLQSGLYTMSSSVTVPSSTWPSQTVTCSVA

HPASSTTVDKKLEPSGPIST wherein N is any amino acid.

FIG. 1C shows the light-chain variable region for this clone, as well as the light-chain constant region as filled in by homology with other antibodies, but not itself sequenced. FIG. 1D shows the heavy-chain variable region for this clone, as well as the heavy-chain constant region as filled in by homology with other antibodies.

2. Synthesis of DNA Encoding the Derived Amino Acid Sequence of Chimeric 3F12

Using a pRK-based plasmid containing the gene for the light-chain of anti-TGF-beta monoclonal antibody 2G7 (WO 2005/97832) as a template, and the amino acid sequences derived above, several rounds of oligonucleotide-directed mutagenesis were performed to derive the gene for the light chain of chimeric antibody 3F12. Similarly, the heavy chain of monoclonal antibody 2G7 was the template for construction of the heavy chain of 3F12. Both light- and heavy-chain templates contained the human constant domains, C kappa for the light chain, and CH1, hinge, CH2, and CH3 of IgG1 isotype, for the heavy chain. The oligonucleotides used in the synthesis are given below for the light and heavy chains.

Oligonucleotides for Synthesis of Chimeric Light Chain of 3F12:

CA1845
(SEQ ID NO: 66)
GCT CAT AGT GAC CTT TTC TCC AAC AGA CAC AGC CAG

AGA TGA TGG CGA CTG TGA CAT CAC GAT ATC TGA ATG

TAC TCC

```
CA1846
                                                    (SEQ ID NO: 67)
GCT GTA AGT CCA GTC AAA GTC TTT TAT ACA GTA CCA

ATC AGA AGA ACT TCT TGG CCT GGT ACC AGC

CA1847
                                                    (SEQ ID NO: 68)
GCG ATC AGG GAC ACC AGA TTC CCT AGT GGA TGC CC

CA1848
                                                    (SEQ ID NO: 69)
GCC ACG TCT TCA GCT TTT ACA CTG CTG ATG G

CA1849
                                                    (SEQ ID NO: 70)
GGT CCC CCC TCC GAA CGT GCG CGG GTA GGA GTA GTA

TTG CTG ACA GTA ATA AAC TGC AGG TC
```

Oligonucleotides for Synthesis of Chimeric Heavy Chain of 3F12:

```
CA1850
                                                    (SEQ ID NO: 71)
GCT GCA GCT GAC CTT CTG AAT GTA CTC C

CA1851
                                                    (SEQ ID NO: 72)
GCC TTG CAG GAG ATC TTC ACT GAA GCC CCA GGC TTC

ATC AGC TCA GCT CC

CA1852
                                                    (SEQ ID NO: 73)
CCC ACT CTA TCC AGT AAC TAG AGA AGG TGT ATC AG

TAG CCT TGC AGG

CA1853
                                                    (SEQ ID NO: 74)
CCA CTT CCA GGA CTA ATC TCT CCA ATC CAC TCA AGG

CCA TGT CCA GGC C

CA1854
                                                    (SEQ ID NO: 75)
GCC CTT GAA CTC CTC ATT GTA ATT AGT ACT ACC ACT

TCC AGG

CA1855
                                                    (SEQ ID NO: 76)
CCG CAG AGT CCT CAG ATG TGA TCA GGC TGC TGA GCT

GGA TGT AGG CAG TGT TGG AGG ATT TGT CTG CAG TGA

ATG TTG CCT TGC C

CA1856
                                                    (SEQ ID NO: 77)
GGC TGA GGA GAC GGT GAC TGT GGT GCC TTG GCC CCA

GTA GCC ATG GTA CCC GTC TGC ACA GTA ATA GAC CTC

CA1871
                                                    (SEQ ID NO: 78)
CCA GAC TGC TGC AGC TGA CCT TGT GAA TGT ACT CCA

GTT GC
```

Since the original 3F12 murine monoclonal antibody had the isotype of IgG2b, the murine constant domains for the light and heavy chains of this isotype were swapped for the human constant domains in the chimera, giving a fully murine antibody. For comparison, the murine IgG2a isotype was also constructed. DNA for the light and heavy chain of each variant was co-transfected into an adenovirus-transformed human embryonic kidney cell line, 293, for transient expression, and protein was purified from conditioned media using Protein A affinity chromatography. Binding to LTα in an ELISA format was compared between the original 3F12 monoclonal antibody from ascites, and the synthetic mulgG2a and mulgG2b variants.

Briefly, a NUNC MAXISORP™ plate was coated with two micrograms per ml of LTα (as described in Example 1 above) in 50 mM carbonate buffer, pH 9.6, overnight at 4° C., and then blocked with 0.5% BSA, 10 PPM PROCLIN™ in PBS at room temperature for 1 hour. Serial dilutions of samples in PBS containing 0.5% BSA, 0.05% TWEEN™, 10 PPM PROCLIN™ were incubated on the plates for 2 hours. After washing, bound antibody was detected with horseradish peroxidase-conjugated anti-human Fc (Jackson ImmunoResearch) using 3,3',5,5'-tetramethyl benzidine (Kirkegaard & Perry Laboratories, Gaithersburg, Md.) as substrate. Absorbance was read at 450 nm. Both the IgG2a- and IgG2b-cloned variants bound similarly to the 3F12 antibody purified from ascites, indicating that the correct sequence had been synthesized.

3. Humanization of 3F12

Using the amino acid sequence of the chimeric clone, the CDR residues of the light and heavy chain were identified (Kabat). Oligonucleotide-directed mutagenesis was used to swap these CDRs onto vectors containing the coding sequences of the light and heavy chains of humanized anti-TGFβ 2G7 version 5 (WO 2005/97832), obtaining the CDRswap version of 3F12. The framework sequences thus derived are for the VL kappa subgroup I and VH subgroup III consensus sequences, respectively:

```
                                                    (SEQ ID NO: 51)
            DIQMTQSPSSLSASVGDRVTITC- (SEQ ID NO: 55)
            L1-WYQQKPGKAPKLLIY- (SEQ ID NO: 53)
            L2-GVPSRFSGSGSGTDFTLTISSLQPEDFATYYC- (SEQ ID NO: 54)
            L3-FGQGTKVEIKR
            and (SEQ ID NO: 46)
            EVQLVESGGGLVQPGGSLRLSCAAS- (SEQ ID NO: 45)
            H1-WVRQAPGKGLEWVG- (SEQ ID NO: 50)
            H2-RATFSADNSKNTAYLQMNSLRAEDTAVYYCAD- (SEQ ID NO: 49)
            H3-WGQGTLVTVSS.
```

After expression and purification as described above, binding of the CDRswap to LTα was compared to that of the chimera. Binding for the CDR swap was almost completely lost.

To restore binding of the humanized antibody, mutations were constructed using DNA from the CDRswap as template. Using a computer-generated model, these mutations were designed to change human framework residues to their murine counterparts at positions where the change might affect CDR conformation of the antibody-antigen surface. Mutants and their relative binding by ELISA as described above are shown in Table 1 below. Changing isoleucine 69 to phenylalanine, to give v2, increased binding significantly, as did the change Leu78Ala, while the change Asn73Lys gave no improvement over the CDRswap. Combining Ile69Phe and Leu78Ala gave version 5, which binds LTα approximately 5-fold less well than the chimera in this ELISA assay format.

Two variants were made to move the framework sequence closer to the human consensus. Version 6, with the changes Lys24Arg and Ser25Ala, was equivalent in binding to version 5. However, an attempt to change the usual aspartic acid at position 94 to the consensus arginine (version 7) resulted in almost complete loss of binding.

TABLE 1

| 3F12 variant | Heavy chain (VH) substitutions | Light chain (VL) substitutions | Relative binding* |
|---|---|---|---|
| Chimera | | | 1 |
| CDRswap | (CDR swap) | (CDR swap) | no binding |
| v2 | I69F | (CDR swap) | >1000x down |
| v3 | N73K | (CDR swap) | >1000x down |
| v4 | L78A | (CDR swap) | >500x down |
| v5 | I68F, L78A | (CDR swap) | 5 to 20 fold down |
| v6 | (CDR swap) | K24R, S25A | 5 to 20 fold down |
| v7 | D94R | (CDR swap) | no binding |

*These values are relative to the original chimera (with heavy chain SEQ ID NO: 35 and heavy-chain variable region set forth in FIG. 1B), which was discovered later to have an "extra" serine in the FR3 of the heavy chain (a serine after the L at position c in SEQ ID NO: 29 in FIG. 3B). This serine was taken out to make chimera2 (having the heavy-chain variable region of SEQ ID NO: 38 in FIG. 1D), and the ELISA binding was found to be the same as above.

All animal studies described below using the 3F12 chimera refer to the original chimera, and not chimera2 as described in the footnote above.

4. Affinity Maturation of Antibody 3F12

For identification of which residues and regions in the CDRs might be most important for binding LTα, and thus candidates for inclusion in phage-display libraries for affinity maturation, partial alanine scanning was performed, using v5 as single-strand template for oligonucleotide-directed mutagenesis.

As shown in Table 2, several residues were found which when mutated to alanine produced a loss or gain in binding to LTβ.

TABLE 2

| version # | Position | relative binding* |
|---|---|---|
| | L1 | |
| 13 | Y31A | 3.40 |
| 14 | T33A | 0.72 |
| 15 | N34A | 0.49 |
| 16 | K36A | 3.70 |
| 17 | F38A | 0.32 |
| | L3 | |
| 18 | Q89A | 4.20 |
| 19 | Y91A | 2.30 |
| 20 | Y92A | 0.71 |
| 21 | S93A | 0.82 |
| 22 | Y94A | 14.30 |
| 23 | R96A | 18.20 |
| | H2 | |
| 24 | G53A | 34.10 |
| 25 | G55A | 1.20 |
| 26 | S56A | 1.07 |
| 27 | N58A | 1.70 |
| 28 | Y59A | 2.73 |
| 29 | N60A | 2.31 |
| 30 | E61A | 1.78 |
| 31 | E62A | 1.93 |
| | H3 | |
| 8 | G95A | >100 |
| 9 | Y99A | 10.00 |
| 10 | H100A | >100 |
| 11 | G101A | |
| 12 | Y102A | 0.81 |

*The ratio of the EC50 of the variant divided by the EC50 of version 5 in plate-based ELISA against LTα. Higher numbers mean weaker binding, numbers >1 mean binding is less than that of version 5.

Thus, versions 14, 15, 17, 20, 21, and 12 have positions where changes could be made to improve binding affinity, and it is expected that conservative substitutions (or even non-conservative in some instances as determined by the skilled artisan by routine testing) could be made at those respective positions to increase binding.

EXAMPLE 3

Preparation of Chimeric Antibody 2C8 and Humanization

1. Preparation of Chimeric Antibody

The variable regions of the heavy and light chains of the murine anti-LTα antibody 2C8 that bound and neutralized LTα3 and LTαβ were cloned and formatted as a murine/human chimeric antibody essentially as described above in Example 1 for the cloning of S5H3.

For RT-PCR, the primers used were as follows:

```
2C8 light chain:
                                        (SEQ ID NO: 79)
5' primer: GCC ATA GAT ATC GTR ATG CAN CAG TCT C (SEQ ID NO: 80)
3' primer: TTT KAT YTC CAG CTT GGT ACC 2C8 heavy chain:
                                        (SEQ ID NO: 81)
5' primer: GAT CGA CGT ACG CTG AGG TYC AGC TSC AGC

TSC AGC AGT CTG G (SEQ ID NO: 82)
3' primer: ACA GAT GGG CCC TTG GTG GAG GCT GMR GAG

ACD GTG ASH RDR GT.
``` wherein K=G or T, S=C or G, D=A or G or T, M=A or C, H=A or C or T, N is T, G, A, or C (any nucleic acid of these four), R=A or G, and Y=C or T.

The variable domain of the light chain was cloned into vector pRK.LPG3.HumanKappa containing the human kappa constant domain, while the heavy-chain variable domain was cloned into expression vector pRK.LPG4.HumanHC encoding the full-length human IgG1 constant domains. These vectors are derivatives of previously described vectors for expression of IgGs in 293 cells (Shields et al., *J Biol Chem,* 276:6591-6604 (2000) and Gorman et al., *DNA Prot Eng Tech,* 2:3-10 (1990)). For transient expression of antibody, these plasmids were co-transfected into 293 cells or CHO mammalian cell lines and the protein was purified as described in Example 1 above.

This chimeric antibody 2C8 was used in the animal experiments described below.

2. Humanization of 2C8

Humanization of the anti-LTα antibody 2C8 was carried out in a series of site-directed mutagenesis steps. Using the sequence of the variable domains of the chimera, the CDR residues of the light and heavy chains were identified by comparing the amino acid sequence of these domains with the sequences of known antibodies (Kabat et al., supra). The CDRs were defined based on sequence hypervariability (Kabat et al., supra) and are shown in FIG. 2.

The CDR swap of 2C8 was made using oligonucleotide site-directed mutagenesis, wherein the CDR regions were put onto separate pRK5-based vectors for the light and heavy chains, respectively. These vectors contain the light-chain human kappa I constant domain, or for the heavy-chain vector, the human IgG1 constant domains CH1, hinge, CH2, and CH3 (Gorman, Current Opinion in Biotechnology, 1, (1), p 36-47 (1990)).

Comparison to other humanized antibodies indicated that the light chain of 2C8 is very similar to the light chain of humanized anti-HER2 antibody 4D5 (U.S. Pat. No. 5,821,337), while the heavy chain of 2C8 is similar in sequence to anti-TGF-β 2G7 (WO 2005/97832). Therefore, a vector containing the light chain of rhuMAb 4D5 was used as the template for the construction of the light chain of 2C8. Site-directed mutagenesis was performed on a deoxyuridine-containing template derived from this vector, using oligonucleotides with light-chain sequences shown in Table 3. Additionally, the oligonucleotide CA1730 was used to revert the framework 3 sequence to that of the human kappa I consensus.

TABLE 3

Oligonucleotides for 2C8 (light chain)

| Substitution | Oligonucleotide sequence |
|---|---|
| CDR-L1 | CC TGG TTT CTG TTG ATA CCA GGC TAC AGC GGA AGA CAC AGC CTG ACT GGC ACG GCA GG (SEQ ID NO: 83) |
| CDR-L2 | GCG AGA AGG GAC TCC AGT GTA ACG GTG GGA TGC AGA GTA AAT CTG TAG TTT CGG AGC (SEQ ID NO: 84) |
| CDR-L3 | GGT ACC CTG TCC GAA CGT CCA AGG AGT AGA ATA ATG TTG CTG ACA GTA ATA AGT TGC (SEQ ID NO: 85) |
| R66G (CA1730) | GGT CAG AGT GAA ATC CGT CCC AGA TCC GGA TCC AGA GAA GCG (SEQ ID NO: 86) |

(All the oligonucleotides were ordered as reverse complements to the coding strand, as the f1 ori in pRK vectors is in the opposite orientation from that in pBR-based vectors.)

For the heavy chain, the deoxyuridine-containing template was derived from a vector containing the heavy chain of humanized antibody 2G7 (WO 2005/97832) using oligonucleotides shown in Table 4. The framework was converted to consensus using oligonucleotides KM55, KM56, and KM61.

TABLE 4

Oligonucleotides for 2C8 (heavy chain)

| | |
|---|---|
| CDR-H1 | GGC CTG ACG GAC CCA ATG GAT CAC ATA GCT GGT GAA TCT GTA GCC AGA AGC TGC (SEQ ID NO: 87) |
| CDR-H2 | CCC CTT GAA CTT CTC GTT ATA GTT GGT GCC GTC GTT ATA AGG ATT GTT ATA ACC AAC CCA CTC GAG GCC (SEQ ID NO: 88) |
| CDR-H3 | GGT TCC TTG ACC CCA GTA GGC GAA CCA TGG GAG CAT TGT GGG TCG AGA ACA ATA ATA GAC GGC AGT GTC CTC AGC (SEQ ID NO: 89) |
| KM55 | CC GTC GTT ATA AGG ATT GTT ATA ACT AAC CCA CTC GAG GCC (SEQ ID NO: 90) |
| KM56 | CAT CTG CAG GTA TAG TGT GTT TTT CGA ATT GTC ACG ACT GAT AGT GAA GCG CCC CTT GAA C (SEQ ID NO: 91) |
| KM61 | CCA TGG GAG CAT TGT GGG TCG AGC ACA ATA ATA GAC GGC AGT GTC C (SEQ ID NO: 92) |

The light and heavy chains comprising the CDR swap, v10, thus derived, were co-transfected into an adenovirus-transformed human embryonic kidney cell line, 293 (Graham et al., supra). Antibodies were purified from culture supernatants using protein A-SEPHAROSE CL-4B™ resin, then buffer-exchanged into 10 mM sodium succinate, 140 mM NaCl, pH 6.0, and concentrated using a CENTRICON-10™ concentrator (Amicon).

For measuring relative binding affinities of the CDR swap, and subsequent 2C8 variants, to human LTα, a plate-based ELISA was used as described above.

As shown in Table 5, the CDR swap, v10, shows no binding in the LTα ELISA. Version 2 and subsequent versions were constructed to regain this binding. Version 2 regains binding equivalent to the chimera, but contains seven non-consensus residues. Further variants were studied to obtain a framework as close to consensus as possible while still retaining or improving binding relative to the chimera. Version 12 has binding equivalent to (by ELISA), or slightly better than (by BIACORE™ analysis), the chimera, and retains only five non-consensus residues. The light- and heavy-chain sequences of versions 7 and 12 are provided in FIG. 2C.

TABLE 5

| 2C8 version | HC | LC | ELISA IC$_{50}$ ratio | BIACORE ™ (rhLTα) | | mutations |
|---|---|---|---|---|---|---|
| | | | | KD | ka/kd | |
| v0 | v0 | v0 | 1 | 0.6 nM | | |
| v2 | v2 | v1 | 1.7 | 0.2 nM | 6e5/1e-4 | |
| v3 | v3 | v1 | 10.2 | | | |
| v4 | v4 | v1 | 27.8 | | | |
| v7 | v2 | v2 | 1.2 | 0.4 nM | 5e5/1.6e-4 | LC.Q46L |
| v8 | v8 | v1 | non-binding | | | HC.G49S.S93A |

TABLE 5-continued

| 2C8 version | HC | LC | ELISA IC$_{50}$ ratio | BIACORE ™ (rhLTα) KD | ka/kd | mutations |
|---|---|---|---|---|---|---|
| v10 | v10 | v1 | non-binding | | | CDRswap |
| v12 | v12 | v2 | 1 | 0.07 nM | 2e6/0.9e−4 | HC.A67F |
| v13 | v13 | v2 | 2.4 | | | HC.S71R |
| v14 | v14 | v2 | 2 | | | HC.K73N |
| v15 | v15 | v2 | 11.1 | | | HC.A93S |
| v16 | v12 | v3 | 0.6 | | | LC.Q46L.E89Q.S90H |
| vX | vX | v3 | 0.3 | | | HC.D53A.A67F |

3. Affinity Maturation of 2C8

A humanized 2C8 monoclonal antibody with improved affinity to LTα was selected from a library of monovalent Fab displayed on phage. A template was generated that displays the humanized 2C8.v2 Fab and contains a stop codon in the CDR-L3. Oligonucleotides (listed in Table 6) were designed to soft-randomize specific CDR-L3 and CDR-H3 residues.

TABLE 6

Soft randomization oligonucleotides for affinity maturation of 2C8 CDR-L3 and CDR-H3

| Oligonucleotide name | Sequence[1] |
|---|---|
| KM73.2C8.phage.v3.LC3.soft | GGA AGA CTT CGC AAC TTA TTA CTG TCA G75 575 885 887 857 8CC T86 6AC GTT CGG ACA GGG TAC CAA GGT GG (SEQ ID NO: 93) |
| KM74.2C8.phage.v3.HC3.soft | G GAC ACT GCC GTC TAT TAT TGT TCT CGA CCC 575 576 787 CCA 866 887 677 TAC TGG GGT CAA GGA ACC CTG G (SEQ ID NO: 94) |

[1]Soft randomization code (A = 5, G = 6, C = 7 and T = 8): each degenerate base is 70% wild-type with 10% equimolar amounts of the remaining three nucleotides added.

Three rounds of sorting on LTα were used to selectively capture high-affinity Fab molecules with less than 2 nM binding to the antigen. For the first round, phage were captured for 2 hours against 2 μg/ml plate-coated LTα at ambient temperature. The second and third rounds of selection were performed at ambient temperature by capturing phage for 30 minutes with 2 nM biotinylated LTα in solution phase, followed by capture on neutravidin-coated plates. The highest affinity clone was identified using a competitive ELISA. Constant concentrations of phage clones (normalized by solid-phase LTα binding OD) were incubated with increasing concentrations of LTα (0-50 nM) in solution before capture on a plate coated with 2 μg/ml LTα. One clone demonstrated a 10-fold improvement in competition with LTα over wild-type 2C8.v2. DNA sequencing of this phagemid clone revealed two amino acid changes from the wild-type 2C8 sequence in CDR-L3: glutamine at position 89 was changed to a glutamic acid, and histidine at position 90 was changed to a serine. These two CDR-L3 changes were made by site-directed mutagenesis on the wild-type 2C8.v7 light chain. When v7 light chain was transfected into 293 cells with the 2C8.v12 heavy chain to give 2C8.v16, the resultant antibody demonstrated a two-fold improvement in IgG binding to LTα by ELISA when compared to 2C8.v2 (Table 5).

To enhance stability, by removing a potential aspartic acid isomerization site, asp 53 in heavy-chain CDR2 was changed to alanine. The resultant 2C8 variant, vX, had a 3.5-fold and 3-fold improvement in binding to LTα by ELISA, compared to the 2C8.v2 and 2C8.chimera, respectively (Table 5).

Table 7 below shows how residue changes in CDR-L3 regions ranked as to ability to bind LTα by ELISA analysis.

TABLE 7

Affinity maturation of 2C8 by phage display: sequence changes in phagemid CDR-L3 regions ranked by ability to compete rhLTα

| Phagemid clone | CDR-L3 Sequence[1,2] | rhLTα Competitive ELISA IC$_{50}$ (nM) |
|---|---|---|
| Wild-type | Q *QHYSTPW* T (SEQ ID NO: 9) | 3.14 |
| A8 | Q *ESYSTPW* T (SEQ ID NO: 10) | 0.32 |
| G7 | Q *ENYSTPW* T (SEQ ID NO: 11) | 0.57 |
| H6 | Q *EVYSTPW* T (SEQ ID NO: 12) | 1.1 |
| C12 | Q *EHYSTPW* T (SEQ ID NO: 95) | 3.41 |
| H9 | Q *QHYYTPW* T (SEQ ID NO: 96) | 3.80 |
| G2 | Q *QYYSTPW* T (SEQ ID NO: 97) | 4.51 |
| G12 | Q *KTFSTPW* T (SEQ ID NO: 98) | 5.34 |
| D8 | Q *QFYSVPW* T (SEQ ID NO: 99) | 136.62 |
| E2 | Q *QKYSTPW* T (SEQ ID NO: 100) | not determined[3] |

[1]Boldface and italicized type shows residues randomized.
[2]All phagemids retained the wild-type CDR-H3 sequence
[3]Clone E2 did not meet rhLTα direct ELISA binding threshold (of OD = 1) necessary for phagemid normalization in competitive ELISA.

It can be seen from this table that the best clones were A8, G7, and H6, which all bound rhLTα with higher affinity than the wild-type clone.

EXAMPLE 4

Anti-LTα Antibody Inhibits Antibody-Induced Arthritis (AIA)

AIA differs from collagen-induced arthritis (CIA), described below, in that instead of injecting the antigen (bovine collagen type II), antibodies recognizing type II collagen are injected. In this way, adaptive B- and T-cell responses are circumvented to directly induce effector functions on macrophages and neutrophils through Fc receptor and complement-mediated activation.

AIA was induced in mice by i.v. injection of a combination of four different monoclonal antibodies generated by the ARTHROGEN-CIA™ mouse B-hybridoma cell lines. Three of the monoclonal antibodies recognize autoantigenic epitopes clustered within an 84-amino-acid residue fragment, LyC2 (the smallest arthritogenic fragment of type II collagen) of CB11, and the fourth monoclonal antibody reacts with LyC1. All four antibodies recognize the conserved epitopes shared by various species of type II collagen and crossreact with homologous and heterologous type II collagen.

All groups (n=5/group) received 2 mg of a cocktail of monoclonal antibodies i.v. in 100 µl PBS on day 0 followed by 25 µg LPS i.p. in 50 µl PBS on day 3. Animals were treated on Day −1 (preventive) or Day 4 (therapeutic) with 10 mg/kg control isotype (anti-ragweed), hamster-murine chimeric LTα antibody S5H3 (as a surrogate for the anti-human LTα antibodies), anti-LT.Fc mutant (an anti-LTα antibody with DANA mutations in the Fc region as described below), or TNFRII.Fc (a TNFR.Ig immunoadhesin) intraperitoneally or subcutaneously. Swelling of the paws was monitored for 14 days. Each paw was given a score of 0-4, for a total maximum of 16 per animal.

DANA mutations in the anti-LT.Fc mutant used in this Example and others below refer to two single-position changes in the Fc region of mouse or human IgG. These changes are D (Aspartic Acid) to A (Alanine) in position 265 and N (Asparagine) to A (Alanine) in position 297. The DANA mutant was constructed by introducing alanine residues into positions 265 and 297 of mouse or human IgG by a PCR-based site-directed mutagenesis method (GENE TAILOR™, Invitrogen Corp.).

FIG. 4A shows the average clinical score for the prophylactic treatment of each group described above as a function of days post-induction. It can be seen that the S5H3 antibody was the most effective in this model of all the treatment groups, including the TNFRII.Fc and anti-LT.Fc mutant molecules. Thus, antibody S5H3 significantly inhibited the development of arthritis in this antibody-induced model. Anti-LTα with the Fc DANA mutation (anti-LT.Fc mutant) had no efficacy, indicating that Fc-mediated killing of LTβ-expressing cells was required for efficacy (FIG. 4A).

Figure 4B:
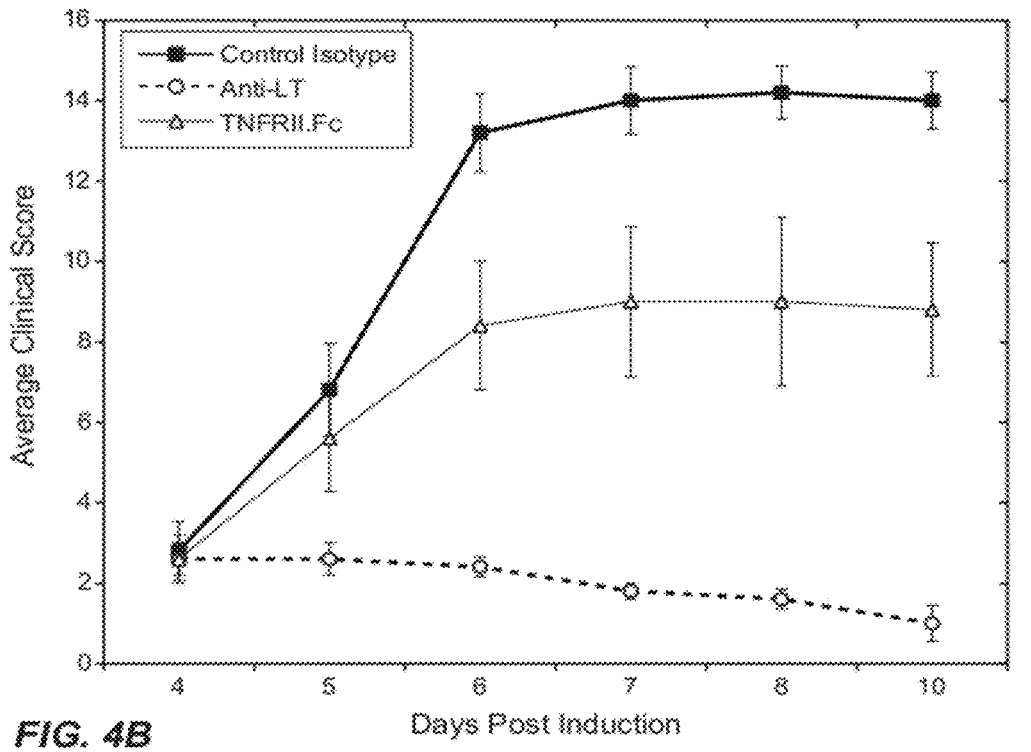

FIG. 4B shows the average clinical score for therapeutic treatment of each group described above as a function of days post-induction. The results show that the S5H3 antibody significantly inhibited the development of arthritis in this antibody-induced model when administered therapeutically, versus the other molecules tested.

In conclusion, animals treated with the hamster-mouse chimera S5H3 had significantly reduced clinical scores as compared to animals treated with S5H3.DANA or control. S5H3 demonstrated both prophylactic and therapeutic efficacy in this animal model.

EXAMPLE 5

Anti-LTα Inhibits Collagen-Induced Arthritis (CIA)

In RA the synovial membrane of multiple joints can become inflamed, leading to destruction of joint tissues including bone and cartilage. The synovium of RA can be highly inflammatory in nature and is typically characterized by lymphocyte and mononuclear cell infiltration, T-cell and antigen-pressing cell (APC) activation, B-cell immunoglobulin (Ig) secretion, and pro-inflammatory cytokine production (Potocnik et al., Scand. J. Immunol., 31:213 (1990); Wernick et al., Arthritis Rheum., 28:742 (1985); Ridley et al., Br. J. Rheumatology, 29:84 (1990); Thomas et al., J. Immunol., 152:2613 (1994); and Thomas et al., J. Immunol., 156:3074 (1996)). Chronically inflamed synovium is usually accompanied by a massive CD4 T-cell infiltration (Pitzalis et al., Eur. J. Immunol., 18:1397 (1988) and Morimoto et al., Am. J. Med., 84:817 (1988)).

Collagen-induced arthritis (CIA) is an animal model for human RA, which resembles human disease, and can be induced in susceptible strains of mice by immunization with heterologous type-II collagen (CII) (Courtenay et al., Nature, 283:665 (1980) and Cathcart et al., Lab. Invest., 54:26 (1986)). Both CD4 T cells and antibodies to CII are required to develop CIA. Transfer of anti-CII to naïve animals only leads to partial histo-pathology that is quite different from CIA, and complete symptoms of CIA do not develop (Holmdahl et al., Agents Action, 19:295 (1986)). In contrast, adoptive transfer of both CD4 T cells and anti-CII antibodies from CII-immunized mice to naïve recipients completely reconstitutes the symptoms of classical CIA (Seki et al., J. Immunol., 148:3093 (1992)). Involvement of both T cells and antibodies in CIA is also consistent with histo-pathological findings of inflamed joints in CIA. Thus, agents that block B-cell or T-cell functions, or inhibit pro-inflammatory cytokines induced by T cells, may be efficacious to prevent or treat arthritis. Indeed, depletion of CD4 T cells, blockade of CD40-CD40L interactions, neutralization of TNF-α, or blocking of IL-1 receptors can lead to prevention of CIA in mice (Maini et al., Immunol. Rev., 144:195 (1995); Joosten et al., Arthritis Rheum., 39:797 (1996); and Durie et al., Science, 261:1328 (1993)).

In the CIA model used herein, DBA-1J mice were immunized with 100 µg bovine collagen type II in 100 µl of Complete Freund's Adjuvant (CFA) on Day 0 and Day 21 intradermally. At Day 24 post-immunization, mice were randomly divided into treatment groups. Animals were subcutaneously treated either with 6 mg/kg in 100 µl anti-ragweed IgG2a monoclonal antibody (control antibody) or with hamster-mouse chimeric anti-LTα antibody (S5H3), anti-LTα.Fc mutant, or murine TNFRII-Ig at 4 mg/kg in 100 PBS. Animals were treated three times weekly for the duration of the study. Limbs of animals were examined daily for signs of joint infiltration using a grading system of 1-4 for each joint, giving a maximum score of 16.

Figure 5A:
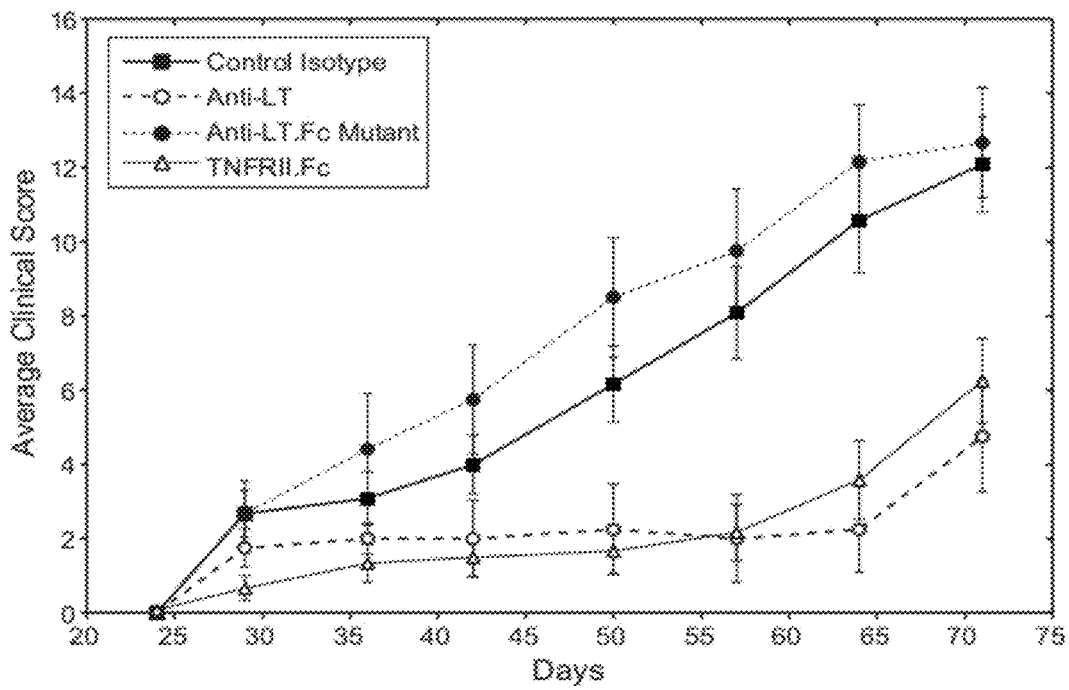
FIGS. 5A and 5B show that hamster-murine chimeric anti-LTα antibody S5H3 inhibits collagen-induced arthritis (CIA).

In a CIA-preventative model, the use of hamster-murine anti-LTα antibody S5H3 and TNFRII.Fc reduced the average clinical score over the period of days up through 70 days versus the anti-S5H3.DANA Fc mutant and isotype control (anti-ragweed IgG2a monoclonal antibody). See FIG. 5A, showing comparable efficacy in the CIA preventative murine model of the antibody S5H3 with TNFR.Ig.

Figure 5B:
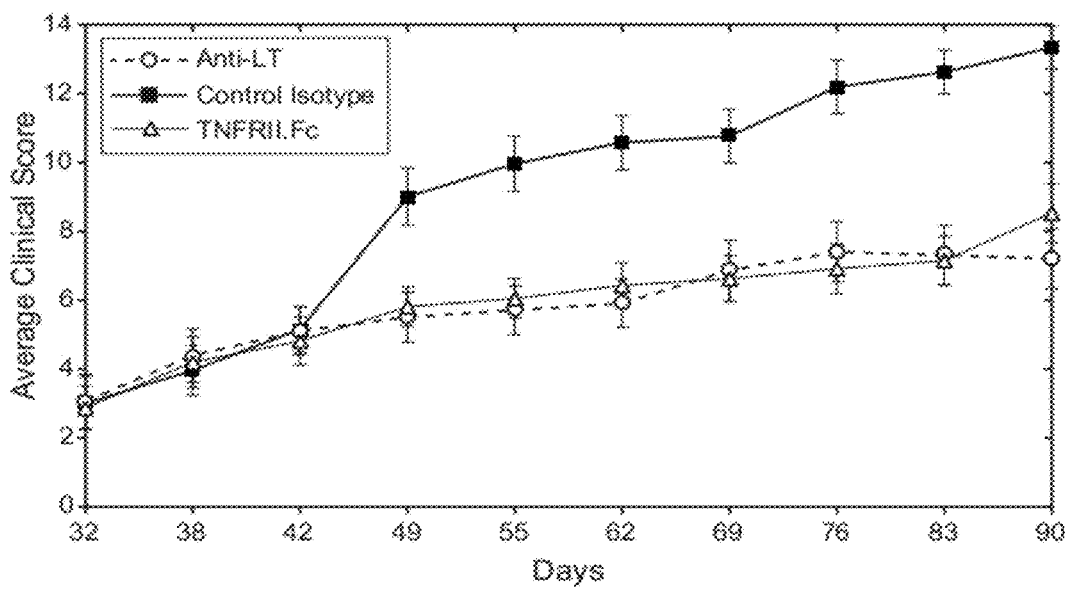

FIG. 5B shows comparable efficacy of the hamster-murine chimeric anti-LTα antibodies (S5H3) with TNFRII.Fc over 90 days in this therapeutic CIA murine model, which efficacy is far better than the isotype control in reducing average clinical score. These results along with those in FIG. 5A show that the antibodies herein are considered useful in preventing and being efficacious in autoimmune diseases such as RA. It is expected that the anti-LTα antibodies herein would be effective in preventing and treating RA in those who are non-responsive to TNF therapies in general, including TNFR.Ig and anti-TNFα antibodies, so that such non-responders could be treated with such antibodies prophylactically and efficaciously.

EXAMPLE 6

Anti-LTα Delays Onset and Severity of Encephalomyelitis (EAE) Disease in MBP-TCR Transgenic Mice Experimental autoimmune/allergic encephalomyelitis (EAE) is an inflammatory condition of the central nervous system with similarities to MS. In both diseases, circulating leukocytes penetrate the blood-brain barrier and damage myelin, resulting in impaired nerve conduction and paralysis. The EAE murine model (transgenic mouse preventative model) has been described as a model for human MS (Grewal et al., *Science,* 273:1864-1867 (1996)).

MBP$_{Acl-11}$ T-cell receptor transgenic mice (10-to-15 week-old male and female adult MBP-TCR transgenic mice bred from an animal breeding pair obtained from Dr. Richard Flavell, Howard Hughes Medical Institute, Yale University) were immunized with 10 μg of MBP$_{Acl-11}$ in 100 μl of CFA subcutaneously. On Days 1 and 2 all mice were additionally injected intraperitoneally with pertussis toxin at 200 ng/10 μl/mouse. On Day 0, mice (n=10/group) received either anti-gp120 IgG1 monoclonal antibody (control antibody) or hamster-mouse chimera anti-LTα antibody S5H3 at 6 mg/kg in 100 μl i.p. and then 6 mg/kg in 100 μl PBS s.c. three times weekly.

Animals were evaluated daily for clinical signs using the following grading system: 0—Normal mouse; no overt signs of disease; 1—Limp-tail or hind-limb weakness, but not both; 2—Limp-tail and hind-limb weakness; 3—Partial hind-limb paralysis; 4—Complete hind-limb paralysis; 5—Moribund.

Figure 6:
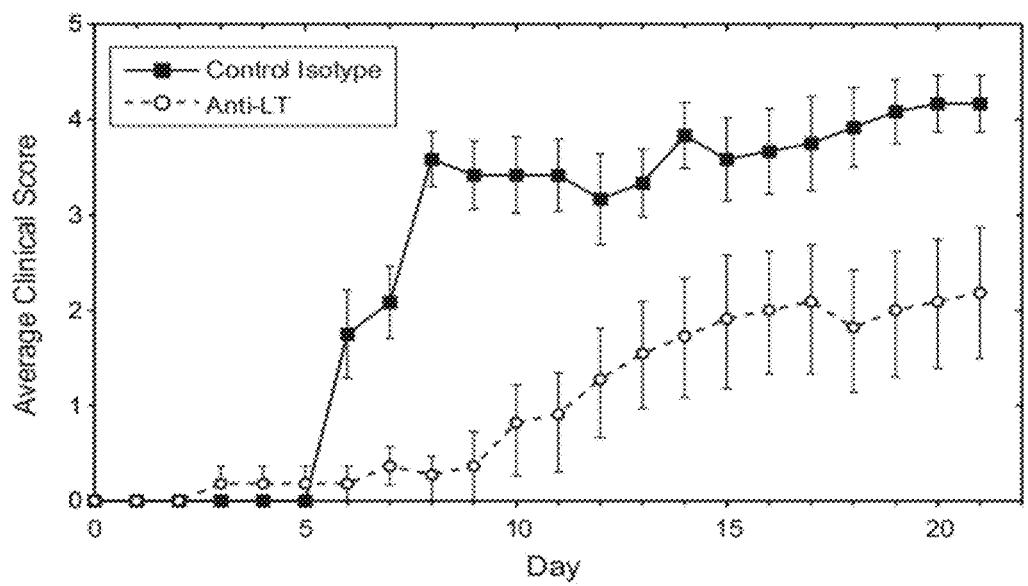
FIG. 6 shows that hamster-murine chimeric anti-LTα antibody S5H3 delays onset and severity of EAE disease in MBP-TCR transgenic mice, versus a control isotype (anti-gp120 IgG1 monoclonal antibody).

The results are shown in FIG. 6. The disease score was lower for the anti-LTα-treated mice than for the control group, only reaching clinical scores of 3 (versus clinical scores of over 4 for the control) during the study. The results show that the antibody S5H3 delayed onset and severity of EAE disease in these transgenic mice, suggesting that the antibody treatment protected the mice from developing overt EAE.

EXAMPLE 7

Anti-LTα Antibody Treatment Does Not Affect T-Cell-Dependent Antibody Isotype Responses, Indicating Safety The immune response to i.v.-injected trinitrophenol (TNP)-FICOLL™ is very high in most mouse strains, allowing one to assay the relative safety of an antibody administered to such mice by measuring various isotype levels in the mice.

BALB/c mice (n=12/group) were treated on Day 0 with either anti-ragweed isotype control, hamster-mouse anti-LTα antibody (S5H3), anti-LT.Fc mutant, or CTLA4-Fc (as a positive control) at 6 mg/kg in 100 μl PBS intra-peritoneally. Treatment continued three times per week for 5 weeks. Mice were immunized on Day 1 with TNP-OVA (100 μg) in 2 mg of alum per mouse intra-peritoneally, and on Day 29 with TNP-OVA (50 μg) in PBS per mouse intra-peritoneally. Serum was collected on Days 0, 14, and 35 for determination of the anti-TNP Ig isotypes IgM, IgG1, and IgG2a by standard ELISA.

Figure 7A:
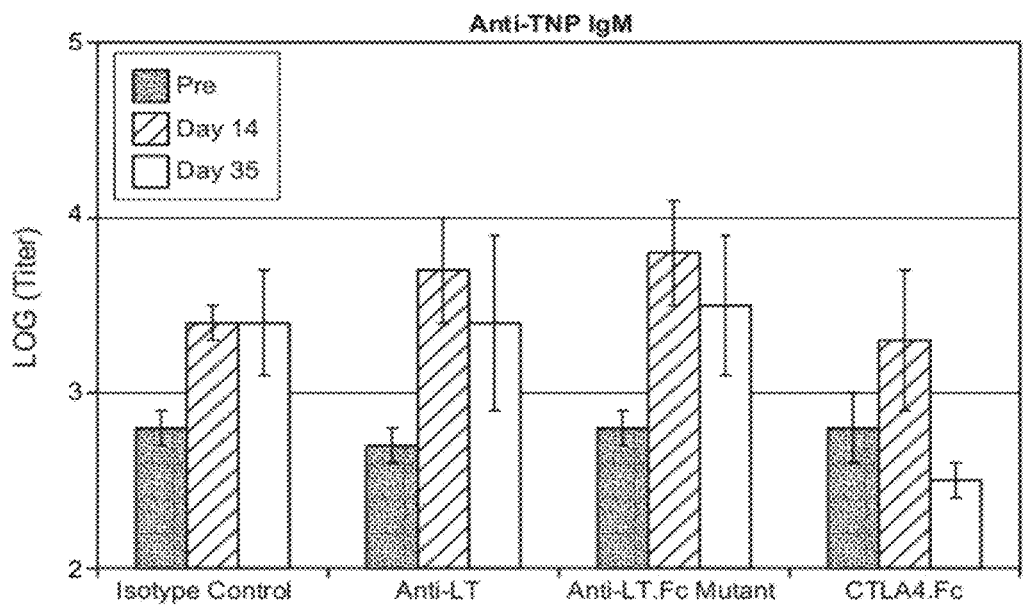
FIGS. 7A, 7B, and 7C show that treatment with hamster-murine chimeric anti-LTα antibody S5H3 does not affect the T-cell-dependent anti-TNP IgM, IgG1, and IgG2a responses, respectively, as compared to isotype control (anti-ragweed), anti-LT.Fc mutant, and CTLA4.Fc (a positive control).
Figure 7B:
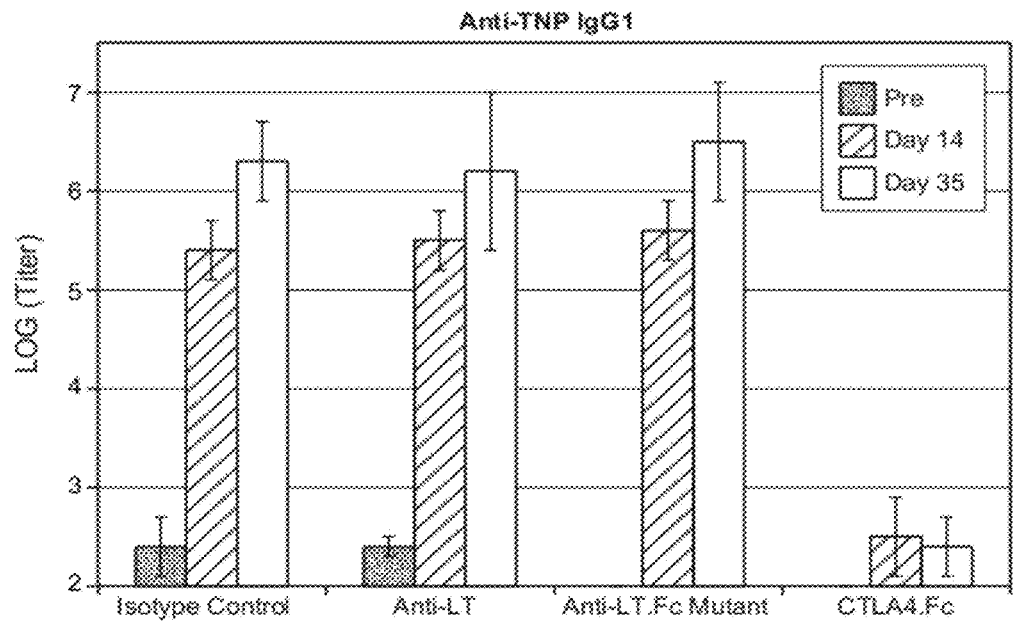
Figure 7C:
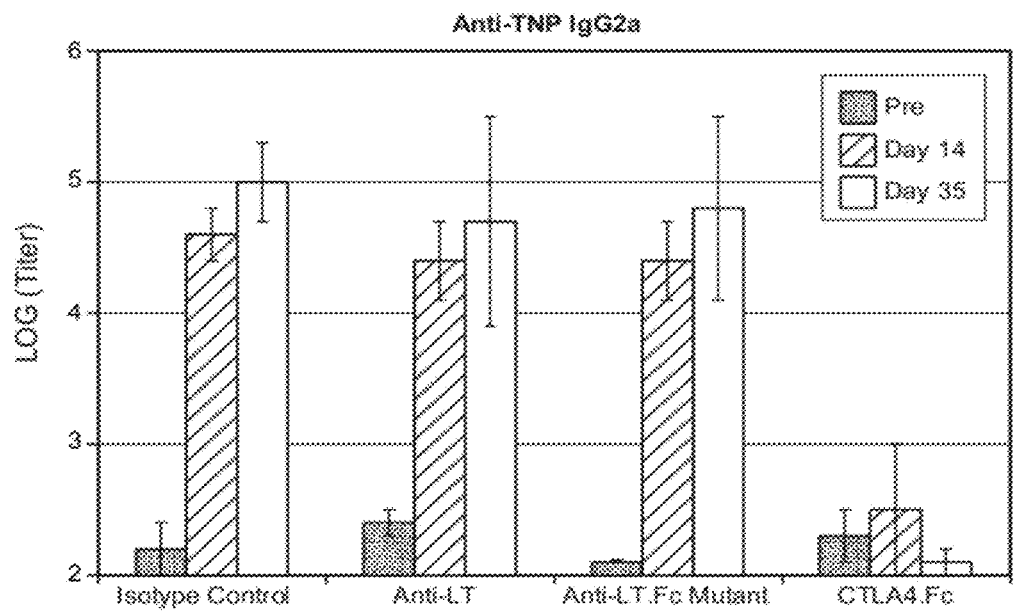

The results, shown in FIGS. 7A-7C, wherein the data are represented as Log 10 titers of anti-TNP IgM, IgG1, and IgG2a, respectively, indicate that the isotype control, S5H3 antibody, and DANA Fc mutant antibody exhibited similar patterns for each of the isotype levels, whereas the CTLA4.Fc immunoadhesin acted differently. This indicates that there would be little, if any, immune response in a patient to the administration of the S5H3 antibody herein.

EXAMPLE 8

Anti-LTα Antibody Treatment Does Not Affect T-Cell-Independent Antibody Isotype Responses, Indicating Safety BALB/c mice (n=10/group) were treated on Day 0 with either anti-ragweed (IgG2a isotype control), hamster-mouse anti-LTα antibody (S5H3), or TNFRII.Fc at 6 mg/kg in 100 μl PBS intra-peritoneally. Treatment continued three times per week for 10 days. Mice were immunized on Day 1 with TNP-FICOLL™ (100 μg) i.p. in 100 μl PBS intra-peritoneally. Serum was collected on Days 0 and 10 for determination of the anti-TNP Ig isotypes IgM, IgG1, IgG2a, and IgG3 by standard ELISA.

Figure 8:
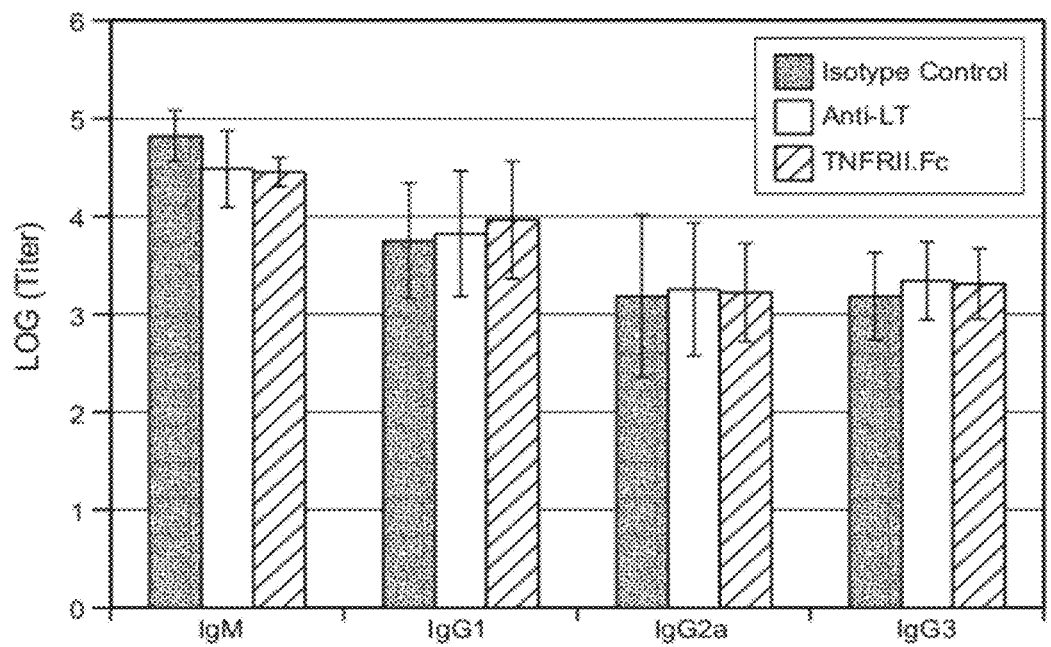
FIG. 8 shows that treatment with hamster-murine chimeric anti-LTα antibody S5H3 does not affect T-cell-independent antibody (IgM, IgG1, IgG2a, and IgG3) responses relative to isotype control (anti-ragweed) and TNFRII.Fc mutant.

FIG. 8, wherein the data are represented as Log 10 titers, shows that the isotype control, the S2C8 antibody, and the TNFRII.Fc immunoadhesin all behaved similarly for the IgM, IgG1, IgG2a, and IgG3 isotypes. This demonstrates further the safety of the antibodies herein for administration in vivo.

EXAMPLE 9

Anti-LTα Antibody Prevents Human SCID Graft-Versus-Host Disease (GVHD)

Graft-versus-host disease (GVHD) occurs when immuno-competent cells are transplanted into immunosuppressed or tolerant patients. The donor T cells recognize host antigens and become activated, secrete cytokines, proliferate, and differentiate into effector cells. This response is known as graft-versus-host-reaction (GVHR). The GVHR response is a multi-organ syndrome, and the effects can vary from life-threatening severe inflammation to mild cases of diarrhea and weight loss. GVHD models in mice have been used to model the clinical disorders of acute and chronic GVHR that occur after bone-marrow transplantation and autoimmune diseases. A general procedure is described in *Current Protocols in Immunology,* supra, unit 4.3.

SCID mice were reconstituted with human PBMCs purified from a LEUKOPACK™ (available from blood banks such as Interstate Blood Bank, Memphis, Tenn.) of a normal donor by FICOLL™ polysaccharide gradient. All mice (n=10/group) were sub-lethally irradiated with 350 rads using a Cesium 137 source. Two hours after irradiation, mice were injected with 50 million human PBMCs/mouse in 200 μl PBS intravenously. Immediately after cell injection, mice were treated i.p. either with 300 μg of trastuzumab (human IgG1 isotype control antibody), anti-LTα chimeric antibody 2C8, or CTLA4-Fc in 100 μl saline two times/week for three weeks. POLYMYXIN™ B (110 mg/liter) and NEOMYCIN™ (1.1 g/liter) antibiotics were added to the drinking water for five days post-irradiation. Mice were monitored for GVHD as indicated by survival.

Figure 9:
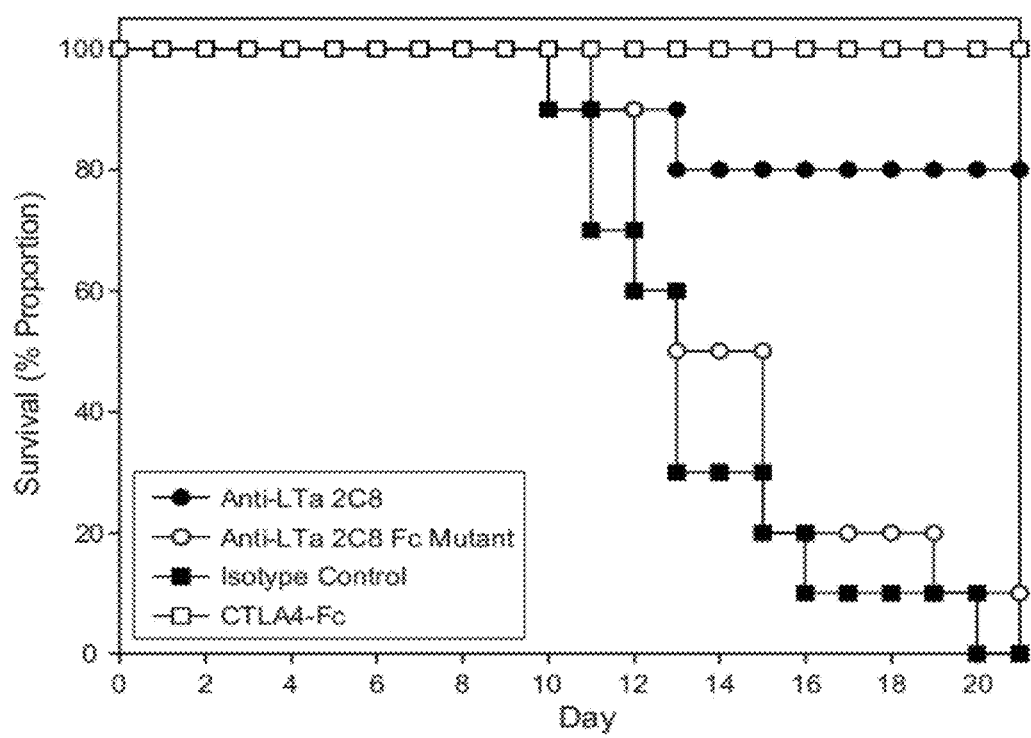
FIG. 9 shows that anti-LTα chimeric monoclonal antibody 2C8 prevents GVHD in human SCID mice as compared to the DANA anti-LTα 2C8 Fc mutant and the isotype control (trastuzumab, human IgG1). CTLA4.Fc mutant was also used as a positive control.

The results are shown in FIG. 9, and indicate that as compared to the isotype control, the 2C8 antibody significantly increased survival of the human SCID mice (preventing GVHD), as compared to anti-LTα 2C8 Fc mutant and the isotype control, with the CTLA4.Fc immunoadhesin being the best in this model of the molecules tested. Thus, the anti-LTα antibodies herein are expected to be useful in the prevention and/or treatment of graft-versus-host disease. Further, the results show that depletion of LTβ-positive cells is required for efficacy in this model, since the 2C8 Fc mutant (DANA) did not show efficacy.

EXAMPLE 10

Anti-LTα Monoclonal Antibodies Bind to LTα3

Microtiter wells were coated with 1 μg/ml human LTα3 in 50 mM carbonate buffer solution (100 μl/well) overnight. The unabsorbed solution was decanted from the wells. Wells were blocked with 150 μL PBS containing 5 mg/ml bovine serum albumin (PBS-BSA) for 1-2 hour. 100 μL of appropriately diluted test sample (anti-LTα chimeric antibody 2C8 or 3F12) diluted in PBS-BSA was added to each well, incubated for one hour, and washed with PBS containing 0.05% TWEEN™-20 surfactant. 100 μL of biotin-labeled rat anti-mouse IgG in PBS-BSA buffer was then added to each well and incubated for one hour. The plate was then washed with PBS/0.05% TWEEN™-20 surfactant, and streptavidin-horseradish peroxidase (SA-HRP) was added for 30 minutes to each well. Each well was washed with PBS/0.05% TWEEN™-20 surfactant, and bound HRP was measured with a solution of tetramethylbenzidine (TMB)/$H_2O_2$. After 15 minutes, the reaction was quenched by the addition of 100 μl of 1M phosphoric acid. The absorbance at 450 nm was read with a reference wavelength of 650 nm.

Figure 10A:
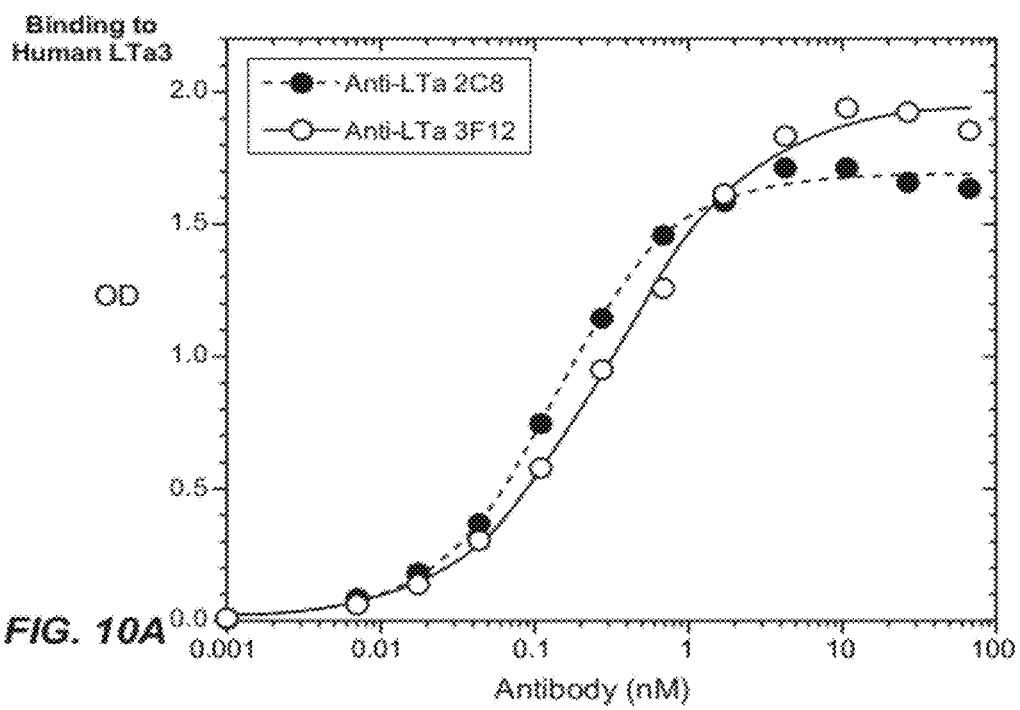
FIG. 10A shows that chimeric anti-LTα antibodies 2C8 and 3F12 bind to human LTα3.

FIG. 10A shows that chimeric anti-LTα antibodies 2C8 and 3F12 bound to human LTα3.

Figure 10B:
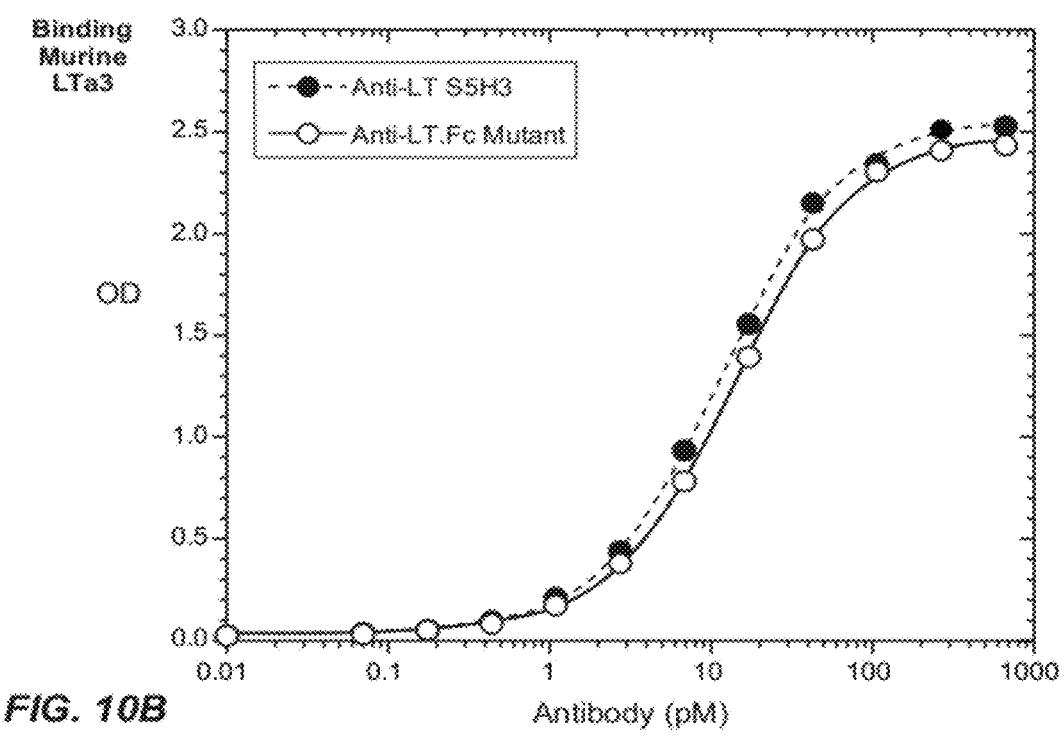
FIG. 10B shows that hamster-murine chimeric anti-LTα antibody S5H3 as well as anti-LT.Fc mutant bind to murine LTα3.

The above procedure was repeated using murine LTα3 instead of human LTα3 and hamster-mouse chimeric anti-LTα antibody S5H3 and anti-LT.Fc mutant as the antibody tested for binding ability. FIG. 10B shows that both S5H3 and the anti-LTα.Fc mutant bound to murine LTα3.

EXAMPLE 11

Anti-LTα Antibodies Bind to LTα1β2

For the LTαβ ELISA, microtiter wells were coated with 1 μg/ml murine LTα1β2 in 50 mM carbonate buffer solution (100 μl /well) overnight. The unabsorbed solution was decanted from the wells. Wells were blocked with 150 μL PBS containing 5 mg/ml bovine serum albumin (PBS-BSA) for 1-2 hours. 100 μL of an appropriately diluted test sample (anti-LTα chimeric antibody S5H3 or anti-LTα.Fc mutant diluted in PBS-BSA) was added to each well, incubated for one hour, and washed with PBS containing 0.05% TWEEN™ 20 surfactant. 100 μL of biotin-labeled rat anti-mouse IgG in PBS-BSA buffer was then added to each well and incubated for one hour. The plate was then washed with PBS/0.05% TWEEN™ 20 surfactant, and streptavidin-horseradish peroxidase (SA-HRP) was added for 30 minutes to each well. Each well was washed with PBS/0.05% TWEEN™ 20 surfactant, and bound HRP was measured with a solution of tetramethylbenzidine (TMB)/$H_2O_2$. After 15 minutes, the reaction was quenched by the addition of 100 μl of 1M phosphoric acid. The absorbance at 450 nm was read with a reference wavelength of 650 mm.

FIG. 11A shows that anti-LTα chimeric antibody S5H3 bound to the murine LTα1β2 complex, as did the anti-LT.Fc mutant.

A FACS assay was used to determine binding of anti-LTα antibody to the LTα on the surface of cells complexed with LTβ. For human LTαβ, 293 cells were transfected with full-length human LTα and human LTαβ (human LTα sequence GenBank Ref NM_000595; human LTβ sequence GenBank Ref NM_002341) to generate stable human LTαβ-expressing cell lines. Cells were incubated with 1-5 μg/ml of anti-LTα chimeric antibody 3F12 or 2C8, human LTβR.huIgG1, or huIgG1 isotype control (trastuzumab) for 20 minutes in PBS with 2% FBS. Cells were washed and incubated with anti-human Ig-PE secondary antibodies for detection.

For murine LTαβ, SVT2 cells were transfected with full-length murine LTα and murine LTαβ (murine LTα sequence GenBank Ref NM_010735; murine LTβ sequence GenBank Ref NM_008518) to generate stable murine LTββ-expressing cell lines. Surface LT was detected with hamster-murine chimera S5H3, anti-LT.S5H3.Fc mutant, muLTβR.IgG2a, or isotype control (anti-IL122 muIgG2a) directly conjugated to ALEXA-647™ fluorophore, for 20 minutes in PBS with 2% FBS. Cells were washed, aspirated, and resuspended in PBS with 2% FBS. Cells were analyzed on a FACSCALIBUR™ (dual laser) using CELLQUEST™ software, and results analyzed on a FLOWJO™ analyzer (Treestar).

FIG. 11B shows how well the chimeric anti-LTα antibodies 3F12 and 2C8 bound to the LTα on the surface of human cells complexed with LTβ. They are compared to LTβ-receptor.huIgG1 and isotype control huIgG1 (trastuzumab). All human antibodies bound surface LTα.

FIG. 11C shows how well hamster-murine anti-LTα antibody S5H3 bound to the LTα on the surface of murine cells complexed with LTβ. It is compared to LTβ-receptor murine IgG2a, anti-LT S5H$_3$Fc mutant, and isotype control (anti-IL122 muIgG2a). All murine antibodies bound surface LTα.

EXAMPLE 12

Anti-LTα Antibodies Bind to Human Th1, Th2, and Th17 Cells

When CD4+ T cells mature from thymus and enter into the peripheral lymph system, they usually maintain their naive phenotype before encountering antigens specific for their T cell receptor (Sprent et al., *Annu Rev Immunol.* 20:551-79 (2002)). The binding to specific antigens presented by APC, causes T cell activation. Depending on the environment and cytokine stimulation, CD4+ T cells differentiate into a Th1 or Th2 phenotype and become effector or memory cells (Sprent et al., supra and Murphy et al., *Nat Rev Immunol.* 2(12):933-44 (2000)). This process is known as primary activation. Having undergone primary activation, CD4+ T cells become effector or memory cells, they maintain their phenotype as Th1 or Th2. Once these cells encounter antigen again, they undergo secondary activation, but this time the response to antigen will be quicker than the primary activation and results in the production of effector cytokines as determined by the primary activation (Sprent et al., supra, and Murphy et al., supra).

For primary activation conditions, naïve T cells were activated by anti-CD3, anti-CD28, and specific cytokines depending on whether Th1 or Th2 was being examined. In particular, human Th1 and Th2 cell lines were generated by stimulating human PBMC with plate-bound anti-CD3 and anti-CD28 (10 μg/ml and 5 μg/ml, respectively; BD PharMingen). On Day 1, to induce Th2 differentiation, interleukin (IL)-4 (5 ng/ml; R&D Systems Inc.), anti-IL-12 (5 μg/ml; R&D Systems Inc., Minneapolis, Minn.), and anti-interferon (IFN)-gamma (5 μg/ml; R&D Systems Inc.) were added. For Th1 differentiation, on Day 1 IL-12 (1 ng/ml; R&D Systems Inc.), IFN-gamma (10 ng/ml; R&D Systems Inc.), and anti-IL-4 (1 μg/ml; R&D Systems Inc.) were added. Cells were restimulated twice at Days 7 and 14.

For FACS analysis cell-surface staining to determine binding of the antibodies to Th1 and Th2, two days after final stimulation, the activated human T-cells (Th1/Th2 cell lines) were incubated with anti-LTα antibody 2C8 (1 μg/ml), 3F12 (1 μg/ml), LTβR.Fc (1 μg/ml), TNFRII.Fc (1 μg/ml) or huIgG1 isotype control (1 μg/ml), all directly conjugated to ALEXA FLUOR® 647 fluorophore (Invitrogen Corp.), for 20 minutes in PBS with 2% FBS. Cells were washed, aspirated, and re-suspended in PBS with 2% FBS. Cells were analyzed on a FACSCALIBUR™ (dual laser) using CELLQUEST™ software, and results analyzed on a FLOWJO™ analyzer (Treestar).

Figure 12A:
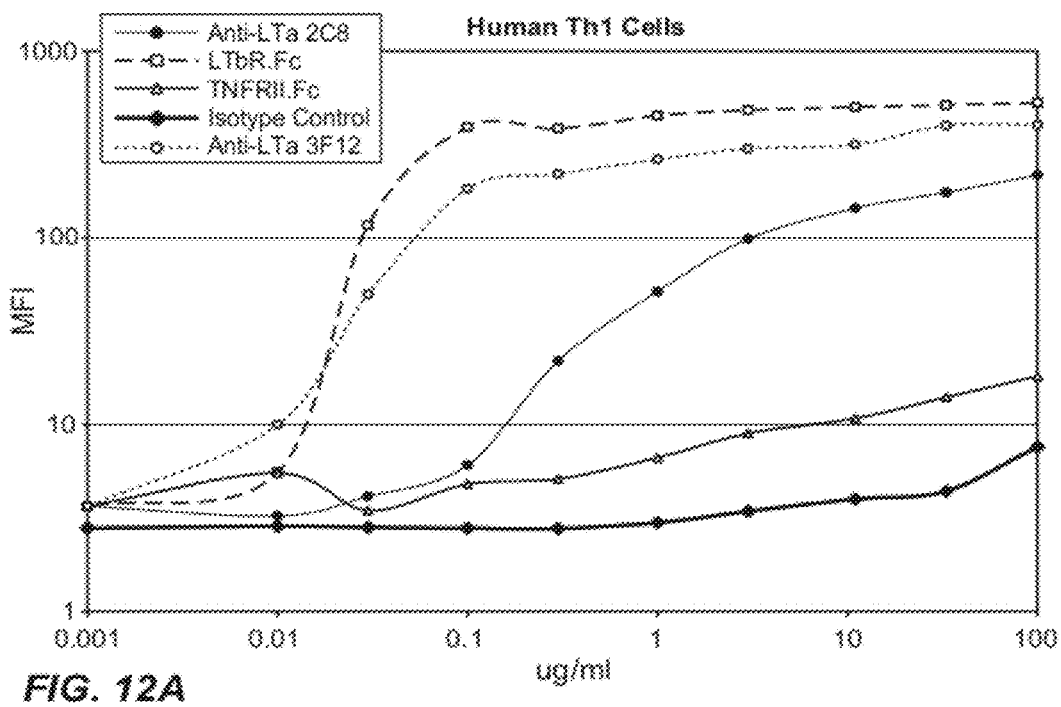
FIGS. 12A and 12B show that chimeric anti-LTα antibodies 2C8 and 3F12 bind to human Th1 and Th2 cells, respectively, and show binding results of LThR.Fc, TNFRII.Fc, and isotype control for comparison.
Figure 12B:
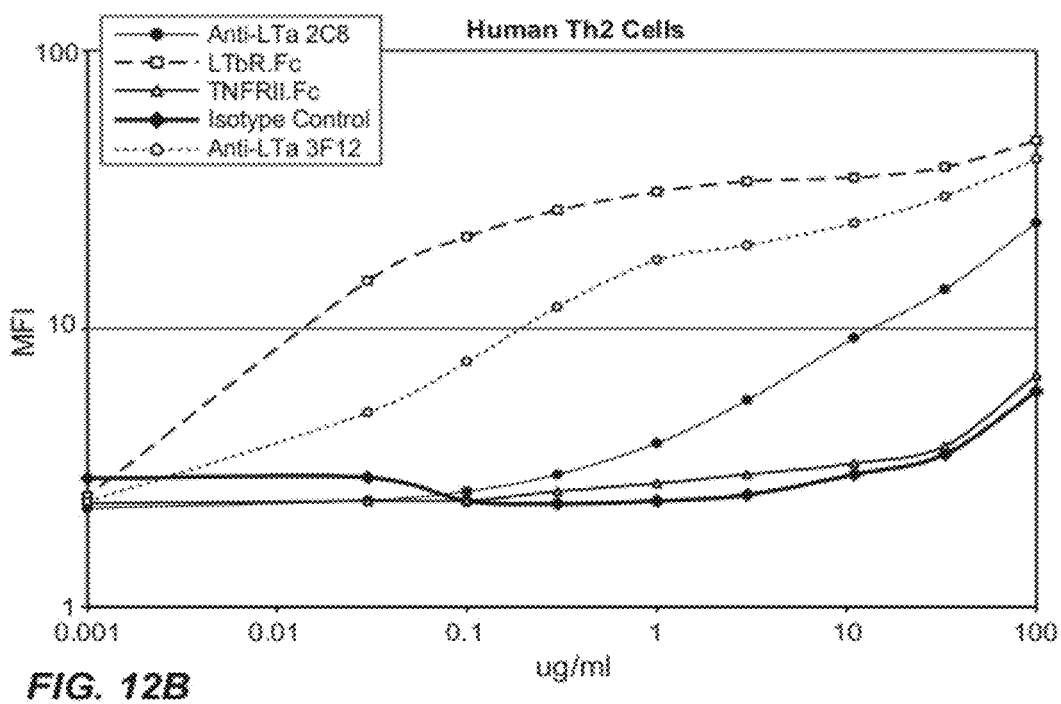

FIGS. 12A and 12B show that chimeric anti-LTα antibodies 2C8 and 3F12 bound to human Th1 and Th2 cells, respectively. The graphs also show the binding results for LTβR.Fc, TNFRII.Fc, and isotype control.

Since LT-α3 and LT-α1β2 were found to be expressed on human Th17 cells as well as human Th1 cells via FACS analysis, it would be expected that the anti-LTα antibodies herein, including chimeric 2C8, 2C8.v2, and 2C8.vX (described in Examples 3 and 18), would (similarly to Th1 and Th2) bind to human Th17 cells and hence be useful in treating many autoimmune diseases, including MS (they drive EAE in murine models) and lupus as well as RA and IBD, such as Crohn's disease and ulcerative colitis.

Figure 12C:
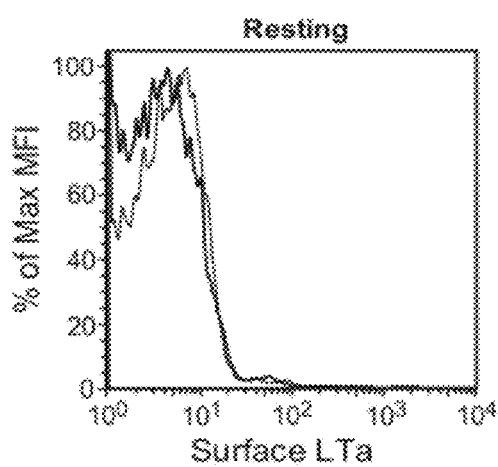
FIG. 12C-12E show that anti-LTα humanized antibody 2C8.vX does not bind to resting cells (FIG. 12C), but does bind to human Th1 and Th17 cells (FIGS. 12D and E, respectively), with a comparison of its binding with that of isotype control.
Figure 12D:
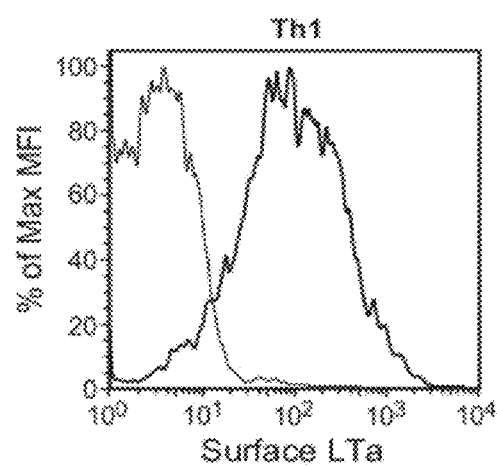
Figure 12E:
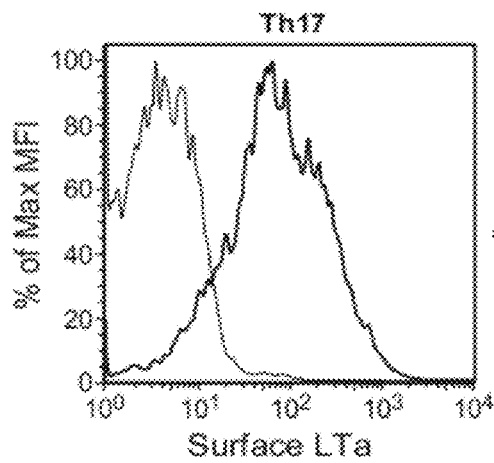

Hence, the same experiment described above was performed, except for using anti-LTα humanized antibody 2C8.vX as the LTα antibody and using a Th17 cell line as well as the Th1 cell line, but not a Th2 cell line. The human Th17 cell lines were generated by stimulating human PBMC with anti-CD3 and anti-CD28 as noted above and with IL-23 (10 ng/ml; R&D Systems Inc.), anti-IFN-gamma (10 μg/ml; R&D Systems Inc.), and anti-IL-12 (10 μg/ml; R&D Systems Inc.). This experiment showed that, in fact, antibody 2C8.vX bound to human Th17 cells as well as human Th1 cells, but not to resting cells. See FIG. 12C-E.

EXAMPLE 13

Anti-LTα Antibodies Bind to Human Cells: T, B and NK A

A FACS assay was used to determine binding of anti-LTα antibodies to the LTα on the surface of primary human cells. Human PBMC were isolated and activated with anti-CD3 and anti-CD28 (10 μg/ml and 5 μg/ml, respectively; BD PharMingen) for two days for activated CD4 and CD8 cells; or anti-IgM (10 μg/ml, R&D Systems Inc.) and IL-4 (20 ng/ml; R&D Systems Inc.) for two days for B cells. NK CD56+ cells were isolated by negative selection (Miltenyi Biotec) and incubated with IL-15 (20 ng/ml; R&D Systems Inc.) for 15 hours.

For FACS analysis, cells were incubated with chimeric anti-LTα antibody 3F12 (1 μg/ml), human LTβR.huIgG1 (1 μg/ml), or huIgG1 isotype control (trastuzumab, 1 μg/ml), all directly conjugated to ALEXA FLUOR® 647 fluorophore (Invitrogen Corp.), for 20 minutes in PBS with 2% FBS. Cells were washed, aspirated, and re-suspended in PBS with 2% FBS. Cells were analyzed on a FACSCALIBUR™ (dual laser) using CELLQUEST™ software, and results analyzed on a FLOWJO™ analyzer (Treestar).

Figure 13A:
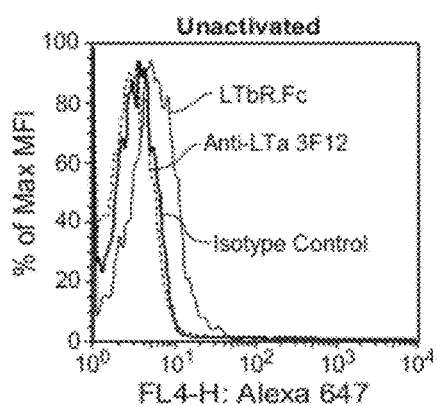
FIG. 13A shows unactivated T cells treated with LTbR.Fc (solid line), chimeric anti-LTα 3F12 antibody (dashed line), and isotype control (shaded area).
Figure 13B:
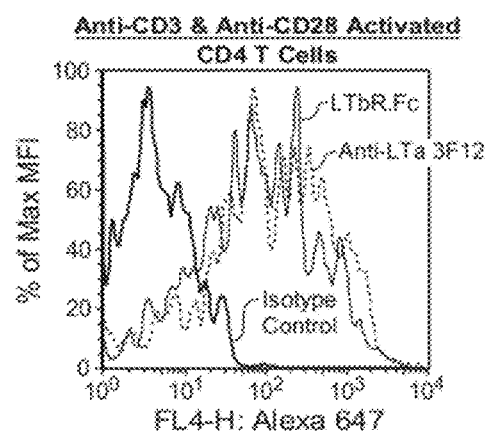
FIG. 13B shows anti-CD3- and anti-CD28-activated CD4 T cells treated with the reagents of FIG. 13A.
Figure 13C:
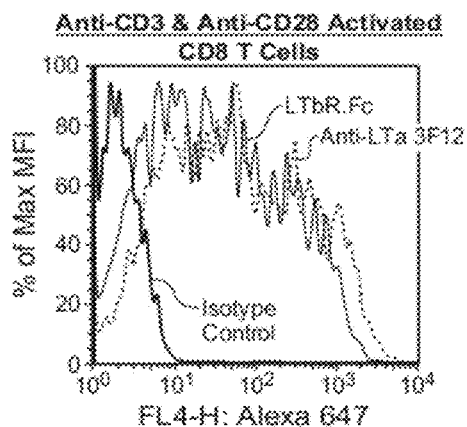
FIG. 13C shows anti-CD3- and anti-CD28-activated CD8 T cells treated with the reagents of FIG. 13A.
Figure 13D:
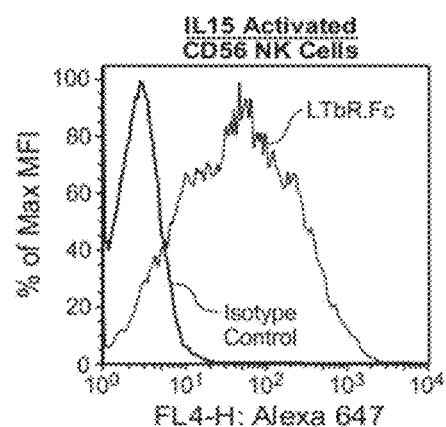
FIG. 13D shows IL15-activated CD56 NK cells treated with the reagents of FIG. 13A.
Figure 13E:
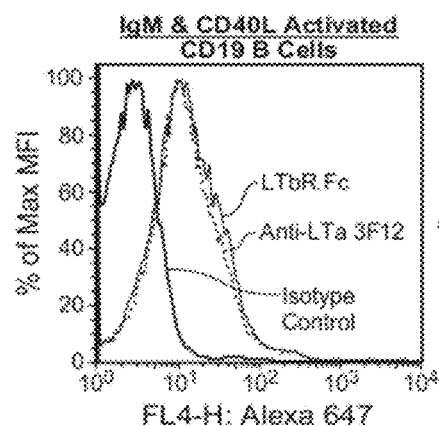
FIG. 13E shows IgM- and CD40L-activated CD19 B cells treated with the reagents of FIG. 13A.

FIGS. 13A-13E show that the antibodies bound to the cells, versus the isotype control. FIG. 13A represents the unactivated cells, FIG. 13B shows the anti-CD3 and anti-CD28-activated CD4 T cells, FIG. 13C shows the CD8 T cells, FIG. 13D shows the IL15-activated CD56 NK cells, and FIG. 13E shows the IgM and CD40L-activated CD19 B cells.

EXAMPLE 14

Anti-LTα Monoclonal Antibodies Functionally Block LTα3

1. Blocking of Human and Murine LTα3

Microtiter wells were coated with 0.7 μg/ml human TNFRII.huIgG1 (ENBREL®) in 50 mM carbonate buffer solution (100 μl/well) overnight. The unabsorbed solution was aspirated from the wells. Biotinylated LTα3 (murine or human) was captured and detected with streptavidin-horseradish peroxidase (HRP). For neutralization of human LTα3, increasing doses of chimeric anti-LTα antibodies 2C8 or 3F12 or control isotype (trastuzumab) were preincubated with the LTα3 at indicated concentrations for one hour before adding to the coated microplate. The same procedure was carried out for neutralization of murine LTα3 using the hamster-mouse chimeric anti-LTα antibody S5H3 or anti-LT.Fc mutant or control isotype (trastuzumab). Each well was washed with PBS/0.05% TWEEN™ 20 surfactant, and bound HRP was measured with a solution of tetramethylbenzidine (TMB)/$H_2O_2$. After 15 minutes, the reaction was quenched by the addition of 100 μl of 1M phosphoric acid to each well. The absorbance at 450 nm was read with a reference wavelength of 650 nm.

Figure 14A:
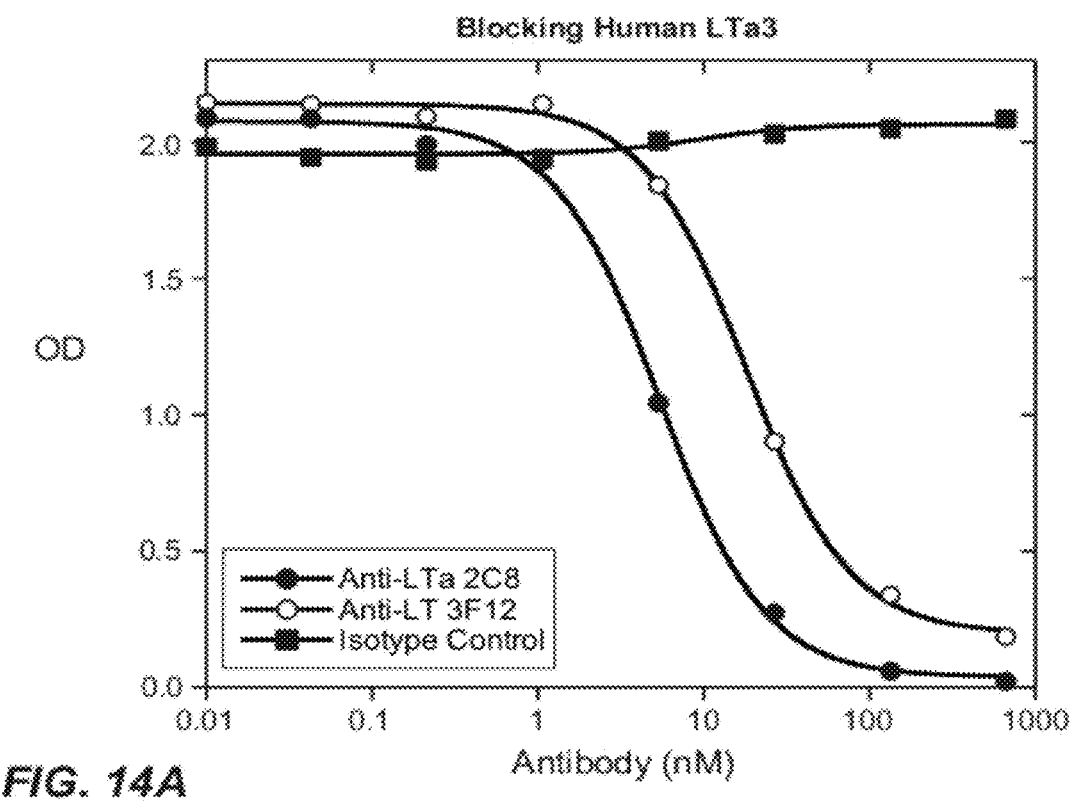
FIG. 14A shows that chimeric anti-LTα antibodies 2C8 and 3F12 functionally block human LTα3 versus the isotype control (trastuzumab).
Figure 14B:
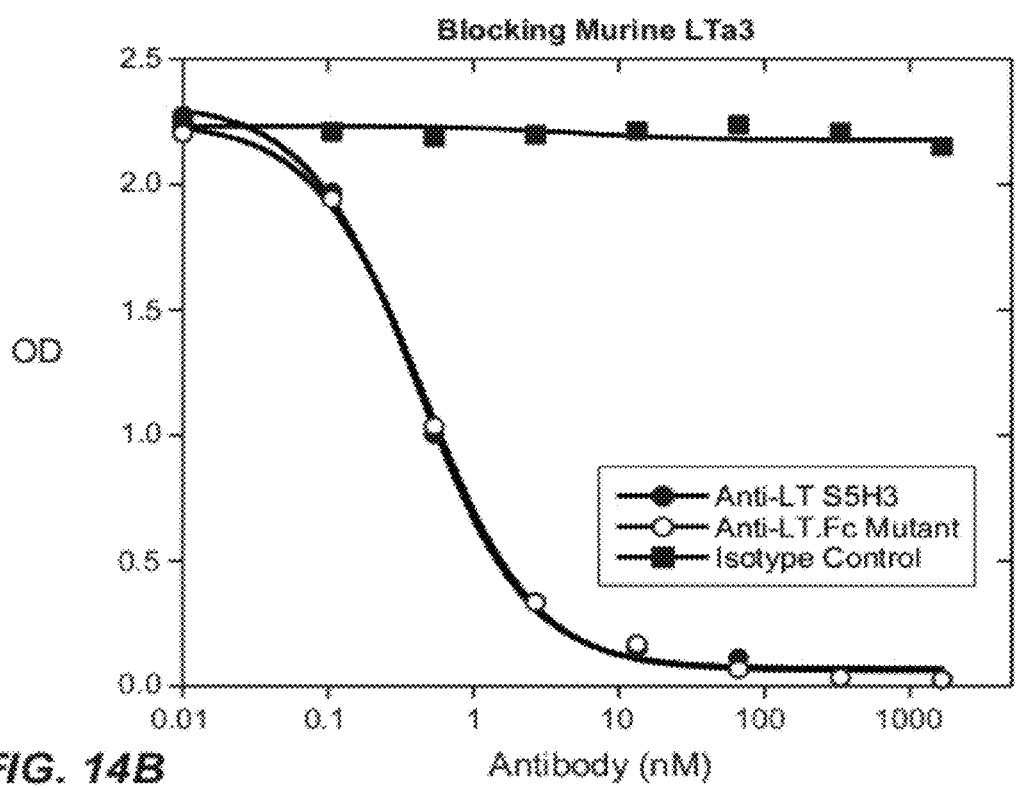
FIG. 14B shows that hamster-murine chimeric anti-LTα antibody S5H3 and the anti-LT.Fc mutant functionally block murine LTα3 versus the isotype control (trastuzumab).

FIG. 14A shows that anti-LTα antibodies 2C8 and 3F12 functionally blocked human LTα3 versus the isotype control. FIG. 14B shows that anti-LTα antibody S5H3 and the anti-LT.Fc mutant functionally blocked murine LTα3 versus the isotype control.

2. Blocking of LTα3-Induced IL-8 in A549 Cells

Epithelial cell lines (A549) were cultured in the presence of LTα3 for 24 hours. Neutralization of the effect of LTα3 with chimeric anti-LTα antibodies 2C8 and 3F12 was determined by serial dilutions of the anti-LTα antibodies (10-0 μg/ml) added to the appropriate wells. Supernatant was used to detect IL-8 in a standard ELISA.

Figure 14C:
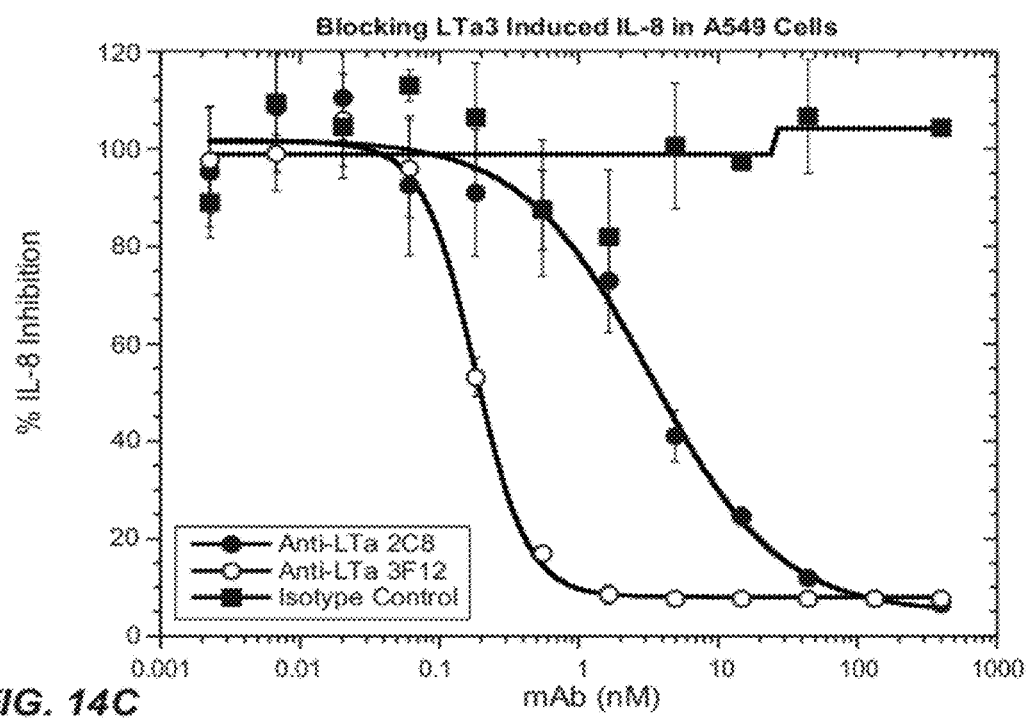
FIG. 14C shows that chimeric anti-LTα antibodies 2C8 and 3F12 block LTα3-induced IL-8 in A549 cells versus the isotype control (trastuzumab).

FIG. 14C shows that chimeric anti-LTα antibodies 2C8 and 3F12 blocked LTα3-induced IL-8 in A549 cells versus the isotype control (trastuzumab IgG1).

3. Blocking of LTα3-Induced ICAM Expression on HUVEC

HUVEC cells were cultured in the presence of LTα3 for 24 hours. Neutralization of the effect of LTα3 with chimeric anti-LTα antibodies 2C8 and 3F12 was determined by serial dilutions of the anti-LTα antibodies (10-0 μg/ml) added to the appropriate wells. Cell-surface expression of ICAM-1 was determined by FACS, shown as mean fluorescent intensity. TNFRII.Fc was used as a control.

Figure 14D:
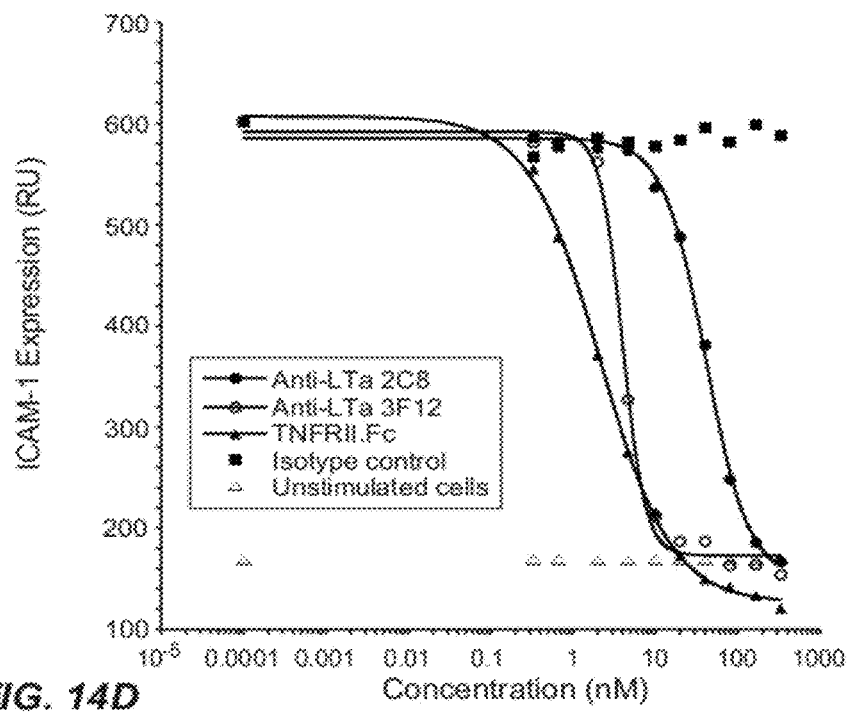
FIG. 14D shows that chimeric anti-LTα antibodies 2C8 and 3F12, as well as TNFRII.Fc mutant, block LTα3-induced ICAM expression on HUVEC versus isotype control (trastuzumab). The response of unstimulated cells is also shown.

FIG. 14D shows that anti-LTα antibodies 2C8 and 3F12, as well as the TNFRII.Fc mutant, blocked LTα3-induced ICAM expression on HUVEC versus the isotype control (trastuzumab IgG1). The effect on unstimulated cells is also shown.

4. Blocking of LTα3-Induced NFkB Activation

To determine if anti-LTα antibodies block signaling of LTα3 through the TNF receptors, 293 cell-lines were cultured in DMEM:F12 50:50 (+10% FBS, glutamine, P/S) to 75% confluency. Cells were transfected with a standard NFkB-RE-luciferase reporter construct using standard transfection techniques (Fugene). After 24 hours, the cells were washed, and then stimulated with LTα3 (100 ng/ml) or with serial dilutions of the chimeric anti-LTα antibody 2C8 (10-0 μg/ml) that were preincubated with LTα3 for 30 minutes. After six hours, the cells were washed with PBS, and luciferase activity was measured as follows: LYSIS BUFFER™ (Promega, 125 μl/well) was added for 15 minutes. Lysates were collected and transferred at 20 μl/well to a 96-well assay plate (high-binding, white polystyrene, COSTAR™) in triplicates and read in a LMAXII™ plate reader (Molecular Devices) after injection of LUCIFERASE ASSAY REAGENT™ and STOP AND GLO BUFFERS™ (Promega). The isotype control used was trastuzumab IgG1.

Figure 14E:
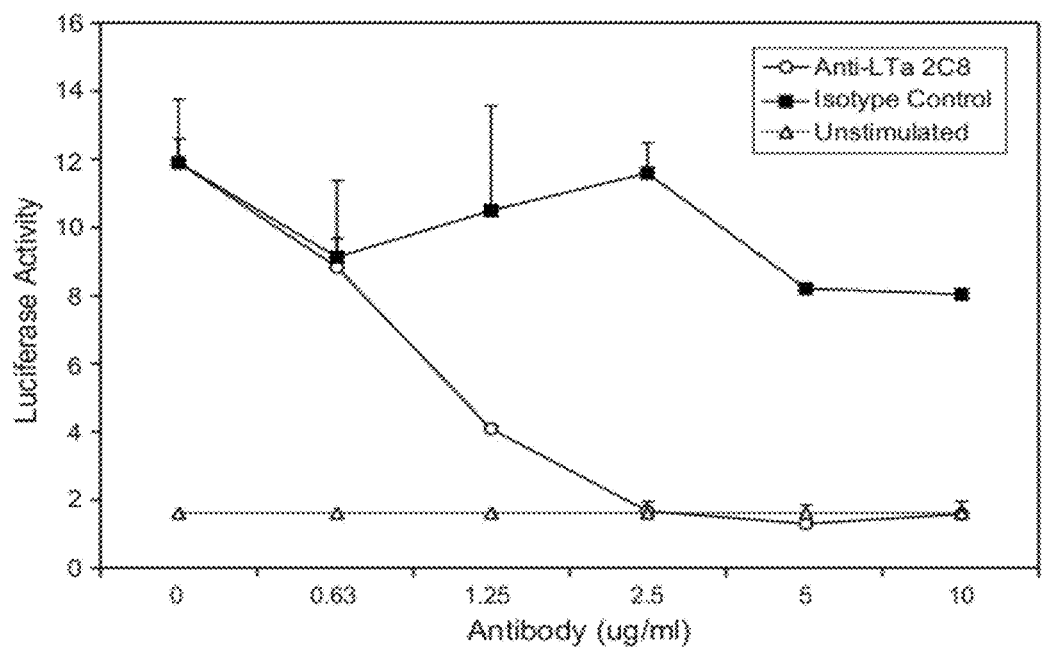
FIG. 14E shows that chimeric anti-LTα antibody 2C8 blocks LTα3-induced NFkB activation, versus the isotype control. The response of unstimulated cells is also shown.

FIG. 14E shows that the anti-LTα antibody 2C8 blocked LTα3-induced NFkB activation, versus the isotype control. The effect on unstimulated cells is also shown.

EXAMPLE 15

Anti-LTα Antibodies Functionally Block LTα1β2

1. Blocking of LTα-Induced NFkB Activation

To determine if anti-LTα antibody blocks signaling of LTα1β2 through the LTβR, 293 cell lines were cultured in DMEM:F12 50:50 (+10% FBS, glutamine, P/S) to 75% confluency. Cells were transfected with standard NFkB-RE-luciferase reporter construct using standard transfection techniques (Fugene). After 24 hours, the cells were washed, and then stimulated with LTα1β2 (R&D Systems Inc.; 100 ng/ml) or with serial dilutions of the chimeric anti-LTα antibody 2C8 (10-0 µg/ml) that were preincubated with LTαβ for 30 minutes. After six hours, the cells were washed with PBS, and luciferase activity was measured as follows: LYSIS BUFFER™ (Promega, 125 µl/well) was added for 15 minutes. Lysates were collected and transferred at 20 µl/well to a 96-well assay plate (high-binding, white polystyrene, COSTAR™) in triplicates and read in a LMAXII™ plate reader (Molecular Devices) after injection of LUCIFERASE ASSAY REAGENT™ and STOP AND GLO BUFFERS™ (Promega). The isotype control used was trastuzumab IgG1.

Figure 15A:
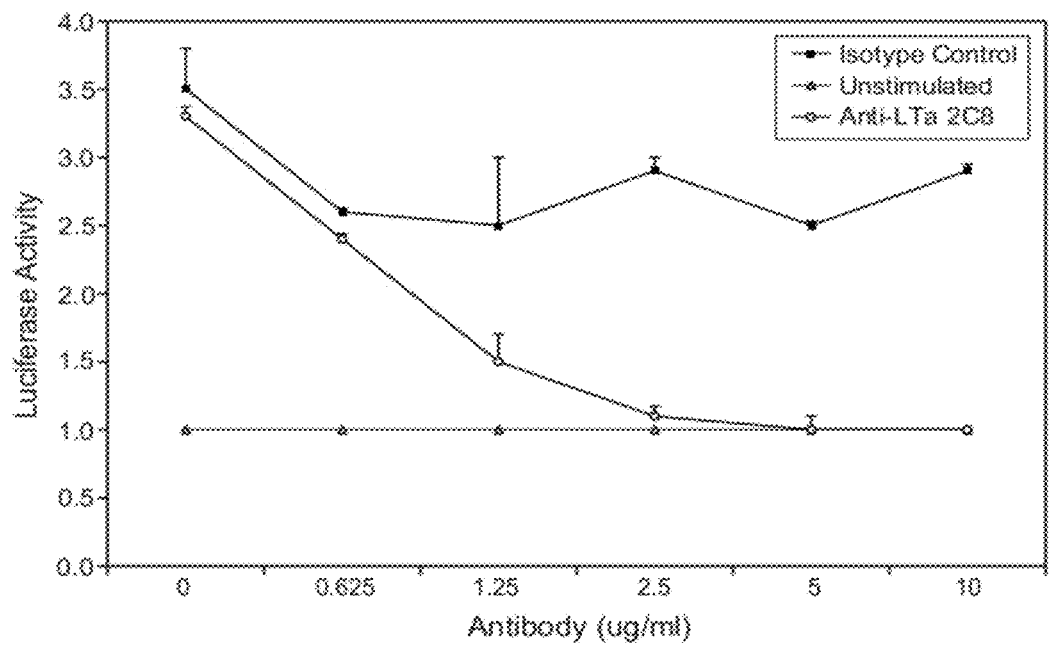
FIG. 15A shows that chimeric anti-LTα antibody 2C8 functionally blocks LTα1β2-induced NFkB activation versus the isotype control. The response of unstimulated cells is also shown.

FIG. 15A shows that anti-LTα antibody 2C8 functionally blocked LTα1β2-induced NFkB activation, versus the isotype control. The response of unstimulated cells is also shown.

2. Blocking of LTα3-, LTα2β1-, and LTα1β2-Induced Cytotoxicity

Test samples were assayed for ability to neutralize the cytolytic activity of LTα3, LTα2β1, and LTα1β2 (R&D Systems Inc.) in a murine L929 cytotoxic assay. L929 cells were cultured in microtiter plates in the presence of one of the three LTα reagents (at the doses indicated in FIGS. 15B-D) and the DNA inhibitor actinomycin-D. Neutralizing chimeric anti-LTα antibody 2C8 was added to the cultures at 10 µg/ml. Cell lysis was determined by standard ALAMARBLUE™ stain of viable cells and represented as relative fluorescence units (RFU).

Figure 15B:
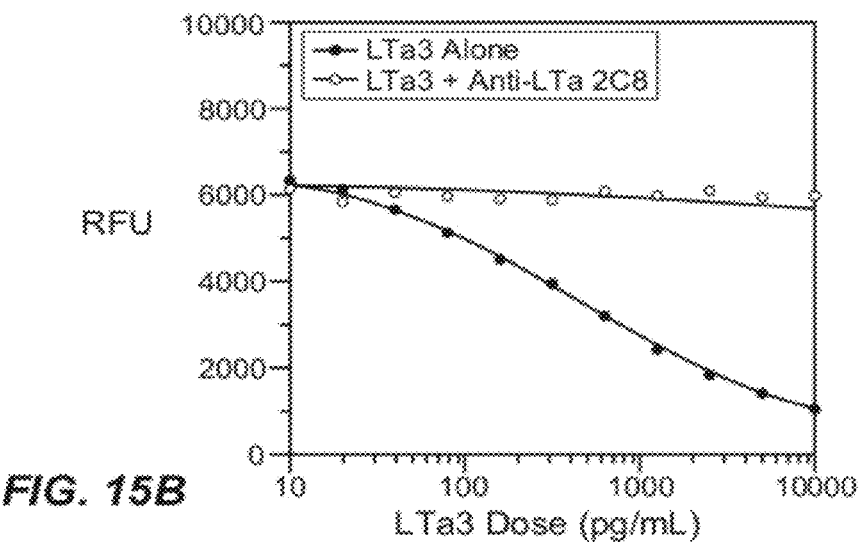
FIGS. 15B, 15C, and 15D show that chimeric anti-LTα antibody 2C8 blocks, respectively, LTα3-, LTα2β1-, and LTα1β2-induced cytotoxicity.
Figure 15C:
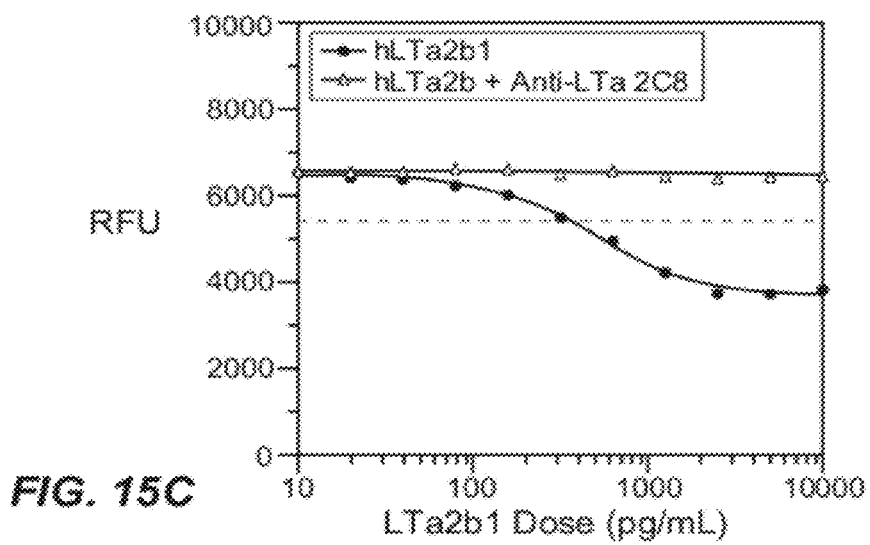
Figure 15D:
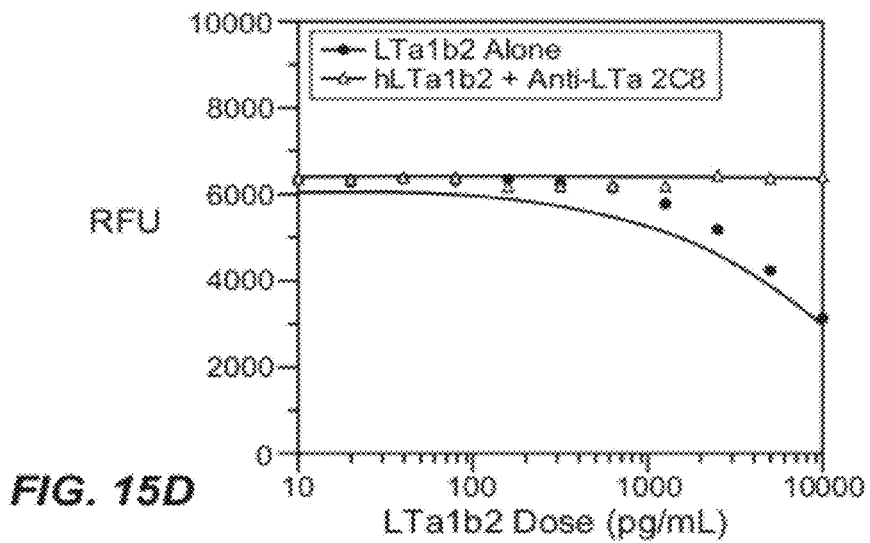

FIGS. 15B, 15C, and 15D show that chimeric anti-LTα antibody 2C8 blocked, respectively, LTα3-, LTα2β1-, and LTα1β2-induced cytotoxicity.

3. Blocking of LTα 1β2-Induced ICAM Expression on HUVEC

HUVEC cells were cultured in the presence of LTα 1β2 (R&D Systems Inc.) for 24 hours. Neutralization of the effect of LTα1β2 with anti-LTα antibodies was determined by serial dilutions of chimeric anti-LTα antibodies 2C8 and 3F12 (10-0 µg/ml) added to the appropriate wells. Cell-surface expression of ICAM-1 was determined by FACS.

Figure 15E:
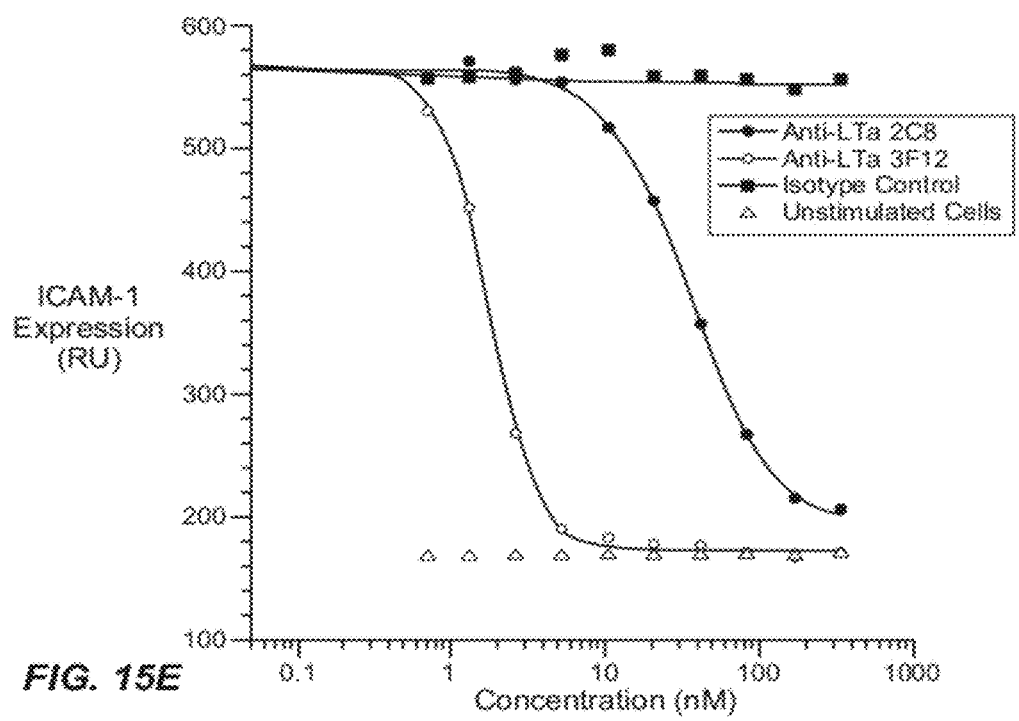
FIG. 15E shows that chimeric anti-LTα antibodies 2C8 and 3F12 block LTα1β2-induced ICAM expression on HUVEC, versus the isotype control. The response of unstimulated cells is also shown.

FIG. 15E shows that chimeric anti-LTα antibodies 2C8 and 3F12 blocked LTα1β2-induced ICAM expression on HUVEC, versus the isotype control (trastuzumab IgG1). The effect on unstimulated cells is also shown.

EXAMPLE 16

Anti-LTα Monoclonal Antibody can Kill LTαβ-Expressing Cells

An ADCC assay was performed in a microtiter plate in duplicate as follows. NK cells were isolated from 100 ml of normal human donor whole blood using negative selection (ROSETTESEP™, #15065, StemCell Technologies). The assay diluent was RPMI™ 1640 and 0.25 mg/mL BSA. Chimeric antibody 2C8 and the Fc mutant thereof, in a serial dilution starting at 100 nM in 50 µl, were incubated with 50 µl of stable 293 cells expressing human LTαβ (20,000) (see Example 11 for details) for 30 minutes at room temperature. 50 µL of NK cells (120,000) were added and incubated for an additional four hours at 37° C. Plates were centrifuged at 1500 rpm for 10 minutes, and 100 µl of supernatant was transferred to a 96-flat-bottom microwell plate. The level of cell lysis was determined by measuring the amount of lactate dehydrogenase (LDH kit, #1-644-793, Roche) released from lysed cells. 100 µl of LDH kit reaction mixture was added to 100 µl of supernatant and incubated for up to 30 minutes. Plates were read at 490 nm. Controls included target:effector cells in the absence of antibody (for antibody-independent lysis), target cells alone with 1% TRITON X-100™ surfactant (for total lysis), and antibody ADCC negative and positive controls.

Figure 16:
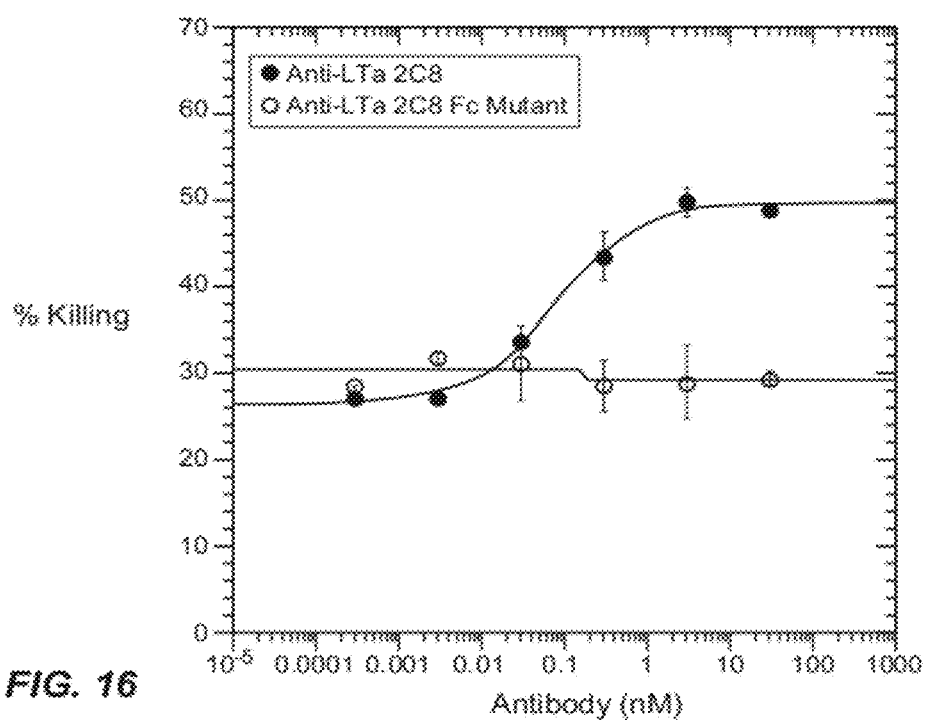
FIG. 16 shows that chimeric anti-LTα antibody 2C8 can kill LTαβ-expressing cells, versus anti-LTα 2C8 Fc mutant.
Figure 17A:
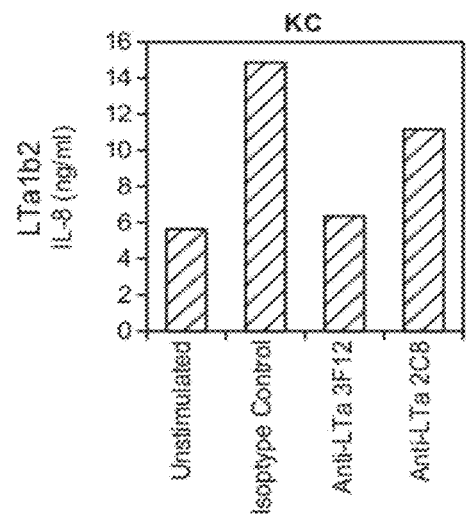
FIG. 17A-H show that chimeric anti-LTα antibody 2C8 blocks cytokine and chemokine secretion in HUVEC cells, with FIGS. 17A-17D respectively showing KC/IL-8, RANTES, IP10, and IL-6 with LTα1β2, and FIGS. 17E-17H respectively showing KC/IL-8, RANTES, IP10, and IL-6 with LTα3 versus control.
Figure 17B:
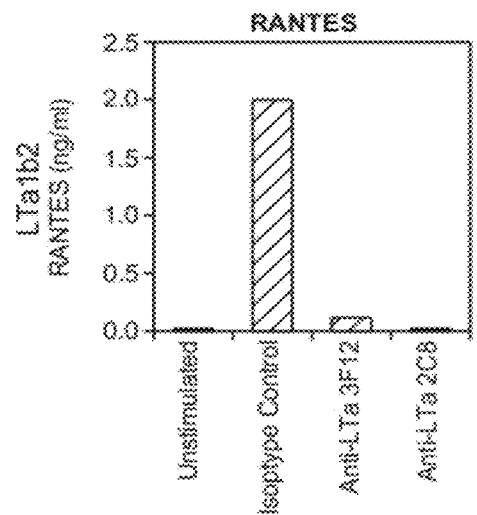
Figure 17C:
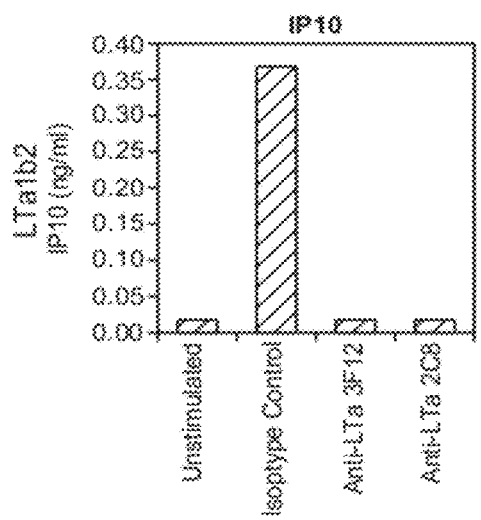
Figure 17D:
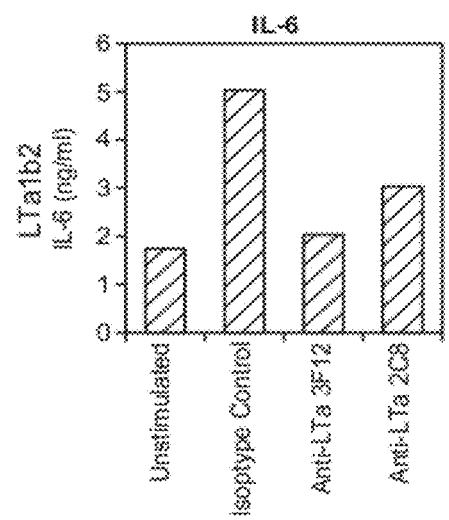
Figure 17E:
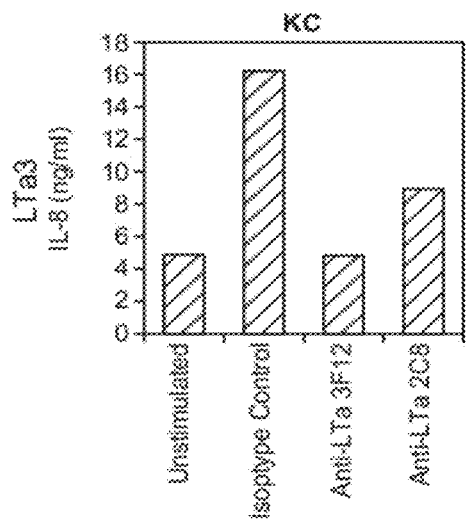
Figure 17F:
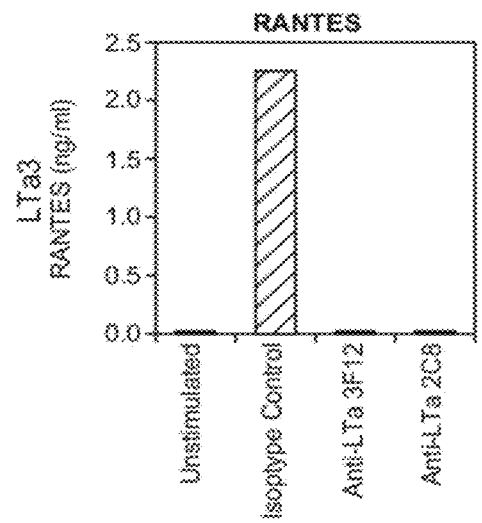
Figure 17G:
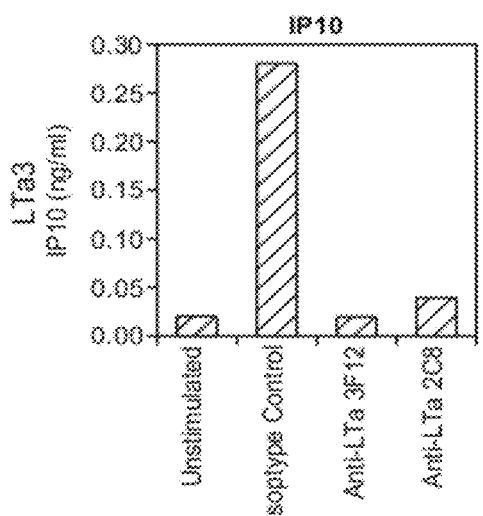
Figure 17H:
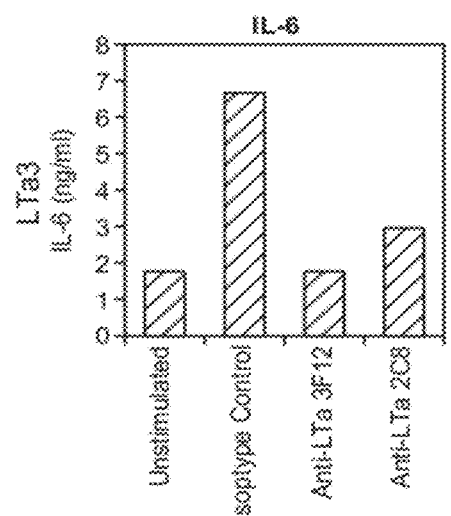
Figure 17I:
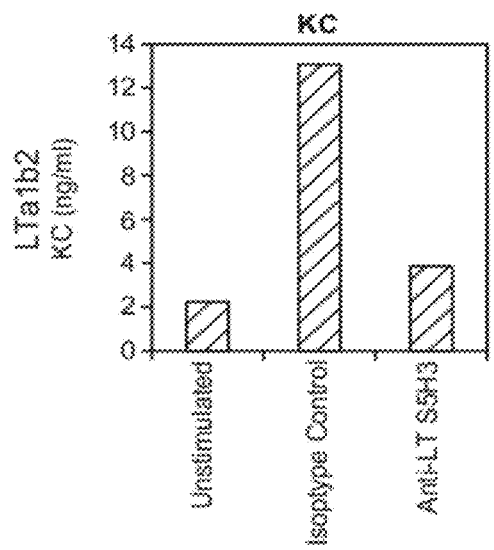
FIG. 17I-P show that hamster-murine chimeric anti-LTα antibody S5H3 blocks cytokine and chemokine secretion in 3T3 cells, with FIGS. 17I-17L respectively showing KC, RANTES, IP10, and IL-6 with LTα1β2, and FIGS. 17M-17P respectively showing KC, RANTES, IP10, and IL-6 with LTα3 versus control.
Figure 17J:
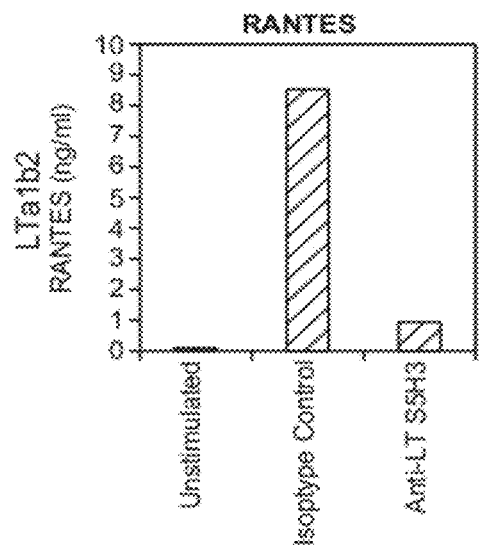
Figure 17K:
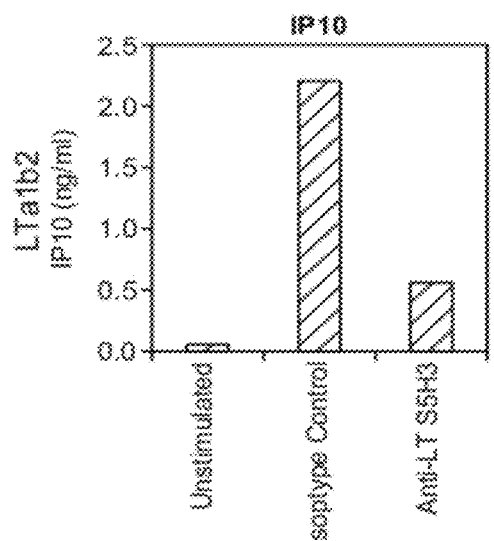
Figure 17L:
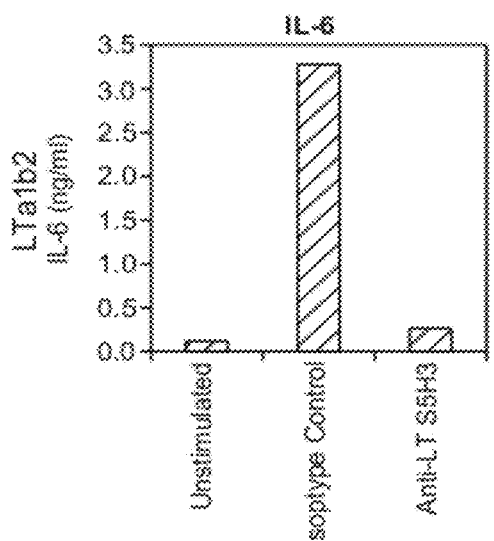
Figure 17M:
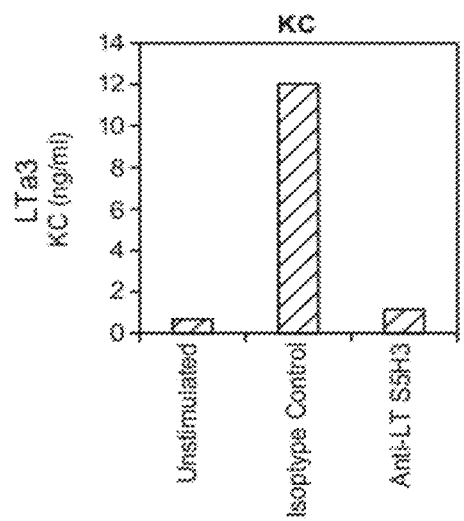
Figure 17N:
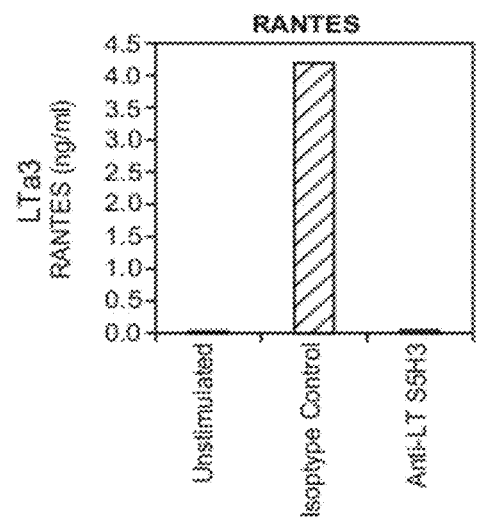
Figure 17O:
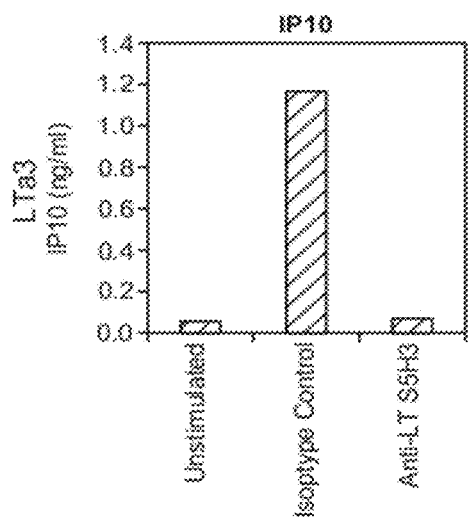
Figure 17P:
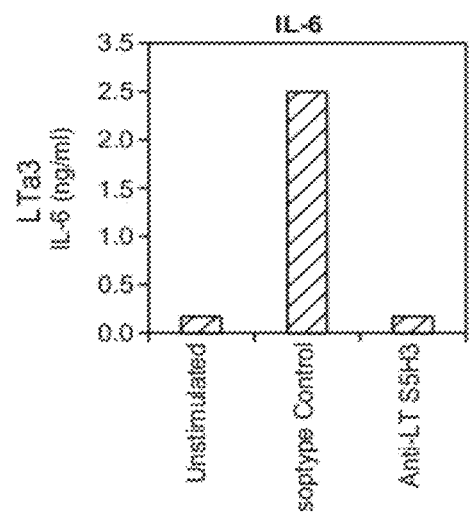
Figure 19A:
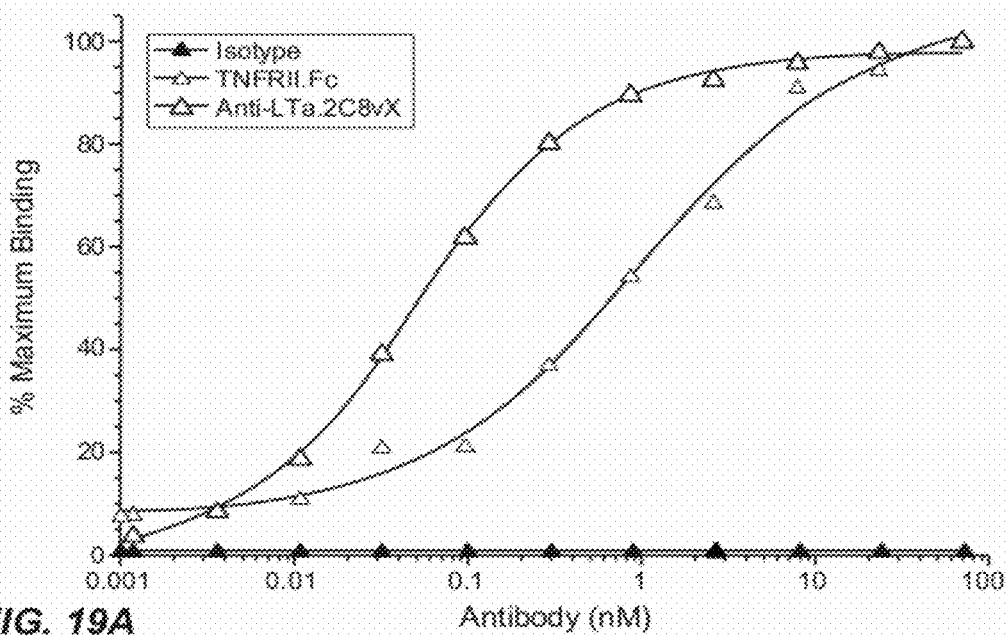
FIGS. 19A and 19B show, respectively, ELISAs of LTα3 and LTα1β2 binding of 2C8.vX antibodies in comparison to TNFRII.Fc/isotype control.
Figure 19B:
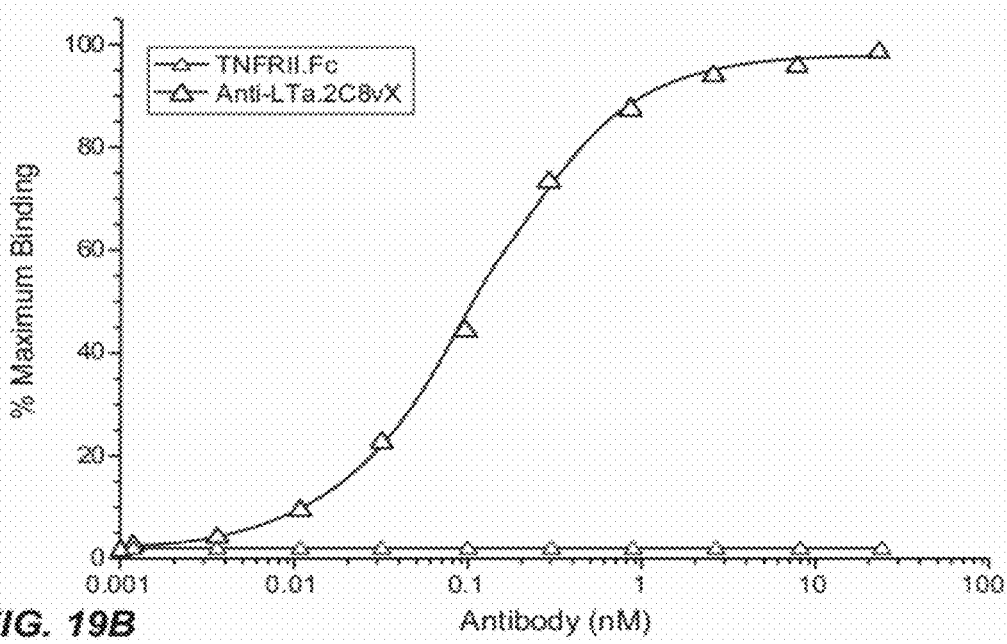
Figure 20A:
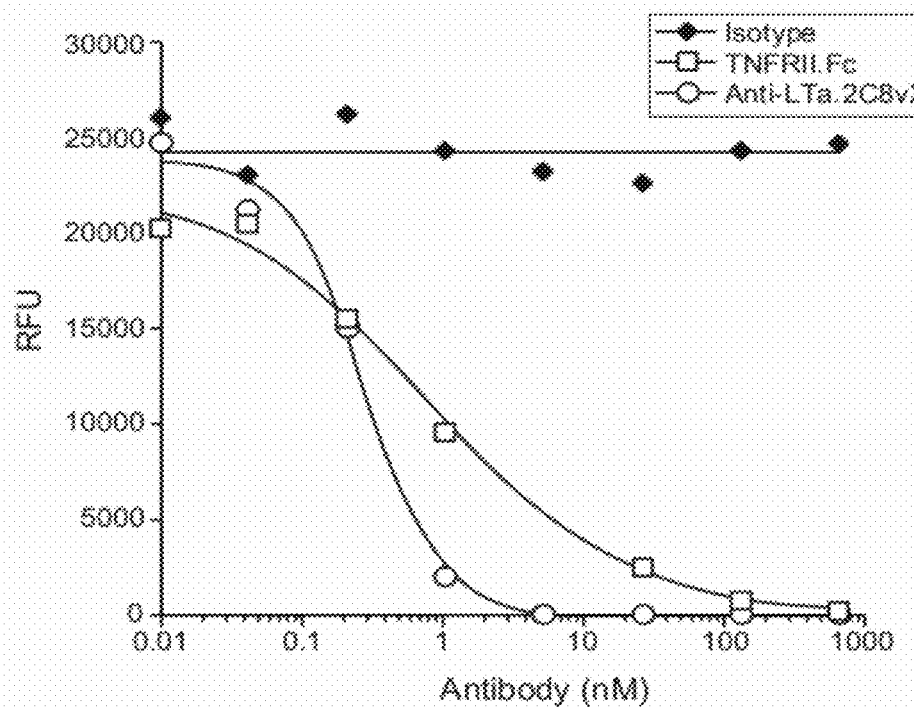
FIGS. 20A and 20B show, respectively, blocking of human LTα3 and LTα1β2 by 2C8vX antibodies in comparison to isotype control/TNFRII.Fc using an assay for testing blocking of human LT-induced cytotoxicity.
Figure 20B:
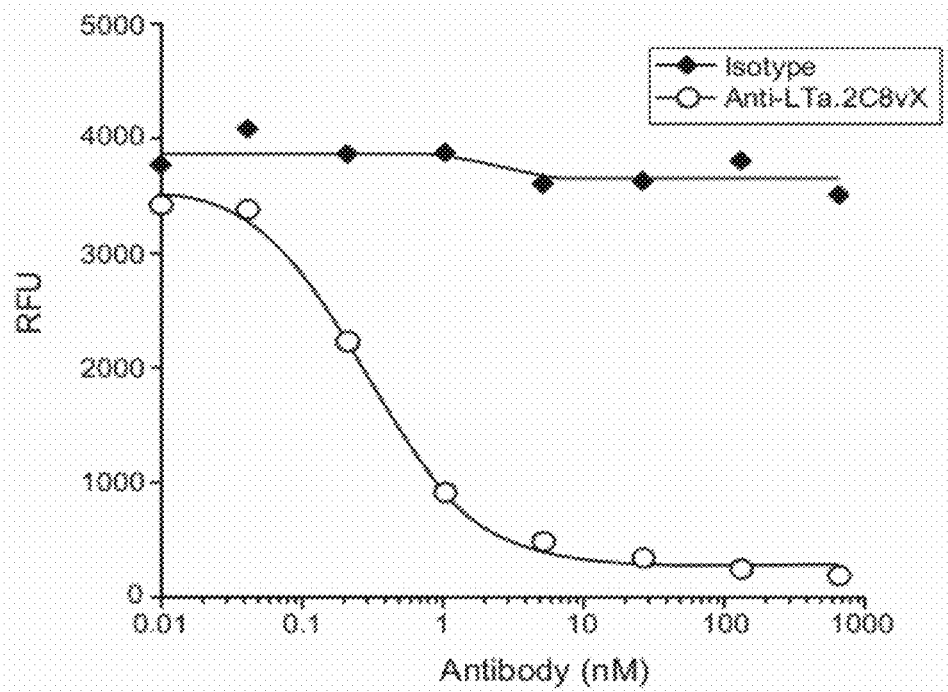
Figure 21:
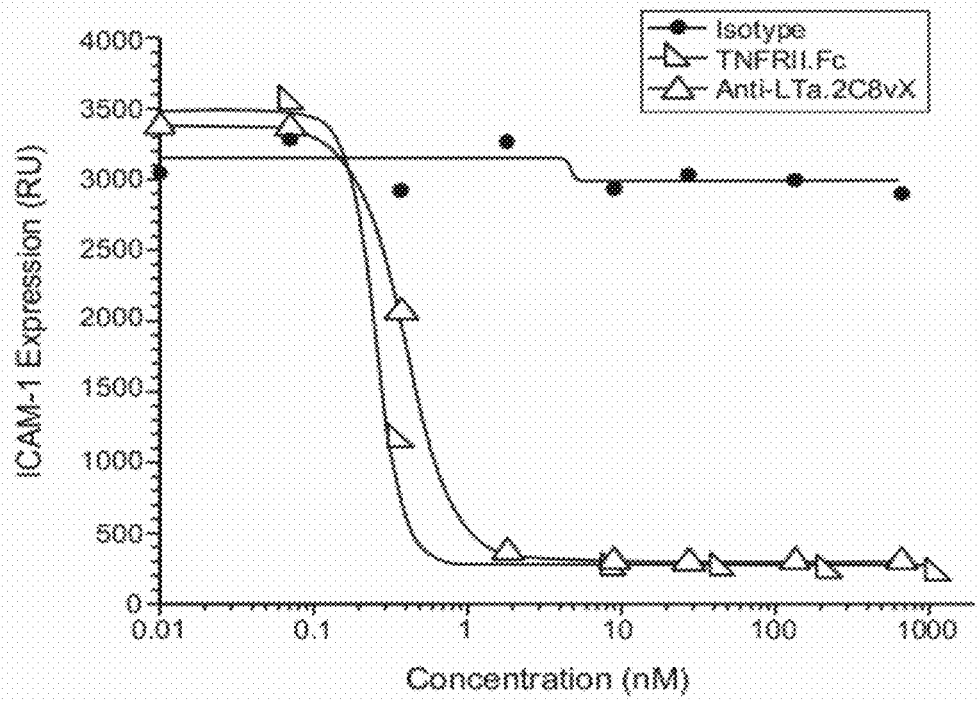
FIG. 21 provides a comparison of how various molecules blocked LTα3 in a functional assay showing inhibition of ICAM1 upregulation by LTα3 on HUVEC cells. Specifically, isotype, 2C8.vX and TNFRII.Fc were compared.
Figure 22:
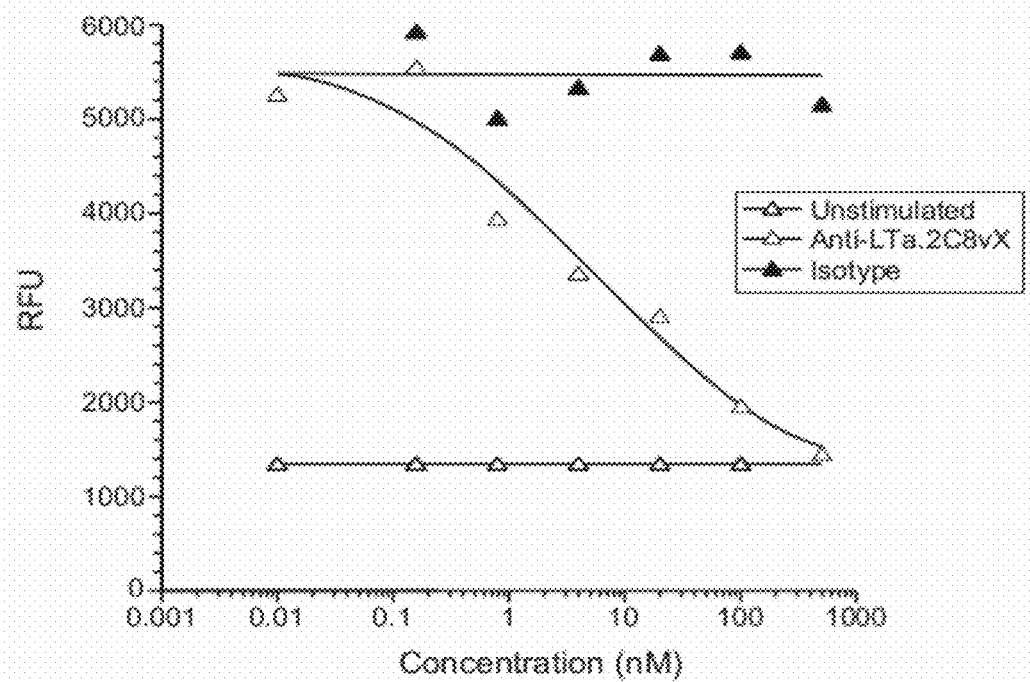
FIG. 22 provides a comparison of how various molecules blocked LTα1β2 in a functional assay showing LTα1β2 blocking using 293-LTβR cells. Specifically, isotype and 2C8.vX were compared along with unstimulated cells.
Figure 23:
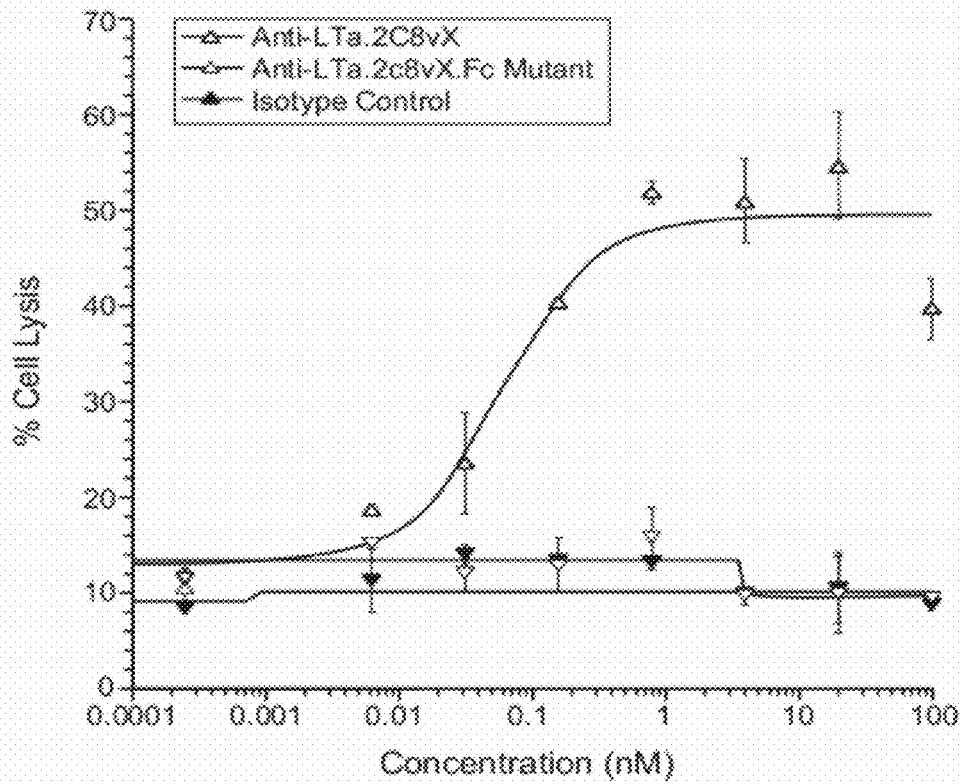
FIG. 23 shows ADCC activity of 2C8.vX using a protocol involving 293-LTα1β2 cells. 2C8.vX was compared with the 2C8.vX DANA mutant (Fc mutant) and isotype control.
Figure 24:
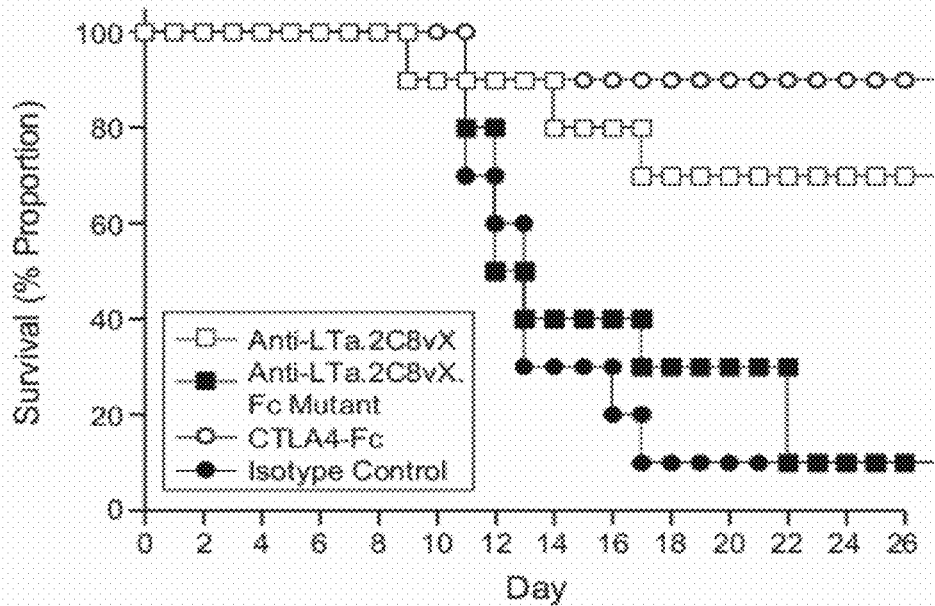
FIG. 24 shows GVHD survival results with 2C8.vX and CTLA4-Fc, as compared to controls (2C8.vX DANA Fc mutant and isotype control), in a human SCID model.
Figure 25A:
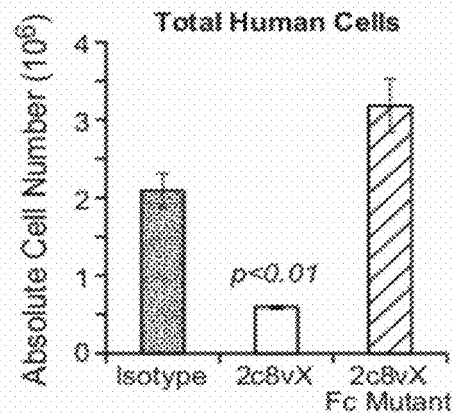
FIG. 25A-D show that the 2C8.vX antibody depletes LTα1β2-expressing T and B cells in the human SCID GVHD model. The results in FIG. 25A show total positive human cells at day 2 for isotype control, 2C8.vX, and 2C8.vX.DANA mutant.
Figure 25B:
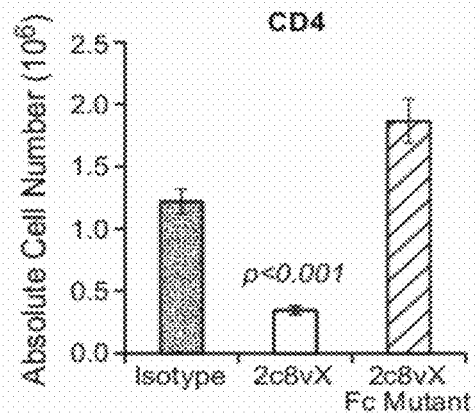
Figure 25C:
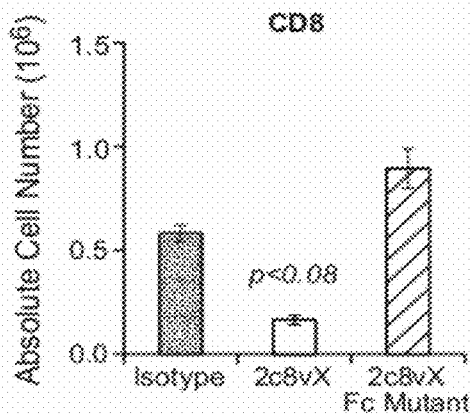
Figure 25D:
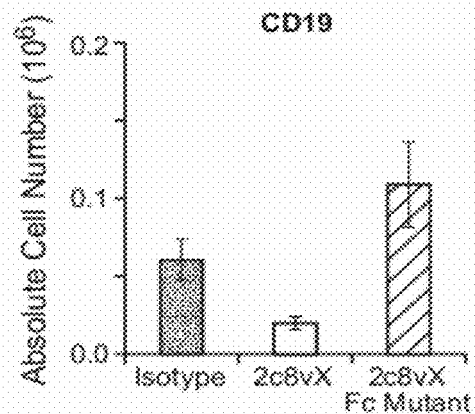

FIG. 16 shows that anti-LTα antibody 2C8 lysed a 293-human LTαβ-expressing cell line in the ADCC assay, but the corresponding Fc mutant monoclonal antibody did not.

EXAMPLE 17

Anti-LTα Monoclonal Antibody Blocks Cytokine and Chemokine Secretion in 3T3 and HUVEC Cells HUVEC and 3T3 cells were cultured in the presence of human LTα3 (100 ng/ml; R&D Systems Inc.) or human LTα1β2 (200 ng/ml; R&D Systems Inc.) for 24 hours using human or murine reagents, respectively. Neutralization of the effect of LTα trimers with chimeric 2C8 or S5H3 anti-LTα antibodies (chimeric 2C8 with HUVEC, and hamster-mouse chimeric S5H3 with murine 3T3 cells) was determined using a static dose of 10-0 µg/ml. Supernatants were assayed for human RANTES, IL-6, IP-10, and IL-8 for the HUVEC evaluation; or murine RANTES, IL-6, IP-10, and KC for the 3T3 evaluation, using standard LINCOPLEX™ kits and read on a LUMINEX™ plate reader.

FIG. 17A-H show that the anti-LTα antibody, versus an isotype control and as compared to unstimulated cells, blocked cytokine and chemokine secretion in HUVEC cells, with FIGS. 17A-17D, respectively, showing KC/IL-8, RANTES, IP10, and IL-6 with LTα1β2, and FIGS. 17E-17H, respectively, showing KC/IL-8, RANTES, IP10, and IL-6 with LTα3.

FIG. 17I-P show that the anti-LTα antibody, versus an isotype control and as compared to unstimulated cells, blocks cytokine and chemokine secretion in 3T3 cells, with FIGS. 17I-17L, respectively, showing KC, RANTES, IP10, and IL-6 with LTα1β2, and FIGS. 17M-17P, respectively, showing KC, RANTES, IP10, and IL-6 with LTα3.

In summary, the preferred antibodies herein against LTα:
1) Block LTα3
2) Deplete LTα-positive cells by binding LTα as target, which is complexed with LTβ on the cell surface. The data that depletion is important are the in vivo data comparing wild-type with the Fc (DANA) mutant—for mouse: CIA, AIA (FIGS. 4 and 5); for human: human SCID mice with 2C8 (FIG. 9) and ADCC assay (FIG. 16)
3) Block LTαβ function
4) Target any cell expressing LTα, including T-, B-, and possibly or likely any Th1- or Th17- or Th2-driven disease (and NK cells), without being limited to any one theory.

Diseases expected to benefit from treatment with the antibodies herein include RA, IBD, psoriasis, MS, Sjögren's syndrome, Hashimoto's thyroiditis, Graves' disease, myasthenia gravis, and lupus, especially, RA, MS, lupus (e.g., SLE and LN), and IBD, including Crohn's disease and UC.

EXAMPLE 18

Affinity-Matured Anti-LTα Antibody 2C8.vX

Affinity maturation of the antibody 2C8 noted in Example 3 led to the humanized antibody 2C8.vX. The light-chain and heavy-chain variable regions and CDRs of this antibody are shown in FIGS. 18A and 18B, respectively, along with the CDRs.

The following is the DNA sequence that encodes the full-length heavy chain of anti-LTα 2C8.vX:

(SEQ ID NO: 104)
GAAGTTCAGCTGGTGGAGTCTGGCGGTGGCCTGGTGCAGCCAGGGGCTC

ACTCCGTTTGTCC

TGTGCAGCT

TCTGGCTACACATTCACCAGCTATGTGATCCATTGGGTCCGTCAGGCCCC

GGGTAAGGGCCTCGAGTGGGTTGGTTATAACAATCCTTATAACGCCGGCA

CCAACTATAACGAGAAGTTCAAGGGGCGCTTCACTATCAGTTCTGACAAG

TCGAAAAACACAGCATACCTGCAGAT

GAACAGCCTGCGTGCTGAGGACACTGCCGTCTATTATTGTTCTCGACCCA

CAATGCTCCCATGGTTCGCCTACTGGGGTCAAGGAACCCTGGTCACCGTC

TCCTCAGCCTCC ACCAAGGGCCC

ATCGGTCTTCCCCCTGGCACCCTCCTCCAAGAGCACCTCTGGGGGCACAG

CGGCCCTGGGC

TGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCT

CAGGACTCTACTCCCTCAG

CAGCGTGGTGACTGTGCCCTCTAGCAGCTTGGGCACCCAGACCTACATCT

GCAACGTGAATCACAAGCCCAGCAACACCAAGGTGGACAAGAAAGTTGAG

CCCAAATCTTGTGACAAAACTCACACA

TGCCCACCGTGCCCAGCACCTGAACTCCTGGGGGGACCGTCAGTCTTCCT

CTTCCCCCC

AAAACCCAAGGACACCCTCATGATCTCCCGGACCCCTGAGGTCACATGCG

TGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCAC

CGTCCTGCACCAGGACTGGCTGAATGGCAAGGAGTACAAGTGCAAGGTCT

CCAACAAAG

CCCTCCCAGCCCCCATCGAGAAAACCATCTCCAAAGCCAAAGGGCAGCCC

CGAGAACCACAGGTGTACACCCTGCCCCCATCCCGGGAAGAGATGACCAA

GAACCAGGTCAGCCTGACCTGCCTGGTCAAAGGCTTCTATCCCAGCGACA

TCGCCGTGGAGTGGGAGAGCAATGGGCAGCCGG

AGAACAACTACAAGACCACGCCTCCCGTGCTGGACTCCGACGGCTCCTTC

TTCCTCTAC

AGCAAGCTCACCGTGGACAAGAGCAGGTGGCAGCAGGGGAACGTCTTCTC

ATGCTCCGTGATGCATGAGGCTCTGCACAACCACTACACGCAGAAGAGCC

TCTCCCTGTCTCCGGGTAAA

The following is the DNA sequence that encodes the full-length light chain of anti-LTα 2C8.vX:

(SEQ ID NO: 105)
GATATCCAGATGACCCAGTCCCCGAGCTCCCTGTCCGCCTCTGTGGGCGA

TAGGGTCACCATCACCTGCCGTGCCAGTCAGGCTGTGTCTTCCGCTGTAG

CCTGGTATCAACAGAAACCAGG

AAAAGCTCCGAAACTACTGATTTACTCTGCATCCCACCGTTACACTGGAG

TCCCTTCTCGCTTCTCTGGATCCGGATCTGGGACGGATTTCACTCTGACC

ATCAGCAGTCTGCAGCCGGAAGACTT

CGCAACTTATTACTGTCAGGAATCTTATTCTACTCCTTGGACGTTCGGAC

AGGGTACCAA

GGTGGAGATCAAACGAACTGTGGCTGCACCATCTGTCTTCATCTTCCCGC

CATCTGATGAGCAGTTGAAATCTGGAACTGCCTCTGTTGTGCCTGCTG

AATAACTTCTATCCCAGAGAGGCCAAAGTACAGTGGAAGGTGGATAACGC

CCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGT

The following is the full-length heavy-chain amino acid sequence for 2C8.vX:

(SEQ ID NO: 106)
EVQLVESGGGLVQPGGSLRLSCAASGYTFTSYVIHWVRQAPGKGLEWVGY

NNPYNAGTNY

NEKFKGRFTISSDKSKNTAYLQMNSLRAEDTAVYYCSRPTMLPWFAYWGQ

GTLVTVSSAS

TKGPSVFPLAPSSKSTSGGTAALGCLVKDYFPEPVTVSWNSGALTSGVHT

FPAVLQSSGL

YSLSSVVTVPSSSLGTQTYICNVNHKPSNTKVDKKVEPKSCDKTHTCPPC

PAPELLGGPS

VFLFPPKPKDTLMISRTPEVTCVVVDVSHEDPEVKFNWYVDGVEVHNAKT

KPREEQYNST

YRVVSVLTVLHQDWLNGKEYKCKVSNKALPAPIEKTISKAKGQPREPQVY

TLPPSREEMT

-continued

```
KNQVSLTCLVKGFYPSDIAVEWESNGQPENNYKTTPPVLDSDGSFFLYSK

LTVDKSRWQQ

GNVFSCSVMHEALHNHYTQKSLSLSPGK
```

The following is the full-length light-chain amino acid sequence for 2C8.vX:

```
                                          (SEQ ID NO: 107)
DIQMTQSPSSLSASVGDRVTITCRASQAVSSAVAWYQQKPGKAPKLLIYS

ASHRYTGVPS

RFSGSGSGTDFTLTISSLQPEDFATYYCQESYSTPWTFGQGTKVEIKRTV

AAPSVFIFPP

SDEQLKSGTASVVCLLNNFYPREAKVQWKVDNALQSGNSQESVTEQDSKD

STYSLSSTLT

LSKADYEKHKVYACEVTHQGLSSPVTKSFNRGEC
```

Epitope mapping indicates that this molecule has a partial overlap with the receptor binding site. Activated rhesus T and B cells express surface LTαβ. The antibody 2C8.vX bound (crossreacted with) rhesus surface LTαβ (as determined by FACS) and rhesus soluble LTα3 (as determined by FORTEBIO™ octet).

FIGS. 19A and 19B show, respectively, ELISAs of LTα3 and LTα1β2 binding of 2C8.vX antibodies in comparison to isotype control/TNFRII.Fc. These ELISAs were performed in the same way as described in Example 10 above using human LTα3 and in Example 11 using LTα1β2. The $EC_{50}$ values of these same antibodies to LTβ3 and LTα1β2 are 1.03 nM for TNFRII.Fc and 0.05 nM for 2C8.vX to LTα3, and no binding of TNFRII.Fc and 0.34 nM for 2C8.vX to LTα1β2. The results show that 2C8.vX bound much better than TNFRII.Fc in both cases.

FIGS. 20A and 20B show, respectively, blocking of human LTα3 and LTα1β2 by 2C8vX antibodies in comparison to isotype control/TNFRII.Fc using the assay for testing blocking of human LT-induced cytotoxicity described in Example 15 above. The $IC_{50}$ values of these same antibodies to LTα3 and LTα1β2 are 0.83 nM for TNFRII.Fc and 0.29 nM for 2C8.vX to LTα3, with no isotype blocking, and 0.31 nM for 2C8.vX to LTα1β2, with no isotype blocking. The results show that 2C8.vX blocked LTα3 better than TNFRII.Fc.

FIG. 21 relates to a functional assay showing inhibition of ICAM1 upregulation by LTα3 on HUVEC cells, using the protocol described in Example 14 above. FIG. 21 shows a comparison of how various molecules blocked LTα3 in this functional assay. Specifically, isotype control, 2C8.vX, and TNFRII.Fc were compared. The results show that both antibodies were able to block LTα3 in this assay.

FIG. 22 relates to a functional assay showing blocking of LTα1β2 using 293-LTβR cells, using the protocol described in Example 15 above. FIG. 22 shows a comparison of how various molecules blocked LTβ1β2 in this functional assay. Specifically, isotype control and 2C8.vX were compared along with unstimulated cells. The results show that 2C8.vX was able to block LTα1β2 in this assay, with an $IC_{50}$ of about 5 nM.

FIG. 23 shows ADCC activity of 2C8.vX using the protocol set forth in Example 16 involving 293-LTα1β2 cells. 2C8.vX was compared with the 2C8.vX DANA mutant and isotype control. The results show that 2C8.vX had ADCC activity, whereas the DANA mutant did not.

FIG. 24 shows GVHD survival results with 2C8.vX and CTLA4-Fc, as compared to controls (Fc mutant and isotype control) in a human SCID model, using the same protocol as described above in Example 9, terminating in three to four weeks. The results indicate that CTLA4-Fc and 2C8.vX prolonged survival in this model, and thus were effective at depleting LTα cells, but not the controls 2C8.vX-DANA mutant and human IgG1 isotype control antibody.

FIG. 25A-D show that the 2C8.vX antibody depleted LTα1β2-expressing T and B cells in the human SCID GVHD model. In this protocol, SCID mice were reconstituted with PBMCs purified from a LEUKOPACK™ (available from blood banks such as Interstate Blood Bank, Memphis, Tenn.) of a normal donor by FICOLL™ polysaccharide gradient. All mice (n=10/group) were sub-lethally irradiated with 350 rads using a Cesium 137 source. Two hours after irradiation, mice were injected with 50 million human PBMCs/mouse in 200 μl PBS intrasplenically. One day after cell injection, mice were treated i.p. either with 300 μg of human IgG1 isotype control antibody, 2C8.vX, or 2C8.vX DANA mutant in 100 μl saline for one day. On Day 2 after irradiation, the splenocytes of the mice were labeled with 5-(and 6-)carboxy fluorescein diacetate succinimidyl ester (CFSE), and the absolute cell number (total CFSE positive cells) was measured and the percentage of cells in CFSE peaks was measured after electronically gating on $CD4^+$, $CD8^+$, and $CD19^+$ cells. For this three-color staining, the following monoclonal antibodies were used: PE-labeled anti-CD4, PE-labeled anti-CD8, and PE-labeled CD19. Stained cells were analyzed on a FACSCAN™ or FACSCALIBUR™ instrument.

The results in FIG. 25A show total CFSE-positive human cells at day 2 for isotype control, 2C8.vX, and 2C8.vX.DANA mutant, and indicate that depletion was best with the vX antibody. FIG. 25B-D show the results of gating using the CD4, CD8, and CD19 antibodies, respectively, indicating that the vX antibody was best at depleting LTαβ-positive T and B cells as compared to isotype control and the DANA mutant.

In summary, the antibody 2C8.vX depletes LT-expressing cells in an in vitro ADCC assay and in vivo in two human SCID GVHD models. It also blocks LTα3 and LTα1β2 in functional cell assays using HUVEC cells and 293-LTβR cells, respectively. Further, it cross-reacts with non-human primate (NHP) lymphotoxin as determined by activated rhesus primary cells and the LTα3 rhesus protein.

EXAMPLE 19

Affinity Matured Anti-LTα Antibody 3F12.v14

Affinity maturation of the antibody 3F12 noted above led to the humanized antibody 3F12.v14. The light-chain and heavy-chain variable regions and CDRs of this antibody are shown in FIGS. 26A and 26B, respectively, along with the CDRs.

When tested for binding and blocking LTα3 and LTα using the assays noted above, 3F12.v14 bound and blocked these molecules as well as did antibody 2c8.vX.

EXAMPLE 20

Afucosylated 2C8.vX

The antibodies herein may be altered so that they lack fucose by culturing them using a cell line or technology disclosed in US 2003/0157108; WO 2000/61739; WO 2001/29246; US 2003/0115614; US 2002/0164328; US 2004/

0093621; US 2004/0132140; US 2004/0110704; US 2004/0110282; US 2004/0109865; WO 2003/085119; WO 2003/084570; WO 2005/035586; WO 2005/035778; WO2005/053742; US 2006/0063254; US 2006/0064781; US 2006/0078990; US 2006/0078991; Okazaki et al. *J. Mol. Biol.* 336:1239-1249 (2004); or Yamane-Ohnuki et al. *Biotech. Bioeng.* 87: 614-622 (2004). Examples of cell lines producing defucosylated antibodies include Lec13 CHO cells deficient in protein fucosylation (Ripka et al., *Arch. Biochem. Biophys.*, 249:533-545 (1986); US 2003/0157108 A1 (Presta) and WO 2004/056312 A1 (Adams et al., especially at Example 11), and knockout cell lines, such as alpha-1,6-fucosyltransferase gene, FUT8, knock-out CHO cells (Yamane-Ohnuki et al. supra).

In fact, the antibody 2C8.vX was afucosylated to produce an antibody called anti-LTa 2C8.vX AF. This molecule was generated using a stable CHO cell line having a FUT8 knock-out gene as described by the method in Yamane-Ohnuki et al., supra It is 100% afucosylated.

Figure 27:
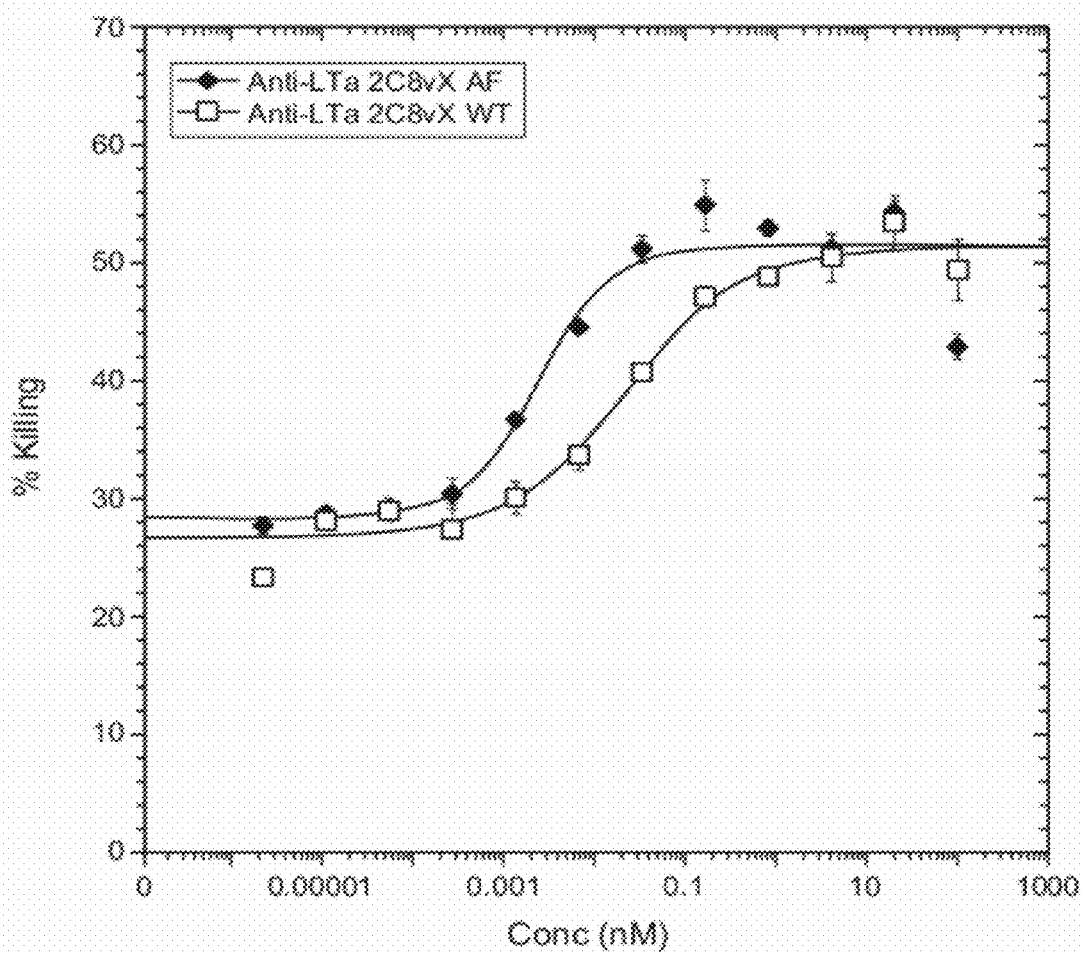
FIG. 27 shows ADCC activity of 2C8.vX and its afucosylated counterpart, wherein AF=afucosylated antibody and WT=regular CHO cell-line production antibody.

The biophysical properties of 2C8.vX (including blocking and binding data) were not substantially changed upon afucosylation thereof, except for the ADCC. The ADCC properties of the wild-type and afucosylated molecules were determined by carrying out the experiments using the protocol set forth in Example 16 involving 293-LTα1β2 cells. The results are shown in FIG. 27. The figure shows that the afucosylated antibody anti-LTa 2C8.vX AF has about a ten-fold increase over the wild-type (WT) antibody (produced in a normal CHO cell line as described above).

EXAMPLE 21

Underfucosylated 2C8.vX

As an alternative way to achieve high yields of non-fucosylated antibodies in mammalian cells, an RNAi approach may be employed to knock down the expression of the FUT8 gene. A plasmid may be used to produce short hairpin siRNA consisting of 19 nt (nucleotide) sense siRNA sequence specific to the gene of FUT8, linked to its reverse complementary antisense siRNA sequence by a short spacer (9nt hairpin loop), followed by 5-6 U's at the 3' end.

Four different RNAi probes are designed to target the different regions based on the available CHO FUT8 DNA sequence.

For testing the efficacy of these RNAi probes, a FLAG-tagged FUT8 fusion protein is constructed using the available CHO FUT8 DNA sequence (Genbank accession no. P_AAC63891). RT-PCR is performed with FUT8 primers and the resulting PCR fragment fused with 5' FLAG tag sequence. The tagged FUT8 fragment is cloned into an expression vector. The RNAi probe plasmid and flag-tagged FUT8 plasmid are cotransfected into CHO cells. Cell lysate is extracted 24 hours after transfection and the FUT8 fusion protein level analyzed using anti-flag M2 antibody by immuno-blotting. In the presence of RNAi probes, the fusion protein expression is expected to be significantly inhibited in most of the cases.

The two probes showing the best inhibitory effect are transfected into a CHO cell line expressing an antibody as described herein, such as 2C8.vX. The expressed anti-LT-alpha antibody is purified by a protein A column and submitted for Matrix-Assisted Laser Desorption/Ionization Time-of-flight (MALDI-TOF) mass spectral analysis of asparagine-linked oligosaccharides (including fucose content) and FcγR binding assay as described below.

Methods for analyzing the oligosaccharides by MALDI-TOF are conducted generally as follows: N-linked oligosaccharides are released from recombinant glycoproteins using the peptide-N-glycosidase-F (PNGase F) procedure of Papac et al., *Glycobiology* 8, 445-454 (1998). Briefly, the wells of a 96-well polyvinylidene difluoride (PVDF)-lined microtitre plate (Millipore, Bedford, Mass.) are conditioned with 100 µl methanol that is drawn through the PVDF membranes by applying vacuum to the MILLIPORE™ multiscreen vacuum manifold. The conditioned PVDF membranes are washed with 3×250 µl water. Between all wash steps the wells are drained completely by applying gentle vacuum to the manifold. The membranes are washed with reduction and carboxymethylation buffer (RCM) consisting of 6 M guanidine hydrochloride, 360 mM TRIS buffer, 2 mM EDTA, pH 8.6. Glycoprotein samples (50 µg) are applied to individual wells, again drawn through the PVDF membranes by gentle vacuum and the wells washed with 2×50 µl of RCM buffer. The immobilized samples are reduced by adding 50 µl of a 0.1 M dithiothreitol (DTT) solution to each well and incubating the microtitre plate at 37° C. for 1 hr. DTT is removed by vacuum and the wells are washed 4×250 µl water. Cysteine residues are carboxylmethylated by the addition of 50 µl of a 0.1 M iodoacetic acid (IAA) solution that is freshly prepared in 1 M NaOH and diluted to 0.1 M with RCM buffer.

Carboxymethylation is accomplished by incubation for 30 min in the dark at ambient temperature. Vacuum is applied to the plate to remove the IAA solution and the wells are washed with 4×250 µl purified water. The PVDF membranes are blocked by the addition of 100 µl of 1% PVP360™ (polyvinylpyrrolidine 360,000 MW) (Sigma) solution and incubation for 30 minutes at ambient temperature. The PVP-360™ solution is removed by gentle vacuum and the wells are washed 4×250 µl water. Peptide: N-Glycosidase F (PNGase F™) amidase (New England Biolabs, Beverly, Mass.), at 25 µl of a 25 Unit/ml solution in 10 mM TRIS acetate, pH 8.3, is added to each well and the digest proceeds for 3 hr at 37° C. After digestion, the samples are transferred to 500 µl EPPENDORF™ tubes and 2.5 µl of a 1.5 M acetic acid solution is added to each sample. The acidified samples are incubated for two hrs at ambient temperature to convert the oligosaccharides from the glycosylamine to the hydroxyl form. Prior to MALDI-TOF mass spectral analysis, the released oligosaccharides are desalted using a 0.7-ml bed of cation-exchange resin (AG50W-X8 resin in the hydrogen form) (Bio-Rad, Hercules, Calif.) slurry packed into compact reaction tubes (US Biochemical, Cleveland, Ohio).

For MALDI-TOF mass-spectral analysis of the samples in the positive mode, the desalted oligosaccharides (0.5 µl aliquots) are applied to the stainless target with 0.5 µl of the 2,5 dihydroxybenzoic acid matrix (sDHB) that is prepared by dissolving 2 mg 2,5 dihydroxybenzoic acid with 0.1 mg of 5-methoxysalicylic acid in 1 ml of 1 mM NaCl in 25% aqueous ethanol. The sample/matrix mixture is vacuum dried and then allowed to absorb atmospheric moisture prior to analysis. Released oligosaccharides are analyzed by MALDI-TOF on a PERSEPTIVE BIOSYSTEMS VOYAGER-ELITE™ mass spectrometer. The mass spectrometer is operated in the positive mode at 20 kV with the linear configuration and utilizing delayed extraction. Data are acquired using a laser power of approximately 1100 and in the data summation mode (240 scans) to improve the signal to noise ratio. The instrument is calibrated with a mixture of standard oligosaccharides and the data are smoothed using a 19-point Savitsky-Golay algorithm before the masses are assigned. Integration of the mass-spectral data is achieved using the CAESAR7.2™ data analysis software package (SciBridge Software).

Binding of control and test materials to the human Fcγ receptors can be assessed using modified versions of procedures originally described by Shields et al., *J Biol Chem*, 276:6591-604 (2001).

For confirmation that the RNAi-transfected cells do have less FUT8 RNA expression, a Northern blot can be performed using RNA samples extracted from the transfected cells 24 hours after transfection. Total RNA from cells containing a control plasmid (random mouse DNA sequence, no homology to any known mouse proteins) and two RNAi plasmids can be purified and hybridized with a 300-bp probe. The knock down of endogenous α 1,6-fucosyltransferase RNA can be further confirmed by quantitative PCR.

Deposit of Material

The following materials have been deposited with the American Type Culture Collection, 10801 University Blvd., Manassas, Va. 20110-2209, USA (ATCC):

| Material | ATCC Dep. No. | Deposit Date |
| --- | --- | --- |
| hybridoma murine Lymphotoxin alpha2 beta1 s5H3.2.2 | PTA-7538 | Apr. 19, 2006 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

What is claimed is:

1. A DNA encoding an isolated anti-lymphotoxin-α(LTα) antibody comprising a light chain comprising the amino acid sequence of SEQ ID NO:107 and a heavy chain comprising the amino acid sequence of SEQ ID NO:106.

2. An isolated nucleic acid encoding the heavy chain of the antibody of claim 1.

3. An expression vector comprising the nucleic acid of claim 2.

4. An isolated host cell comprising the nucleic acid of claim 2.

5. A method of producing a heavy chain of an antibody comprising culturing the host cell of claim 4 under conditions to produce the heavy chain of the antibody and recovering the heavy chain of the antibody.

6. An isolated nucleic acid encoding the light chain of the antibody of claim 1.

7. An expression vector comprising the nucleic acid of claim 6.

8. An isolated host cell comprising the nucleic acid of claim 6.

9. A method of producing a light chain of an antibody comprising culturing the host cell of claim 8 under conditions to produce the light chain of the antibody and recovering the light chain of the antibody.

10. A method of producing an antibody comprising:
   a. culturing a host cell comprising nucleic acid encoding an anti-lymphotoxin-α antibody having the light chain comprising SEQ ID NO:107 and a heavy chain comprising SEQ ID NO:106 under conditions to produce the antibody; and
   b. recovering the antibody.

11. The method of claim 10 wherein the light and heavy chains are encoded on separate vectors.

12. The method of claim 10 wherein the light and heavy chains are encoded on the same vector.

13. An antibody produced by the method of claim 10.

\* \* \* \* \*

SEQUENCE LISTING

```
<160> NUMBER OF SEQ ID NOS: 110

<210> SEQ ID NO 1
<211> LENGTH: 11
<212> TYPE: PRT
<213> ORGANISM: Artificial sequence
<220> FEATURE:
<223> OTHER INFORMATION: Sequence is synthesized

<400> SEQUENCE: 1

Lys Ala Ser Gln Ala Val Ser Ser Ala Val Ala
                5                   10

<210> SEQ ID NO 2
<211> LENGTH: 11
<212> TYPE: PRT
<213> ORGANISM: Artificial sequence
<220> FEATURE:
<223> OTHER INFORMATION: Sequence is synthesized

<400> SEQUENCE: 2

Arg Ala Ser Gln Ala Val Ser Ser Ala Val Ala
                5                   10

<210> SEQ ID NO 3
<211> LENGTH: 17
<212> TYPE: PRT
<213> ORGANISM: Artificial sequence
<220> FEATURE:
<223> OTHER INFORMATION: Sequence is synthesized

<400> SEQUENCE: 3

Lys Ser Ser Gln Ser Leu Leu Tyr Ser Thr Asn Gln Lys Asn Phe
```

```
                1               5                  10                  15

Leu Ala

<210> SEQ ID NO 4
<211> LENGTH: 17
<212> TYPE: PRT
<213> ORGANISM: Artificial sequence
<220> FEATURE:
<223> OTHER INFORMATION: Sequence is synthesized

<400> SEQUENCE: 4

Lys Ser Ser Gln Ser Leu Leu Tyr Ser Ala Asn Gln Lys Asn Phe
  1               5                  10                  15

Leu Ala

<210> SEQ ID NO 5
<211> LENGTH: 17
<212> TYPE: PRT
<213> ORGANISM: Artificial sequence
<220> FEATURE:
<223> OTHER INFORMATION: Sequence is synthesized

<400> SEQUENCE: 5

Lys Ser Ser Gln Ser Leu Leu Tyr Ser Thr Ala Gln Lys Asn Phe
  1               5                  10                  15

Leu Ala

<210> SEQ ID NO 6
<211> LENGTH: 17
<212> TYPE: PRT
<213> ORGANISM: Artificial sequence
<220> FEATURE:
<223> OTHER INFORMATION: Sequence is synthesized

<400> SEQUENCE: 6

Lys Ser Ser Gln Ser Leu Leu Tyr Ser Thr Asn Gln Lys Asn Ala
  1               5                  10                  15

Leu Ala

<210> SEQ ID NO 7
<211> LENGTH: 7
<212> TYPE: PRT
<213> ORGANISM: Artificial sequence
<220> FEATURE:
<223> OTHER INFORMATION: Sequence is synthesized

<400> SEQUENCE: 7

Ser Ala Ser His Arg Tyr Thr
                  5

<210> SEQ ID NO 8
<211> LENGTH: 7
<212> TYPE: PRT
<213> ORGANISM: Artificial sequence
<220> FEATURE:
<223> OTHER INFORMATION: Sequence is synthesized

<400> SEQUENCE: 8

Trp Ala Ser Thr Arg Asp Ser
                  5

<210> SEQ ID NO 9
<211> LENGTH: 9
<212> TYPE: PRT
<213> ORGANISM: Artificial sequence
```

```
<220> FEATURE:
<223> OTHER INFORMATION: Sequence is synthesized

<400> SEQUENCE: 9

Gln Gln His Tyr Ser Thr Pro Trp Thr
                5

<210> SEQ ID NO 10
<211> LENGTH: 9
<212> TYPE: PRT
<213> ORGANISM: Artificial sequence
<220> FEATURE:
<223> OTHER INFORMATION: Sequence is synthesized

<400> SEQUENCE: 10

Gln Glu Ser Tyr Ser Thr Pro Trp Thr
                5

<210> SEQ ID NO 11
<211> LENGTH: 9
<212> TYPE: PRT
<213> ORGANISM: Artificial sequence
<220> FEATURE:
<223> OTHER INFORMATION: Sequence is synthesized

<400> SEQUENCE: 11

Gln Glu Asn Tyr Ser Thr Pro Trp Thr
                5

<210> SEQ ID NO 12
<211> LENGTH: 9
<212> TYPE: PRT
<213> ORGANISM: Artificial sequence
<220> FEATURE:
<223> OTHER INFORMATION: Sequence is synthesized

<400> SEQUENCE: 12

Gln Glu Val Tyr Ser Thr Pro Trp Thr
                5

<210> SEQ ID NO 13
<211> LENGTH: 9
<212> TYPE: PRT
<213> ORGANISM: Artificial sequence
<220> FEATURE:
<223> OTHER INFORMATION: Sequence is synthesized

<400> SEQUENCE: 13

Gln Gln Tyr Tyr Ser Tyr Pro Arg Thr
                5

<210> SEQ ID NO 14
<211> LENGTH: 9
<212> TYPE: PRT
<213> ORGANISM: Artificial sequence
<220> FEATURE:
<223> OTHER INFORMATION: Sequence is synthesized

<400> SEQUENCE: 14

Gln Gln Tyr Ala Ser Tyr Pro Arg Thr
                5

<210> SEQ ID NO 15
<211> LENGTH: 9
<212> TYPE: PRT
<213> ORGANISM: Artificial sequence
<220> FEATURE:
<223> OTHER INFORMATION: Sequence is synthesized
```

```
<400> SEQUENCE: 15

Gln Gln Tyr Tyr Ala Tyr Pro Arg Thr
                5

<210> SEQ ID NO 16
<211> LENGTH: 10
<212> TYPE: PRT
<213> ORGANISM: Artificial sequence
<220> FEATURE:
<223> OTHER INFORMATION: Sequence is synthesized

<400> SEQUENCE: 16

Gly Tyr Thr Phe Thr Ser Tyr Val Ile His
                5                   10

<210> SEQ ID NO 17
<211> LENGTH: 10
<212> TYPE: PRT
<213> ORGANISM: Artificial sequence
<220> FEATURE:
<223> OTHER INFORMATION: Sequence is synthesized

<400> SEQUENCE: 17

Gly Tyr Thr Phe Ser Ser Tyr Trp Ile Glu
                5                   10

<210> SEQ ID NO 18
<211> LENGTH: 17
<212> TYPE: PRT
<213> ORGANISM: Artificial sequence
<220> FEATURE:
<223> OTHER INFORMATION: Sequence is synthesized

<400> SEQUENCE: 18

Tyr Asn Asn Pro Tyr Asn Asp Gly Thr Asn Tyr Asn Glu Lys Phe
  1               5                  10                  15

Lys Gly

<210> SEQ ID NO 19
<211> LENGTH: 17
<212> TYPE: PRT
<213> ORGANISM: Artificial sequence
<220> FEATURE:
<223> OTHER INFORMATION: Sequence is synthesized

<400> SEQUENCE: 19

Glu Ile Ser Pro Gly Ser Gly Ser Thr Asn Tyr Asn Glu Glu Phe
  1               5                  10                  15

Lys Gly

<210> SEQ ID NO 20
<211> LENGTH: 9
<212> TYPE: PRT
<213> ORGANISM: Artificial sequence
<220> FEATURE:
<223> OTHER INFORMATION: Sequence is synthesized

<400> SEQUENCE: 20

Pro Thr Met Leu Pro Trp Phe Ala Tyr
                5

<210> SEQ ID NO 21
<211> LENGTH: 5
<212> TYPE: PRT
<213> ORGANISM: Artificial sequence
```

```
<220> FEATURE:
<223> OTHER INFORMATION: Sequence is synthesized

<400> SEQUENCE: 21

Gly Tyr His Gly Tyr
                5

<210> SEQ ID NO 22
<211> LENGTH: 5
<212> TYPE: PRT
<213> ORGANISM: Artificial sequence
<220> FEATURE:
<223> OTHER INFORMATION: Sequence is synthesized

<400> SEQUENCE: 22

Gly Tyr His Gly Ala
                5

<210> SEQ ID NO 23
<211> LENGTH: 108
<212> TYPE: PRT
<213> ORGANISM: Artificial sequence
<220> FEATURE:
<223> OTHER INFORMATION: Sequence is synthesized

<400> SEQUENCE: 23

Asp Ile Val Met Thr Gln Ser His Lys Phe Met Ser Thr Ser Val
  1               5                  10                  15

Gly Asp Arg Val Ser Ile Thr Cys Lys Ala Ser Gln Ala Val Ser
                 20                  25                  30

Ser Ala Val Ala Trp Tyr Gln Gln Lys Pro Gly Gln Ser Pro Lys
                 35                  40                  45

Leu Gln Ile Tyr Ser Ala Ser His Arg Tyr Thr Gly Val Pro Asp
                 50                  55                  60

Arg Phe Thr Gly Ser Gly Ser Gly Thr Asp Phe Thr Phe Thr Ile
                 65                  70                  75

Ser Ser Val Gln Ala Glu Asp Leu Ala Val Tyr Tyr Cys Gln Gln
                 80                  85                  90

His Tyr Ser Thr Pro Trp Thr Phe Gly Gly Gly Thr Lys Val Glu
                 95                 100                 105

Ile Lys Arg

<210> SEQ ID NO 24
<211> LENGTH: 108
<212> TYPE: PRT
<213> ORGANISM: Artificial sequence
<220> FEATURE:
<223> OTHER INFORMATION: Sequence is synthesized

<400> SEQUENCE: 24

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ala Val Ser
                 20                  25                  30

Ser Ala Val Ala Trp Tyr Gln Gln Lys Pro Gly Lys Ala Pro Lys
                 35                  40                  45

Leu Gln Ile Tyr Ser Ala Ser His Arg Tyr Thr Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
```

```
                    80                  85                  90

His Tyr Ser Thr Pro Trp Thr Phe Gly Gln Gly Thr Lys Val Glu
                95                 100                 105

Ile Lys Arg

<210> SEQ ID NO 25
<211> LENGTH: 118
<212> TYPE: PRT
<213> ORGANISM: Artificial sequence
<220> FEATURE:
<223> OTHER INFORMATION: Sequence is synthesized

<400> SEQUENCE: 25

Glu Val Gln Leu Gln Gln Ser Gly Pro Glu Leu Val Lys Pro Gly
 1               5                  10                  15

Ala Ser Val Lys Leu Ser Cys Lys Ala Ser Gly Tyr Thr Phe Thr
                20                  25                  30

Ser Tyr Val Ile His Trp Val Lys Gln Lys Pro Gly Gln Gly Leu
                35                  40                  45

Glu Trp Ile Gly Tyr Asn Asn Pro Tyr Asn Asp Gly Thr Asn Tyr
                50                  55                  60

Asn Glu Lys Phe Lys Gly Lys Ala Thr Leu Thr Ser Asp Lys Ser
                65                  70                  75

Ser Ser Thr Ala Tyr Met Glu Leu Ser Ser Leu Thr Ser Glu Asp
                80                  85                  90

Ser Ala Val Tyr Tyr Cys Ser Arg Pro Thr Met Leu Pro Trp Phe
                95                 100                 105

Ala Tyr Trp Gly Gln Gly Thr Thr Leu Thr Val Ser Ala
               110                 115

<210> SEQ ID NO 26
<211> LENGTH: 118
<212> TYPE: PRT
<213> ORGANISM: Artificial sequence
<220> FEATURE:
<223> OTHER INFORMATION: Sequence is synthesized

<400> SEQUENCE: 26

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Val Ile His Trp Val Arg Gln Ala Pro Gly Lys Gly Leu
                35                  40                  45

Glu Trp Val Gly Tyr Asn Asn Pro Tyr Asn Asp Gly Thr Asn Tyr
                50                  55                  60

Asn Glu Lys Phe Lys Gly Arg Ala Thr Ile Ser Ser Asp Lys Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Pro Thr Met Leu Pro Trp Phe
                95                 100                 105

Ala Tyr Trp Gly Gln Gly Thr Leu Val Thr Val Ser Ser
               110                 115

<210> SEQ ID NO 27
<211> LENGTH: 114
<212> TYPE: PRT
<213> ORGANISM: Artificial sequence
```

```
<220> FEATURE:
<223> OTHER INFORMATION: Sequence is synthesized

<400> SEQUENCE: 27

Asp Ile Val Met Ser Gln Ser Pro Ser Leu Ala Val Ser Val
 1               5                  10                  15

Gly Glu Lys Val Thr Met Ser Cys Lys Ser Ser Gln Ser Leu Leu
                20                  25                  30

Tyr Ser Thr Asn Gln Lys Asn Phe Leu Ala Trp Tyr Gln Gln Lys
                35                  40                  45

Pro Gly Gln Ser Pro Lys Leu Leu Ile Tyr Trp Ala Ser Thr Arg
                50                  55                  60

Asp Ser Gly Val Pro Asp Arg Phe Thr Gly Ser Gly Ser Gly Thr
                65                  70                  75

Asp Phe Thr Leu Thr Ile Ser Ser Val Lys Ala Glu Asp Leu Ala
                80                  85                  90

Val Tyr Tyr Cys Gln Gln Tyr Tyr Ser Tyr Pro Arg Thr Phe Gly
                95                 100                 105

Gly Gly Thr Lys Leu Glu Ile Lys Arg
                110

<210> SEQ ID NO 28
<211> LENGTH: 114
<212> TYPE: PRT
<213> ORGANISM: Artificial sequence
<220> FEATURE:
<223> OTHER INFORMATION: Sequence is synthesized

<400> SEQUENCE: 28

Asp Ile Gln Met Thr Gln Ser Pro Ser Ser Leu Ser Ala Ser Val
 1               5                  10                  15

Gly Asp Arg Val Thr Ile Thr Cys Lys Ser Ser Gln Ser Leu Leu
                20                  25                  30

Tyr Ser Thr Asn Gln Lys Asn Phe Leu Ala Trp Tyr Gln Gln Lys
                35                  40                  45

Pro Gly Lys Ala Pro Lys Leu Leu Ile Tyr Trp Ala Ser Thr Arg
                50                  55                  60

Asp Ser Gly Val Pro Ser Arg Phe Ser Gly Ser Gly Ser Gly Thr
                65                  70                  75

Asp Phe Thr Leu Thr Ile Ser Ser Leu Gln Pro Glu Asp Phe Ala
                80                  85                  90

Thr Tyr Tyr Cys Gln Gln Tyr Tyr Ser Tyr Pro Arg Thr Phe Gly
                95                 100                 105

Gln Gly Thr Lys Val Glu Ile Lys Arg
                110

<210> SEQ ID NO 29
<211> LENGTH: 116
<212> TYPE: PRT
<213> ORGANISM: Artificial sequence
<220> FEATURE:
<223> OTHER INFORMATION: Sequence is synthesized

<400> SEQUENCE: 29

Gln Gly Gln Leu Gln Gln Ser Gly Ala Glu Leu Met Lys Pro Gly
 1               5                  10                  15

Ala Ser Val Lys Ile Ser Cys Lys Ala Thr Gly Tyr Thr Phe Ser
                20                  25                  30

Ser Tyr Trp Ile Glu Trp Val Lys Gln Arg Pro Gly His Gly Leu
```

```
                    35                  40                  45

Glu Trp Ile Gly Glu Ile Ser Pro Gly Ser Gly Ser Thr Asn Tyr
            50                  55                  60

Asn Glu Glu Phe Lys Gly Lys Ala Thr Phe Thr Ala Asp Lys Ser
            65                  70                  75

Ser Asn Thr Ala Tyr Ile Gln Leu Ser Ser Leu Ser Thr Ser Glu
            80                  85                  90

Asp Ser Ala Val Tyr Tyr Cys Ala Asp Gly Tyr His Gly Tyr Trp
            95                 100                 105

Gly Gln Gly Thr Thr Leu Thr Val Ser Ser Ala
            110                 115

<210> SEQ ID NO 30
<211> LENGTH: 115
<212> TYPE: PRT
<213> ORGANISM: Artificial sequence
<220> FEATURE:
<223> OTHER INFORMATION: Sequence is synthesized

<400> SEQUENCE: 30

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
            20                  25                  30

Ser Tyr Trp Ile Glu Trp Val Arg Gln Ala Pro Gly Lys Gly Leu
            35                  40                  45

Glu Trp Val Gly Glu Ile Ser Pro Gly Ser Gly Ser Thr Asn Tyr
            50                  55                  60

Asn Glu Glu Phe Lys Gly Arg Ala Thr Phe Ser Ala Asp Asn Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Asp Gly Tyr His Gly Tyr Trp Gly
            95                 100                 105

Gln Gly Thr Leu Val Thr Val Ser Ser Ala
            110                 115

<210> SEQ ID NO 31
<211> LENGTH: 115
<212> TYPE: PRT
<213> ORGANISM: Artificial sequence
<220> FEATURE:
<223> OTHER INFORMATION: Sequence is synthesized

<400> SEQUENCE: 31

Gln Gly Gln Leu Gln Gln Ser Gly Ala Glu Leu Met Lys Pro Gly
 1               5                  10                  15

Ala Ser Val Lys Ile Ser Cys Lys Ala Thr Gly Tyr Thr Phe Ser
            20                  25                  30

Ser Tyr Trp Ile Glu Trp Val Lys Gln Arg Pro Gly His Gly Leu
            35                  40                  45

Glu Trp Ile Gly Glu Ile Ser Pro Gly Ser Gly Ser Thr Asn Tyr
            50                  55                  60

Asn Glu Glu Phe Lys Gly Lys Ala Thr Phe Thr Ala Asp Lys Ser
            65                  70                  75

Ser Asn Thr Ala Tyr Ile Gln Leu Ser Ser Leu Ser Thr Ser Glu
            80                  85                  90

Asp Ser Ala Val Tyr Tyr Cys Ala Asp Gly Tyr His Gly Tyr Trp
```

```
                   95                  100                 105

Gly Gln Gly Thr Thr Leu Thr Val Ser Ser
                110                 115

<210> SEQ ID NO 32
<211> LENGTH: 214
<212> TYPE: PRT
<213> ORGANISM: Artificial sequence
<220> FEATURE:
<223> OTHER INFORMATION: Sequence is synthesized

<400> SEQUENCE: 32

Asp Ile Val Met Thr Gln Ser His Lys Phe Met Ser Thr Ser Val
  1               5                  10                  15

Gly Asp Arg Val Ser Ile Thr Cys Lys Ala Ser Gln Ala Val Ser
                 20                  25                  30

Ser Ala Val Ala Trp Tyr Gln Gln Lys Pro Gly Gln Ser Pro Lys
                 35                  40                  45

Leu Gln Ile Tyr Ser Ala Ser His Arg Tyr Thr Gly Val Pro Asp
                 50                  55                  60

Arg Phe Thr Gly Ser Gly Ser Gly Thr Asp Phe Thr Phe Thr Ile
                 65                  70                  75

Ser Ser Val Gln Ala Glu Asp Leu Ala Val Tyr Tyr Cys Gln Gln
                 80                  85                  90

His Tyr Ser Thr Pro Trp Thr Phe Gly Gly Gly Thr Lys Val Glu
                 95                 100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 33
<211> LENGTH: 448
<212> TYPE: PRT
<213> ORGANISM: Artificial sequence
<220> FEATURE:
<223> OTHER INFORMATION: Sequence is synthesized

<400> SEQUENCE: 33

Glu Val Gln Leu Gln Gln Ser Gly Pro Glu Leu Val Lys Pro Gly
  1               5                  10                  15

Ala Ser Val Lys Leu Ser Cys Lys Ala Ser Gly Tyr Thr Phe Thr
                 20                  25                  30

Ser Tyr Val Ile His Trp Val Lys Gln Lys Pro Gly Gln Gly Leu
                 35                  40                  45

Glu Trp Ile Gly Tyr Asn Asn Pro Tyr Asn Asp Gly Thr Asn Tyr
                 50                  55                  60
```

```
Asn Glu Lys Phe Lys Gly Lys Ala Thr Leu Thr Ser Asp Lys Ser
                65                  70                  75

Ser Ser Thr Ala Tyr Met Glu Leu Ser Ser Leu Thr Ser Glu Asp
                80                  85                  90

Ser Ala Val Tyr Tyr Cys Ser Arg Pro Thr Met Leu Pro Trp Phe
                95                 100                 105

Ala Tyr Trp Gly Gln Gly Thr Thr Leu Thr Val Ser Ala Ala Ser
               110                 115                 120

Thr Lys Gly Pro Ser Val Phe Pro Leu Ala Pro Ser Ser Lys Ser
               125                 130                 135

Thr Ser Gly Gly Thr Ala Ala Leu Gly Cys Leu Val Lys Asp Tyr
               140                 145                 150

Phe Pro Glu Pro Val Thr Val Ser Trp Asn Ser Gly Ala Leu Thr
               155                 160                 165

Ser Gly Val His Thr Phe Pro Ala Val Leu Gln Ser Ser Gly Leu
               170                 175                 180

Tyr Ser Leu Ser Ser Val Val Thr Val Pro Ser Ser Ser Leu Gly
               185                 190                 195

Thr Gln Thr Tyr Ile Cys Asn Val Asn His Lys Pro Ser Asn Thr
               200                 205                 210

Lys Val Asp Lys Lys Val Glu Pro Lys Ser Cys Asp Lys Thr His
               215                 220                 225

Thr Cys Pro Pro Cys Pro Ala Pro Glu Leu Leu Gly Gly Pro Ser
               230                 235                 240

Val Phe Leu Phe Pro Pro Lys Pro Lys Asp Thr Leu Met Ile Ser
               245                 250                 255

Arg Thr Pro Glu Val Thr Cys Val Val Asp Val Ser His Glu
               260                 265                 270

Asp Pro Glu Val Lys Phe Asn Trp Tyr Val Asp Gly Val Glu Val
               275                 280                 285

His Asn Ala Lys Thr Lys Pro Arg Glu Glu Gln Tyr Asn Ser Thr
               290                 295                 300

Tyr Arg Val Val Ser Val Leu Thr Val Leu His Gln Asp Trp Leu
               305                 310                 315

Asn Gly Lys Glu Tyr Lys Cys Lys Val Ser Asn Lys Ala Leu Pro
               320                 325                 330

Ala Pro Ile Glu Lys Thr Ile Ser Lys Ala Lys Gly Gln Pro Arg
               335                 340                 345

Glu Pro Gln Val Tyr Thr Leu Pro Pro Ser Arg Glu Glu Met Thr
               350                 355                 360

Lys Asn Gln Val Ser Leu Thr Cys Leu Val Lys Gly Phe Tyr Pro
               365                 370                 375

Ser Asp Ile Ala Val Glu Trp Glu Ser Asn Gly Gln Pro Glu Asn
               380                 385                 390

Asn Tyr Lys Thr Thr Pro Pro Val Leu Asp Ser Asp Gly Ser Phe
               395                 400                 405

Phe Leu Tyr Ser Lys Leu Thr Val Asp Lys Ser Arg Trp Gln Gln
               410                 415                 420

Gly Asn Val Phe Ser Cys Ser Val Met His Glu Ala Leu His Asn
               425                 430                 435

His Tyr Thr Gln Lys Ser Leu Ser Leu Ser Pro Gly Lys
               440                 445
```

```
<210> SEQ ID NO 34
<211> LENGTH: 220
<212> TYPE: PRT
<213> ORGANISM: Artificial sequence
<220> FEATURE:
<223> OTHER INFORMATION: Sequence is synthesized

<400> SEQUENCE: 34

Asp Ile Val Met Ser Gln Ser Pro Ser Ser Leu Ala Val Ser Val
 1               5                  10                  15

Gly Glu Lys Val Thr Met Ser Cys Lys Ser Ser Gln Ser Leu Leu
                20                  25                  30

Tyr Ser Thr Asn Gln Lys Asn Phe Leu Ala Trp Tyr Gln Gln Lys
                35                  40                  45

Pro Gly Gln Ser Pro Lys Leu Leu Ile Tyr Trp Ala Ser Thr Arg
                50                  55                  60

Asp Ser Gly Val Pro Asp Arg Phe Thr Gly Ser Gly Ser Gly Thr
                65                  70                  75

Asp Phe Thr Leu Thr Ile Ser Ser Val Lys Ala Glu Asp Leu Ala
                80                  85                  90

Val Tyr Tyr Cys Gln Gln Tyr Tyr Ser Tyr Pro Arg Thr Phe Gly
                95                 100                 105

Gly Gly Thr Lys Leu Glu Ile Lys Arg Thr Val Ala Ala Pro Ser
               110                 115                 120

Val Phe Ile Phe Pro Pro Ser Asp Glu Gln Leu Lys Ser Gly Thr
               125                 130                 135

Ala Ser Val Val Cys Leu Leu Asn Asn Phe Tyr Pro Arg Glu Ala
               140                 145                 150

Lys Val Gln Trp Lys Val Asp Asn Ala Leu Gln Ser Gly Asn Ser
               155                 160                 165

Gln Glu Ser Val Thr Glu Gln Asp Ser Lys Asp Ser Thr Tyr Ser
               170                 175                 180

Leu Ser Ser Thr Leu Thr Leu Ser Lys Ala Asp Tyr Glu Lys His
               185                 190                 195

Lys Val Tyr Ala Cys Glu Val Thr His Gln Gly Leu Ser Ser Pro
               200                 205                 210

Val Thr Lys Ser Phe Asn Arg Gly Glu Cys
               215                 220

<210> SEQ ID NO 35
<211> LENGTH: 445
<212> TYPE: PRT
<213> ORGANISM: Artificial sequence
<220> FEATURE:
<223> OTHER INFORMATION: Sequence is synthesized

<400> SEQUENCE: 35

Gln Gly Gln Leu Gln Gln Ser Gly Ala Glu Leu Met Lys Pro Gly
 1               5                  10                  15

Ala Ser Val Lys Ile Ser Cys Lys Ala Thr Gly Tyr Thr Phe Ser
                20                  25                  30

Ser Tyr Trp Ile Glu Trp Val Lys Gln Arg Pro Gly His Gly Leu
                35                  40                  45

Glu Trp Ile Gly Glu Ile Ser Pro Gly Ser Gly Ser Thr Asn Tyr
                50                  55                  60

Asn Glu Glu Phe Lys Gly Lys Ala Thr Phe Thr Ala Asp Lys Ser
                65                  70                  75

Ser Asn Thr Ala Tyr Ile Gln Leu Ser Ser Leu Ser Thr Ser Glu
```

```
            80                  85                  90
Asp Ser Ala Val Tyr Tyr Cys Ala Asp Gly Tyr His Gly Tyr Trp
                95                 100                 105
Gly Gln Gly Thr Thr Leu Thr Val Ser Ala Lys Thr Thr Gly
            110                 115                 120
Pro Ser Val Phe Pro Leu Ala Pro Ser Ser Lys Ser Thr Ser Gly
                125                 130                 135
Gly Thr Ala Ala Leu Gly Cys Leu Val Lys Asp Tyr Phe Pro Glu
            140                 145                 150
Pro Val Thr Val Ser Trp Asn Ser Gly Ala Leu Thr Ser Gly Val
                155                 160                 165
His Thr Phe Pro Ala Val Leu Gln Ser Ser Gly Leu Tyr Ser Leu
            170                 175                 180
Ser Ser Val Val Thr Val Pro Ser Ser Ser Leu Gly Thr Gln Thr
                185                 190                 195
Tyr Ile Cys Asn Val Asn His Lys Pro Ser Asn Thr Lys Val Asp
                200                 205                 210
Lys Lys Val Glu Pro Lys Ser Cys Asp Lys Thr His Thr Cys Pro
                215                 220                 225
Pro Cys Pro Ala Pro Glu Leu Leu Gly Gly Pro Ser Val Phe Leu
                230                 235                 240
Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu
                260                 265                 270
Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val
                290                 295                 300
Val Ser Val Leu Thr Val Leu His Gln Asp Trp Leu Asn Gly Lys
                305                 310                 315
Glu Tyr Lys Cys Lys Val Ser Asn Lys Ala Leu Pro Ala Pro Ile
                320                 325                 330
Glu Lys Thr Ile Ser Lys Ala Lys Gly Gln Pro Arg Glu Pro Gln
                335                 340                 345
Val Tyr Thr Leu Pro Pro Ser Arg Glu Glu Met Thr Lys Asn Gln
                350                 355                 360
Val Ser Leu Thr Cys Leu Val Lys Gly Phe Tyr Pro Ser Asp Ile
                365                 370                 375
Ala Val Glu Trp Glu Ser Asn Gly Gln Pro Glu Asn Asn Tyr Lys
                380                 385                 390
Thr Thr Pro Pro Val Leu Asp Ser Asp Gly Ser Phe Phe Leu Tyr
                395                 400                 405
Ser Lys Leu Thr Val Asp Lys Ser Arg Trp Gln Gln Gly Asn Val
                410                 415                 420
Phe Ser Cys Ser Val Met His Glu Ala Leu His Asn His Tyr Thr
                425                 430                 435
Gln Lys Ser Leu Ser Leu Ser Pro Gly Lys
                440                 445

<210> SEQ ID NO 36
<211> LENGTH: 113
<212> TYPE: PRT
<213> ORGANISM: Artificial sequence
<220> FEATURE:
```

<223> OTHER INFORMATION: Sequence is synthesized

<400> SEQUENCE: 36

```
Asp Ile Val Met Ser Gln Ser Pro Ser Ser Leu Ala Val Ser Val
  1               5                  10                  15

Gly Glu Lys Val Thr Met Ser Cys Lys Ser Ser Gln Ser Leu Leu
                 20                  25                  30

Tyr Ser Thr Asn Gln Lys Asn Phe Leu Ala Trp Tyr Gln Gln Lys
                 35                  40                  45

Pro Gly Gln Ser Pro Lys Leu Leu Ile Tyr Trp Ala Ser Thr Arg
                 50                  55                  60

Asp Ser Gly Val Pro Asp Arg Phe Thr Gly Ser Gly Ser Gly Thr
                 65                  70                  75

Asp Phe Thr Leu Thr Ile Ser Ser Val Lys Ala Glu Asp Leu Ala
                 80                  85                  90

Val Tyr Tyr Cys Gln Gln Tyr Tyr Ser Tyr Pro Arg Thr Phe Gly
                 95                 100                 105

Gly Gly Thr Lys Leu Glu Ile Lys
                110
```

<210> SEQ ID NO 37
<211> LENGTH: 107
<212> TYPE: PRT
<213> ORGANISM: Artificial sequence
<220> FEATURE:
<223> OTHER INFORMATION: Sequence is synthesized

<400> SEQUENCE: 37

```
Arg Ala Asp Ala Ala Pro Thr Val Ser Ile Phe Pro Pro Ser Ser
  1               5                  10                  15

Glu Gln Leu Thr Ser Gly Gly Ala Ser Val Val Cys Phe Leu Asn
                 20                  25                  30

Asn Phe Tyr Pro Lys Asp Ile Asn Val Lys Trp Lys Ile Asp Gly
                 35                  40                  45

Ser Glu Arg Gln Asn Gly Val Leu Asn Ser Trp Thr Asp Gln Asp
                 50                  55                  60

Ser Lys Asp Ser Thr Tyr Ser Met Ser Ser Thr Leu Thr Leu Thr
                 65                  70                  75

Lys Asp Glu Tyr Glu Arg His Asn Ser Tyr Thr Cys Glu Ala Thr
                 80                  85                  90

His Lys Thr Ser Thr Ser Pro Ile Val Lys Ser Phe Asn Arg Asn
                 95                 100                 105

Glu Cys
```

<210> SEQ ID NO 38
<211> LENGTH: 114
<212> TYPE: PRT
<213> ORGANISM: Artificial sequence
<220> FEATURE:
<223> OTHER INFORMATION: Sequence is synthesized

<400> SEQUENCE: 38

```
Gln Gly Gln Leu Gln Gln Ser Gly Ala Glu Leu Met Lys Pro Gly
  1               5                  10                  15

Ala Ser Val Lys Ile Ser Cys Lys Ala Thr Gly Tyr Thr Phe Ser
                 20                  25                  30

Ser Tyr Trp Ile Glu Trp Val Lys Gln Arg Pro Gly His Gly Leu
                 35                  40                  45
```

```
Glu Trp Ile Gly Glu Ile Ser Pro Gly Ser Gly Ser Thr Asn Tyr
             50                  55                  60

Asn Glu Glu Phe Lys Gly Lys Ala Thr Phe Thr Ala Asp Lys Ser
             65                  70                  75

Ser Asn Thr Ala Tyr Ile Gln Leu Ser Ser Leu Thr Ser Glu Asp
             80                  85                  90

Ser Ala Val Tyr Tyr Cys Ala Asp Gly Tyr His Gly Tyr Trp Gly
             95                 100                 105

Gln Gly Thr Thr Leu Thr Val Ser Ser
            110

<210> SEQ ID NO 39
<211> LENGTH: 335
<212> TYPE: PRT
<213> ORGANISM: Artificial sequence
<220> FEATURE:
<223> OTHER INFORMATION: Sequence is synthesized

<400> SEQUENCE: 39

Ala Lys Thr Thr Pro Pro Ser Val Tyr Pro Leu Ala Pro Gly Cys
  1               5                  10                  15

Gly Asp Thr Thr Gly Ser Ser Val Thr Leu Gly Cys Leu Val Lys
             20                  25                  30

Gly Tyr Phe Pro Glu Ser Val Thr Val Thr Trp Asn Ser Gly Ser
             35                  40                  45

Leu Ser Ser Ser Val His Thr Phe Pro Ala Leu Leu Gln Ser Gly
             50                  55                  60

Leu Tyr Thr Met Ser Ser Ser Val Thr Val Pro Ser Ser Thr Trp
             65                  70                  75

Pro Ser Gln Thr Val Thr Cys Ser Val Ala His Pro Ala Ser Ser
             80                  85                  90

Thr Thr Val Asp Lys Lys Leu Glu Pro Ser Gly Pro Ile Ser Thr
             95                 100                 105

Ile Asn Pro Cys Pro Pro Cys Lys Glu Cys His Lys Cys Pro Ala
            110                 115                 120

Pro Asn Leu Glu Gly Gly Pro Ser Val Phe Ile Phe Pro Pro Asn
            125                 130                 135

Ile Lys Asp Val Leu Met Ile Ser Leu Thr Pro Lys Val Thr Cys
            140                 145                 150

Val Val Val Asp Val Ser Glu Asp Pro Asp Val Gln Ile Ser
            155                 160                 165

Trp Phe Val Asn Asn Val Glu Val His Thr Ala Gln Thr Gln Thr
            170                 175                 180

His Arg Glu Asp Tyr Asn Ser Thr Ile Arg Val Val Ser Thr Leu
            185                 190                 195

Pro Ile Gln His Gln Asp Trp Met Ser Gly Lys Glu Phe Lys Cys
            200                 205                 210

Lys Val Asn Asn Lys Asp Leu Pro Ser Pro Ile Glu Arg Thr Ile
            215                 220                 225

Ser Lys Ile Lys Gly Leu Val Arg Ala Pro Gln Val Tyr Ile Leu
            230                 235                 240

Pro Pro Pro Ala Glu Gln Leu Ser Arg Lys Asp Val Ser Leu Thr
            245                 250                 255

Cys Leu Val Val Gly Phe Asn Pro Gly Asp Ile Ser Val Glu Trp
            260                 265                 270

Thr Ser Asn Gly His Thr Glu Glu Asn Tyr Lys Asp Thr Ala Pro
```

```
                    275                 280                 285

Val Leu Asp Ser Asp Gly Ser Tyr Phe Ile Tyr Ser Lys Leu Asn
                290                 295                 300

Met Lys Thr Ser Lys Trp Glu Lys Thr Asp Ser Phe Ser Cys Asn
            305                 310                 315

Val Arg His Glu Gly Leu Lys Asn Tyr Tyr Leu Lys Lys Thr Ile
        320                 325                 330

Ser Arg Ser Pro Gly
            335

<210> SEQ ID NO 40
<211> LENGTH: 108
<212> TYPE: PRT
<213> ORGANISM: Artificial sequence
<220> FEATURE:
<223> OTHER INFORMATION: Sequence is synthesized

<400> SEQUENCE: 40

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ser Ile Ser
                 20                  25                  30

Asn Tyr Leu Ala Trp Tyr Gln Gln Lys Pro Gly Lys Ala Pro Lys
             35                  40                  45

Leu Leu Ile Tyr Ala Ala Ser Ser Leu Glu Ser Gly Val Pro Ser
         50                  55                  60

Arg Phe Ser Gly Ser Gly Ser Gly Thr Asp Phe Thr Leu Thr Ile
     65                  70                  75

Ser Ser Leu Gln Pro Glu Asp Phe Ala Thr Tyr Tyr Cys Gln Gln
                 80                  85                  90

Tyr Asn Ser Leu Pro Trp Thr Phe Gly Gln Gly Thr Lys Val Glu
             95                 100                 105

Ile Lys Arg

<210> SEQ ID NO 41
<211> LENGTH: 118
<212> TYPE: PRT
<213> ORGANISM: Artificial sequence
<220> FEATURE:
<223> OTHER INFORMATION: Sequence is synthesized

<400> SEQUENCE: 41

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu
             35                  40                  45

Glu Trp Val Ser Val Ile Ser Gly Asp Gly Gly Ser Thr Tyr Tyr
         50                  55                  60

Ala Asp Ser Val Lys Gly Arg Phe Thr Ile Ser Arg Asp Asn Ser
     65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Gly Arg Gly Gly Ser Asp
             95                 100                 105

Tyr Trp Gly Gln Gly Thr Leu Val Thr Val Ser Ser Ala
         110                 115
```

<210> SEQ ID NO 42
<211> LENGTH: 214
<212> TYPE: PRT
<213> ORGANISM: Artificial sequence
<220> FEATURE:
<223> OTHER INFORMATION: Sequence is synthesized

<400> SEQUENCE: 42

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ala Val Ser
                20                  25                  30

Ser Ala Val Ala Trp Tyr Gln Gln Lys Pro Gly Lys Ala Pro Lys
                35                  40                  45

Leu Leu Ile Tyr Ser Ala Ser His Arg Tyr Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Ser Thr Pro Trp Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys

<210> SEQ ID NO 43
<211> LENGTH: 448
<212> TYPE: PRT
<213> ORGANISM: Artificial sequence
<220> FEATURE:
<223> OTHER INFORMATION: Sequence is synthesized

<400> SEQUENCE: 43

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Val Ile His Trp Val Arg Gln Ala Pro Gly Lys Gly Leu
                35                  40                  45

Glu Trp Val Gly Tyr Asn Asn Pro Tyr Asn Asp Gly Thr Asn Tyr
                50                  55                  60

Asn Glu Lys Phe Lys Gly Arg Ala Thr Ile Ser Ser Asp Lys Ser
                65                  70                  75

```
Lys Asn Thr Ala Tyr Leu Gln Met Asn Ser Leu Arg Ala Glu Asp
             80                  85                  90
Thr Ala Val Tyr Tyr Cys Ser Arg Pro Thr Met Leu Pro Trp Phe
             95                 100                 105
Ala Tyr Trp Gly Gln Gly Thr Leu Val Thr Val Ser Ser Ala Ser
            110                 115                 120
Thr Lys Gly Pro Ser Val Phe Pro Leu Ala Pro Ser Ser Lys Ser
            125                 130                 135
Thr Ser Gly Gly Thr Ala Ala Leu Gly Cys Leu Val Lys Asp Tyr
            140                 145                 150
Phe Pro Glu Pro Val Thr Val Ser Trp Asn Ser Gly Ala Leu Thr
            155                 160                 165
Ser Gly Val His Thr Phe Pro Ala Val Leu Gln Ser Ser Gly Leu
            170                 175                 180
Tyr Ser Leu Ser Ser Val Val Thr Val Pro Ser Ser Ser Leu Gly
            185                 190                 195
Thr Gln Thr Tyr Ile Cys Asn Val Asn His Lys Pro Ser Asn Thr
            200                 205                 210
Lys Val Asp Lys Lys Val Glu Pro Lys Ser Cys Asp Lys Thr His
            215                 220                 225
Thr Cys Pro Pro Cys Pro Ala Pro Glu Leu Leu Gly Gly Pro Ser
            230                 235                 240
Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu
            305                 310                 315
Asn Gly Lys Glu Tyr Lys Cys Lys Val Ser Asn Lys Ala Leu Pro
            320                 325                 330
Ala Pro Ile Glu Lys Thr Ile Ser Lys Ala Lys Gly Gln Pro Arg
            335                 340                 345
Glu Pro Gln Val Tyr Thr Leu Pro Pro Ser Arg Glu Glu Met Thr
            350                 355                 360
Lys Asn Gln Val Ser Leu Thr Cys Leu Val Lys Gly Phe Tyr Pro
            365                 370                 375
Ser Asp Ile Ala Val Glu Trp Glu Ser Asn Gly Gln Pro Glu Asn
            380                 385                 390
Asn Tyr Lys Thr Thr Pro Pro Val Leu Asp Ser Asp Gly Ser Phe
            395                 400                 405
Phe Leu Tyr Ser Lys Leu Thr Val Asp Lys Ser Arg Trp Gln Gln
            410                 415                 420
Gly Asn Val Phe Ser Cys Ser Val Met His Glu Ala Leu His Asn
            425                 430                 435
His Tyr Thr Gln Lys Ser Leu Ser Leu Ser Pro Gly Lys
            440                 445

<210> SEQ ID NO 44
<211> LENGTH: 214
<212> TYPE: PRT
<213> ORGANISM: Artificial sequence
```

<220> FEATURE:
<223> OTHER INFORMATION: Sequence is synthesized

<400> SEQUENCE: 44

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ala Val Ser
                20                  25                  30

Ser Ala Val Ala Trp Tyr Gln Gln Lys Pro Gly Lys Ala Pro Lys
            35                  40                  45

Leu Leu Ile Tyr Ser Ala Ser His Arg Tyr Thr Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

His Tyr Ser Thr Pro Trp Thr Phe Gly Gln Gly Thr Lys Val Glu
            95                  100                 105

Ile Lys Arg Thr Val Ala Ala Pro Ser Val Phe Ile Phe Pro Pro
        110                 115                 120

Ser Asp Glu Gln Leu Lys Ser Gly Thr Ala Ser Val Val Cys Leu
    125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
        170                 175                 180

Leu Ser Lys Ala Asp Tyr Glu Lys His Lys Val Tyr Ala Cys Glu
    185                 190                 195

Val Thr His Gln Gly Leu Ser Ser Pro Val Thr Lys Ser Phe Asn
                200                 205                 210

Arg Gly Glu Cys

<210> SEQ ID NO 45
<211> LENGTH: 448
<212> TYPE: PRT
<213> ORGANISM: Artificial sequence
<220> FEATURE:
<223> OTHER INFORMATION: Sequence is synthesized

<400> SEQUENCE: 45

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Val Ile His Trp Val Arg Gln Ala Pro Gly Lys Gly Leu
            35                  40                  45

Glu Trp Val Gly Tyr Asn Asn Pro Tyr Asn Asp Gly Thr Asn Tyr
        50                  55                  60

Asn Glu Lys Phe Lys Gly Arg Phe Thr Ile Ser Ser Asp Lys Ser
65                  70                  75

Lys Asn Thr Ala Tyr Leu Gln Met Asn Ser Leu Arg Ala Glu Asp
                80                  85                  90

Thr Ala Val Tyr Tyr Cys Ser Arg Pro Thr Met Leu Pro Trp Phe
            95                  100                 105

```
Ala Tyr Trp Gly Gln Gly Thr Leu Val Thr Val Ser Ser Ala Ser
                110                 115                 120

Thr Lys Gly Pro Ser Val Phe Pro Leu Ala Pro Ser Ser Lys Ser
                125                 130                 135

Thr Ser Gly Gly Thr Ala Ala Leu Gly Cys Leu Val Lys Asp Tyr
                140                 145                 150

Phe Pro Glu Pro Val Thr Val Ser Trp Asn Ser Gly Ala Leu Thr
                155                 160                 165

Ser Gly Val His Thr Phe Pro Ala Val Leu Gln Ser Ser Gly Leu
                170                 175                 180

Tyr Ser Leu Ser Ser Val Val Thr Val Pro Ser Ser Ser Leu Gly
                185                 190                 195

Thr Gln Thr Tyr Ile Cys Asn Val Asn His Lys Pro Ser Asn Thr
                200                 205                 210

Lys Val Asp Lys Lys Val Glu Pro Lys Ser Cys Asp Lys Thr His
                215                 220                 225

Thr Cys Pro Pro Cys Pro Ala Pro Glu Leu Leu Gly Gly Pro Ser
                230                 235                 240

Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu
                305                 310                 315

Asn Gly Lys Glu Tyr Lys Cys Lys Val Ser Asn Lys Ala Leu Pro
                320                 325                 330

Ala Pro Ile Glu Lys Thr Ile Ser Lys Ala Lys Gly Gln Pro Arg
                335                 340                 345

Glu Pro Gln Val Tyr Thr Leu Pro Pro Ser Arg Glu Glu Met Thr
                350                 355                 360

Lys Asn Gln Val Ser Leu Thr Cys Leu Val Lys Gly Phe Tyr Pro
                365                 370                 375

Ser Asp Ile Ala Val Glu Trp Glu Ser Asn Gly Gln Pro Glu Asn
                380                 385                 390

Asn Tyr Lys Thr Thr Pro Pro Val Leu Asp Ser Asp Gly Ser Phe
                395                 400                 405

Phe Leu Tyr Ser Lys Leu Thr Val Asp Lys Ser Arg Trp Gln Gln
                410                 415                 420

Gly Asn Val Phe Ser Cys Ser Val Met His Glu Ala Leu His Asn
                425                 430                 435

His Tyr Thr Gln Lys Ser Leu Ser Leu Ser Pro Gly Lys
                440                 445

<210> SEQ ID NO 46
<211> LENGTH: 25
<212> TYPE: PRT
<213> ORGANISM: Artificial sequence
<220> FEATURE:
<223> OTHER INFORMATION: Sequence is synthesized

<400> SEQUENCE: 46

Glu Val Gln Leu Val Glu Ser Gly Gly Gly Leu Val Gln Pro Gly
```

```
                 1               5                  10                  15
Gly Ser Leu Arg Leu Ser Cys Ala Ala Ser
                20                  25

<210> SEQ ID NO 47
<211> LENGTH: 14
<212> TYPE: PRT
<213> ORGANISM: Artificial sequence
<220> FEATURE:
<223> OTHER INFORMATION: Sequence is synthesized

<400> SEQUENCE: 47

Trp Val Arg Gln Ala Pro Gly Lys Gly Leu Glu Trp Val Gly
                 5                  10

<210> SEQ ID NO 48
<211> LENGTH: 32
<212> TYPE: PRT
<213> ORGANISM: Artificial sequence
<220> FEATURE:
<223> OTHER INFORMATION: Sequence is synthesized

<400> SEQUENCE: 48

Arg Phe Thr Ile Ser Arg Asp Asn Ser Lys Asn Thr Leu Tyr Leu
  1               5                  10                  15
Gln Met Asn Ser Leu Arg Ala Glu Asp Thr Ala Val Tyr Tyr Cys
                20                  25                  30
Ala Arg

<210> SEQ ID NO 49
<211> LENGTH: 11
<212> TYPE: PRT
<213> ORGANISM: Artificial sequence
<220> FEATURE:
<223> OTHER INFORMATION: Sequence is synthesized

<400> SEQUENCE: 49

Trp Gly Gln Gly Thr Leu Val Thr Val Ser Ser
                 5                  10

<210> SEQ ID NO 50
<211> LENGTH: 32
<212> TYPE: PRT
<213> ORGANISM: Artificial sequence
<220> FEATURE:
<223> OTHER INFORMATION: Sequence is synthesized

<400> SEQUENCE: 50

Arg Ala Thr Phe Ser Ala Asp Asn Ser Lys Asn Thr Ala Tyr Leu
  1               5                  10                  15
Gln Met Asn Ser Leu Arg Ala Glu Asp Thr Ala Val Tyr Tyr Cys
                20                  25                  30
Ala Asp

<210> SEQ ID NO 51
<211> LENGTH: 23
<212> TYPE: PRT
<213> ORGANISM: Artificial sequence
<220> FEATURE:
<223> OTHER INFORMATION: Sequence is synthesized

<400> SEQUENCE: 51

Asp Ile Gln Met Thr Gln Ser Pro Ser Ser Leu Ser Ala Ser Val
  1               5                  10                  15
```

```
Gly Asp Arg Val Thr Ile Thr Cys
            20
```

<210> SEQ ID NO 52
<211> LENGTH: 15
<212> TYPE: PRT
<213> ORGANISM: Artificial sequence
<220> FEATURE:
<223> OTHER INFORMATION: Sequence is synthesized

<400> SEQUENCE: 52

```
Trp Tyr Gln Gln Lys Pro Gly Lys Ala Pro Lys Leu Gln Ile Tyr
 1               5                  10                  15
```

<210> SEQ ID NO 53
<211> LENGTH: 32
<212> TYPE: PRT
<213> ORGANISM: Artificial sequence
<220> FEATURE:
<223> OTHER INFORMATION: Sequence is synthesized

<400> SEQUENCE: 53

```
Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys
```

<210> SEQ ID NO 54
<211> LENGTH: 11
<212> TYPE: PRT
<213> ORGANISM: Artificial sequence
<220> FEATURE:
<223> OTHER INFORMATION: Sequence is synthesized

<400> SEQUENCE: 54

```
Phe Gly Gln Gly Thr Lys Val Glu Ile Lys Arg
 1               5                  10
```

<210> SEQ ID NO 55
<211> LENGTH: 15
<212> TYPE: PRT
<213> ORGANISM: Artificial sequence
<220> FEATURE:
<223> OTHER INFORMATION: Sequence is synthesized

<400> SEQUENCE: 55

```
Trp Tyr Gln Gln Lys Pro Gly Lys Ala Pro Lys Leu Leu Ile Tyr
 1               5                  10                  15
```

<210> SEQ ID NO 56
<211> LENGTH: 35
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 15, 30
<223> OTHER INFORMATION: R = A or G
<220> FEATURE:
<221> NAME/KEY: Unknown
<222> LOCATION: 18, 24, 27, 33
<223> OTHER INFORMATION: N= A, G, C, and T
<220> FEATURE:
<221> NAME/KEY: Unknown
<222> LOCATION: 22
<223> OTHER INFORMATION: Y = C or T

<400> SEQUENCE: 56
ggatcatcga tacarctngt vytncancar tcncc                    35

<210> SEQ ID NO 57
<211> LENGTH: 33
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 3
<223> OTHER INFORMATION: R = A or G
<220> FEATURE:
<221> NAME/KEY: Unknown
<222> LOCATION: 18
<223> OTHER INFORMATION: Y = C or T

<400> SEQUENCE: 57
aarggtggta gaagactygc cgcgcggcaa tgg                      33

<210> SEQ ID NO 58
<211> LENGTH: 33
<212> TYPE: DNA
<213> ORGANISM: Artificial sequence
<220> FEATURE:
<223> OTHER INFORMATION: Sequence is synthesized

<400> SEQUENCE: 58
ggatccgata tccagctggt attgacccaa tct                      33

<210> SEQ ID NO 59
<211> LENGTH: 33
<212> TYPE: DNA
<213> ORGANISM: Artificial sequence
<220> FEATURE:
<223> OTHER INFORMATION: Sequence is synthesized

<400> SEQUENCE: 59
cccagcacac aaaaaccgtc gccatggact agg                      33

<210> SEQ ID NO 60
<211> LENGTH: 30
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 14, 24, 30
<223> OTHER INFORMATION: R = A or G
<220> FEATURE:
<221> NAME/KEY: Unknown
<222> LOCATION: 17, 27
<223> OTHER INFORMATION: N = A, G, C, and T

<400> SEQUENCE: 60
tgataatcga tgargtncca tttrgtngar                          30

<210> SEQ ID NO 61
<211> LENGTH: 36
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 6
<223> OTHER INFORMATION: R = A or G
<220> FEATURE:

```
<221> NAME/KEY: Unknown
<222> LOCATION: 9, 12
<223> OTHER INFORMATION: N = A, G, C, and T

<400> SEQUENCE: 61
accttragnc cnagggactg gtccgcgcgg  aatgat                            36

<210> SEQ ID NO 62
<211> LENGTH: 32
<212> TYPE: DNA
<213> ORGANISM: Artificial sequence
<220> FEATURE:
<223> OTHER INFORMATION: Sequence is synthesized

<400> SEQUENCE: 62
tgatcgcgta cgctgaggtt caattggttg  ag                                32

<210> SEQ ID NO 63
<211> LENGTH: 35
<212> TYPE: DNA
<213> ORGANISM: Artificial sequence
<220> FEATURE:
<223> OTHER INFORMATION: Sequence is synthesized

<400> SEQUENCE: 63
ggcagaggag tcggtgttgt ttcccgggtg  ctagt                             35

<210> SEQ ID NO 64
<211> LENGTH: 220
<212> TYPE: PRT
<213> ORGANISM: Artificial sequence
<220> FEATURE:
<223> OTHER INFORMATION: Sequence is synthesized

<400> SEQUENCE: 64
```

Asp Ile Val Met Ser Gln Ser Pro Ser Leu Ala Val Ser Val
 1               5                  10                  15

Gly Glu Lys Val Thr Met Ser Cys Lys Ser Ser Gln Ser Leu Leu
            20                  25                  30

Tyr Ser Thr Asn Gln Lys Asn Phe Leu Ala Trp Tyr Gln Gln Lys
            35                  40                  45

Pro Gly Gln Ser Pro Lys Leu Leu Ile Tyr Trp Ala Ser Thr Arg
            50                  55                  60

Asp Ser Gly Val Pro Asp Arg Phe Thr Gly Ser Gly Ser Gly Thr
            65                  70                  75

Asp Phe Thr Leu Thr Ile Ser Ser Val Lys Ala Glu Asp Leu Ala
            80                  85                  90

Val Tyr Tyr Cys Gln Gln Tyr Tyr Ser Tyr Pro Arg Thr Phe Gly
            95                 100                 105

Gly Gly Thr Lys Leu Glu Ile Lys Arg Ala Asp Ala Ala Pro Thr
           110                 115                 120

Val Ser Ile Phe Pro Pro Ser Ser Glu Gln Leu Thr Ser Gly Gly
           125                 130                 135

Ala Ser Val Val Cys Phe Leu Asn Asn Phe Tyr Pro Lys Asp Ile
           140                 145                 150

Asn Val Lys Trp Lys Ile Asp Gly Ser Glu Arg Gln Asn Gly Val
           155                 160                 165

Leu Asn Ser Trp Thr Asp Gln Asp Ser Lys Asp Ser Thr Tyr Ser
           170                 175                 180

Met Ser Ser Thr Leu Thr Leu Thr Lys Asp Glu Tyr Glu Arg His
           185                 190                 195

```
Asn Ser Tyr Thr Cys Glu Ala Thr His Lys Thr Ser Thr Ser Pro
            200                 205                 210

Ile Val Lys Ser Phe Asn Arg Asn Glu Cys
            215                 220

<210> SEQ ID NO 65
<211> LENGTH: 220
<212> TYPE: PRT
<213> ORGANISM: Artificial sequence
<220> FEATURE:
<223> OTHER INFORMATION: Sequence is synthesized

<400> SEQUENCE: 65

Gln Gly Gln Leu Gln Gln Ser Gly Ala Glu Leu Met Lys Pro Gly
  1               5                  10                  15

Ala Ser Val Lys Ile Ser Cys Lys Ala Thr Gly Tyr Thr Phe Ser
                 20                  25                  30

Ser Tyr Trp Ile Glu Trp Val Lys Gln Arg Pro Gly His Gly Leu
                 35                  40                  45

Glu Trp Ile Gly Glu Ile Ser Pro Gly Ser Gly Ser Thr Asn Tyr
                 50                  55                  60

Asn Glu Glu Phe Lys Gly Lys Ala Thr Phe Thr Ala Asp Lys Ser
                 65                  70                  75

Ser Asn Thr Ala Tyr Ile Gln Leu Ser Ser Leu Ser Thr Ser Glu
                 80                  85                  90

Asp Ser Ala Val Tyr Tyr Cys Ala Asp Gly Tyr His Gly Tyr Trp
                 95                 100                 105

Gly Gln Gly Thr Thr Leu Thr Val Ser Ser Ala Lys Thr Thr Pro
                110                 115                 120

Pro Ser Val Tyr Pro Leu Ala Pro Gly Cys Gly Asp Thr Thr Gly
                125                 130                 135

Ser Ser Val Thr Leu Gly Cys Leu Val Lys Gly Tyr Phe Pro Glu
                140                 145                 150

Ser Val Thr Val Thr Trp Asn Ser Gly Ser Leu Ser Ser Ser Val
                155                 160                 165

His Thr Phe Pro Ala Leu Leu Gln Ser Gly Leu Tyr Thr Met Ser
                170                 175                 180

Ser Ser Val Thr Val Pro Ser Ser Thr Trp Pro Ser Gln Thr Val
                185                 190                 195

Thr Cys Ser Val Ala His Pro Ala Ser Ser Thr Thr Val Asp Lys
                200                 205                 210

Lys Leu Glu Pro Ser Gly Pro Ile Ser Thr
                215                 220

<210> SEQ ID NO 66
<211> LENGTH: 78
<212> TYPE: DNA
<213> ORGANISM: Artificial sequence
<220> FEATURE:
<223> OTHER INFORMATION: Sequence is synthesized

<400> SEQUENCE: 66
gctcatagtg acctttctc caacagacac agccagagat gatggcgact          50
gtgacatcac gatatctgaa tgtactcc                                 78

<210> SEQ ID NO 67
<211> LENGTH: 66
<212> TYPE: DNA
```

```
<213> ORGANISM: Artificial sequence
<220> FEATURE:
<223> OTHER INFORMATION: Sequence is synthesized

<400> SEQUENCE: 67
gctgtaagtc cagtcaaagt cttttataca gtaccaatca gaagaacttc          50
ttggcctggt  accagc                                              66

<210> SEQ ID NO 68
<211> LENGTH: 35
<212> TYPE: DNA
<213> ORGANISM: Artificial sequence
<220> FEATURE:
<223> OTHER INFORMATION: Sequence is synthesized

<400> SEQUENCE: 68
gcgatcaggg acaccagatt ccctagtgga tgccc                          35

<210> SEQ ID NO 69
<211> LENGTH: 31
<212> TYPE: DNA
<213> ORGANISM: Artificial sequence
<220> FEATURE:
<223> OTHER INFORMATION: Sequence is synthesized

<400> SEQUENCE: 69
gccacgtctt cagcttttac actgctgatg g                              31

<210> SEQ ID NO 70
<211> LENGTH: 63
<212> TYPE: DNA
<213> ORGANISM: Artificial sequence
<220> FEATURE:
<223> OTHER INFORMATION: Sequence is synthesized

<400> SEQUENCE: 70 ggtccccct ccgaacgtgc gcgggtagga gtagtattgc tgacagtaat           50
aaactgccag  gtc                                                 63

<210> SEQ ID NO 71
<211> LENGTH: 28
<212> TYPE: DNA
<213> ORGANISM: Artificial sequence
<220> FEATURE:
<223> OTHER INFORMATION: Sequence is synthesized

<400> SEQUENCE: 71
gctgcagctg accttctgaa tgtactcc                                  28

<210> SEQ ID NO 72
<211> LENGTH: 50
<212> TYPE: DNA
<213> ORGANISM: Artificial sequence
<220> FEATURE:
<223> OTHER INFORMATION: Sequence is synthesized

<400> SEQUENCE: 72
gccttgcagg agatcttcac tgaagcccca ggcttcatca gctcagctcc          50

<210> SEQ ID NO 73
<211> LENGTH: 48
<212> TYPE: DNA
<213> ORGANISM: Artificial sequence
<220> FEATURE:
<223> OTHER INFORMATION: Sequence is synthesized
```

<400> SEQUENCE: 73
cccactctat ccagtaacta gagaaggtgt atccagtagc cttgcagg                48

<210> SEQ ID NO 74
<211> LENGTH: 49
<212> TYPE: DNA
<213> ORGANISM: Artificial sequence
<220> FEATURE:
<223> OTHER INFORMATION: Sequence is synthesized

<400> SEQUENCE: 74
ccacttccag gactaatctc tccaatccac tcaaggccat gtccaggcc               49

<210> SEQ ID NO 75
<211> LENGTH: 42
<212> TYPE: DNA
<213> ORGANISM: Artificial sequence
<220> FEATURE:
<223> OTHER INFORMATION: Sequence is synthesized

<400> SEQUENCE: 75
gcccttgaac tcctcattgt aattagtact accacttcca gg                     42

<210> SEQ ID NO 76
<211> LENGTH: 85
<212> TYPE: DNA
<213> ORGANISM: Artificial sequence
<220> FEATURE:
<223> OTHER INFORMATION: Sequence is synthesized

<400> SEQUENCE: 76
ccgcagagtc ctcagatgtg atcaggctgc tgagctggat gtaggcagtg              50
ttggaggatt tgtctgcagt gaatgttgcc ttgcc                              85

<210> SEQ ID NO 77
<211> LENGTH: 72
<212> TYPE: DNA
<213> ORGANISM: Artificial sequence
<220> FEATURE:
<223> OTHER INFORMATION: Sequence is synthesized

<400> SEQUENCE: 77
ggctgaggag acggtgactg tggtgccttg gccccagtag ccatggtacc              50
cgtctgcaca gtaatagacc tc                                            72

<210> SEQ ID NO 78
<211> LENGTH: 41
<212> TYPE: DNA
<213> ORGANISM: Artificial sequence
<220> FEATURE:
<223> OTHER INFORMATION: Sequence is synthesized

<400> SEQUENCE: 78
ccagactgct gcagctgacc ttgtgaatgt actccagttg c                       41

<210> SEQ ID NO 79
<211> LENGTH: 28
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 15
<223> OTHER INFORMATION: R = A or G
<220> FEATURE:

```
<221> NAME/KEY: Unknown
<222> LOCATION: 21
<223> OTHER INFORMATION: N = T, G, A or C

<400> SEQUENCE: 79
gccatagata tcgtratgca ncagtctc                                          28

<210> SEQ ID NO 80
<211> LENGTH: 21
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 15
<223> OTHER INFORMATION: Y = C or T
<220> FEATURE:
<221> NAME/KEY: Unknown
<222> LOCATION: 18
<223> OTHER INFORMATION: K = G or T

<400> SEQUENCE: 80
ccatggttcg acctytaktt t                                                 21

<210> SEQ ID NO 81
<211> LENGTH: 43
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 20
<223> OTHER INFORMATION: Y = C or T
<220> FEATURE:
<221> NAME/KEY: Unknown
<222> LOCATION: 26
<223> OTHER INFORMATION: S = C or G

<400> SEQUENCE: 81
gatcgacgta cgctgaggty cagctscagc tscagcagtc tgg                         43

<210> SEQ ID NO 82
<211> LENGTH: 44
<212> TYPE: DNA
<213> ORGANISM: Artificial sequence
<220> FEATURE:
<223> OTHER INFORMATION: Sequence is synthesized
<220> FEATURE:
<221> NAME/KEY: Unknown
<222> LOCATION: 3, 5, 18
<223> OTHER INFORMATION: R = A or G
<220> FEATURE:
<221> NAME/KEY: Unknown
<222> LOCATION: 4, 12
<223> OTHER INFORMATION: D = A or G or T
<220> FEATURE:
<221> NAME/KEY: Unknown
<222> LOCATION: 6
<223> OTHER INFORMATION: H = A or C or T
<220> FEATURE:
<221> NAME/KEY: Unknown
<222> LOCATION: 7
<223> OTHER INFORMATION: S = C or G
<220> FEATURE:
<221> NAME/KEY: Unknown
<222> LOCATION: 19
<223> OTHER INFORMATION: M = A or C

<400> SEQUENCE: 82
tgrdrhsagt gdcagagrmg tcggaggtgg ttcccgggta gaca                        44
```

```
<210> SEQ ID NO 83
<211> LENGTH: 58
<212> TYPE: DNA
<213> ORGANISM: Artificial sequence
<220> FEATURE:
<223> OTHER INFORMATION: Sequence is synthesized

<400> SEQUENCE: 83
cctggtttct gttgatacca ggctacagcg aagacacag cctgactggc        50 acggcagg                                                      58

<210> SEQ ID NO 84
<211> LENGTH: 57
<212> TYPE: DNA
<213> ORGANISM: Artificial sequence
<220> FEATURE:
<223> OTHER INFORMATION: Sequence is synthesized

<400> SEQUENCE: 84
gcgagaaggg actccagtgt aacggtggga tgcagagtaa atctgtagtt        50
tcggagc                                                       57

<210> SEQ ID NO 85
<211> LENGTH: 57
<212> TYPE: DNA
<213> ORGANISM: Artificial sequence
<220> FEATURE:
<223> OTHER INFORMATION: Sequence is synthesized

<400> SEQUENCE: 85
ggtaccctgt ccgaacgtcc aaggagtaga ataatgttgc tgacagtaat        50
aagttgc                                                       57

<210> SEQ ID NO 86
<211> LENGTH: 42
<212> TYPE: DNA
<213> ORGANISM: Artificial sequence
<220> FEATURE:
<223> OTHER INFORMATION: Sequence is synthesized

<400> SEQUENCE: 86
ggtcagagtg aaatccgtcc cagatccgga tccagagaag  cg               42

<210> SEQ ID NO 87
<211> LENGTH: 54
<212> TYPE: DNA
<213> ORGANISM: Artificial sequence
<220> FEATURE:
<223> OTHER INFORMATION: Sequence is synthesized

<400> SEQUENCE: 87
ggcctgacgg acccaatgga tcacatagct ggtgaatctg tagccagaag        50
ctgc                                                          54

<210> SEQ ID NO 88
<211> LENGTH: 69
<212> TYPE: DNA
<213> ORGANISM: Artificial sequence
<220> FEATURE:
<223> OTHER INFORMATION: Sequence is synthesized

<400> SEQUENCE: 88 cccccttgaac ttctcgttat agttggtgcc gtcgttataa ggattgttat       50
```

-continued

```
aaccaaccca  ctcgaggcc                                              69

<210> SEQ ID NO 89
<211> LENGTH: 75
<212> TYPE: DNA
<213> ORGANISM: Artificial sequence
<220> FEATURE:
<223> OTHER INFORMATION: Sequence is synthesized

<400> SEQUENCE: 89
ggttccttga ccccagtagg cgaaccatgg gagcattgtg ggtcgagaac              50
aataatagac ggcagtgtcc  tcagc                                       75

<210> SEQ ID NO 90
<211> LENGTH: 41
<212> TYPE: DNA
<213> ORGANISM: Artificial sequence
<220> FEATURE:
<223> OTHER INFORMATION: Sequence is synthesized

<400> SEQUENCE: 90
ccgtcgttat aaggattgtt ataactaacc cactcgaggc  c                     41

<210> SEQ ID NO 91
<211> LENGTH: 61
<212> TYPE: DNA
<213> ORGANISM: Artificial sequence
<220> FEATURE:
<223> OTHER INFORMATION: Sequence is synthesized

<400> SEQUENCE: 91
catctgcagg tatagtgtgt ttttcgaatt gtcacgactg atagtgaagc              50
gccccttgaa  c                                                      61

<210> SEQ ID NO 92
<211> LENGTH: 46
<212> TYPE: DNA
<213> ORGANISM: Artificial sequence
<220> FEATURE:
<223> OTHER INFORMATION: Sequence is synthesized

<400> SEQUENCE: 92
ccatgggagc attgtgggtc gagcacaata atagacggca  gtgtcc                46

<210> SEQ ID NO 93
<211> LENGTH: 74
<212> TYPE: DNA
<213> ORGANISM: Artificial sequence
<220> FEATURE:
<223> OTHER INFORMATION: Sequence is synthesized

<400> SEQUENCE: 93
ggaagacttc gcaacttatt actgtcagca acattattct actccttgga              50
cgttcggaca gggtaccaag  gtgg                                        74

<210> SEQ ID NO 94
<211> LENGTH: 74
<212> TYPE: DNA
<213> ORGANISM: Artificial sequence
<220> FEATURE:
<223> OTHER INFORMATION: Sequence is synthesized

<400> SEQUENCE: 94
ggacactgcc gtctattatt gttctcgacc cacaacgctc ccatggttcg              50
```

-continued cctactgggg tcaaggaacc ctgg                                              74

<210> SEQ ID NO 95
<211> LENGTH: 9
<212> TYPE: PRT
<213> ORGANISM: Artificial sequence
<220> FEATURE:
<223> OTHER INFORMATION: Sequence is synthesized

<400> SEQUENCE: 95

Gln Glu His Tyr Ser Thr Pro Trp Thr
                5

<210> SEQ ID NO 96
<211> LENGTH: 9
<212> TYPE: PRT
<213> ORGANISM: Artificial sequence
<220> FEATURE:
<223> OTHER INFORMATION: Sequence is synthesized

<400> SEQUENCE: 96

Gln Gln His Tyr Tyr Thr Pro Trp Thr
                5

<210> SEQ ID NO 97
<211> LENGTH: 9
<212> TYPE: PRT
<213> ORGANISM: Artificial sequence
<220> FEATURE:
<223> OTHER INFORMATION: Sequence is synthesized

<400> SEQUENCE: 97

Gln Gln Tyr Tyr Ser Thr Pro Trp Thr
                5

<210> SEQ ID NO 98
<211> LENGTH: 9
<212> TYPE: PRT
<213> ORGANISM: Artificial sequence
<220> FEATURE:
<223> OTHER INFORMATION: Sequence is synthesized

<400> SEQUENCE: 98

Gln Lys Thr Phe Ser Thr Pro Trp Thr
                5

<210> SEQ ID NO 99
<211> LENGTH: 9
<212> TYPE: PRT
<213> ORGANISM: Artificial sequence
<220> FEATURE:
<223> OTHER INFORMATION: Sequence is synthesized

<400> SEQUENCE: 99

Gln Gln Phe Tyr Ser Val Pro Trp Thr
                5

<210> SEQ ID NO 100
<211> LENGTH: 9
<212> TYPE: PRT
<213> ORGANISM: Artificial sequence
<220> FEATURE:
<223> OTHER INFORMATION: Sequence is synthesized

<400> SEQUENCE: 100

Gln Gln Lys Tyr Ser Thr Pro Trp Thr
                5

```
<210> SEQ ID NO 101
<211> LENGTH: 17
<212> TYPE: PRT
<213> ORGANISM: Artificial sequence
<220> FEATURE:
<223> OTHER INFORMATION: Sequence is synthesized

<400> SEQUENCE: 101

Tyr Asn Asn Pro Tyr Asn Ala Gly Thr Asn Tyr Asn Glu Lys Phe
 1               5                  10                  15

Lys Gly

<210> SEQ ID NO 102
<211> LENGTH: 108
<212> TYPE: PRT
<213> ORGANISM: Artificial sequence
<220> FEATURE:
<223> OTHER INFORMATION: Sequence is synthesized

<400> SEQUENCE: 102

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ala Val Ser
                20                  25                  30

Ser Ala Val Ala Trp Tyr Gln Gln Lys Pro Gly Lys Ala Pro Lys
            35                  40                  45

Leu Leu Ile Tyr Ser Ala Ser His Arg Tyr Thr Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Glu
                80                  85                  90

Ser Tyr Ser Thr Pro Trp Thr Phe Gly Gln Gly Thr Lys Val Glu
            95                  100                 105

Ile Lys Arg

<210> SEQ ID NO 103
<211> LENGTH: 118
<212> TYPE: PRT
<213> ORGANISM: Artificial sequence
<220> FEATURE:
<223> OTHER INFORMATION: Sequence is synthesized

<400> SEQUENCE: 103

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Thr
                20                  25                  30

Ser Tyr Val Ile His Trp Val Arg Gln Ala Pro Gly Lys Gly Leu
            35                  40                  45

Glu Trp Val Gly Tyr Asn Asn Pro Tyr Asn Ala Gly Thr Asn Tyr
        50                  55                  60

Asn Glu Lys Phe Lys Gly Arg Phe Thr Ile Ser Ser Asp Lys Ser
65                  70                  75

Lys Asn Thr Ala Tyr Leu Gln Met Asn Ser Leu Arg Ala Glu Asp
                80                  85                  90

Thr Ala Val Tyr Tyr Cys Ser Arg Pro Thr Met Leu Pro Trp Phe
            95                  100                 105

Ala Tyr Trp Gly Gln Gly Thr Leu Val Thr Val Ser Ser
```

110                 115

<210> SEQ ID NO 104
<211> LENGTH: 1344
<212> TYPE: PRT
<213> ORGANISM: Artificial sequence
<220> FEATURE:
<223> OTHER INFORMATION: Sequence is synthesized

<400> SEQUENCE: 104

Gly Ala Ala Gly Thr Thr Cys Ala Gly Cys Thr Gly Gly Thr Gly
 1               5                  10                  15

Gly Ala Gly Thr Cys Thr Gly Gly Cys Gly Gly Thr Gly Gly Cys
                20                  25                  30

Cys Thr Gly Gly Thr Gly Cys Ala Gly Cys Cys Ala Gly Gly Gly
                35                  40                  45

Gly Gly Cys Thr Cys Ala Cys Thr Cys Gly Thr Thr Thr Gly
                50                  55                  60

Thr Cys Cys Thr Gly Thr Gly Cys Ala Gly Cys Thr Cys Thr
            65                  70                  75

Gly Gly Cys Thr Ala Cys Ala Cys Ala Thr Thr Cys Ala Cys Cys
                80                  85                  90

Ala Gly Cys Thr Ala Thr Gly Thr Gly Ala Thr Cys Cys Ala Thr
                95                  100                 105

Thr Gly Gly Gly Thr Cys Cys Gly Thr Cys Ala Gly Gly Cys Cys
                110                 115                 120

Cys Cys Gly Gly Gly Thr Ala Ala Gly Gly Cys Cys Thr Cys
                125                 130                 135

Gly Ala Gly Thr Gly Gly Gly Thr Thr Gly Gly Thr Thr Ala Thr
                140                 145                 150

Ala Ala Cys Ala Ala Thr Cys Thr Thr Ala Thr Ala Ala Cys
                155                 160                 165

Gly Cys Cys Gly Gly Cys Ala Cys Cys Ala Ala Cys Thr Ala Thr
                170                 175                 180

Ala Ala Cys Gly Ala Gly Ala Ala Gly Thr Thr Cys Ala Ala Gly
                185                 190                 195

Gly Gly Gly Cys Gly Cys Thr Thr Cys Ala Cys Thr Ala Thr Cys
                200                 205                 210

Ala Gly Thr Thr Cys Thr Gly Ala Cys Ala Ala Gly Thr Cys Gly
                215                 220                 225

Ala Ala Ala Ala Ala Cys Ala Cys Ala Gly Cys Ala Thr Ala Cys
                230                 235                 240

Cys Thr Gly Cys Ala Gly Ala Thr Gly Ala Ala Cys Ala Gly Cys
                245                 250                 255

Cys Thr Gly Cys Gly Thr Gly Cys Thr Gly Ala Gly Gly Ala Cys
                260                 265                 270

Ala Cys Thr Gly Cys Cys Gly Thr Cys Thr Ala Thr Ala Thr Thr
                275                 280                 285

Thr Gly Thr Thr Cys Thr Cys Gly Ala Cys Cys Ala Cys Ala
            290                 295                 300

Ala Thr Gly Cys Thr Cys Cys Ala Thr Gly Gly Thr Thr Cys
                305                 310                 315

Gly Cys Cys Thr Ala Cys Thr Gly Gly Gly Thr Cys Ala Ala
                320                 325                 330

Gly Gly Ala Ala Cys Cys Cys Thr Gly Gly Thr Cys Ala Cys Cys
                335                 340                 345

-continued

```
Gly Thr Cys Thr Cys Cys Thr Cys Ala Gly Cys Cys Thr Cys Cys
            350                 355                 360
Ala Cys Cys Ala Ala Gly Gly Cys Cys Ala Thr Cys Gly
            365                 370                 375
Gly Thr Cys Thr Thr Cys Cys Cys Cys Thr Gly Gly Cys Ala
            380                 385                 390
Cys Cys Cys Thr Cys Thr Cys Cys Ala Ala Gly Ala Gly Cys
            395                 400                 405
Ala Cys Cys Thr Cys Thr Gly Gly Gly Gly Cys Ala Cys Ala
            410                 415                 420
Gly Cys Gly Gly Cys Cys Cys Thr Gly Gly Cys Thr Gly Cys
            425                 430                 435
Cys Thr Gly Gly Thr Cys Ala Ala Gly Ala Cys Thr Ala Cys
            440                 445                 450
Thr Thr Cys Cys Cys Cys Gly Ala Ala Cys Cys Gly Gly Thr Gly
            455                 460                 465
Ala Cys Gly Gly Thr Gly Thr Cys Gly Thr Gly Gly Ala Ala Cys
            470                 475                 480
Thr Cys Ala Gly Gly Cys Gly Cys Cys Cys Thr Gly Ala Cys Cys
            485                 490                 495
Ala Gly Cys Gly Gly Cys Gly Thr Gly Cys Ala Cys Ala Cys Cys
            500                 505                 510
Thr Thr Cys Cys Cys Gly Gly Cys Thr Gly Thr Cys Cys Thr Ala
            515                 520                 525
Cys Ala Gly Thr Cys Cys Thr Cys Ala Gly Gly Ala Cys Thr Cys
            530                 535                 540
Thr Ala Cys Thr Cys Cys Cys Thr Cys Ala Gly Cys Ala Gly Cys
            545                 550                 555
Gly Thr Gly Gly Thr Gly Ala Cys Thr Gly Thr Gly Cys Cys Cys
            560                 565                 570
Thr Cys Thr Ala Gly Cys Ala Gly Cys Thr Thr Gly Gly Gly Cys
            575                 580                 585
Ala Cys Cys Cys Ala Gly Ala Cys Cys Thr Ala Cys Ala Thr Cys
            590                 595                 600
Thr Gly Cys Ala Ala Cys Gly Thr Gly Ala Ala Thr Cys Ala Cys
            605                 610                 615
Ala Ala Gly Cys Cys Ala Gly Cys Ala Ala Cys Ala Cys Cys
            620                 625                 630
Ala Ala Gly Gly Thr Gly Gly Ala Cys Ala Ala Gly Ala Ala Ala
            635                 640                 645
Gly Thr Thr Gly Ala Gly Cys Cys Cys Ala Ala Ala Thr Cys Thr
            650                 655                 660
Thr Gly Thr Gly Ala Cys Ala Ala Ala Cys Thr Cys Ala Cys
            665                 670                 675
Ala Cys Ala Thr Gly Cys Cys Cys Ala Cys Cys Gly Thr Gly Cys
            680                 685                 690
Cys Cys Ala Gly Cys Ala Cys Cys Thr Gly Ala Ala Cys Thr Cys
            695                 700                 705
Cys Thr Gly Gly Gly Gly Gly Ala Cys Cys Gly Thr Cys Ala
            710                 715                 720
Gly Thr Cys Thr Thr Cys Cys Thr Cys Thr Thr Cys Cys Cys Cys
            725                 730                 735
Cys Cys Ala Ala Ala Ala Cys Cys Cys Ala Ala Gly Gly Ala Cys
```

740                 745                 750
Ala Cys Cys Cys Thr Cys Ala Thr Gly Ala Thr Cys Thr Cys Cys
                    755                 760                 765
Cys Gly Gly Ala Cys Cys Cys Thr Gly Ala Gly Gly Thr Cys
                    770                 775                 780
Ala Cys Ala Thr Gly Cys Gly Thr Gly Gly Thr Gly Thr Gly
                    785                 790                 795
Gly Ala Cys Gly Thr Gly Ala Gly Cys Ala Cys Gly Ala Ala
                    800                 805                 810
Gly Ala Cys Cys Thr Gly Ala Gly Gly Thr Cys Ala Ala Gly
                    815                 820                 825
Thr Thr Cys Ala Ala Cys Thr Gly Gly Thr Ala Cys Gly Thr
                    830                 835                 840
Gly Ala Cys Gly Gly Cys Gly Thr Gly Gly Ala Gly Gly Thr
                    845                 850                 855
Cys Ala Thr Ala Ala Thr Gly Cys Cys Ala Ala Gly Ala Cys Ala
                    860                 865                 870
Ala Ala Gly Cys Cys Gly Cys Gly Gly Ala Gly Gly Ala Gly
                    875                 880                 885
Cys Ala Gly Thr Ala Cys Ala Ala Cys Ala Gly Cys Ala Cys Gly
                    890                 895                 900
Thr Ala Cys Cys Gly Thr Gly Thr Gly Gly Thr Cys Ala Gly Cys
                    905                 910                 915
Gly Thr Cys Cys Thr Cys Ala Cys Cys Gly Thr Cys Thr Gly
                    920                 925                 930
Cys Ala Cys Cys Ala Gly Gly Ala Cys Thr Gly Gly Cys Thr Gly
                    935                 940                 945
Ala Ala Thr Gly Gly Cys Ala Ala Gly Ala Gly Thr Ala Cys
                    950                 955                 960
Ala Ala Gly Thr Gly Cys Ala Ala Gly Gly Thr Cys Thr Cys Cys
                    965                 970                 975
Ala Ala Cys Ala Ala Ala Gly Cys Cys Thr Cys Cys Ala
                    980                 985                 990
Gly Cys Cys Cys Cys Ala Thr Cys Gly Ala Gly Ala Ala Ala
                    995                1000                1005
Ala Cys Cys Ala Thr Cys Thr Cys Cys Ala Ala Ala Gly Cys Cys
                   1010                1015                1020
Ala Ala Ala Gly Gly Gly Cys Ala Gly Cys Cys Cys Cys Gly Ala
                   1025                1030                1035
Gly Ala Ala Cys Cys Ala Cys Ala Gly Gly Thr Gly Thr Ala Cys
                   1040                1045                1050
Ala Cys Cys Cys Thr Gly Cys Cys Cys Cys Cys Ala Thr Cys Cys
                   1055                1060                1065
Cys Gly Gly Gly Ala Thr Gly Ala Gly Ala Thr Gly Ala Cys Cys
                   1070                1075                1080
Ala Ala Gly Ala Ala Cys Cys Ala Gly Thr Cys Ala Gly Cys
                   1085                1090                1095
Cys Thr Gly Ala Cys Cys Thr Gly Cys Cys Thr Gly Gly Thr Cys
                   1100                1105                1110
Ala Ala Ala Gly Gly Cys Thr Thr Cys Thr Ala Thr Cys Cys
                   1115                1120                1125
Ala Gly Cys Gly Ala Cys Ala Thr Cys Gly Cys Cys Gly Thr Gly
                   1130                1135                1140

```
Gly Ala Gly Thr Gly Gly Gly Ala Gly Ala Gly Cys Ala Ala Thr
                1145                1150                1155

Gly Gly Gly Cys Ala Gly Cys Cys Gly Gly Ala Gly Ala Ala Cys
                1160                1165                1170

Ala Ala Cys Thr Ala Cys Ala Ala Gly Ala Cys Cys Ala Cys Gly
                1175                1180                1185

Cys Cys Thr Cys Cys Cys Gly Thr Gly Cys Thr Gly Gly Ala Cys
                1190                1195                1200

Thr Cys Cys Gly Ala Cys Gly Gly Cys Thr Cys Cys Thr Thr Cys
                1205                1210                1215

Thr Thr Cys Cys Thr Cys Thr Ala Cys Ala Gly Cys Ala Ala Gly
                1220                1225                1230

Cys Thr Cys Ala Cys Cys Gly Thr Gly Gly Ala Cys Ala Ala Gly
                1235                1240                1245

Ala Gly Cys Ala Gly Gly Thr Gly Gly Cys Ala Gly Cys Ala Gly
                1250                1255                1260

Gly Gly Gly Ala Ala Cys Gly Thr Cys Thr Thr Cys Thr Cys Ala
                1265                1270                1275

Thr Gly Cys Thr Cys Cys Gly Thr Gly Ala Thr Gly Cys Ala Thr
                1280                1285                1290

Gly Ala Gly Gly Cys Thr Cys Thr Gly Cys Ala Cys Ala Ala Cys
                1295                1300                1305

Cys Ala Cys Thr Ala Cys Ala Cys Gly Cys Ala Gly Ala Ala Gly
                1310                1315                1320

Ala Gly Cys Cys Thr Cys Thr Cys Cys Cys Thr Gly Thr Cys Thr
                1325                1330                1335

Cys Cys Gly Gly Gly Thr Ala Ala Ala
                1340

<210> SEQ ID NO 105
<211> LENGTH: 642
<212> TYPE: PRT
<213> ORGANISM: Artificial sequence
<220> FEATURE:
<223> OTHER INFORMATION: Sequence is synthesized

<400> SEQUENCE: 105

Gly Ala Thr Ala Thr Cys Cys Ala Gly Ala Thr Gly Ala Cys Cys
  1               5                   10                  15

Cys Ala Gly Thr Cys Cys Cys Cys Gly Ala Gly Cys Thr Cys Cys
                 20                   25                  30

Cys Thr Gly Thr Cys Cys Gly Cys Cys Thr Cys Thr Gly Thr Gly
                 35                   40                  45

Gly Gly Cys Gly Ala Thr Ala Gly Gly Gly Thr Cys Ala Cys Cys
                 50                   55                  60

Ala Thr Cys Ala Cys Cys Thr Gly Cys Cys Gly Thr Gly Cys Cys
                 65                   70                  75

Ala Gly Thr Cys Ala Gly Gly Cys Thr Gly Thr Gly Thr Cys Thr
                 80                   85                  90

Thr Cys Cys Gly Cys Thr Gly Thr Ala Gly Cys Cys Thr Gly Gly
                 95                  100                 105

Thr Ala Thr Cys Ala Ala Cys Ala Gly Ala Ala Ala Cys Cys Ala
                110                  115                 120

Gly Gly Ala Ala Ala Ala Gly Cys Thr Cys Cys Gly Ala Ala Ala
                125                  130                 135

Cys Thr Ala Cys Thr Gly Ala Thr Thr Thr Ala Cys Thr Cys Thr
```

-continued

```
                140                 145                 150

Gly Cys Ala Thr Cys Cys Cys Ala Cys Cys Gly Thr Thr Ala Cys
                155                 160                 165

Ala Cys Thr Gly Gly Ala Gly Thr Cys Cys Cys Thr Thr Cys Thr
                170                 175                 180

Cys Gly Cys Thr Thr Cys Thr Cys Thr Gly Gly Ala Thr Cys Cys
                185                 190                 195

Gly Gly Ala Thr Cys Thr Gly Gly Gly Ala Cys Gly Gly Ala Thr
                200                 205                 210

Thr Thr Cys Ala Cys Thr Cys Thr Gly Ala Cys Cys Ala Thr Cys
                215                 220                 225

Ala Gly Cys Ala Gly Thr Cys Thr Gly Cys Ala Gly Cys Cys Gly
                230                 235                 240

Gly Ala Ala Gly Ala Cys Thr Thr Cys Gly Cys Ala Ala Cys Thr
                245                 250                 255

Thr Ala Thr Thr Ala Cys Thr Gly Thr Cys Ala Gly Gly Ala Ala
                260                 265                 270

Thr Cys Thr Thr Ala Thr Thr Cys Thr Ala Cys Thr Cys Cys Thr
                275                 280                 285

Thr Gly Gly Ala Cys Gly Thr Thr Cys Gly Gly Ala Cys Ala Gly
                290                 295                 300

Gly Gly Thr Ala Cys Cys Ala Ala Gly Gly Thr Gly Gly Ala Gly
                305                 310                 315

Ala Thr Cys Ala Ala Ala Cys Gly Ala Ala Cys Thr Gly Thr Gly
                320                 325                 330

Gly Cys Thr Gly Cys Ala Cys Cys Ala Thr Cys Thr Gly Thr Cys
                335                 340                 345

Thr Thr Cys Ala Thr Cys Thr Thr Cys Cys Cys Gly Cys Cys Ala
                350                 355                 360

Thr Cys Thr Gly Ala Thr Gly Ala Gly Cys Ala Gly Thr Thr Gly
                365                 370                 375

Ala Ala Ala Thr Cys Thr Gly Gly Ala Ala Cys Thr Gly Cys Cys
                380                 385                 390

Thr Cys Thr Gly Thr Thr Gly Thr Gly Thr Gly Cys Cys Thr Gly
                395                 400                 405

Cys Thr Gly Ala Ala Thr Ala Ala Cys Thr Thr Cys Thr Ala Thr
                410                 415                 420

Cys Cys Cys Ala Gly Ala Gly Ala Gly Gly Cys Cys Ala Ala Ala
                425                 430                 435

Gly Thr Ala Cys Ala Gly Thr Gly Gly Ala Ala Gly Gly Thr Gly
                440                 445                 450

Gly Ala Thr Ala Ala Cys Gly Cys Cys Cys Thr Cys Cys Ala Ala
                455                 460                 465

Thr Cys Gly Gly Gly Thr Ala Ala Cys Thr Cys Cys Cys Ala Gly
                470                 475                 480

Gly Ala Gly Ala Gly Thr Gly Thr Cys Ala Cys Ala Gly Ala Gly
                485                 490                 495

Cys Ala Gly Gly Ala Cys Ala Gly Cys Ala Ala Gly Gly Ala Cys
                500                 505                 510

Ala Gly Cys Ala Cys Cys Thr Ala Cys Ala Gly Cys Cys Thr Cys
                515                 520                 525

Ala Gly Cys Ala Gly Cys Ala Cys Cys Cys Thr Gly Ala Cys Gly
                530                 535                 540
```

-continued

```
Cys Thr Gly Ala Gly Cys Ala Ala Gly Cys Ala Gly Cys
            545                 550                 555
Thr Ala Cys Gly Ala Gly Ala Ala Cys Ala Cys Ala Ala Ala
            560                 565                 570
Gly Thr Cys Thr Ala Cys Gly Cys Cys Thr Gly Cys Gly Ala Ala
            575                 580                 585
Gly Thr Cys Ala Cys Cys Cys Ala Thr Cys Ala Gly Gly Cys
            590                 595                 600
Cys Thr Gly Ala Gly Cys Thr Cys Gly Cys Cys Cys Gly Thr Cys
            605                 610                 615
Ala Cys Ala Ala Ala Gly Ala Gly Cys Thr Thr Cys Ala Ala Cys
            620                 625                 630
Ala Gly Gly Gly Gly Ala Gly Ala Gly Thr Gly Thr
            635                 640

<210> SEQ ID NO 106
<211> LENGTH: 448
<212> TYPE: PRT
<213> ORGANISM: Artificial sequence
<220> FEATURE:
<223> OTHER INFORMATION: Sequence is synthesized

<400> SEQUENCE: 106

Glu Val Gln Leu Val Glu Ser Gly Gly Gly Leu Val Gln Pro Gly
 1               5                  10                  15
Gly Ser Leu Arg Leu Ser Cys Ala Ala Ser Gly Tyr Thr Phe Thr
                20                  25                  30
Ser Tyr Val Ile His Trp Val Arg Gln Ala Pro Gly Lys Gly Leu
                35                  40                  45
Glu Trp Val Gly Tyr Asn Asn Pro Tyr Asn Ala Gly Thr Asn Tyr
                50                  55                  60
Asn Glu Lys Phe Lys Gly Arg Phe Thr Ile Ser Ser Asp Lys Ser
                65                  70                  75
Lys Asn Thr Ala Tyr Leu Gln Met Asn Ser Leu Arg Ala Glu Asp
                80                  85                  90
Thr Ala Val Tyr Tyr Cys Ser Arg Pro Thr Met Leu Pro Trp Phe
                95                  100                 105
Ala Tyr Trp Gly Gln Gly Thr Leu Val Thr Val Ser Ser Ala Ser
                110                 115                 120
Thr Lys Gly Pro Ser Val Phe Pro Leu Ala Pro Ser Ser Lys Ser
                125                 130                 135
Thr Ser Gly Gly Thr Ala Ala Leu Gly Cys Leu Val Lys Asp Tyr
                140                 145                 150
Phe Pro Glu Pro Val Thr Val Ser Trp Asn Ser Gly Ala Leu Thr
                155                 160                 165
Ser Gly Val His Thr Phe Pro Ala Val Leu Gln Ser Ser Gly Leu
                170                 175                 180
Tyr Ser Leu Ser Ser Val Val Thr Val Pro Ser Ser Ser Leu Gly
                185                 190                 195
Thr Gln Thr Tyr Ile Cys Asn Val Asn His Lys Pro Ser Asn Thr
                200                 205                 210
Lys Val Asp Lys Lys Val Glu Pro Lys Ser Cys Asp Lys Thr His
                215                 220                 225
Thr Cys Pro Pro Cys Pro Ala Pro Glu Leu Leu Gly Gly Pro Ser
                230                 235                 240
Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu
                260                 265                 270

Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu
            305                 310                 315

Asn Gly Lys Glu Tyr Lys Cys Lys Val Ser Asn Lys Ala Leu Pro
            320                 325                 330

Ala Pro Ile Glu Lys Thr Ile Ser Lys Ala Lys Gly Gln Pro Arg
            335                 340                 345

Glu Pro Gln Val Tyr Thr Leu Pro Pro Ser Arg Glu Glu Met Thr
            350                 355                 360

Lys Asn Gln Val Ser Leu Thr Cys Leu Val Lys Gly Phe Tyr Pro
            365                 370                 375

Ser Asp Ile Ala Val Glu Trp Glu Ser Asn Gly Gln Pro Glu Asn
            380                 385                 390

Asn Tyr Lys Thr Thr Pro Pro Val Leu Asp Ser Asp Gly Ser Phe
            395                 400                 405

Phe Leu Tyr Ser Lys Leu Thr Val Asp Lys Ser Arg Trp Gln Gln
            410                 415                 420

Gly Asn Val Phe Ser Cys Ser Val Met His Glu Ala Leu His Asn
            425                 430                 435

His Tyr Thr Gln Lys Ser Leu Ser Leu Ser Pro Gly Lys
            440                 445

<210> SEQ ID NO 107
<211> LENGTH: 214
<212> TYPE: PRT
<213> ORGANISM: Artificial sequence
<220> FEATURE:
<223> OTHER INFORMATION: Sequence is synthesized

<400> SEQUENCE: 107

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Ala Val Ser
                 20                  25                  30

Ser Ala Val Ala Trp Tyr Gln Gln Lys Pro Gly Lys Ala Pro Lys
             35                  40                  45

Leu Leu Ile Tyr Ser Ala Ser His Arg Tyr Thr Gly Val Pro Ser
             50                  55                  60

Arg Phe Ser Gly Ser Gly Ser Gly Thr Asp Phe Thr Leu Thr Ile
             65                  70                  75

Ser Ser Leu Gln Pro Glu Asp Phe Ala Thr Tyr Tyr Cys Gln Glu
             80                  85                  90

Ser Tyr Ser Thr Pro Trp Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150
```

```
Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
        170                 175                 180

Leu Ser Lys Ala Asp Tyr Glu Lys His Lys Val Tyr Ala Cys Glu
        185                 190                 195

Val Thr His Gln Gly Leu Ser Ser Pro Val Thr Lys Ser Phe Asn
        200                 205                 210

Arg Gly Glu Cys

<210> SEQ ID NO 108
<211> LENGTH: 114
<212> TYPE: PRT
<213> ORGANISM: Artificial sequence
<220> FEATURE:
<223> OTHER INFORMATION: Sequence is synthesized

<400> SEQUENCE: 108

Asp Ile Gln Met Thr Gln Ser Pro Ser Ser Leu Ser Ala Ser Val
 1               5                  10                  15

Gly Asp Arg Val Thr Ile Thr Cys Lys Ser Ser Gln Ser Leu Leu
            20                  25                  30

Tyr Ser Thr Asn Gln Lys Asn Phe Leu Ala Trp Tyr Gln Gln Lys
        35                  40                  45

Pro Gly Lys Ala Pro Lys Leu Leu Ile Tyr Trp Ala Ser Thr Arg
        50                  55                  60

Asp Ser Gly Val Pro Ser Arg Phe Ser Gly Ser Gly Ser Gly Thr
        65                  70                  75

Asp Phe Thr Leu Thr Ile Ser Ser Leu Gln Pro Glu Asp Phe Ala
        80                  85                  90

Thr Tyr Tyr Cys Gln Gln Tyr Tyr Ser Tyr Pro Arg Thr Phe Gly
        95                  100                 105

Gln Gly Thr Lys Val Glu Ile Lys Arg
            110

<210> SEQ ID NO 109
<211> LENGTH: 114
<212> TYPE: PRT
<213> ORGANISM: Artificial sequence
<220> FEATURE:
<223> OTHER INFORMATION: Sequence is synthesized

<400> SEQUENCE: 109

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Thr Phe Ser
            20                  25                  30

Ser Tyr Trp Ile Glu Trp Val Arg Gln Ala Pro Gly Lys Gly Leu
        35                  40                  45

Glu Trp Val Gly Glu Ile Asn Pro Gly Ser Gly Ser Thr Ile Tyr
        50                  55                  60

Asn Glu Lys Phe Lys Gly Arg Ala Thr Phe Ser Ala Asp Asn Ser
        65                  70                  75

Lys Asn Thr Ala Tyr Leu Gln Met Asn Ser Leu Arg Ala Glu Asp
        80                  85                  90

Thr Ala Val Tyr Tyr Cys Ala Asp Gly Tyr His Gly Tyr Trp Gly
        95                  100                 105
```

```
Gln Gly Thr Leu Val Thr Val Ser Ser
                110

<210> SEQ ID NO 110
<211> LENGTH: 17
<212> TYPE: PRT
<213> ORGANISM: Artificial sequence
<220> FEATURE:
<223> OTHER INFORMATION: Sequence is synthesized

<400> SEQUENCE: 110

Glu Ile Asn Pro Gly Ser Gly Ser Thr Ile Tyr Asn Glu Lys Phe
  1               5                  10                  15

Lys Gly
```